US012599660B2

(12) United States Patent
Sahin et al.

(10) Patent No.: US 12,599,660 B2
(45) Date of Patent: Apr. 14, 2026

(54) THERAPEUTIC RNA FOR HPV-POSITIVE CANCER

(71) Applicants: BioNTech SE, Mainz (DE); TRON-Translationale Onkologie an der Universitätsmedizin der Johannes Gutenberg-Universität Mainz Gemeinnützige GMBH, Mainz (DE)

(72) Inventors: Ugur Sahin, Mainz (DE); Sebastian Kreiter, Mainz (DE); Mustafa Diken, Mainz (DE); Fulvia Vascotto, Mainz (DE); Nadja Salomon, Mainz (DE); Christian Grunwitz, Mainz (DE)

(73) Assignees: BiòNTech SE, Mainz (DE); TRON—Translationale Onkologie an der Universitätsmedizin Der Johannes Gutenberg-Universität Mainz gGmbH, Mainz (DE)

( * ) Notice: Subject to any disclaimer, the term of this patent is extended or adjusted under 35 U.S.C. 154(b) by 644 days.

(21) Appl. No.: 18/012,366

(22) PCT Filed: Jul. 6, 2021

(86) PCT No.: PCT/EP2021/068680
§ 371 (c)(1),
(2) Date: Dec. 22, 2022

(87) PCT Pub. No.: WO2022/008519
PCT Pub. Date: Jan. 13, 2022

(65) Prior Publication Data

US 2025/0262293 A1 Aug. 21, 2025

(30) Foreign Application Priority Data

Jul. 7, 2020 (WO) ................ PCT/EP2020/069146

(51) Int. Cl.
*A61K 39/12* (2006.01)
*A61K 33/243* (2019.01)
*A61K 39/395* (2006.01)
*A61P 35/00* (2006.01)
*A61K 39/00* (2006.01)

(52) U.S. Cl.
CPC ............ *A61K 39/12* (2013.01); *A61K 33/243* (2019.01); *A61K 39/3955* (2013.01); *A61P 35/00* (2018.01); *A61K 2039/505* (2013.01); *A61K 2039/53* (2013.01); *A61K 2039/54* (2013.01); *A61K 2039/55555* (2013.01); *A61K 2039/605* (2013.01); *C12N 2710/20034* (2013.01)

(58) Field of Classification Search
None
See application file for complete search history.

(56) References Cited

U.S. PATENT DOCUMENTS

| | | | | |
|---|---|---|---|---|
| 8,178,653 B2 * | 5/2012 | Tureci | A61P 31/14 530/403 |
| 2018/0296662 A1 * | 10/2018 | Ciaramella | A61P 31/14 |
| 2023/0114808 A1 * | 4/2023 | Weber | A61K 39/3955 424/185.1 |

FOREIGN PATENT DOCUMENTS

| | | | |
|---|---|---|---|
| CN | 109568574 | A | 4/2019 |
| WO | 2011015347 | A1 | 2/2011 |
| WO | 2013113326 | A1 | 8/2013 |
| WO | 2013143683 | A1 | 10/2013 |
| WO | 2015024664 | A1 | 2/2015 |
| WO | 2015103602 | A1 | 7/2015 |
| WO | 2016005324 | A1 | 1/2016 |
| WO | 2017060314 | A2 | 4/2017 |
| WO | 2017070616 | A2 | 4/2017 |
| WO | 2018081459 | A1 | 5/2018 |
| WO | 2019063565 | A1 | 4/2019 |
| WO | 2022008519 | A1 | 1/2022 |

OTHER PUBLICATIONS

Derbie et al. (Jama, 2025, pp. 1-3).*
International Search Report for International Patent Application No. PCT/EP2021/068680, dated Oct. 8, 2021, 8 pages.
Written Opinion for International Patent Application No. PCT/EP2021/068680, dated Oct. 8, 2021, 8 pages.
Grunwitz C et al, "Preclinical evaluation of an mRNA-based immunotherapy against HPV16+ Head and neck squamous cell carcinoma", May 1, 2015 (May 1, 2015), p. 36, Retrieved from the Internet: URL:http://www.meeting.cimt.eu/cms/diskfiles/download/82/97bc7316432d6e3be01f682fa66f1640/CIMT_Abstracts_2015.pdf [retrieved on Sep. 27, 2021].
Lena M. Kranz et al, "Systemic RNA delivery to dendritic cells exploits antiviral defence for cancer Immunotherapy", Nature, vol. 534, No. 7607, Jun. 16, 2016 (Jun. 16, 2016), p. 396-401.

(Continued)

*Primary Examiner* — Agnieszka Boesen
(74) *Attorney, Agent, or Firm* — Neal, Gerber & Eisenberg LLP

(57) ABSTRACT

This disclosure relates to the field of therapeutic RNA to treat HPV-positive cancer, in particular anogenital, cervical and penile cancers and cancer in the head and neck region such as cancer in the genital region and head and neck squamous cell carcinoma (HNSCC). Disclosed herein are compositions, uses, and methods for treatment of HPV-positive cancers. Administration of therapeutic RNAs to a patient having HPV-positive cancer disclosed herein can reduce tumor size, prolong time to progressive disease, and/or protect against metastasis and/or recurrence of the tumor and ultimately extend survival time.

27 Claims, 21 Drawing Sheets

Specification includes a Sequence Listing.

(56) References Cited

OTHER PUBLICATIONS

Rafi-Janajreh A et al, "Influence of adjuvants in inducing immune responses to different epitopes included in a multiepitope, multivalent, multistage Plasmodium falciparum candidate vaccine (FALVAC-1) in outbred mice", Experimental Parasitology, New York, NY, US, vol. 101, No. 1, May 1, 2002 (May 1, 2002), p. 3-12.

Lund L H et al, "Signal sequence deletion and fusion to tetanus toxoid epitope augment antitumor immune responses to a human carcinoembryonic antigen (CEA) plasmid DNA vaccine in a murine test system", Cancer Gene Therapy, Appleton & Lange, New York, vol. 10, No. 5, May 1, 2003 (May 1, 2003), p. 365-376.

USPTO, Office Action in co-pending U.S. Appl. No. 19/091,130 dated Aug. 21, 2025 (10 pages).

* cited by examiner

A.2

B

C

SEQUENCE LISTING

```
<160> NUMBER OF SEQ ID NOS: 35

<210> SEQ ID NO 1
<211> LENGTH: 338
<212> TYPE: PRT
<213> ORGANISM: Human papillomavirus type 16

<400> SEQUENCE: 1

Met Arg Val Met Ala Pro Arg Thr Leu Ile Leu Leu Leu Ser Gly Ala
1               5                   10                  15
```

-continued

```
Leu Ala Leu Thr Glu Thr Trp Ala Gly Ser Gly Gly Ser Gly Gly Gly
            20                  25                  30

Gly Ser Gly Gly Met His Gln Lys Arg Thr Ala Met Phe Gln Asp Pro
        35                  40                  45

Gln Glu Arg Pro Arg Lys Leu Pro Gln Leu Cys Thr Glu Leu Gln Thr
    50                  55                  60

Thr Ile His Asp Ile Ile Leu Glu Cys Val Tyr Cys Lys Gln Gln Leu
65                  70                  75                  80

Leu Arg Arg Glu Val Tyr Asp Phe Ala Phe Arg Asp Leu Cys Ile Val
                85                  90                  95

Tyr Arg Asp Gly Asn Pro Tyr Ala Val Cys Asp Lys Cys Leu Lys Phe
            100                 105                 110

Tyr Ser Lys Ile Ser Glu Tyr Arg His Tyr Cys Tyr Ser Leu Tyr Gly
        115                 120                 125

Thr Thr Leu Glu Gln Gln Tyr Asn Lys Pro Leu Cys Asp Leu Leu Ile
    130                 135                 140

Arg Cys Ile Asn Cys Gln Lys Pro Leu Cys Pro Glu Glu Lys Gln Arg
145                 150                 155                 160

His Leu Asp Lys Lys Gln Arg Phe His Asn Ile Arg Gly Arg Trp Thr
                165                 170                 175

Gly Arg Cys Met Ser Cys Cys Arg Ser Ser Arg Thr Arg Arg Glu Thr
            180                 185                 190

Gln Leu Gly Gly Ser Gly Gly Gly Gly Ser Gly Gly Lys Lys Gln Tyr
        195                 200                 205

Ile Lys Ala Asn Ser Lys Phe Ile Gly Ile Thr Glu Leu Lys Lys Leu
    210                 215                 220

Gly Gly Gly Lys Arg Gly Gly Gly Lys Lys Met Thr Asn Ser Val Asp
225                 230                 235                 240

Asp Ala Leu Ile Asn Ser Thr Lys Ile Tyr Ser Tyr Phe Pro Ser Val
                245                 250                 255

Ile Ser Lys Val Asn Gln Gly Ala Gln Gly Lys Lys Leu Gly Ser Ser
            260                 265                 270

Gly Gly Gly Gly Ser Pro Gly Gly Gly Ser Ser Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 2
<211> LENGTH: 1499
<212> TYPE: RNA
<213> ORGANISM: Human papillomavirus type 16

<400> SEQUENCE: 2

gggcgaacua guauucuucu ggucccccaca gacucagaga gaacccgcca ccaugagagu      60

gauggccccc agaacccuga uccugcugcu gucuggcgcc cuggcccuga cagagacaug     120

ggccggaagc ggcggcucug gaggaggcgg cuccggaggc augcaccaaa agagaacugc     180

aauguuucag gacccacagg agcgacccag aaaguuacca caguuaugca cagagcugca     240
```

-continued

```
aacaacuaua caugauauaa uauuagaaug uguguacugc aagcaacagu uacugcgacg    300

ugagguauau gacuuugcuu uucgggauuu augcauagua uauagagaug ggaauccaua    360

ugcuguaugu gauaaauguu uaaaguuuua uucuaaaauu agugaguaua gacauuauug    420

uuauaguuug uauggaacaa cauuagaaca gcaauacaac aaaccguugu gugauuuguu    480

aauuaggugu auuaacuguc aaaagccacu guguccugaa gaaaagcaaa gacaucugga    540

caaaaagcaa agauuccaua auauaagggg ucgguggacc ggucgaugua ugucuuguug    600

cagaucauca agaacacgua gagaaaccca gcugggagga uccgguggug gcggcagcgg    660

cggcaagaag caguacauca aggccaacag caaguucauc ggcaucaccg agcugaagaa    720

gcugggaggg ggcaaacggg gaggcggcaa aaagaugacc aacagcgugg acgacgcccu    780

gaucaacagc accaagaucu acagcuacuu ccccagcgug aucagcaaag ugaaccaggg    840

cgcucagggc aagaaacugg gcucuagcgg agggggaggc ucuccuggcg gggaucuag    900

caucguggga auuguggcag gacuggcagu gcuggccgug guggugaucg gagccguggu    960

ggcuaccgug augugcagac ggaaguccag cggaggcaag ggcggcagcu acagccaggc   1020

cgccagcucu gauagcgccc agggcagcga cgugucacug acagccuagu aacucgagcu   1080

gguacugcau gcacgcaaug cuagcugccc cuuucccguc cuggguaccc cgagucuccc   1140

ccgaccucgg gucccaggua ugcucccacc uccaccugcc ccacucacca ccucugcuag   1200

uuccagacac cucccaagca cgcagcaaug cagcucaaaa cgcuuagccu agccacaccc   1260

ccacgggaaa cagcagugau uaaccuuuag caauaaacga aaguuuaacu aagcuauacu   1320

aaccccaggg uuggucaauu ucgugccagc cacaccgaga ccugguccag agucgcuagc   1380

cgcgucgcua aaaaaaaaaa aaaaaaaaaa aaaaaaaaag cauaugacua aaaaaaaaaa   1440

aaaaaaaaaa aaaaaaaaaa aaaaaaaaaa aaaaaaaaaa aaaaaaaaaa aaaaaaaaa    1499
```

<210> SEQ ID NO 3
<211> LENGTH: 278
<212> TYPE: PRT
<213> ORGANISM: Human papillomavirus type 16

<400> SEQUENCE: 3

```
Met Arg Val Met Ala Pro Arg Thr Leu Ile Leu Leu Leu Ser Gly Ala
1               5                   10                  15

Leu Ala Leu Thr Glu Thr Trp Ala Gly Ser Gly Gly Ser Gly Gly Gly
            20                  25                  30

Gly Ser Gly Gly Met His Gly Asp Thr Pro Thr Leu His Glu Tyr Met
        35                  40                  45

Leu Asp Leu Gln Pro Glu Thr Thr Asp Leu Tyr Cys Tyr Glu Gln Leu
    50                  55                  60

Asn Asp Ser Ser Glu Glu Glu Asp Glu Ile Asp Gly Pro Ala Gly Gln
65                  70                  75                  80

Ala Glu Pro Asp Arg Ala His Tyr Asn Ile Val Thr Phe Cys Cys Lys
                85                  90                  95

Cys Asp Ser Thr Leu Arg Leu Cys Val Gln Ser Thr His Val Asp Ile
            100                 105                 110

Arg Thr Leu Glu Asp Leu Leu Met Gly Thr Leu Gly Ile Val Cys Pro
        115                 120                 125

Ile Cys Ser Gln Lys Pro Gly Gly Ser Gly Gly Gly Gly Ser Gly Gly
    130                 135                 140

Lys Lys Gln Tyr Ile Lys Ala Asn Ser Lys Phe Ile Gly Ile Thr Glu
145                 150                 155                 160
```

```
Leu Lys Lys Leu Gly Gly Gly Lys Arg Gly Gly Gly Lys Lys Met Thr
                165                 170                 175

Asn Ser Val Asp Asp Ala Leu Ile Asn Ser Thr Lys Ile Tyr Ser Tyr
            180                 185                 190

Phe Pro Ser Val Ile Ser Lys Val Asn Gln Gly Ala Gln Gly Lys Lys
        195                 200                 205

Leu Gly Ser Ser Gly Gly Gly Gly Ser Pro Gly Gly Gly Ser Ser Ile
    210                 215                 220

Val Gly Ile Val Ala Gly Leu Ala Val Leu Ala Val Val Val Ile Gly
225                 230                 235                 240

Ala Val Val Ala Thr Val Met Cys Arg Arg Lys Ser Ser Gly Gly Lys
                245                 250                 255

Gly Gly Ser Tyr Ser Gln Ala Ala Ser Ser Asp Ser Ala Gln Gly Ser
            260                 265                 270

Asp Val Ser Leu Thr Ala
        275


<210> SEQ ID NO 4
<211> LENGTH: 1319
<212> TYPE: RNA
<213> ORGANISM: Human papillomavirus type 16

<400> SEQUENCE: 4

gggcgaacua guauucuucu gguccccaca gacucagaga gaacccgcca ccaugagagu      60

gauggccccc agaacccuga uccugcugcu gucuggcgcc cuggcccuga cagagacaug     120

ggccggaagc ggcggcucug gaggaggcgg cuccggaggc augcauggcg acacaccaac     180

acuucacgaa uauaugcugg auuugcagcc ugaaaccacc gaucuguacu gcuaugaaca     240

gcugaaugau ucuucugaag aagaagauga aauugauggu ccugcuggac aagcagaacc     300

ugauagagcc cacuacaaca uugugacauu uugcugcaaa ugugauucaa cccuuagacu     360

uuguguucag uccacacaug uugacauaag aacucuggaa gaucugcuga ugggaacucu     420

uggaauugug ugucccauuu gcucacagaa accuggagga uccggugug gcggcagcgg     480

cggcaagaag caguacauca aggccaacag caaguucauc ggcaucaccg agcugaagaa     540

gcugggaggg ggcaaacggg gaggcggcaa aaagaugacc aacagcgugg acgacgcccu     600

gaucaacagc accaagaucu acagcuacuu ccccagcgug aucagcaaag ugaaccaggg     660

cgcucagggc aagaaacugg gcucuagcgg agggggaggc ucuccuggcg ggggaucuag     720

caucguggga auuguggcag gacuggcagu gcuggccgug guggugaucg gagccguggu     780

ggcuaccgug augugcagac ggaaguccag cggaggcaag ggcggcagcu acagccaggc     840

cgccagcucu gauagcgccc agggcagcga cgugucacug acagccuagu aacucgagcu     900

gguacugcau gcacgcaaug cuagcugccc cuuucccguc cuggguaccc cgagucuccc     960

ccgaccucgg gucccaggua ugcucccacc uccaccugcc ccacucacca ccucugcuag    1020

uuccagacac cucccaagca cgcagcaaug cagcucaaaa cgcuuagccu agccacaccc    1080

ccacgggaaa cagcagugau uaaccuuuag caauaaacga aaguuuaacu aagcuauacu    1140

aaccccaggg uuggucaauu ucgugccagc cacaccgaga ccugguccag agucgcuagc    1200

cgcgucgcua aaaaaaaaaa aaaaaaaaaa aaaaaaaaag cauaugacua aaaaaaaaaa    1260

aaaaaaaaaa aaaaaaaaaa aaaaaaaaaa aaaaaaaaaa aaaaaaaaaa aaaaaaaaa     1319


<210> SEQ ID NO 5
```

-continued

<211> LENGTH: 338
<212> TYPE: PRT
<213> ORGANISM: Human papillomavirus type 18

<400> SEQUENCE: 5

```
Met Arg Val Met Ala Pro Arg Thr Leu Ile Leu Leu Leu Ser Gly Ala
1               5                   10                  15

Leu Ala Leu Thr Glu Thr Trp Ala Gly Ser Gly Gly Ser Gly Gly Gly
            20                  25                  30

Gly Ser Gly Gly Met Ala Arg Phe Glu Asp Pro Thr Arg Arg Pro Tyr
        35                  40                  45

Lys Leu Pro Asp Leu Cys Thr Glu Leu Asn Thr Ser Leu Gln Asp Ile
    50                  55                  60

Glu Ile Thr Cys Val Tyr Cys Lys Thr Val Leu Glu Leu Thr Glu Val
65                  70                  75                  80

Phe Glu Phe Ala Phe Lys Asp Leu Phe Val Val Tyr Arg Asp Ser Ile
                85                  90                  95

Pro His Ala Ala Cys His Lys Cys Ile Asp Phe Tyr Ser Arg Ile Arg
            100                 105                 110

Glu Leu Arg His Tyr Ser Asp Ser Val Tyr Gly Asp Thr Leu Glu Lys
        115                 120                 125

Leu Thr Asn Thr Gly Leu Tyr Asn Leu Leu Ile Arg Cys Leu Arg Cys
    130                 135                 140

Gln Lys Pro Leu Asn Pro Ala Glu Lys Leu Arg His Leu Asn Glu Lys
145                 150                 155                 160

Arg Arg Phe His Asn Ile Ala Gly His Tyr Arg Gly Gln Cys His Ser
                165                 170                 175

Cys Cys Asn Arg Ala Arg Gln Glu Arg Leu Gln Arg Arg Arg Glu Thr
            180                 185                 190

Gln Val Gly Gly Ser Gly Gly Gly Gly Ser Gly Gly Lys Lys Gln Tyr
        195                 200                 205

Ile Lys Ala Asn Ser Lys Phe Ile Gly Ile Thr Glu Leu Lys Lys Leu
    210                 215                 220

Gly Gly Gly Lys Arg Gly Gly Gly Lys Lys Met Thr Asn Ser Val Asp
225                 230                 235                 240

Asp Ala Leu Ile Asn Ser Thr Lys Ile Tyr Ser Tyr Phe Pro Ser Val
                245                 250                 255

Ile Ser Lys Val Asn Gln Gly Ala Gln Gly Lys Lys Leu Gly Ser Ser
            260                 265                 270

Gly Gly Gly Gly Ser Pro Gly Gly Gly Ser Ser Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 6
<211> LENGTH: 1499
<212> TYPE: RNA
<213> ORGANISM: Human papillomavirus type 18

<400> SEQUENCE: 6

-continued

```
gggcgaacua guauucuucu gguccccaca gacucagaga gaacccgcca ccaugagagu      60

gauggccccc agaacccuga uccugcugcu gucuggcgcc cuggcccuga cagagacaug     120

ggccggaagc ggcggcucug gaggaggcgg cuccggaggc auggcaagau uugaagaucc     180

aacaagaaga ccauacaaac ugcccgaucu gugcacagaa cugaacaccu cucugcaaga     240

uauugaaauc accugugugu acuguaaaac cgugcuggaa cugaccgaag uguuugaauu     300

ugcuuuuaaa gaccuguuug ugguguacag agauuccauu ccucaugcag caugucacaa     360

auguauugau uuuuacucaa gaaucagaga acugagacau uauucugauu cuguguaugg     420

agauacacug gagaaacuga caaauacagg acuguacaau cugcugauua gaugucugag     480

augucagaaa ccucugaacc cugcugagaa acugagacau cugaaugaga aaagaagauu     540

ucacaacauu gcuggccauu acagaggcca gugucauucu uguuguaaua gagcaagaca     600

ggaaagacug caaagaagaa gggaaaccca ggugggagga uccgguggug gcggcagcgg     660

cggcaagaag caguacauca aggccaacag caaguucauc ggcaucaccg agcugaagaa     720

gcugggaggg ggcaaacggg gaggcggcaa aaagaugacc aacagcgugg acgacgcccu     780

gaucaacagc accaagaucu acagcuacuu ccccagcgug aucagcaaag ugaaccaggg     840

cgcucagggc aagaaacugg gcucuagcgg agggggaggc ucuccuggcg ggggaucuag     900

caucguggga auuguggcag gacuggcagu gcuggccgug guggugaucg gagccguggu     960

ggcuaccgug augugcagac ggaaguccag cggaggcaag ggcggcagcu acagccaggc    1020

cgccagcucu gauagcgccc agggcagcga cgugucacug acagccuagu aacucgagcu    1080

gguacugcau gcacgcaaug cuagcugccc cuuucccguc cuggguaccc cgagucuccc    1140

ccgaccucgg gucccaggua ugcucccacc uccaccugcc ccacucacca ccucugcuag    1200

uuccagacac cucccaagca cgcagcaaug cagcucaaaa cgcuuagccu agccacaccc    1260

ccacgggaaa cagcagugau uaaccuuuag caauaaacga aaguuuaacu aagcuauacu    1320

aaccccaggg uuggucaauu ucgugccagc cacaccgaga ccugguccag agucgcuagc    1380

cgcgucgcua aaaaaaaaaa aaaaaaaaaa aaaaaaaaag cauaugacua aaaaaaaaaa    1440

aaaaaaaaaa aaaaaaaaaa aaaaaaaaaa aaaaaaaaaa aaaaaaaaaa aaaaaaaaa     1499
```

<210> SEQ ID NO 7
<211> LENGTH: 285
<212> TYPE: PRT
<213> ORGANISM: Human papillomavirus type 18

<400> SEQUENCE: 7

```
Met Arg Val Met Ala Pro Arg Thr Leu Ile Leu Leu Leu Ser Gly Ala
1               5                   10                  15

Leu Ala Leu Thr Glu Thr Trp Ala Gly Ser Gly Gly Ser Gly Gly Gly
            20                  25                  30

Gly Ser Gly Gly Met His Gly Pro Lys Ala Thr Leu Gln Asp Ile Val
        35                  40                  45

Leu His Leu Glu Pro Gln Asn Glu Ile Pro Val Asp Leu Leu Cys His
    50                  55                  60

Glu Gln Leu Ser Asp Ser Glu Glu Glu Asn Asp Glu Ile Asp Gly Val
65                  70                  75                  80

Asn His Gln His Leu Pro Ala Arg Arg Ala Glu Pro Gln Arg His Thr
                85                  90                  95

Met Leu Cys Met Cys Cys Lys Cys Glu Ala Arg Ile Glu Leu Val Val
            100                 105                 110
```

-continued

```
Glu Ser Ser Ala Asp Asp Leu Arg Ala Phe Gln Gln Leu Phe Leu Asn
        115                 120                 125

Thr Leu Ser Phe Val Cys Pro Trp Cys Ala Ser Gln Gln Gly Gly Ser
    130                 135                 140

Gly Gly Gly Gly Ser Gly Gly Lys Lys Gln Tyr Ile Lys Ala Asn Ser
145                 150                 155                 160

Lys Phe Ile Gly Ile Thr Glu Leu Lys Lys Leu Gly Gly Gly Lys Arg
                165                 170                 175

Gly Gly Gly Lys Lys Met Thr Asn Ser Val Asp Asp Ala Leu Ile Asn
            180                 185                 190

Ser Thr Lys Ile Tyr Ser Tyr Phe Pro Ser Val Ile Ser Lys Val Asn
        195                 200                 205

Gln Gly Ala Gln Gly Lys Lys Leu Gly Ser Ser Gly Gly Gly Gly Ser
    210                 215                 220

Pro Gly Gly Gly Ser Ser Ile Val Gly Ile Val Ala Gly Leu Ala Val
225                 230                 235                 240

Leu Ala Val Val Val Ile Gly Ala Val Val Ala Thr Val Met Cys Arg
                245                 250                 255

Arg Lys Ser Ser Gly Gly Lys Gly Gly Ser Tyr Ser Gln Ala Ala Ser
            260                 265                 270

Ser Asp Ser Ala Gln Gly Ser Asp Val Ser Leu Thr Ala
        275                 280                 285


<210> SEQ ID NO 8
<211> LENGTH: 1340
<212> TYPE: RNA
<213> ORGANISM: Human papillomavirus type 18

<400> SEQUENCE: 8

gggcgaacua guauucuucu gguccccaca gacucagaga gaacccgcca ccaugagagu      60

gauggccccc agaacccuga uccugcugcu gucuggcgcc cuggcccuga cagagacaug     120

ggccggaagc ggcggcucug gaggaggcgg cuccggaggc augcauggac cuaaggcaac     180

auugcaagac auuguauugc auuuagagcc ccaaaaugaa auuccgguug accuucuaug     240

ucacgagcaa uuaagcgacu cagaggaaga aaacgaugaa auagauggag uuaaucauca     300

acauuuacca gcccgacgag ccgaaccaca acgucacaca auguugugua uguguuguaa     360

gugugaagcc agaauugagc uaguaguaga aagcucagca gacgaccuuc gagcauucca     420

gcagcuguuu cugaacaccc uguccuuugu guguccgugg ugugcauccc agcagggagg     480

auccgguggu ggcggcagcg gcggcaagaa gcaguacauc aaggccaaca gcaaguucau     540

cggcaucacc gagcugaaga agcugggagg gggcaaacgg ggaggcggca aaaagaugac     600

caacagcgug gacgacgccc ugaucaacag caccaagauc uacagcuacu uccccagcgu     660

gaucagcaaa gugaaccagg gcgcucaggg caagaaacug ggcucuagcg gagggggagg     720

cucuccuggc gggggaucua gcaucguggg aauuguggca ggacuggcag ugcuggccgu     780

gguggugauc ggagccgugg uggcuaccgu gaugugcaga cggaagucca gcggaggcaa     840

gggcggcagc uacagccagg ccgccagcuc ugauagcgcc cagggcagcg acgugucacu     900

gacagccuag uaacucgagc ugguacugca ugcacgcaau gcuagcugcc ccuuucccgu     960

ccuggguacc ccgagucucc cccgaccucg ggucccaggu augcucccac cuccaccugc    1020

cccacucacc accucugcua guuccagaca ccucccaagc acgcagcaau gcagcucaaa    1080

acgcuuagcc uagccacacc cccacgggaa acagcaguga uuaaccuuua gcaauaaacg    1140
```

-continued

```
aaaguuuaac uaagcuauac uaaccccagg guuggucaau uucgugccag ccacaccgag   1200

accuggucca gagucgcuag ccgcgucgcu aaaaaaaaaa aaaaaaaaaa aaaaaaaaaa   1260

gcauaugacu aaaaaaaaaa aaaaaaaaaa aaaaaaaaaa aaaaaaaaaa aaaaaaaaaa   1320

aaaaaaaaaa aaaaaaaaaa                                               1340


<210> SEQ ID NO 9
<211> LENGTH: 329
<212> TYPE: PRT
<213> ORGANISM: Human papillomavirus type 31

<400> SEQUENCE: 9

Met Arg Val Met Ala Pro Arg Thr Leu Ile Leu Leu Leu Ser Gly Ala
1               5                   10                  15

Leu Ala Leu Thr Glu Thr Trp Ala Gly Ser Gly Gly Ser Gly Gly Gly
            20                  25                  30

Gly Ser Gly Gly Met Phe Lys Asn Pro Ala Glu Arg Pro Arg Lys Leu
        35                  40                  45

His Glu Leu Ser Ser Ala Leu Glu Ile Pro Tyr Asp Glu Leu Arg Leu
    50                  55                  60

Asn Cys Val Tyr Cys Lys Gly Gln Leu Thr Glu Thr Glu Val Leu Asp
65                  70                  75                  80

Phe Ala Phe Thr Asp Leu Thr Ile Val Tyr Arg Asp Asp Thr Pro Tyr
                85                  90                  95

Gly Val Cys Thr Lys Cys Leu Arg Phe Tyr Ser Lys Val Ser Glu Phe
            100                 105                 110

Arg Trp Tyr Arg Tyr Ser Val Tyr Gly Thr Thr Leu Glu Lys Leu Thr
        115                 120                 125

Asn Lys Gly Ile Cys Asp Leu Leu Ile Arg Cys Ile Thr Cys Gln Arg
    130                 135                 140

Pro Leu Cys Pro Glu Glu Lys Gln Arg His Leu Asp Lys Lys Lys Arg
145                 150                 155                 160

Phe His Asn Ile Gly Gly Arg Trp Thr Gly Arg Cys Ile Val Cys Trp
                165                 170                 175

Arg Arg Pro Arg Thr Glu Thr Gln Val Gly Gly Ser Gly Gly Gly Gly
            180                 185                 190

Ser Gly Gly Lys Lys Gln Tyr Ile Lys Ala Asn Ser Lys Phe Ile Gly
        195                 200                 205

Ile Thr Glu Leu Lys Lys Leu Gly Gly Gly Lys Arg Gly Gly Gly Lys
    210                 215                 220

Lys Met Thr Asn Ser Val Asp Asp Ala Leu Ile Asn Ser Thr Lys Ile
225                 230                 235                 240

Tyr Ser Tyr Phe Pro Ser Val Ile Ser Lys Val Asn Gln Gly Ala Gln
                245                 250                 255

Gly Lys Lys Leu Gly Ser Ser Gly Gly Gly Gly Ser Pro Gly Gly Gly
            260                 265                 270

Ser Ser Ile Val Gly Ile Val Ala Gly Leu Ala Val Leu Ala Val Val
        275                 280                 285

Val Ile Gly Ala Val Val Ala Thr Val Met Cys Arg Arg Lys Ser Ser
    290                 295                 300

Gly Gly Lys Gly Gly Ser Tyr Ser Gln Ala Ala Ser Ser Asp Ser Ala
305                 310                 315                 320

Gln Gly Ser Asp Val Ser Leu Thr Ala
                325
```

-continued

<210> SEQ ID NO 10
<211> LENGTH: 1472
<212> TYPE: RNA
<213> ORGANISM: Human papillomavirus type 31

<400> SEQUENCE: 10
gggcgaacua guauucuucu gguccccaca gacucagaga gaacccgcca ccaugagagu 60
gauggccccc agaacccuga uccugcugcu gucuggcgcc cuggcccuga cagagacaug 120
ggccggaagc ggcggcucug gaggaggcgg cuccggaggc auguuuaaaa auccagcaga 180
aagaccaaga aaacugcaug aacugucuuc ugcucuggaa auuccuuaug augaacugag 240
acugaauugu guguauugua aaggacagcu gacagaaaca gaagugcugg auuuugcuuu 300
uacagaucug acaauugugu auagagauga uacaccuuau ggagugugua caaaaugucu 360
gagauuuuau uccaaagugu cugaauuuag augguauaga uauucugugu auggaacaac 420
auuggaaaaa uugacaaaua aaggaauuug ugaucugcug auuagaugua uuacauguca 480
gagaccucug uguccugaag aaaaacagag acaucuggau aaaaagaaaa gauuucauaa 540
uauuggagga agauggacag gaagauguau ugugugUugg agaagaccaa gaacagaaac 600
acagguggga ggauccggug guggcggcag cggcggcaag aagcaguaca ucaaggccaa 660
cagcaaguuc aucggcauca ccgagcugaa gaagcuggga gggggcaaac ggggaggcgg 720
caaaaagaug accaacagcg uggacgacgc ccugaucaac agcaccaaga ucuacagcua 780
cuuccccagc gugaucagca aagugaacca gggcgcucag ggcaagaaac ugggcucuag 840 cggagggggga ggcucuccug gcgggggauc uagcaucgug ggaauugugg caggacuggc 900
agugcuggcc guggugguga ucggagccgu gguggcuacc gugaugugca gacggaaguc 960
cagcggaggc aagggcggca gcuacagcca ggccgccagc ucugauagcg cccagggcag 1020
cgacguguca cugacagccu aguaacucga gcugguacug caugcacgca augcuagcug 1080
ccccuuuccc guccugggua ccccgagucu cccccgaccu cgggucccag guaugcuccc 1140
accuccaccu gccccacuca ccaccucugc uaguuccaga caccucccaa gcacgcagca 1200
augcagcuca aaacgcuuag ccuagccaca cccccacggg aaacagcagu gauuaaccuu 1260
uagcaauaaa cgaaaguuua acuaagcuau acuaacccca ggguugguca auuucgugcc 1320
agccacaccg agaccugguc cagagucgcu agccgcgucg cuaaaaaaaa aaaaaaaaaa 1380
aaaaaaaaaa aagcauauga cuaaaaaaaa aaaaaaaaaa aaaaaaaaaa aaaaaaaaaa 1440
aaaaaaaaaa aaaaaaaaaa aaaaaaaaaa aa 1472

<210> SEQ ID NO 11
<211> LENGTH: 278
<212> TYPE: PRT
<213> ORGANISM: Human papillomavirus type 31

<400> SEQUENCE: 11

Met Arg Val Met Ala Pro Arg Thr Leu Ile Leu Leu Leu Ser Gly Ala
1 5 10 15

Leu Ala Leu Thr Glu Thr Trp Ala Gly Ser Gly Gly Ser Gly Gly Gly
20 25 30

Gly Ser Gly Gly Met Arg Gly Glu Thr Pro Thr Leu Gln Asp Tyr Val
35 40 45

Leu Asp Leu Gln Pro Glu Ala Thr Asp Leu His Cys Tyr Glu Gln Leu
50 55 60

Pro Asp Ser Ser Asp Glu Glu Asp Val Ile Asp Ser Pro Ala Gly Gln

-continued

```
65                  70                  75                  80

Ala Lys Pro Asp Thr Ser Asn Tyr Asn Ile Val Thr Phe Cys Cys Gln
                85                  90                  95

Cys Glu Ser Thr Leu Arg Leu Cys Val Gln Ser Thr Gln Val Asp Ile
            100                 105                 110

Arg Ile Leu Gln Glu Leu Leu Met Gly Ser Phe Gly Ile Val Cys Pro
        115                 120                 125

Asn Cys Ser Thr Arg Leu Gly Gly Ser Gly Gly Gly Gly Ser Gly Gly
    130                 135                 140

Lys Lys Gln Tyr Ile Lys Ala Asn Ser Lys Phe Ile Gly Ile Thr Glu
145                 150                 155                 160

Leu Lys Lys Leu Gly Gly Gly Lys Arg Gly Gly Gly Lys Lys Met Thr
                165                 170                 175

Asn Ser Val Asp Asp Ala Leu Ile Asn Ser Thr Lys Ile Tyr Ser Tyr
            180                 185                 190

Phe Pro Ser Val Ile Ser Lys Val Asn Gln Gly Ala Gln Gly Lys Lys
        195                 200                 205

Leu Gly Ser Ser Gly Gly Gly Gly Ser Pro Gly Gly Gly Ser Ser Ile
    210                 215                 220

Val Gly Ile Val Ala Gly Leu Ala Val Leu Ala Val Val Val Ile Gly
225                 230                 235                 240

Ala Val Val Ala Thr Val Met Cys Arg Arg Lys Ser Ser Gly Gly Lys
                245                 250                 255

Gly Gly Ser Tyr Ser Gln Ala Ala Ser Ser Asp Ser Ala Gln Gly Ser
            260                 265                 270

Asp Val Ser Leu Thr Ala
        275


<210> SEQ ID NO 12
<211> LENGTH: 1319
<212> TYPE: RNA
<213> ORGANISM: Human papillomavirus type 31

<400> SEQUENCE: 12

gggcgaacua guauucuucu gguccccaca gacucagaga gaacccgcca ccaugagagu      60

gauggccccc agaacccuga uccugcugcu gucuggcgcc cuggcccuga cagagacaug     120

ggccggaagc ggcggcucug gaggaggcgg cuccggaggc augagaggag agacacccac     180

auugcaggau uauguguugg auuugcaacc ugaggcaacu gaucugcacu guuaugaaca     240

gcugcccgau ucuucugacg aagaagaugu gauugauucu ccagcaggac aggcaaaacc     300

agauaccucc aauuacaaua uugugaccuu uuguugucag ugugaaagca cacugagacu     360

gugugugcag agcacacagg uggauauuag aauucugcaa gaacugcuga ugggcucuuu     420

uggaauugug uguccaaauu guucaacaag acugggagga uccgguggug gcggcagcgg     480

cggcaagaag caguacauca aggccaacag caaguucauc ggcaucaccg agcugaagaa     540

gcugggaggg ggcaaacggg gaggcggcaa aaagaugacc aacagcgugg acgacgcccu     600

gaucaacagc accaagaucu acagcuacuu ccccagcgug aucagcaaag ugaaccaggg     660

cgcucagggc aagaaacugg gcucuagcgg agggggaggc ucuccuggcg gggaucuag     720

caucguggga auuguggcag gacuggcagu gcuggccgug guggugaucg gagccguggu     780

ggcuaccgug augugcagac ggaaguccag cggaggcaag ggcggcagcu acagccaggc     840

cgccagcucu gauagcgccc agggcagcga cgugucacug acagccuagu aacucgagcu     900
```

-continued

```
gguacugcau gcacgcaaug cuagcugccc cuuuccccguc cuggguaccc cgagucuccc    960

ccgaccucgg gucccaggua ugcucccacc uccaccugcc ccacucacca ccucugcuag   1020

uuccagacac cucccaagca cgcagcaaug cagcucaaaa cgcuuagccu agccacaccc   1080

ccacgggaaa cagcagugau uaaccuuuag caauaaacga aaguuuaacu aagcuauacu   1140

aaccccaggg uuggucaauu ucgugccagc cacaccgaga ccugguccag agucgcuagc   1200

cgcgucgcua aaaaaaaaaa aaaaaaaaaa aaaaaaaaag cauaugacua aaaaaaaaaa   1260

aaaaaaaaaa aaaaaaaaaa aaaaaaaaaa aaaaaaaaaa aaaaaaaaaa aaaaaaaaa    1319


<210> SEQ ID NO 13
<211> LENGTH: 329
<212> TYPE: PRT
<213> ORGANISM: Human papillomavirus type 33

<400> SEQUENCE: 13

Met Arg Val Met Ala Pro Arg Thr Leu Ile Leu Leu Leu Ser Gly Ala
1               5                   10                  15

Leu Ala Leu Thr Glu Thr Trp Ala Gly Ser Gly Gly Ser Gly Gly Gly
            20                  25                  30

Gly Ser Gly Gly Met Phe Gln Asp Thr Glu Glu Lys Pro Arg Thr Leu
        35                  40                  45

His Asp Leu Cys Gln Ala Leu Glu Thr Thr Ile His Asn Ile Glu Leu
    50                  55                  60

Gln Cys Val Glu Cys Lys Lys Pro Leu Gln Arg Ser Glu Val Tyr Asp
65                  70                  75                  80

Phe Ala Phe Ala Asp Leu Thr Val Val Tyr Arg Glu Gly Asn Pro Phe
                85                  90                  95

Gly Ile Cys Lys Leu Cys Leu Arg Phe Leu Ser Lys Ile Ser Glu Tyr
            100                 105                 110

Arg His Tyr Asn Tyr Ser Leu Tyr Gly Asn Thr Leu Glu Gln Thr Val
        115                 120                 125

Lys Lys Pro Leu Asn Glu Ile Leu Ile Arg Cys Met Ile Cys Gln Arg
    130                 135                 140

Pro Leu Cys Pro Gln Glu Lys Lys Arg His Val Asp Leu Asn Lys Arg
145                 150                 155                 160

Phe His Asn Ile Ser Gly Arg Trp Ala Gly Arg Cys Ala Val Cys Trp
                165                 170                 175

Arg Ser Arg Arg Arg Glu Thr Ala Leu Gly Gly Ser Gly Gly Gly Gly
            180                 185                 190

Ser Gly Gly Lys Lys Gln Tyr Ile Lys Ala Asn Ser Lys Phe Ile Gly
        195                 200                 205

Ile Thr Glu Leu Lys Lys Leu Gly Gly Gly Lys Arg Gly Gly Gly Lys
    210                 215                 220

Lys Met Thr Asn Ser Val Asp Asp Ala Leu Ile Asn Ser Thr Lys Ile
225                 230                 235                 240

Tyr Ser Tyr Phe Pro Ser Val Ile Ser Lys Val Asn Gln Gly Ala Gln
                245                 250                 255

Gly Lys Lys Leu Gly Ser Ser Gly Gly Gly Gly Ser Pro Gly Gly Gly
            260                 265                 270

Ser Ser Ile Val Gly Ile Val Ala Gly Leu Ala Val Leu Ala Val Val
        275                 280                 285

Val Ile Gly Ala Val Val Ala Thr Val Met Cys Arg Arg Lys Ser Ser
    290                 295                 300
```

-continued

```
Gly Gly Lys Gly Gly Ser Tyr Ser Gln Ala Ala Ser Ser Asp Ser Ala
305                 310                 315                 320

Gln Gly Ser Asp Val Ser Leu Thr Ala
                325


<210> SEQ ID NO 14
<211> LENGTH: 1472
<212> TYPE: RNA
<213> ORGANISM: Human papillomavirus type 33

<400> SEQUENCE: 14

gggcgaacua guauucuucu gguccccaca gacucagaga gaacccgcca ccaugagagu      60

gauggccccc agaacccuga uccugcugcu gucuggcgcc cuggcccuga cagagacaug     120

ggccggaagc ggcggcucug gaggaggcgg cucccggaggc auguuucagg auacagaaga     180

aaaaccaaga acacuucaug aucuuuguca ggcucuugaa acaacaauuc acaauauuga     240

auugcagugu guggaaugua agaaaccuuu gcagagaucu gaaguguaug auuuugcuuu     300

ugcugaucug acaguggugu acagagaagg aaauccuuuu ggaauuugua aacugugucu     360

gagauuucug ucaaaaauuu cugaauacag acauuauaau uauucucugu auggaaauac     420

acuggaacag acagugaaaa aaccucugaa ugaaauucug auuagaugua ugauuuguca     480

gagaccauua uguccacagg aaaagaaaag acauguggau cugaauaaaa gauuucauaa     540

uauuucugga agaugggcug gaagaugugc uguguguugg agaucaagaa gaagggaaac     600

agcucuugga ggauccggug guggcggcag cggcggcaag aagcaguaca ucaaggccaa     660

cagcaaguuc aucggcauca ccgagcugaa gaagcuggga gggggcaaac ggggaggcgg     720

caaaaagaug accaacagcg uggacgacgc ccugaucaac agcaccaaga ucuacagcua     780

cuuccccagc gugaucagca aagugaacca gggcgcucag ggcaagaaac ugggcucuag     840

cggaggggga ggcucuccug gcgggggauc uagcaucgug ggaauugugg caggacuggc     900

agugcuggcc guggugguga ucggagccgu gguggcuacc gugaugugca gacggaaguc     960

cagcggaggc aagggcggca gcuacagcca ggccgccagc ucugauagcg cccagggcag    1020

cgacguguca cugacagccu aguaacucga gcugguacug caugcacgca augcuagcug    1080

ccccuuuccc guccugggua ccccgagucu cccccgaccu cgggucccag guaugcuccc    1140

accuccaccu gccccacuca ccaccucugc uaguuccaga caccucccaa gcacgcagca    1200

augcagcuca aaacgcuuag ccuagccaca cccccacggg aaacagcagu gauuaaccuu    1260

uagcaauaaa cgaaaguuua acuaagcuau acuaacccca ggguugguca auuucgugcc    1320

agccacaccg agaccugguc cagagucgcu agccgcgucg cuaaaaaaaa aaaaaaaaaa    1380

aaaaaaaaaa aagcauauga cuaaaaaaaa aaaaaaaaaa aaaaaaaaaa aaaaaaaaaa    1440

aaaaaaaaaa aaaaaaaaaa aaaaaaaaaa aa                                  1472


<210> SEQ ID NO 15
<211> LENGTH: 277
<212> TYPE: PRT
<213> ORGANISM: Human papillomavirus type 33

<400> SEQUENCE: 15

Met Arg Val Met Ala Pro Arg Thr Leu Ile Leu Leu Leu Ser Gly Ala
1               5                   10                  15

Leu Ala Leu Thr Glu Thr Trp Ala Gly Ser Gly Gly Ser Gly Gly Gly
            20                  25                  30

Gly Ser Gly Gly Met Arg Gly His Lys Pro Thr Leu Lys Glu Tyr Val
```

-continued

```
            35                  40                  45

Leu Asp Leu Tyr Pro Glu Pro Thr Asp Leu Tyr Cys Tyr Glu Gln Leu
    50                  55                  60

Ser Asp Ser Ser Asp Glu Asp Glu Gly Leu Asp Arg Pro Asp Gly Gln
65                  70                  75                  80

Ala Gln Pro Ala Thr Ala Asp Tyr Tyr Ile Val Thr Cys Cys His Thr
                85                  90                  95

Cys Asn Ala Thr Val Arg Leu Cys Val Asn Ser Thr Ala Ser Asp Leu
            100                 105                 110

Arg Thr Ile Gln Gln Leu Leu Met Gly Thr Val Asn Ile Val Cys Pro
        115                 120                 125

Ser Cys Ala Gln Pro Gly Gly Ser Gly Gly Gly Gly Ser Gly Gly Lys
    130                 135                 140

Lys Gln Tyr Ile Lys Ala Asn Ser Lys Phe Ile Gly Ile Thr Glu Leu
145                 150                 155                 160

Lys Lys Leu Gly Gly Gly Lys Arg Gly Gly Gly Lys Lys Met Thr Asn
                165                 170                 175

Ser Val Asp Asp Ala Leu Ile Asn Ser Thr Lys Ile Tyr Ser Tyr Phe
            180                 185                 190

Pro Ser Val Ile Ser Lys Val Asn Gln Gly Ala Gln Gly Lys Lys Leu
        195                 200                 205

Gly Ser Ser Gly Gly Gly Gly Ser Pro Gly Gly Gly Ser Ser Ile Val
    210                 215                 220

Gly Ile Val Ala Gly Leu Ala Val Leu Ala Val Val Val Ile Gly Ala
225                 230                 235                 240

Val Val Ala Thr Val Met Cys Arg Arg Lys Ser Ser Gly Gly Lys Gly
                245                 250                 255

Gly Ser Tyr Ser Gln Ala Ala Ser Ser Asp Ser Ala Gln Gly Ser Asp
            260                 265                 270

Val Ser Leu Thr Ala
        275


<210> SEQ ID NO 16
<211> LENGTH: 1316
<212> TYPE: RNA
<213> ORGANISM: Human papillomavirus type 33

<400> SEQUENCE: 16

gggcgaacua guauucuucu gguccccaca gacucagaga gaacccgcca ccaugagagu      60

gauggccccc agaacccuga uccugcugcu gucuggcgcc cuggcccuga cagagacaug     120

ggccggaagc ggcggcucug gaggaggcgg cuccggaggc augagaggac acaagccaac     180

guuaaaggaa uauguuuuag auuuauaucc ugaaccaacu gaccuauacu gcuaugagca     240

auuaagugac agcucagaug aggaugaagg cuuggaccgg ccagauggac aagcacaacc     300

agccacagcu gauuacuaca uuguaaccug uugucacacu uguaacgcca caguucguuu     360

augugucaac aguacagcaa gugaccuacg aaccauacag caacuacuua ugggcacagu     420

uaauauugug ugcccuagcu gugcacaacc aggaggaucc gguggugggcg gcagcggcgg     480

caagaagcag uacaucaagg ccaacagcaa guucaucggc aucaccgagc ugaagaagcu     540

gggagggggc aaacggggag gcggcaaaaa gaugaccaac agcguggacg acgcccugau     600

caacagcacc aagaucuaca gcuacuuccc cagcgugauc agcaaaguga accagggcgc     660

ucagggcaag aaacugggcu cuagcggagg gggaggcucu ccuggcgggg gaucuagcau     720
```

-continued

```
cgugggaauu guggcaggac uggcagugcu ggccguggug gugaucggag ccgugguggc    780

uaccgugaug ugcagacgga aguccagcgg aggcaagggc ggcagcuaca gccaggccgc    840

cagcucugau agcgcccagg gcagcgacgu gucacugaca gccuaguaac ucgagcuggu    900

acugcaugca cgcaaugcua gcugccccuu ucccguccug gguaccccga gucucccccg    960

accucggguc ccagguaugc ucccaccucc accugcccca cucaccaccu cugcuaguuc   1020

cagacaccuc ccaagcacgc agcaaugcag cucaaaacgc uuagccuagc cacaccccca   1080

cgggaaacag cagugauuaa ccuuuagcaa uaaacgaaag uuuaacuaag cuauacuaac   1140

cccaggguug gucaauuucg ugccagccac accgagaccu gguccagagu cgcuagccgc   1200

gucgcuaaaa aaaaaaaaaa aaaaaaaaaa aaaaaagcau augacuaaaa aaaaaaaaaa   1260

aaaaaaaaaa aaaaaaaaaa aaaaaaaaaa aaaaaaaaaa aaaaaaaaaa aaaaaa       1316


<210> SEQ ID NO 17
<211> LENGTH: 338
<212> TYPE: PRT
<213> ORGANISM: Human papillomavirus type 45

<400> SEQUENCE: 17

Met Arg Val Met Ala Pro Arg Thr Leu Ile Leu Leu Leu Ser Gly Ala
1               5                   10                  15

Leu Ala Leu Thr Glu Thr Trp Ala Gly Ser Gly Gly Ser Gly Gly Gly
            20                  25                  30

Gly Ser Gly Gly Met Ala Arg Phe Asp Asp Pro Thr Gln Arg Pro Tyr
        35                  40                  45

Lys Leu Pro Asp Leu Cys Thr Glu Leu Asn Thr Ser Leu Gln Asp Val
    50                  55                  60

Ser Ile Ala Cys Val Tyr Cys Lys Ala Thr Leu Glu Arg Thr Glu Val
65                  70                  75                  80

Tyr Gln Phe Ala Phe Lys Asp Leu Phe Ile Val Tyr Arg Asp Cys Ile
                85                  90                  95

Ala Tyr Ala Ala Cys His Lys Cys Ile Asp Phe Tyr Ser Arg Ile Arg
            100                 105                 110

Glu Leu Arg Tyr Tyr Ser Asn Ser Val Tyr Gly Glu Thr Leu Glu Lys
        115                 120                 125

Ile Thr Asn Thr Glu Leu Tyr Asn Leu Leu Ile Arg Cys Leu Arg Cys
    130                 135                 140

Gln Lys Pro Leu Asn Pro Ala Glu Lys Arg Arg His Leu Lys Asp Lys
145                 150                 155                 160

Arg Arg Phe His Ser Ile Ala Gly Gln Tyr Arg Gly Gln Cys Asn Thr
                165                 170                 175

Cys Cys Asp Gln Ala Arg Gln Glu Arg Leu Arg Arg Arg Arg Glu Thr
            180                 185                 190

Gln Val Gly Gly Ser Gly Gly Gly Gly Ser Gly Gly Lys Lys Gln Tyr
        195                 200                 205

Ile Lys Ala Asn Ser Lys Phe Ile Gly Ile Thr Glu Leu Lys Lys Leu
    210                 215                 220

Gly Gly Gly Lys Arg Gly Gly Gly Lys Lys Met Thr Asn Ser Val Asp
225                 230                 235                 240

Asp Ala Leu Ile Asn Ser Thr Lys Ile Tyr Ser Tyr Phe Pro Ser Val
                245                 250                 255

Ile Ser Lys Val Asn Gln Gly Ala Gln Gly Lys Lys Leu Gly Ser Ser
            260                 265                 270
```

-continued

```
Gly Gly Gly Gly Ser Pro Gly Gly Gly Ser Ser Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 18
<211> LENGTH: 1499
<212> TYPE: RNA
<213> ORGANISM: Human papillomavirus type 45

<400> SEQUENCE: 18

gggcgaacua guauucuucu gguccccaca gacucagaga gaacccgcca ccaugagagu      60

gauggccccc agaacccuga uccugcugcu gucuggcgcc cuggcccuga cagagacaug     120

ggccggaagc ggcggcucug gaggaggcgg cuccggaggc auggcaagau uugaugaucc     180

aacacagaga ccauacaaac ugcccgaucu guguacagaa cugaauacau cucugcaaga     240

cgugagcauu gccugugugu auuguaaagc cacacuggaa agaacagaag uguaccaguu     300

ugcuuuuaaa gaccuguuua ucguguauag agacuguauu gcuuaugcug cuugucacaa     360

auguauugau uuuuauucua gaauuagaga acugagauau uauuccaauu cuguguaugg     420

agaaacacug gagaaaauca caaauacaga gcuguacaau cugcugauua gaugucugag     480

augucagaaa ccacugaacc cagcugagaa aagaagacau cuuaaagaua aaagaagauu     540

ucauuccauu gcuggacagu acagaggaca guguaauacc uguugugacc aggccagaca     600

ggaaagacug agaagaagga gagaaacaca ggugggagga uccggugug gcggcagcgg      660

cggcaagaag caguacauca aggccaacag caaguucauc ggcaucaccg agcugaagaa     720

gcugggaggg ggcaaacggg gaggcggcaa aaagaugacc aacagcgugg acgacgcccu     780

gaucaacagc accaagaucu acagcuacuu ccccagcgug aucagcaaag ugaaccaggg     840

cgcucagggc aagaaacugg gcucuagcgg agggggaggc ucuccuggcg ggggaucuag     900

caucguggga auuguggcag gacuggcagu gcuggccgug guggugaucg gagccguggu     960

ggcuaccgug augugcagac ggaaguccag cggaggcaag ggcggcagcu acagccaggc    1020

cgccagcucu gauagcgccc agggcagcga cgugucacug acagccuagu aacucgagcu    1080

gguacugcau gcacgcaaug cuagcugccc cuuucccguc cuggguaccc cgagucuccc    1140

ccgaccucgg gucccaggua ugcucccacc uccaccugcc ccacucacca ccucugcuag    1200

uuccagacac cucccaagca cgcagcaaug cagcucaaaa cgcuuagccu agccacaccc    1260

ccacgggaaa cagcagugau uaaccuuuag caauaaacga aaguuuaacu aagcuauacu    1320

aaccccaggg uuggucaauu ucgugccagc cacaccgaga ccugguccag agucgcuagc    1380

cgcgucgcua aaaaaaaaaa aaaaaaaaaa aaaaaaaaag cauaugacua aaaaaaaaaa    1440

aaaaaaaaaa aaaaaaaaaa aaaaaaaaaa aaaaaaaaaa aaaaaaaaaa aaaaaaaaa     1499


<210> SEQ ID NO 19
<211> LENGTH: 286
<212> TYPE: PRT
<213> ORGANISM: Human papillomavirus type 45

<400> SEQUENCE: 19
```

```
Met Arg Val Met Ala Pro Arg Thr Leu Ile Leu Leu Leu Ser Gly Ala
1               5                   10                  15

Leu Ala Leu Thr Glu Thr Trp Ala Gly Ser Gly Gly Ser Gly Gly Gly
            20                  25                  30

Gly Ser Gly Gly Met His Gly Pro Gln Ala Thr Leu Gln Glu Ile Val
        35                  40                  45

Leu His Leu Glu Pro Gln Asn Glu Leu Asp Pro Val Asp Leu Leu Cys
    50                  55                  60

Tyr Glu Gln Leu Ser Glu Ser Glu Glu Glu Asn Asp Glu Ala Asp Gly
65                  70                  75                  80

Val Ser His Ala Gln Leu Pro Ala Arg Arg Ala Glu Pro Gln Arg His
                85                  90                  95

Lys Ile Leu Cys Val Cys Cys Lys Cys Asp Gly Arg Ile Glu Leu Thr
            100                 105                 110

Val Glu Ser Ser Ala Asp Asp Leu Arg Thr Leu Gln Gln Leu Phe Leu
        115                 120                 125

Ser Thr Leu Ser Phe Val Cys Pro Trp Cys Ala Thr Asn Gln Gly Gly
    130                 135                 140

Ser Gly Gly Gly Gly Ser Gly Gly Lys Lys Gln Tyr Ile Lys Ala Asn
145                 150                 155                 160

Ser Lys Phe Ile Gly Ile Thr Glu Leu Lys Lys Leu Gly Gly Gly Lys
                165                 170                 175

Arg Gly Gly Gly Lys Lys Met Thr Asn Ser Val Asp Asp Ala Leu Ile
            180                 185                 190

Asn Ser Thr Lys Ile Tyr Ser Tyr Phe Pro Ser Val Ile Ser Lys Val
        195                 200                 205

Asn Gln Gly Ala Gln Gly Lys Lys Leu Gly Ser Ser Gly Gly Gly Gly
    210                 215                 220

Ser Pro Gly Gly Gly Ser Ser Ile Val Gly Ile Val Ala Gly Leu Ala
225                 230                 235                 240

Val Leu Ala Val Val Val Ile Gly Ala Val Val Ala Thr Val Met Cys
                245                 250                 255

Arg Arg Lys Ser Ser Gly Gly Lys Gly Gly Ser Tyr Ser Gln Ala Ala
            260                 265                 270

Ser Ser Asp Ser Ala Gln Gly Ser Asp Val Ser Leu Thr Ala
        275                 280                 285
```

<210> SEQ ID NO 20
<211> LENGTH: 1343
<212> TYPE: RNA
<213> ORGANISM: Human papillomavirus type 45

<400> SEQUENCE: 20

```
gggcgaacua guauucuucu gguccccaca gacucagaga gaacccgcca ccaugagagu     60

gauggccccc agaacccuga uccugcugcu gucuggcgcc cuggcccuga cagagacaug    120

ggccggaagc ggcggcucug gaggaggcgg cuccggaggc augcauggac cucaggcaac    180

acuucaggaa auugugcuuc aucuggaacc ucagaaugaa cuugacccug uggaucugcu    240

guguuaugag cagcugucug agucugagga ggagaaugau gaggcagaug gagugucuca    300

ugcacagcug ccugcaagaa gggcagaacc ucagagacac aaaauucugu gugugugu ug    360

uaaaugugau ggaagaauug aacugacagu ggaaucuucu gcugaugauc ugagaacacu    420

gcaacagcug uuucugucua cacugucuuu uguguguccu uggugugcaa caaaucaggg    480
```

-continued

```
aggauccggu gguggcggca gcggcggcaa gaagcaguac aucaaggcca acagcaaguu    540

caucggcauc accgagcuga agaagcuggg agggggcaaa cggggaggcg gcaaaaagau    600

gaccaacagc guggacgacg cccugaucaa cagcaccaag aucuacagcu acuuccccag    660

cgugaucagc aaagugaacc agggcgcuca gggcaagaaa cugggcucua gcggaggggg    720

aggcucuccu ggcgggggau cuagcaucgu gggaauugug gcaggacugg cagugcuggc    780

cgugguggug aucggagccg ugguggcuac cgugaugugc agacggaagu ccagcggagg    840

caagggcggc agcuacagcc aggccgccag cucugauagc gcccagggca gcgacguguc    900

acugacagcc uaguaacucg agcugguacu gcaugcacgc aaugcuagcu gccccuuucc    960

cguccugggu accccgaguc ucccccgacc ucgggucccca gguaugcucc caccuccacc   1020

ugccccacuc accaccucug cuaguuccag acaccuccca agcacgcagc aaugcagcuc   1080

aaaacgcuua gccuagccac accccccacgg gaaacagcag ugauuaaccu uuagcaauaa   1140

acgaaaguuu aacuaagcua uacuaacccc aggguugguc aauuucgugc cagccacacc   1200

gagaccuggu ccagagucgc uagccgcguc gcuaaaaaaa aaaaaaaaaa aaaaaaaaaa   1260

aaagcauaug acuaaaaaaa aaaaaaaaaa aaaaaaaaaa aaaaaaaaaa aaaaaaaaaa   1320

aaaaaaaaaa aaaaaaaaaa aaa                                            1343
```

```
<210> SEQ ID NO 21
<211> LENGTH: 329
<212> TYPE: PRT
<213> ORGANISM: Human papillomavirus type 58

<400> SEQUENCE: 21

Met Arg Val Met Ala Pro Arg Thr Leu Ile Leu Leu Leu Ser Gly Ala
1               5                   10                  15

Leu Ala Leu Thr Glu Thr Trp Ala Gly Ser Gly Gly Ser Gly Gly Gly
            20                  25                  30

Gly Ser Gly Gly Met Phe Gln Asp Ala Glu Glu Lys Pro Arg Thr Leu
        35                  40                  45

His Asp Leu Cys Gln Ala Leu Glu Thr Ser Val His Glu Ile Glu Leu
    50                  55                  60

Lys Cys Val Glu Cys Lys Lys Thr Leu Gln Arg Ser Glu Val Tyr Asp
65                  70                  75                  80

Phe Thr Phe Ala Asp Leu Arg Ile Val Tyr Arg Asp Gly Asn Pro Phe
                85                  90                  95

Ala Val Cys Lys Val Cys Leu Arg Leu Leu Ser Lys Ile Ser Glu Tyr
            100                 105                 110

Arg His Tyr Asn Tyr Ser Leu Tyr Gly Asp Thr Leu Glu Gln Thr Leu
        115                 120                 125

Lys Lys Arg Leu Glu Glu Ile Leu Ile Arg Cys Ile Ile Cys Gln Arg
    130                 135                 140

Pro Leu Cys Pro Gln Glu Lys Lys Arg His Val Asp Leu Asn Lys Arg
145                 150                 155                 160

Phe His Asn Ile Ser Gly Arg Trp Thr Gly Arg Cys Ala Val Cys Trp
                165                 170                 175

Arg Pro Arg Arg Arg Gln Thr Gln Val Gly Gly Ser Gly Gly Gly Gly
            180                 185                 190

Ser Gly Gly Lys Lys Gln Tyr Ile Lys Ala Asn Ser Lys Phe Ile Gly
        195                 200                 205

Ile Thr Glu Leu Lys Lys Leu Gly Gly Gly Lys Arg Gly Gly Gly Lys
    210                 215                 220
```

-continued

```
Lys Met Thr Asn Ser Val Asp Asp Ala Leu Ile Asn Ser Thr Lys Ile
225                 230                 235                 240

Tyr Ser Tyr Phe Pro Ser Val Ile Ser Lys Val Asn Gln Gly Ala Gln
                245                 250                 255

Gly Lys Lys Leu Gly Ser Ser Gly Gly Gly Gly Ser Pro Gly Gly Gly
            260                 265                 270

Ser Ser Ile Val Gly Ile Val Ala Gly Leu Ala Val Leu Ala Val Val
        275                 280                 285

Val Ile Gly Ala Val Val Ala Thr Val Met Cys Arg Arg Lys Ser Ser
    290                 295                 300

Gly Gly Lys Gly Gly Ser Tyr Ser Gln Ala Ala Ser Ser Asp Ser Ala
305                 310                 315                 320

Gln Gly Ser Asp Val Ser Leu Thr Ala
                325
```

<210> SEQ ID NO 22
<211> LENGTH: 1472
<212> TYPE: RNA
<213> ORGANISM: Human papillomavirus type 58

<400> SEQUENCE: 22

```
gggcgaacua guauucuucu gguccccaca gacucagaga gaacccgcca ccaugagagu     60

gauggccccc agaacccuga uccugcugcu gucuggcgcc cuggcccuga cagagacaug    120

ggccggaagc ggcggcucug gaggaggcgg cuccggaggc auguuucagg augcugaaga    180

aaaaccaaga acacugcaug aucuguguca ggcucuggaa acaucugugc augaaauuga    240

acugaaaugu guggaaugua agaaaacauu acagagaucu gaaguguaug auuuuacauu    300

ugcugaucug agaauugugu acagagaugg aaauccuuuu gcugugugua aagugugucu    360

gagacugcug ucuaaaauuu cugaauacag acauuacaau uacucacugu auggagauac    420

acuggaacag acacugaaga aaagacugga agaaauucug auuagaugua uuauuuguca    480

gagaccuuua uguccucagg aaaagaaaag acauguggau cugaauaaaa gauuucauaa    540

uauuucugga agauggacag gaagaugugc ugugugguugg agaccaagaa gaagacagac    600

acagguggga ggauccggug guggcggcag cggcggcaag aagcaguaca ucaaggccaa    660

cagcaaguuc aucggcauca ccgagcugaa gaagcuggga gggggcaaac ggggaggcgg    720

caaaaagaug accaacagcg uggacgacgc ccugaucaac agcaccaaga ucuacagcua    780

cuuccccagc gugaucagca aagugaacca gggcgcucag ggcaagaaac ugggcucuag    840

cggagggggga ggcucuccug gcgggggauc uagcaucgug ggaauugugg caggacuggc    900

agugcuggcc gugguggugga ucggagccgu gguggcuacc gugaugugca gacggaaguc    960

cagcggaggc aagggcggca gcuacagcca ggccgccagc ucugauagcg cccagggcag   1020

cgacguguca cugacagccu aguaacucga gcugguacug caugcacgca augcuagcug   1080

ccccuuuccc guccugggua ccccgagucu cccccgaccu cgggucccag guaugcuccc   1140

accuccaccu gccccacuca ccaccucugc uaguuccaga caccucccaa gcacgcagca   1200

augcagcuca aaacgcuuag ccuagccaca cccccacggg aaacagcagu gauuaaccuu   1260

uagcaauaaa cgaaaguuua acuaagcuau acuaacccca ggguugguca auuucgugcc   1320

agccacaccg agaccugguc cagagucgcu agccgcgucg cuaaaaaaaa aaaaaaaaaa   1380

aaaaaaaaaa aagcauauga cuaaaaaaaa aaaaaaaaaa aaaaaaaaaa aaaaaaaaaa   1440

aaaaaaaaaa aaaaaaaaaa aaaaaaaaaa aa                                 1472
```

<210> SEQ ID NO 23
<211> LENGTH: 278
<212> TYPE: PRT
<213> ORGANISM: Human papillomavirus type 58

<400> SEQUENCE: 23

Met Arg Val Met Ala Pro Arg Thr Leu Ile Leu Leu Leu Ser Gly Ala
1 5 10 15

Leu Ala Leu Thr Glu Thr Trp Ala Gly Ser Gly Gly Ser Gly Gly Gly
20 25 30

Gly Ser Gly Gly Met Arg Gly Asn Asn Pro Thr Leu Arg Glu Tyr Ile
35 40 45

Leu Asp Leu His Pro Glu Pro Thr Asp Leu Phe Cys Tyr Glu Gln Leu
50 55 60

Cys Asp Ser Ser Asp Glu Asp Glu Ile Gly Leu Asp Gly Pro Asp Gly
65 70 75 80

Gln Ala Gln Pro Ala Thr Ala Asn Tyr Tyr Ile Val Thr Cys Cys Tyr
85 90 95

Thr Cys Asp Ala Thr Val Arg Leu Cys Ile Asn Ser Thr Ala Thr Glu
100 105 110

Val Arg Thr Leu Gln Gln Leu Leu Met Gly Thr Cys Thr Ile Val Cys
115 120 125

Pro Ser Cys Ala Gln Gln Gly Gly Ser Gly Gly Gly Gly Ser Gly Gly
130 135 140

Lys Lys Gln Tyr Ile Lys Ala Asn Ser Lys Phe Ile Gly Ile Thr Glu
145 150 155 160

Leu Lys Lys Leu Gly Gly Gly Lys Arg Gly Gly Gly Lys Lys Met Thr
165 170 175

Asn Ser Val Asp Asp Ala Leu Ile Asn Ser Thr Lys Ile Tyr Ser Tyr
180 185 190

Phe Pro Ser Val Ile Ser Lys Val Asn Gln Gly Ala Gln Gly Lys Lys
195 200 205

Leu Gly Ser Ser Gly Gly Gly Gly Ser Pro Gly Gly Gly Ser Ser Ile
210 215 220

Val Gly Ile Val Ala Gly Leu Ala Val Leu Ala Val Val Val Ile Gly
225 230 235 240

Ala Val Val Ala Thr Val Met Cys Arg Arg Lys Ser Ser Gly Gly Lys
245 250 255

Gly Gly Ser Tyr Ser Gln Ala Ala Ser Ser Asp Ser Ala Gln Gly Ser
260 265 270

Asp Val Ser Leu Thr Ala
275

<210> SEQ ID NO 24
<211> LENGTH: 1319
<212> TYPE: RNA
<213> ORGANISM: Human papillomavirus type 58

<400> SEQUENCE: 24
gggcgaacua guauucuucu ggucccccaca gacucagaga gaacccgcca ccaugagagu 60
gauggccccc agaacccuga uccugcugcu gucuggcgcc cuggcccuga cagagacaug 120
ggccggaagc ggcggcucug gaggaggcgg cuccggaggc augagaggaa auaauccaac 180
acugagagaa uacauucugg aucugcaucc agaaccaacc gaccuguuuu guuaugaaca 240

-continued

```
guuaugugac agcagcgaug aagaugaaau uggacuggau ggaccagaug gacaggcaca    300

gccagcaaca gcaaauuauu acauugugac auguuguuac acaugugaug caacagugag    360

acuguguauc aauuccacag ccacagaagu gagaacacug caacagcugc ugaugggaac    420

augcaccauu gugugucccu cuugugccca gcagggagga uccggguggug gcggcagcgg    480

cggcaagaag caguacauca aggccaacag caaguucauc ggcaucaccg agcugaagaa    540

gcugggaggg ggcaaacggg gaggcggcaa aaagaugacc aacagcgugg acgacgcccu    600

gaucaacagc accaagaucu acagcuacuu ccccagcgug aucagcaaag ugaaccaggg    660

cgcucagggc aagaaacugg gcucuagcgg agggggaggc ucuccuggcg ggggaucuag    720

caucguggga auuguggcag gacuggcagu gcuggccgug guggugaucg gagccguggu    780

ggcuaccgug augugcagac ggaaguccag cggaggcaag ggcggcagcu acagccaggc    840

cgccagcucu gauagcgccc agggcagcga cgugucacug acagccuagu aacucgagcu    900

gguacugcau gcacgcaaug cuagcugccc cuuucccguc cuggguaccc cgagucuccc    960

ccgaccucgg gucccaggua ugcucccacc uccaccugcc ccacucacca ccucugcuag   1020

uuccagacac cucccaagca cgcagcaaug cagcucaaaa cgcuuagccu agccacaccc   1080

ccacgggaaa cagcagugau uaaccuuuag caauaaacga aaguuuaacu aagcuauacu   1140

aaccccaggg uuggucaauu ucgugccagc cacaccgaga ccugguccag agucgcuagc   1200

cgcgucgcua aaaaaaaaaa aaaaaaaaaa aaaaaaaaag cauaugacua aaaaaaaaaa   1260

aaaaaaaaaa aaaaaaaaaa aaaaaaaaaa aaaaaaaaaa aaaaaaaaaa aaaaaaaaa    1319
```

```
<210> SEQ ID NO 25
<211> LENGTH: 26
<212> TYPE: PRT
<213> ORGANISM: Artificial Sequence
<220> FEATURE:
<223> OTHER INFORMATION: Sec

<400> SEQUENCE: 25

Met Arg Val Met Ala Pro Arg Thr Leu Ile Leu Leu Leu Ser Gly Ala
1               5                   10                  15

Leu Ala Leu Thr Glu Thr Trp Ala Gly Ser
            20                  25


<210> SEQ ID NO 26
<211> LENGTH: 55
<212> TYPE: PRT
<213> ORGANISM: Artificial Sequence
<220> FEATURE:
<223> OTHER INFORMATION: MITD

<400> SEQUENCE: 26

Ile Val Gly Ile Val Ala Gly Leu Ala Val Leu Ala Val Val Val Ile
1               5                   10                  15

Gly Ala Val Val Ala Thr Val Met Cys Arg Arg Lys Ser Ser Gly Gly
            20                  25                  30

Lys Gly Gly Ser Tyr Ser Gln Ala Ala Ser Ser Asp Ser Ala Gln Gly
        35                  40                  45

Ser Asp Val Ser Leu Thr Ala
    50                  55


<210> SEQ ID NO 27
<211> LENGTH: 65
<212> TYPE: PRT
<213> ORGANISM: Artificial Sequence
```

<220> FEATURE:
<223> OTHER INFORMATION: P2P16

<400> SEQUENCE: 27

Lys Lys Gln Tyr Ile Lys Ala Asn Ser Lys Phe Ile Gly Ile Thr Glu
1               5                   10                  15

Leu Lys Lys Leu Gly Gly Gly Lys Arg Gly Gly Gly Lys Lys Met Thr
            20                  25                  30

Asn Ser Val Asp Asp Ala Leu Ile Asn Ser Thr Lys Ile Tyr Ser Tyr
        35                  40                  45

Phe Pro Ser Val Ile Ser Lys Val Asn Gln Gly Ala Gln Gly Lys Lys
    50                  55                  60

Leu
65

<210> SEQ ID NO 28
<211> LENGTH: 10
<212> TYPE: PRT
<213> ORGANISM: Artificial Sequence
<220> FEATURE:
<223> OTHER INFORMATION: GS Linker

<400> SEQUENCE: 28

Gly Gly Ser Gly Gly Gly Gly Ser Gly Gly
1               5                   10

<210> SEQ ID NO 29
<211> LENGTH: 14
<212> TYPE: PRT
<213> ORGANISM: Artificial Sequence
<220> FEATURE:
<223> OTHER INFORMATION: GS Linker

<400> SEQUENCE: 29

Gly Ser Ser Gly Gly Gly Gly Ser Pro Gly Gly Gly Ser Ser
1               5                   10

<210> SEQ ID NO 30
<211> LENGTH: 47
<212> TYPE: RNA
<213> ORGANISM: Artificial Sequence
<220> FEATURE:
<223> OTHER INFORMATION: 5'-UTR

<400> SEQUENCE: 30
aacuaguauu cuucuggucc ccacagacuc agagagaacc cgccacc 47

<210> SEQ ID NO 31
<211> LENGTH: 278
<212> TYPE: RNA
<213> ORGANISM: Artificial Sequence
<220> FEATURE:
<223> OTHER INFORMATION: 3'-UTR

<400> SEQUENCE: 31
cugguacugc augcacgcaa ugcuagcugc cccuuucccg uccuggguac cccgagucuc 60
ccccgaccuc gggucccagg uaugcuccca ccuccaccug ccccacucac caccucugcu 120
aguuccagac accucccaag cacgcagcaa ugcagcucaa aacgcuuagc cuagccacac 180
ccccacggga aacagcagug auuaaccuuu agcaauaaac gaaaguuuaa cuaagcuaua 240
cuaaccccag gguuggucaa uuucgugcca gccacacc 278

-continued

```
<210> SEQ ID NO 32
<211> LENGTH: 110
<212> TYPE: RNA
<213> ORGANISM: Artificial Sequence
<220> FEATURE:
<223> OTHER INFORMATION: A30L70

<400> SEQUENCE: 32

aaaaaaaaaa aaaaaaaaaa aaaaaaaaaa gcauaugacu aaaaaaaaaa aaaaaaaaaa      60

aaaaaaaaaa aaaaaaaaaa aaaaaaaaaa aaaaaaaaaa aaaaaaaaaa                110


<210> SEQ ID NO 33
<211> LENGTH: 15
<212> TYPE: PRT
<213> ORGANISM: Artificial Sequence
<220> FEATURE:
<223> OTHER INFORMATION: P2

<400> SEQUENCE: 33

Gln Tyr Ile Lys Ala Asn Ser Lys Phe Ile Gly Ile Thr Glu Leu
1               5                   10                  15


<210> SEQ ID NO 34
<211> LENGTH: 32
<212> TYPE: PRT
<213> ORGANISM: Artificial Sequence
<220> FEATURE:
<223> OTHER INFORMATION: P16

<400> SEQUENCE: 34

Met Thr Asn Ser Val Asp Asp Ala Leu Ile Asn Ser Thr Lys Ile Tyr
1               5                   10                  15

Ser Tyr Phe Pro Ser Val Ile Ser Lys Val Asn Gln Gly Ala Gln Gly
            20                  25                  30


<210> SEQ ID NO 35
<211> LENGTH: 9
<212> TYPE: PRT
<213> ORGANISM: Artificial Sequence
<220> FEATURE:
<223> OTHER INFORMATION: Peptide

<400> SEQUENCE: 35

Arg Ala His Tyr Asn Ile Val Thr Phe
1               5
```

THERAPEUTIC RNA FOR HPV-POSITIVE CANCER

CROSS-REFERENCE TO RELATED APPLICATIONS

This application is a National Stage Entry of International Application Number PCT/EP2021/068680, which was filed on Jul. 6, 2021 and claimed priority to International Application Number PCT/EP2020/069146, which was filed on Jul. 7, 2020. The contents of each of the aforementioned applications are incorporated herein by reference in their entireties.

SEQUENCE LISTING

The instant application contains a Sequence Listing which has been submitted in a ASCII text file via EFS-Web and is hereby incorporated by reference in its entirety. Said text file, created on Dec. 14, 2022, is named "028320-8047_Sequence_Listing.txt", and is 59,574 bytes in size.

This disclosure relates to the field of therapeutic RNA to treat HPV-positive cancer, in particular anogenital, cervical and penile cancers and cancer in the head and neck region such as cancer in the genital region and head and neck squamous cell carcinoma (HNSCC).

Disclosed herein are compositions, uses, and methods for treatment of HPV-positive cancers. Administration of therapeutic RNAs to a patient having HPV-positive cancer disclosed herein can reduce tumor size, prolong time to progressive disease, and/or protect against metastasis and/or recurrence of the tumor and ultimately extend survival time.

In the past decade, infections with oncogenic human papillomavirus (HPV) types have been established as being causative for a variety of cancers including head and neck squamous cell carcinoma (HNSCC), cervical and anogenital cancers (IARC Working Group. Human Papillomaviruses. IARC Monographs on the evaluation of carcinogenic risks to humans. 90, (2007)).

The most prevalent HPV subtype in HPV-positive HNSCC is HPV16. HPV-positive HNSCC is clinically, histo-pathologically and molecularly distinct (Lawrence, M. S. M. S. et al., *Nature* 517, 576-582 (2015)) with increasing incidence and a significantly better prognosis than HPV-negative HNSCC, independent of the treatment modality (Ang, K. K. et al., *N. Engl. J. Med.* 363, 24-35 (2010); Dayyani, F. et al., *Head Neck Oncol.* 2, (2010)). In HNSCC the standard of care includes surgery, radiotherapy and chemotherapy and is associated with long-term physical, functional and psychosocial impairments, strongly affecting the patient's quality of life. Despite aggressive treatment, about 50% of patients die of their disease (Argiris, A., Karamouzis, M. V, Raben, D. & Ferris, R. L. Seminar: Head and neck cancer. *Lancet* (2008). doi: 10.1016/S0140-6736 (08) 60728-X; Razzaghi, H. et al., *Cancer* 124, 203-211 (2018)). Alternative therapies are needed to improve survival while reducing treatment-associated morbidity.

Interest in exploring immunological approaches has increased since the recent approval of immune checkpoint blockade therapy targeting the PD-1/PD-L1 axis for the treatment of patients with recurrent or metastatic HNSCC (Soulieres, D. et al. Abstract CT115: Updated survival results of the KEYNOTE-040 study of pembrolizumab vs standard-of-care chemotherapy for recurrent or metastatic head and neck squamous cell carcinoma. *Cancer Res.* (2018). doi: 10.1158/1538-7445.AM2018-CT115). The HPV oncoproteins E6 and E7, which drive malignant transformation and are constitutively expressed by the cancer cells (Mesri, E. A., Feitelson, M. A. & Munger, K., *Cell Host and Microbe* (2014). doi: 10.1016/j.chom.2014.02.011), are ideal targets for immunotherapy. This is further supported by the observation that spontaneously occurring T cells against HPV16 oncoproteins are critical for viral clearance and regression of HPV-positive premalignant lesions (Kenter, G. G. et al., *N. Engl. J. Med.* 361, 1838-1847 (2009)), and that the density of tumor-infiltrating lymphocytes (TIL) is a strong predictor for the outcome of HPV-positive HNSCC (Ward, M. J. et al., *Br. J. Cancer* 110, 489-500 (2014)).

In clinical trials, therapeutic HPV16 vaccines have demonstrated the feasibility of inducing a systemic $CD8^+$ T cell response against E6 and E7 through immunization (Kenter, G. G. et al., *N. Engl. J. Med.* 361, 1838-1847 (2009); Trimble, C. L. et al., *Lancet* 386, 2078-2088 (2015); Welters, M. J. P. et al., *Clin. Cancer Res.* 24, 634-647 (2018)).

The ultimate goal of cancer vaccines is the induction of potent, durable and clinically relevant immune responses by delivering the antigen to antigen-presenting cells preferentially in the lymph node for its presentation under optimal immune-stimulatory conditions (Melero, I. et al., *Nat. Rev. Clin. Oncol.* 11, 509-24 (2014)).

Synthetic mRNA is emerging as an attractive vaccine format due to its advantageous characteristics: mRNA is non-integrating and therefore considered as safe. It delivers the encoded antigen in an HLA-independent manner, is a natural adjuvant due to its TLR7/8 ligand activity and its production is time- and cost-efficient.

Here we present the characterization of HPV16 E6 and E7 RNA-LPX the first intravenously administered RNA-based therapeutic HPV16 vaccine, in mouse models. Vaccination with HPV16 E6 and E7 RNA-LPX in humanized, HLA-transgenic A2DR1 mice (expressing human HLA-A*0201 and HLA-DRB1*01 molecules) induces strong T cell responses against the vaccine encoded antigen. As there are no naturally processed and presented $CD8^+$ T cell epitopes derived from the E6 oncoprotein in mice, therapeutic experiments focus on the E7 oncoprotein to therapeutically evaluate our HPV16 RNA-LPX vaccine.

We show the induction of strong T cell immunity by E7 RNA-LPX in C57BL/6 mice, which results in durable remission of murine HPV16-positive TC-1 and C3 tumors through E7 RNA-LPX-mediated infiltration of E7-specific CD8 T cells, CD4 T cells, NK cells and proinflammatory (iNOS-secreting) macrophages. E7 RNA-LPX vaccination enhances TC-1 and C3 tumor rejection, prevents relapse and further synergizes with immune checkpoint blockade therapy such as PD-L1 inhibitors.

Furthermore, we show that E7 RNA-LPX synergizes with local radiotherapy (LRT), being the the standard of care for many HPV+ cancer patients. Combined E7 RNA-LPX/LRT mediate superior regression of both $HPV16^+$TC-1 and C3 tumor models, which was not seen after either monotherapy.

Whereas the E7 RNA-LPX vaccine dominantly induced E7-specific tumor-infiltrating $CD8^+$ T cells, LRT further augmented tumor cell death, reduced local immune suppression and rendered vaccine-primed cytotoxic T cells more potent.

The recruitment of immunosuppressive Tregs was equal in E7 RNA-LPX-treated tumors whether they received LRT or not, as was the expression of PD-L1, a negative T cell regulator on tumor cells. E7 RNA-LPX and combination therapy treated mice displayed high levels of PD-L1, which is likely a result of continuous IFNγ secretion in the TME by E7-specific T cells. E7 RNA-LPX vaccination increased the expression of PD-1 and Tim-3 and NKG2AB on E7-specific CD8 TIL, whereas combined LRT further elevated NKG2AB expression. Data presented herein suggest that besides LRT, checkpoint blockage such anti-PD-1/PD-L1 CPI could be an attractive combination partner of treatments involving HPV-based vaccines such as HPV16 E6/E7 RNA-LPX.

In addition, we show that cisplatin augments the antitumor effects of E7 RNA-LPX vaccination. RNA-LPX vaccines and platinum-based chemotherapies can therefore be used as synergistic combination partners for improved cancer therapies.

SUMMARY

The present invention generally embraces the immunotherapeutic treatment of a subject comprising the administration of (i) RNA, i.e., vaccine RNA, encoding an amino acid sequence, i.e., a vaccine antigen, comprising HPV E6 protein, an immunogenic variant thereof, or an immunogenic fragment of the HPV E6 protein or the immunogenic variant thereof, i.e., an antigenic peptide or protein, and (ii) RNA, i.e., vaccine RNA, encoding an amino acid sequence, i.e., a vaccine antigen, comprising HPV E7 protein, an immunogenic variant thereof, or an immunogenic fragment of the HPV E7 protein or the immunogenic variant thereof, i.e., an antigenic peptide or protein. Thus, the vaccine antigen comprises an epitope of HPV E6 protein or HPV E7 protein for inducing an immune response against HPV E6 protein or HPV E7 protein, in the subject. RNA encoding vaccine antigen is administered to provide (following expression of the polynucleotide by appropriate target cells) antigen for induction, i.e., stimulation, priming and/or expansion, of an immune response, e.g., antibodies and/or immune effector cells, which is targeted to target antigen (HPV E6 protein or HPV E7 protein) or a procession product thereof. In one embodiment, the immune response which is to be induced according to the present disclosure is a B cell-mediated immune response, i.e., an antibody-mediated immune response. Additionally or alternatively, in one embodiment, the immune response which is to be induced according to the present disclosure is a T cell-mediated immune response. In one embodiment, the immune response is an anti-HPV immune response. The vaccine described herein comprises as the active principle single-stranded RNA that may be translated into the respective protein upon entering cells of a recipient. In addition to wildtype or codon-optimized sequences encoding the antigen sequence, the RNA may contain one or more structural elements optimized for maximal efficacy of the RNA with respect to stability and translational efficiency (5' cap, 5' UTR, 3' UTR, poly(A)-tail). In one embodiment, the RNA contains all of these elements. In one embodiment, beta-S-ARCA (D1) ($m_2^{7,2'-O}$GppSpG) may be utilized as specific capping structure at the 5'-end of the RNA drug substances. As 5'-UTR sequence, the 5'-UTR sequence of the human alpha-globin mRNA, optionally with an optimized 'Kozak sequence' to increase translational efficiency may be used. As 3'-UTR sequence, a combination of two sequence elements (FI element) derived from the "amino terminal enhancer of split" (AES) mRNA (called F) and the mitochondrial encoded 12S ribosomal RNA (called I) placed between the coding sequence and the poly(A)-tail to assure higher maximum protein levels and prolonged persistence of the mRNA may be used. These were identified by an ex vivo selection process for sequences that confer RNA stability and augment total protein expression (see WO 2017/060314, herein incorporated by reference). Furthermore, a poly(A)-tail measuring 110 nucleotides in length, consisting of a stretch of 30 adenosine residues, followed by a 10 nucleotide linker sequence (of random nucleotides) and another 70 adenosine residues may be used. This poly(A)-tail sequence was designed to enhance RNA stability and translational efficiency.

Furthermore, see (secretory signal peptide) and/or MITD (MHC class I trafficking domain) may be fused to the antigen-encoding regions in a way that the respective elements are translated as N or C terminal tag, respectively. Fusion-protein tags derived from the sequence encoding the human MHC class I complex (HLA-B51, haplotype A2, B27/B51, Cw2/Cw3), have been shown to improve antigen processing and presentation. Sec may correspond to the 78 bp fragment coding for the secretory signal peptide, which guides translocation of the nascent polypeptide chain into the endoplasmatic reticulum. MITD may correspond to the transmembrane and cytoplasmic domain of the MHC class I molecule, also called MHC class I trafficking domain. Sequences coding for short linker peptides predominantly consisting of the amino acids glycine (G) and serine(S), as commonly used for fusion proteins may be used as GS/Linkers.

The antigen may be administered in combination with helper epitopes to break immunological tolerance. The helper epitopes may be tetanus toxoid-derived, e.g., P2P16 amino acid sequences derived from the tetanus toxoid (TT) of *Clostridium tetani*. These sequences may support to overcome tolerance mechanisms by providing tumor-unspecific T-cell help during priming. The tetanus toxoid heavy chain includes epitopes that can bind promiscuously to MHC class II alleles and induce $CD4^+$ memory T cells in almost all tetanus vaccinated individuals. In addition, the combination of TT helper epitopes with tumor-associated antigens is known to improve the immune stimulation compared to the application of tumor-associated antigen alone by providing CD4+ mediated T-cell help during priming. To reduce the risk of stimulating CD8+ T cells, two peptide sequences known to contain promiscuously binding helper epitopes may be used to ensure binding to as many MHC class II alleles as possible, e.g., P2 and P16.

In one embodiment, a vaccine antigen comprises an amino acid sequence which breaks immunological tolerance. In one embodiment, the amino acid sequence which breaks immunological tolerance comprises helper epitopes, preferably tetanus toxoid-derived helper epitopes. The amino acid sequence which breaks immunological tolerance may be fused to the C-terminus of the vaccine sequence, e.g., antigen sequence, either directly or separated by a linker. Optionally, the amino acid sequence which breaks immunological tolerance may link the vaccine sequence and the MITD. The amino acid sequence which breaks immunological tolerance may be RNA encoded. In one embodiment, the antigen-targeting RNAs are applied together with RNA coding for a helper-epitope to boost the resulting immune response. This RNA coding for a helper-epitope may contain structural elements optimized for maximal efficacy of the RNA with respect to stability and translational efficiency (5' cap, 5' UTR, 3' UTR, poly(A)-tail) described above for the antigen-encoding RNA.

The vaccine RNA may be complexed with liposomes to generate serum-stable RNA-lipoplexes (LPX) for intravenous (i.v.) administration. If a combination of different RNAs is used, the RNAs may be separately complexed with liposomes to generate serum-stable RNA-lipoplexes for intravenous (i.v.) administration. RNA-lipoplexes may target antigen-presenting cells (APCs) in lymphoid organs which results in an efficient stimulation of the immune system.

The RNA lipoplex particles may be prepared using liposomes that may be obtained by injecting a solution of lipids in ethanol into water or a suitable aqueous phase. In one embodiment, the aqueous phase has an acidic pH. In one embodiment, the aqueous phase comprises acetic acid, e.g., in an amount of about 5 mM. Liposomes may be used for preparing RNA lipoplex particles by mixing the liposomes with RNA. In one embodiment, the liposomes and RNA lipoplex particles comprise at least one cationic lipid and at least one additional lipid. In one embodiment, the at least one cationic lipid comprises 1,2-di-O-octadecenyl-3-trimethylammonium propane (DOTMA). In one embodiment, the at least one additional lipid comprises 1,2-di-(9Z-octadecenoyl)-sn-glycero-3-phosphoethanolamine (DOPE). In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE). In one embodiment, the liposomes and RNA lipoplex particles comprise 1,2-di-O-octadecenyl-3-trimethylammonium propane (DOTMA) and 1,2-di-(9Z-octadecenoyl)-sn-glycero-3-phosphoethanolamine (DOPE). In one embodiment, the molar ratio of the at least one cationic lipid to the at least one additional lipid is about 2:1. In one embodiment, at physiological pH, the charge ratio of positive charges to negative charges in the RNA lipoplex particles is from about 1.6:2 to about 1:2, or about 1.6:2 to about 1.1:2. In specific embodiments, the charge ratio of positive charges to negative charges in the RNA lipoplex particles at physiological pH is about 1.6:2.0, about 1.5:2.0, about 1.4:2.0, about 1.3:2.0, about 1.2:2.0, about 1.1:2.0, or about 1:2.0. In one embodiment, vaccine RNA is co-formulated as lipoplex particles with an RNA encoding an amino acid sequence which breaks immunological tolerance.

In one aspect, the invention relates to a composition or medical preparation comprising at least one RNA, wherein the at least one RNA encodes:

(i) an amino acid sequence comprising human papillomavirus (HPV) E6 protein, an immunogenic variant thereof, or an immunogenic fragment of the HPV E6 protein or the immunogenic variant thereof; and (ii) an amino acid sequence comprising HPV E7 protein, an immunogenic variant thereof, or an immunogenic fragment of the HPV E7 protein or the immunogenic variant thereof.

In one embodiment, each of the amino acid sequences under (i), or (ii) is encoded by a separate RNA.

In one embodiment, (i) the RNA encoding the amino acid sequence under (i) comprises the nucleotide sequence of SEQ ID NO: 2, or a nucleotide sequence having at least 99%, 98%, 97%, 96%, 95%, 90%, 85%, or 80% identity to the nucleotide sequence of SEQ ID NO: 2; and/or (ii) the amino acid sequence under (i) comprises the amino acid sequence of SEQ ID NO: 1, or an amino acid sequence having at least 99%, 98%, 97%, 96%, 95%, 90%, 85%, or 80% identity to the amino acid sequence of SEQ ID NO: 1.

In one embodiment, (i) the RNA encoding the amino acid sequence under (ii) comprises the nucleotide sequence of SEQ ID NO: 4, or a nucleotide sequence having at least 99%, 98%, 97%, 96%, 95%, 90%, 85%, or 80% identity to the nucleotide sequence of SEQ ID NO: 4; and/or (ii) the amino acid sequence under (ii) comprises the amino acid sequence of SEQ ID NO: 3, or an amino acid sequence having at least 99%, 98%, 97%, 96%, 95%, 90%, 85%, or 80% identity to the amino acid sequence of SEQ ID NO: 3.

In one embodiment, at least one amino acid sequence under (i), or (ii) comprises an amino acid sequence enhancing antigen processing and/or presentation.

In one embodiment, each amino acid sequence under (i), or (ii) comprises an amino acid sequence enhancing antigen processing and/or presentation.

In one embodiment, the amino acid sequence enhancing antigen processing and/or presentation comprises an amino acid sequence corresponding to the transmembrane and cytoplasmic domain of a MHC molecule, preferably a MHC class I molecule.

In one embodiment, the amino acid sequence enhancing antigen processing and/or presentation comprises the amino acid sequence of SEQ ID NO: 26, or an amino acid sequence having at least 99%, 98%, 97%, 96%, 95%, 90%, 85%, or 80% identity to the amino acid sequence of SEQ ID NO: 26.

In one embodiment, the amino acid sequence enhancing antigen processing and/or presentation further comprises an amino acid sequence coding for a secretory signal peptide. In one embodiment, the secretory signal peptide comprises the amino acid sequence of SEQ ID NO: 25, or an amino acid sequence having at least 99%, 98%, 97%, 96%, 95%, 90%, 85%, or 80% identity to the amino acid sequence of SEQ ID NO: 25.

In one embodiment, at least one amino acid sequence under (i), or (ii) comprises an amino acid sequence which breaks immunological tolerance and/or at least one RNA is co-administered with RNA encoding an amino acid sequence which breaks immunological tolerance.

In one embodiment, each amino acid sequence under (i), or (ii) comprises an amino acid sequence which breaks immunological tolerance and/or each RNA is co-administered with RNA encoding an amino acid sequence which breaks immunological tolerance.

In one embodiment, the amino acid sequence which breaks immunological tolerance comprises helper epitopes, preferably tetanus toxoid-derived helper epitopes.

In one embodiment, the amino acid sequence which breaks immunological tolerance comprises the amino acid sequence of SEQ ID NO: 27, or an amino acid sequence having at least 99%, 98%, 97%, 96%, 95%, 90%, 85%, or 80% identity to the amino acid sequence of SEQ ID NO: 27.

In one embodiment, at least one of the amino acid sequences under (i), or (ii) is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

In one embodiment, each of the amino acid sequences under (i), or (ii) is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

In one embodiment, at least one RNA is a modified RNA, in particular a stabilized mRNA. In one embodiment, at least one RNA comprises a modified nucleoside in place of at least one uridine. In one embodiment, at least one RNA comprises a modified nucleoside in place of each uridine. In one embodiment, each RNA comprises a modified nucleoside in place of at least one uridine. In one embodiment, each RNA comprises a modified nucleoside in place of each uridine. In one embodiment, the modified nucleoside is independently selected from pseudouridine (ψ), N1-methyl-pseudouridine (m1ψ), and 5-methyl-uridine (m5U).

In one embodiment, at least one RNA comprises the 5' cap $m_2^{7,2'-O}$Gppsp (5')G.

In one embodiment, each RNA comprises the 5' cap $m_2^{7,2'-O}$Gppsp (5')G.

In one embodiment, at least one RNA comprises a 5' UTR comprising the nucleotide sequence of SEQ ID NO: 30, or a nucleotide sequence having at least 99%, 98%, 97%, 96%, 95%, 90%, 85%, or 80% identity to the nucleotide sequence of SEQ ID NO: 30.

In one embodiment, each RNA comprises a 5' UTR comprising the nucleotide sequence of SEQ ID NO: 30, or a nucleotide sequence having at least 99%, 98%, 97%, 96%, 95%, 90%, 85%, or 80% identity to the nucleotide sequence of SEQ ID NO: 30.

In one embodiment, at least one RNA comprises a 3' UTR comprising the nucleotide sequence of SEQ ID NO: 31, or a nucleotide sequence having at least 99%, 98%, 97%, 96%, 95%, 90%, 85%, or 80% identity to the nucleotide sequence of SEQ ID NO: 31.

In one embodiment, each RNA comprises a 3' UTR comprising the nucleotide sequence of SEQ ID NO: 31, or a nucleotide sequence having at least 99%, 98%, 97%, 96%, 95%, 90%, 85%, or 80% identity to the nucleotide sequence of SEQ ID NO: 31.

In one embodiment, at least one RNA comprises a poly-A sequence.

In one embodiment, each RNA comprises a poly-A sequence.

In one embodiment, the poly-A sequence comprises at least 100 nucleotides.

In one embodiment, the poly-A sequence comprises or consists of the nucleotide sequence of SEQ ID NO: 32.

In one embodiment, the amino acid sequence under (i), i.e., the amino acid sequence comprising HPV E6 protein, an immunogenic variant thereof, or an immunogenic fragment of the HPV E6 protein or the immunogenic variant thereof, comprises from N-terminus to C-terminus: N-secretory signal peptide-E6-amino acid sequence which breaks immunological tolerance-amino acid sequence enhancing antigen processing and/or presentation-C.

In one embodiment, the amino acid sequence under (ii), i.e., the amino acid sequence comprising HPV E7 protein, an immunogenic variant thereof, or an immunogenic fragment of the HPV E7 protein or the immunogenic variant thereof, comprises from N-terminus to C-terminus: N-secretory signal peptide-E7-amino acid sequence which breaks immunological tolerance-amino acid sequence enhancing antigen processing and/or presentation-C.

In one embodiment, the RNA is formulated as a liquid, formulated as a solid, or a combination thereof.

In one embodiment, the RNA is formulated for injection.

In one embodiment, the RNA is formulated for intravenous administration.

In one embodiment, the RNA is formulated or is to be formulated as lipoplex particles.

In one embodiment, the RNA lipoplex particles are obtainable by mixing the RNA with liposomes.

In one embodiment, the composition or medical preparation further comprises an immune checkpoint inhibitor.

In one embodiment, the immune checkpoint inhibitor is selected from a PD-1 inhibitor, and a PD-L1 inhibitor.

In one embodiment, the immune checkpoint inhibitor is selected from an anti-PD-1 antibody, and an anti-PD-L1 antibody.

In one embodiment, the immune checkpoint inhibitor is an anti-PD-1 antibody.

In one embodiment, the anti-PD-1 antibody is pembrolizumab (KEYTRUDA; MK-3475), nivolumab (OPDIVO; BMS-936558), pidilizumab (CT-011), cemiplimab (LIBTAYO, REGN2810), spartalizumab (PDR001), MEDI0680 (AMP-514), dostarlimab (TSR-042), cetrelimab (JNJ 63723283), toripalimab (JS001), AMP-224 (GSK-2661380), PF-06801591, tislelizumab (BGB-A317), ABBV-181, BI 754091, or SHR-1210.

In one embodiment, the immune checkpoint inhibitor is an anti-PD-L1 antibody.

In one embodiment, the anti-PD-L1 antibody is atezolizumab (TECENTRIQ; RG7446; MPDL3280A; R05541267), durvalumab (MEDI4736), BMS-936559, avelumab (bavencio), lodapolimab (LY3300054), CX-072 (Proclaim-CX-072), FAZ053, KN035, or MDX-1105.

In one embodiment, the composition or medical preparation further comprises a platinum compound.

In one embodiment, the platinum compound comprises cisplatin.

In one embodiment, the composition or medical preparation comprises an immune checkpoint inhibitor and a platinum compound.

In one embodiment, the composition or medical preparation is a pharmaceutical composition.

In one embodiment, the pharmaceutical composition further comprises one or more pharmaceutically acceptable carriers, diluents and/or excipients.

In one embodiment, the medical preparation is a kit.

In one embodiment, the RNAs and optionally the immune checkpoint inhibitor are in separate vials.

In one embodiment, the composition or medical preparation further comprises instructions for use of the RNAs and optionally the immune checkpoint inhibitor for treating or preventing HPV-positive cancer.

In one aspect, the invention relates to the composition or medical preparation described herein for pharmaceutical use.

In one embodiment, the pharmaceutical use comprises a therapeutic or prophylactic treatment of a disease or disorder.

In one embodiment, the therapeutic or prophylactic treatment of a disease or disorder comprises treating or preventing HPV-positive cancer.

In one embodiment, the composition or medical preparation described herein is for administration to a human.

In one embodiment, the therapeutic or prophylactic treatment of a disease or disorder further comprises administering radiotherapy, preferably local radiotherapy.

In one embodiment, the therapeutic or prophylactic treatment of a disease or disorder further comprises administering a further therapy. In one embodiment, the further therapy comprises surgery to excise, resect, or debulk a tumor, and/or chemotherapy. In one embodiment, the further therapy comprises administering a further therapeutic agent. In one embodiment, the further therapeutic agent comprises an anti-cancer therapeutic agent.

In one aspect, the invention relates to a method of treating HPV-positive cancer in a subject comprising administering at least one RNA to the subject, wherein the at least one RNA encodes:

(i) an amino acid sequence comprising human papillomavirus (HPV) E6 protein, an immunogenic variant thereof, or an immunogenic fragment of the HPV E6 protein or the immunogenic variant thereof; and (ii) an amino acid sequence comprising HPV E7 protein, an immunogenic variant thereof, or an immunogenic fragment of the HPV E6 protein or the immunogenic variant thereof.

In one embodiment, each of the amino acid sequences under (i), or (ii) is encoded by a separate RNA.

In one embodiment, (i) the RNA encoding the amino acid sequence under (i) comprises the nucleotide sequence of SEQ ID NO: 2, or a nucleotide sequence having at least 99%, 98%, 97%, 96%, 95%, 90%, 85%, or 80% identity to the nucleotide sequence of SEQ ID NO: 2; and/or (ii) the amino acid sequence under (i) comprises the amino acid sequence of SEQ ID NO: 1, or an amino acid sequence having at least 99%, 98%, 97%, 96%, 95%, 90%, 85%, or 80% identity to the amino acid sequence of SEQ ID NO: 1.

In one embodiment, (i) the RNA encoding the amino acid sequence under (ii) comprises the nucleotide sequence of SEQ ID NO: 4, or a nucleotide sequence having at least 99%, 98%, 97%, 96%, 95%, 90%, 85%, or 80% identity to the nucleotide sequence of SEQ ID NO: 4; and/or (ii) the amino acid sequence under (ii) comprises the amino acid sequence of SEQ ID NO: 3, or an amino acid sequence having at least 99%, 98%, 97%, 96%, 95%, 90%, 85%, or 80% identity to the amino acid sequence of SEQ ID NO: 3.

In one embodiment, at least one amino acid sequence under (i), or (ii) comprises an amino acid sequence enhancing antigen processing and/or presentation.

In one embodiment, each amino acid sequence under (i), or (ii) comprises an amino acid sequence enhancing antigen processing and/or presentation.

In one embodiment, the amino acid sequence enhancing antigen processing and/or presentation comprises an amino acid sequence corresponding to the transmembrane and cytoplasmic domain of a MHC molecule, preferably a MHC class I molecule.

In one embodiment, the amino acid sequence enhancing antigen processing and/or presentation comprises the amino acid sequence of SEQ ID NO: 26, or an amino acid sequence having at least 99%, 98%, 97%, 96%, 95%, 90%, 85%, or 80% identity to the amino acid sequence of SEQ ID NO: 26.

In one embodiment, the amino acid sequence enhancing antigen processing and/or presentation further comprises an amino acid sequence coding for a secretory signal peptide.

In one embodiment, the secretory signal peptide comprises the amino acid sequence of SEQ ID NO: 25, or an amino acid sequence having at least 99%, 98%, 97%, 96%, 95%, 90%, 85%, or 80% identity to the amino acid sequence of SEQ ID NO: 25.

In one embodiment, at least one amino acid sequence under (i), or (ii) comprises an amino acid sequence which breaks immunological tolerance and/or at least one RNA is co-administered with RNA encoding an amino acid sequence which breaks immunological tolerance.

In one embodiment, each amino acid sequence under (i), or (ii) comprises an amino acid sequence which breaks immunological tolerance and/or each RNA is co-administered with RNA encoding an amino acid sequence which breaks immunological tolerance.

In one embodiment, the amino acid sequence which breaks immunological tolerance comprises helper epitopes, preferably tetanus toxoid-derived helper epitopes.

In one embodiment, the amino acid sequence which breaks immunological tolerance comprises the amino acid sequence of SEQ ID NO: 27, or an amino acid sequence having at least 99%, 98%, 97%, 96%, 95%, 90%, 85%, or 80% identity to the amino acid sequence of SEQ ID NO: 27.

In one embodiment, at least one of the amino acid sequences under (i), or (ii) is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

In one embodiment, each of the amino acid sequences under (i), or (ii) is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

In one embodiment, at least one RNA is a modified RNA, in particular a stabilized mRNA. In one embodiment, at least one RNA comprises a modified nucleoside in place of at least one uridine. In one embodiment, at least one RNA comprises a modified nucleoside in place of each uridine. In one embodiment, each RNA comprises a modified nucleoside in place of at least one uridine. In one embodiment, each RNA comprises a modified nucleoside in place of each uridine. In one embodiment, the modified nucleoside is independently selected from pseudouridine (ψ), N1-methyl-pseudouridine (m1), and 5-methyl-uridine (m5U).

In one embodiment, at least one RNA comprises the 5' cap $m_2^{7,2'-O}$Gppsp (5')G.

In one embodiment, each RNA comprises the 5' cap $m_2^{7,2'-O}$Gppsp (5')G.

In one embodiment, at least one RNA comprises a 5' UTR comprising the nucleotide sequence of SEQ ID NO: 30, or a nucleotide sequence having at least 99%, 98%, 97%, 96%, 95%, 90%, 85%, or 80% identity to the nucleotide sequence of SEQ ID NO: 30.

In one embodiment, each RNA comprises a 5' UTR comprising the nucleotide sequence of SEQ ID NO: 30, or a nucleotide sequence having at least 99%, 98%, 97%, 96%, 95%, 90%, 85%, or 80% identity to the nucleotide sequence of SEQ ID NO: 30.

In one embodiment, at least one RNA comprises a 3' UTR comprising the nucleotide sequence of SEQ ID NO: 31, or a nucleotide sequence having at least 99%, 98%, 97%, 96%, 95%, 90%, 85%, or 80% identity to the nucleotide sequence of SEQ ID NO: 31.

In one embodiment, each RNA comprises a 3' UTR comprising the nucleotide sequence of SEQ ID NO: 31, or a nucleotide sequence having at least 99%, 98%, 97%, 96%, 95%, 90%, 85%, or 80% identity to the nucleotide sequence of SEQ ID NO: 31.

In one embodiment, at least one RNA comprises a poly-A sequence.

In one embodiment, each RNA comprises a poly-A sequence.

In one embodiment, the poly-A sequence comprises at least 100 nucleotides.

In one embodiment, the poly-A sequence comprises or consists of the nucleotide sequence of SEQ ID NO: 32.

In one embodiment, the amino acid sequence under (i), i.e., the amino acid sequence comprising HPV E6 protein, an immunogenic variant thereof, or an immunogenic fragment of the HPV E6 protein or the immunogenic variant thereof, comprises from N-terminus to C-terminus: N-secretory signal peptide-E6-amino acid sequence which breaks immunological tolerance-amino acid sequence enhancing antigen processing and/or presentation-C.

In one embodiment, the amino acid sequence under (ii), i.e., the amino acid sequence comprising HPV E7 protein, an immunogenic variant thereof, or an immunogenic fragment of the HPV E7 protein or the immunogenic variant thereof, comprises from N-terminus to C-terminus: N-secretory signal peptide-E7-amino acid sequence which breaks immunological tolerance-amino acid sequence enhancing antigen processing and/or presentation-C.

In one embodiment, the RNA is administered by injection.

In one embodiment, the RNA is administered by intravenous administration.

In one embodiment, the RNA is formulated as lipoplex particles.

In one embodiment, the RNA lipoplex particles are obtainable by mixing the RNA with liposomes.

In one embodiment, the method described herein further comprises administering to the subject an immune checkpoint inhibitor.

In one embodiment, the immune checkpoint inhibitor is selected from a PD-1 inhibitor, and a PD-L1 inhibitor.

In one embodiment, the immune checkpoint inhibitor is selected from an anti-PD-1 antibody, and an anti-PD-L1 antibody.

In one embodiment, the immune checkpoint inhibitor is an anti-PD-1 antibody.

In one embodiment, the anti-PD-1 antibody is pembrolizumab (KEYTRUDA; MK-3475), nivolumab (OPDIVO; BMS-936558), pidilizumab (CT-011), cemiplimab (LIBTAYO, REGN2810), spartalizumab (PDR001), MEDI0680 (AMP-514), dostarlimab (TSR-042), cetrelimab (JNJ 63723283), toripalimab (JS001), AMP-224 (GSK-2661380), PF-06801591, tislelizumab (BGB-A317), ABBV-181, BI 754091, or SHR-1210.

In one embodiment, the immune checkpoint inhibitor is an anti-PD-L1 antibody.

In one embodiment, the anti-PD-L1 antibody is atezolizumab (TECENTRIQ; RG7446; MPDL3280A; R05541267), durvalumab (MEDI4736), BMS-936559, avelumab (bavencio), lodapolimab (LY3300054), CX-072 (Proclaim-CX-072), FAZ053, KN035, or MDX-1105.

In one embodiment, the subject is a human.

In one embodiment, the method described herein further comprises administering to the subject radiotherapy, preferably local radiotherapy.

In one embodiment, the method described herein comprises administering to the subject radiotherapy, preferably local radiotherapy, and an immune checkpoint inhibitor.

In one embodiment, the method further comprises administering a further therapy. In one embodiment, the further therapy comprises surgery to excise, resect, or debulk a tumor, and/or chemotherapy. In one embodiment, the further therapy comprises administering a further therapeutic agent. In one embodiment, the further therapeutic agent comprises an anti-cancer therapeutic agent.

In one embodiment, the method described herein further comprises administering to the subject a platinum compound.

In one embodiment, the platinum compound comprises cisplatin.

In one embodiment, the method described herein comprises administering to the subject an immune checkpoint inhibitor and a platinum compound.

In one embodiment, the method described herein comprises administering to the subject radiotherapy, preferably local radiotherapy, and a platinum compound.

In one embodiment, the method described herein comprises administering to the subject radiotherapy, preferably local radiotherapy, an immune checkpoint inhibitor and a platinum compound.

In one aspect, provided herein is RNA described herein, e.g., (i) RNA encoding an amino acid sequence comprising HPV E6 protein, an immunogenic variant thereof, or an immunogenic fragment of the HPV E6 protein or the immunogenic variant thereof; and (ii) RNA encoding an amino acid sequence comprising HPV E7 protein, an immunogenic variant thereof, or an immunogenic fragment of the HPV E7 protein or the immunogenic variant thereof, for use in a method described herein.

(A-F) Flow cytometric characterization of tumor cells from s.c. TC-1 tumor-bearing C57BL/6 mice (n=6-7/group) vaccinated with E7 or control ($OVA_{257-264}$) RNA-LPX at a mean tumor volume of 125 $mm^3$ and locally irradiated with 12 Gy. (A) TC-1 tumor cell count per mg tumor tissue. (B) Fraction of cleaved caspase-3$^+$ TC-1 tumor cells. (C-F) Expression of (C) Fas, (D) MHC class I (pan H-2), (E) PD-L1 and (F) Qa-$1^b$ on TC-1 tumor cells. (G) Immunofluorescence staining of hypoxic tumor areas in TC-1 tumor sections from TC-1 tumor-bearing C57BL/6 mice (n=4/group), immunized with E7 or control ($OVA_{257-264}$) RNA-LPX at a mean tumor volume of 160 $mm^3$ and locally irradiated with 12 Gy. The hypoxia probe pimonidazole was injected one hour prior tumor excision. Pimonidazole$^+$ area determined as a fraction of the total tumor area. (H) Fraction of $BrdU^+$ CD4 and CD8 TIL from s.c. TC-1 tumor-bearing C57BL/6 mice (n=6/group), vaccinated with E7 or control ($OVA_{257-264}$) RNA-LPX at a mean tumor volume of 165 $mm^3$ and locally irradiated with 12 Gy as determined by in vivo labelling with bromdeoxyuridine (BrdU). Mice were injected with 1 mg BrdU base-analog one day prior organ excision. Significance in (A-F) was determined using one-way ANOVA, Tukey's multiple comparison test and in (G, H) unpaired, two-tailed Student's t-test. Mean±SEM. MFI=median fluorescent intensity.

Figure 8:
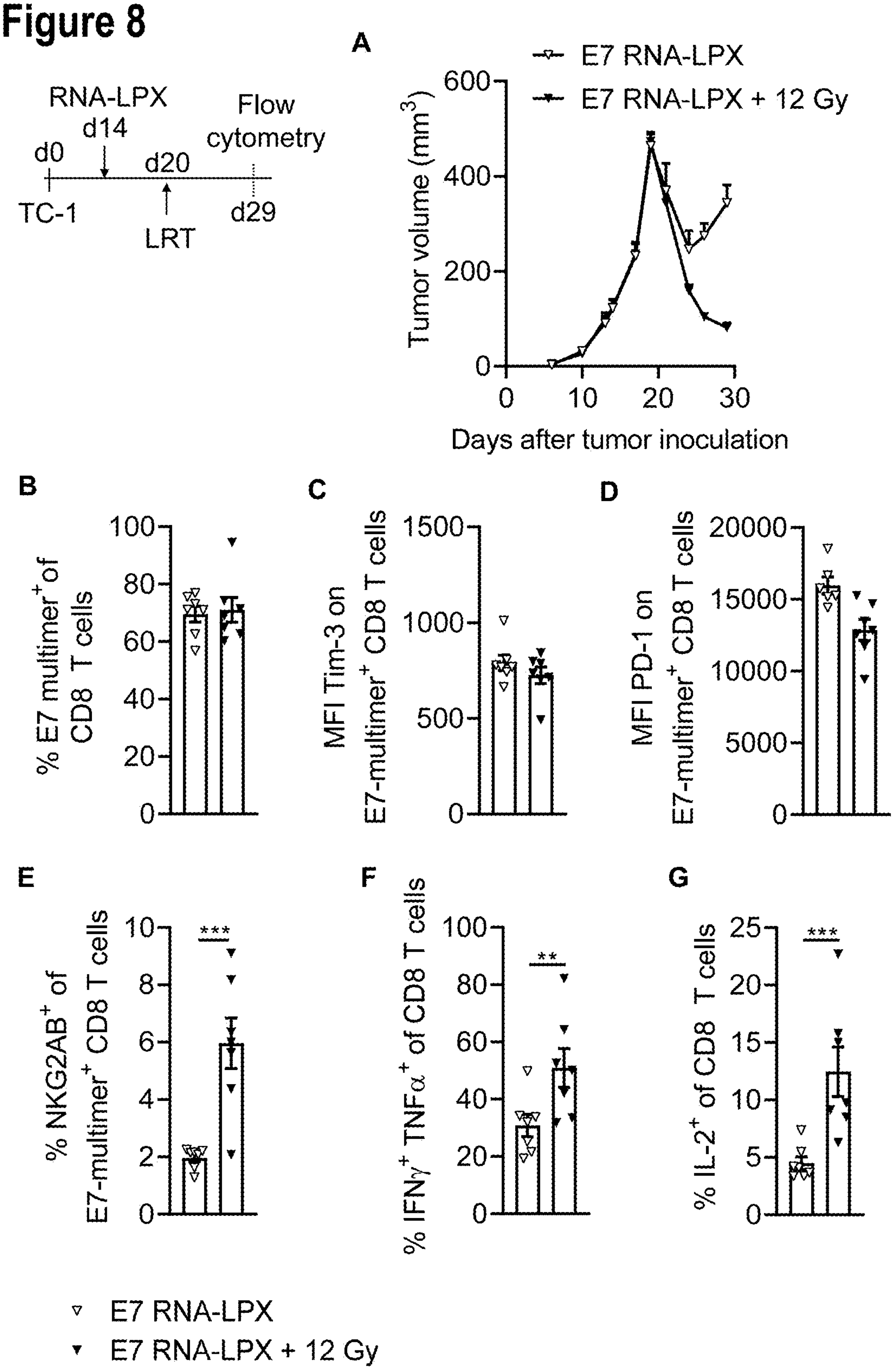

FIG. 8: LRT renders E7-specific $CD8^+$ T cell responses more potent and long-lasting.

Flow cytometric characterization of tumor-infiltrating CD8 T cells from s.c. TC-1 tumors-bearing C57BL/6 mice (n=7/group), vaccinated with E7 RNA-LPX at a mean tumor volume of 120 $mm^3$ and locally irradiated with 12 Gy. (A) Mean tumor growth curves. (B) Fraction of E7-specific $CD8^+$ TIL in TC-1 tumors. (C-E) Expression of (C) TIM-3, (D) PD-1, and fraction of (E) $NKG2AB^+$ cells in E7-specific $CD8^+$ TIL. (F-G) Intracellular cytokine staining of (F) IFNγ and TNFα, and (G) IL-2 in MACS-sorted $CD8^+$ TIL restimulated ex vivo with $E7_{49-57}$ peptide-loaded C57BL/6 BMDC. Significance in (B-G) was determined by unpaired, two-tailed Student's t-test. Mean±SEM. MFI=median fluorescent intensity.

Figure 9:
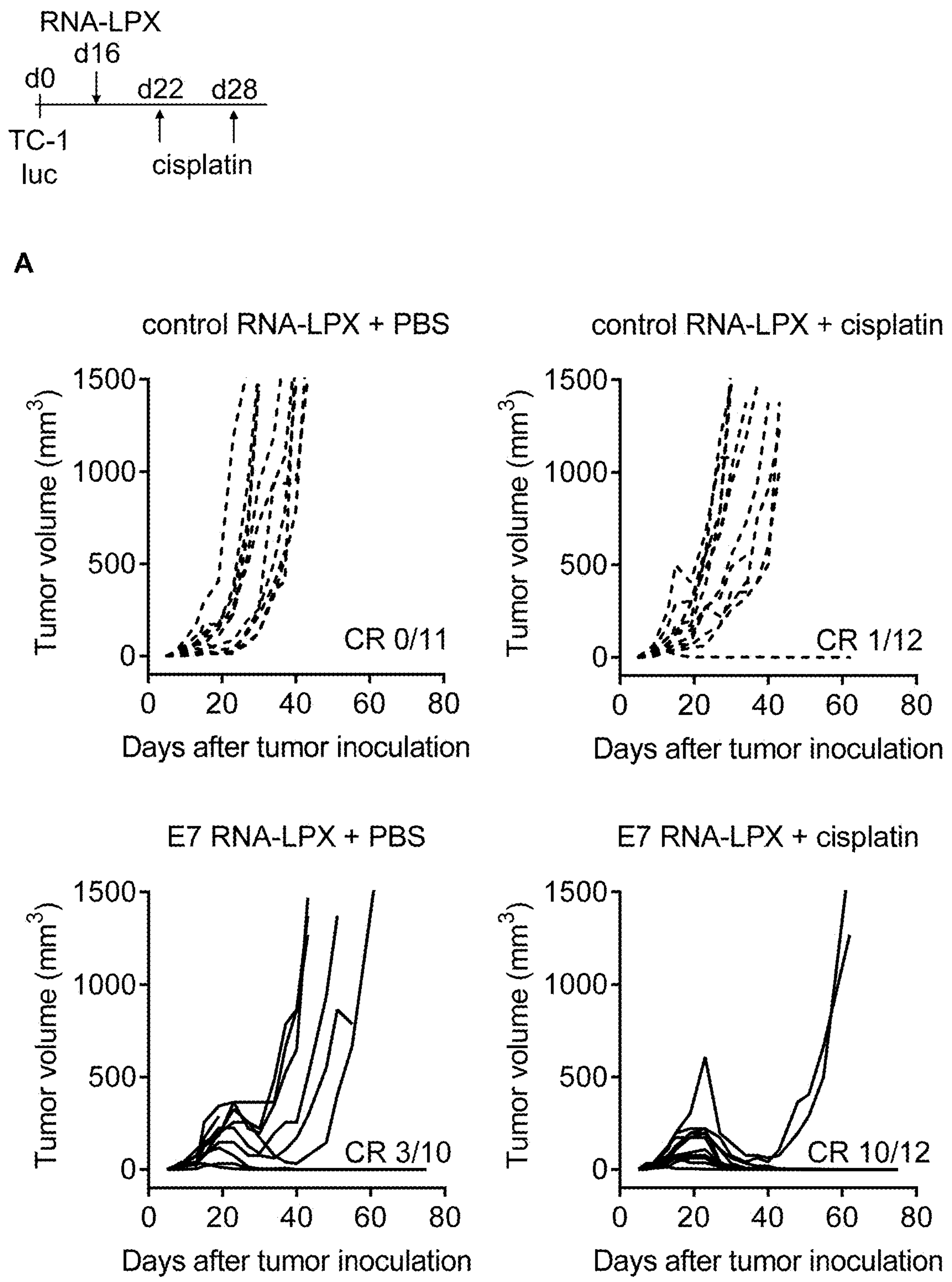
Figure 9:
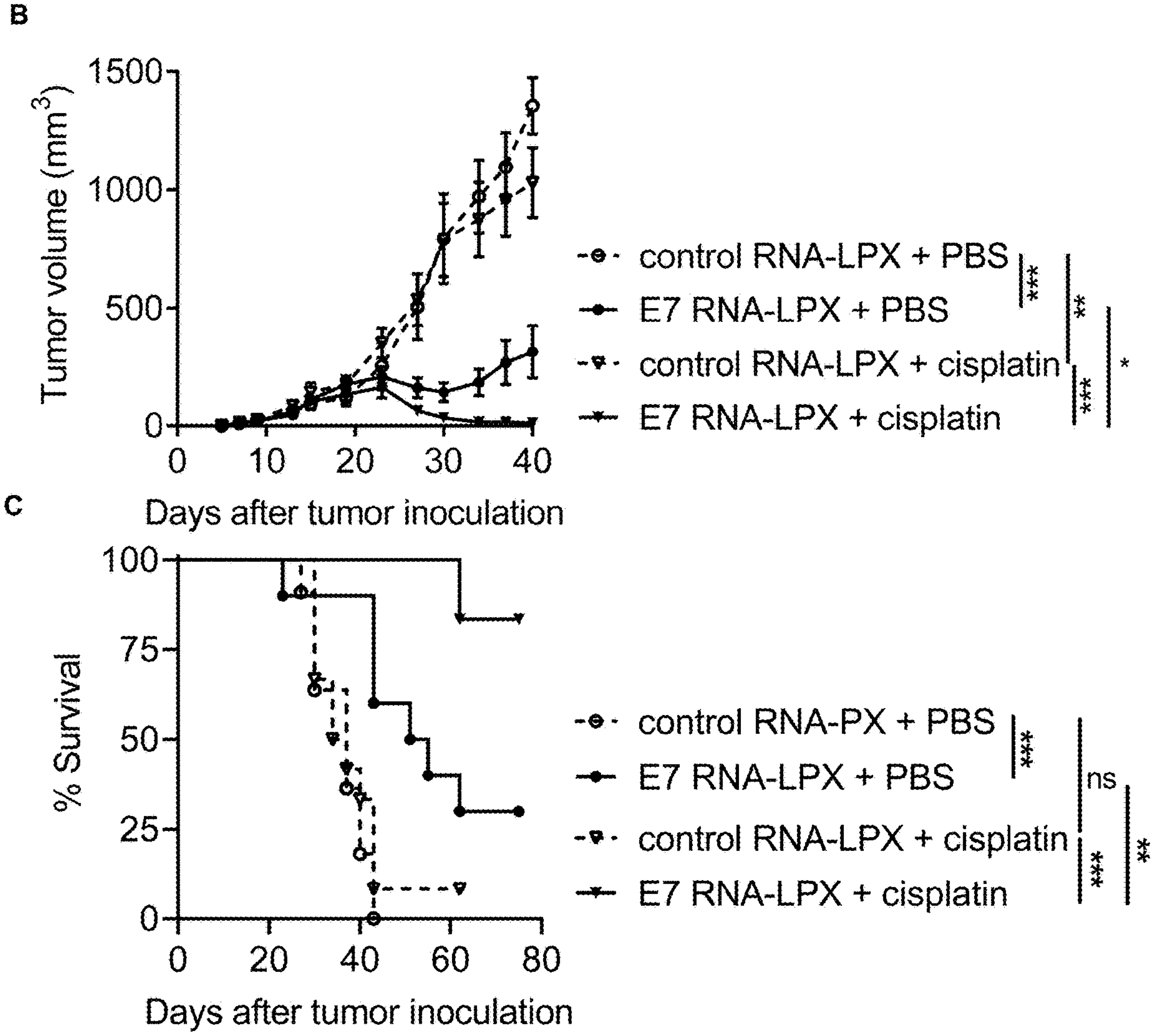

FIG. 9: E7 RNA-LPX and cisplatin chemotherapy synergize to reject $HPV16^+$ TC-1 tumors. TC-1 luc tumor-bearing C57BL/6 mice were immunized with 40 μg E7 RNA-LPX or control (OVA) RNA-LPX on day 16 and treated with 80 μg cisplatin or PBS i.p. on day 22 and 28 (n=10-12 mice/group). A) Individual tumor growth curves. B) Mean tumor growth until day 40, when the number of mice in the control RNA-LPX+PBS group declined to 45% (LOCF as long as n≥5 mice). Two-way ANOVA with Tukey's multiple comparisons test (day 40 results shown). Mean±SEM. C) Survival. Log-rank test without Bonferroni correction. LOCF=last observation carried forward; OVA=chicken ovalbumin; RNA LPX=ribonucleic acid lipoplex; SEM=standard error of the mean.

DESCRIPTION OF THE SEQUENCES

The following table provides a listing of certain sequences referenced herein.

TABLE 1

DESCRIPTION OF THE SEQUENCES

| SEQ ID NO: | Description | SEQUENCE |
|---|---|---|
| | | HPV 16 |
| 1 | E6 | MRVMAPRTLILLLSGALALTETWAGSGGSGGGGSGGMHQKRTAMFQDPQERPRKLPQLCTELQTTIHDIILECVYCKQQLLRREVYDFAFRDLCIV<br>YRDGNPYAVCDKCLKFYSKISEYRHYCYSLYGTTLEQQYNKPLCDLLIRCINCQKPLCPEEKQRHLDKKQRFHNIRGRWTGRCMSCCRSSRTRRETQ<br>LGGSGGGGSGGKKQYIKANSKFIGITELKKLGGGKRGGGKKMTNSVDDALINSTKIYSYFPSVISKVNQGAQGKKLGSSGGGGSPGGGSSIVGIVA<br>GLAVLAVVVIGAVVATVMCRRKSSGGKGGSYSQAASSDSAQGSDVSLTA |
| 2 | E6 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGCACCAAAAGAGAA<br>CUGCAAUGUUUCAGGACCCACAGGAGCGACCCAGAAAGUUACCACAGUUAUGCACAGAGCUGCAAACAACUAUACAUGAUAUAAUAU<br>UAGAAUGUGUGUACUGCAAGCAACAGUUACUGCGACGUGAGGUAUAUGACUUUGCUUUUCGGGAUUUAUGCAUAGUAUAUAGAGA<br>UGGGAAUCCAUAUGCUGUAUGUGAUAAAUGUUUAAAGUUUUAUUCUAAAAUUAGUGAGUAUAGACAUUAUUGUUAUAGUUUGUA<br>UGGAACAACAUUAGAACAGCAAUACAACAAACCGUUGUGUGAUUUGUUAAUUAGGUGUAUUAACUGUCAAAAGCCACUGUGUCCUG<br>AAGAAAAGCAAAGACAUCUGGACAAAAAGCAAAGAUUCCAUAAUAUAAGGGGUCGGUGGACCGGUCGAUGUAUGUCUUGUUGCAGA<br>UCAUCAAGAACACGUAGAGAAACCCAGCUGGGAGGAUCCGGUGGUGGCGGCAGCGGCGGCAAGAAGCAGUACAUCAAGGCCAACAGC<br>AAGUUCAUCGGCAUCACCGAGCUGAAGAAGCUGGGAGGGGGCAAACGGGGAGGCGGCAAAAAGAUGACCAACAGCGUGGACGACGCC<br>CUGAUCAACAGCACCAAGAUCUACAGCUACUUCCCCAGCGUGAUCAGCAAAGUGAACCAGGGCGCUCAGGGCAAGAAACUGGGCUCUA<br>GCGGAGGGGGAGGCUCUCCUGGCGGGGGAUCUAGCAUCGUGGGAAUUGUGGCAGGACUGGCAGUGCUGGCCGUGGUGGUGAUCGG<br>AGCCGUGGUGGCUACCGUGAUGUGCAGACGGAAGUCCAGCGGAGGCAAGGGCGGCAGCUACAGCCAGGCCGCCAGCUCUGAUAGCGCC<br>CAGGGCAGCGACGUGUCACUGACAGCCUAGUAACUCGAGCUGGUACUGCAUGCACGCAAUGCUAGCUGCCCCUUUCCCGUCCUGGGUA<br>CCCCGAGUCUCCCCCGACCUCGGGUCCCAGGUAUGCUCCCACCUCCACCUGCCCCACUCACCACCUCUGCUAGUUCCAGACACCUCCCAAG<br>CACGCAGCAAUGCAGCUCAAAACGCUUAGCCUAGCCACACCCCCACGGGAAACAGCAGUGAUUAACCUUUAGCAAUAAACGAAAGUUU<br>AACUAAGCUAUACUAACCCCAGGGUUGGUCAAUUUCGUGCCAGCCACACCGAGACCUGGUCCAGAGUCGCUAGCCGCGUCGCUAAAAA<br>AAAAAAAAAAAAAAAAAAAAAAAAAAAAGCAUAUGACUAAAAAAAAAAAAAAAAAAAAAAAAAAAAAAAAAAAAAAAAAAAAAAAAAA<br>AAAAAAAAAAAAAAAAAA |
| 3 | E7 | MRVMAPRTLILLLSGALALTETWAGSGGSGGGGSGGMHGDTPTLHEYMLDLQPETTDLYCYEQLNDSSEEEDEIDGPAGQAEPDRAHYNIVTFCC<br>KCDSTLRLCVQSTHVDIRTLEDLLMGTLGIVCPICSQKPGGSGGGGSGGKKQYIKANSKFIGITELKKLGGGKRGGGKKMTNSVDDALINSTKIYSYF<br>PSVISKVNQGAQGKKLGSSGGGGSPGGGSSIVGIVAGLAVLAVVVIGAVVATVMCRRKSSGGKGGSYSQAASSDSAQGSDVSLTA |
| 4 | E7 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGCAUGGCGACACAC<br>CAACACUUCACGAAUAUAUGCUGGAUUUGCAGCCUGAAACCACCGAUCUGUACUGCUAUGAACAGCUGAAUGAUUCUUCUGAAGAAG<br>AAGAUGAAAUUGAUGGUCCUGCUGGACAAGCAGAACCUGAUAGAGCCCACUACAACAUUGUGACAUUUUGCUGCAAAUGUGAUUCA<br>ACCCUUAGACUUUGUGUUCAGUCCACACAUGUUGACAUAAGAACUCUGGAAGAUCUGCUGAUGGGAACUCUUGGAAUUGUGUGUCC<br>CAUUUGCUCACAGAAACCUGGAGGAUCCGGUGGUGGCGGCAGCGGCGGCAAGAAGCAGUACAUCAAGGCCAACAGCAAGUUCAUCGG<br>CAUCACCGAGCUGAAGAAGCUGGGAGGGGGCAAACGGGGAGGCGGCAAAAAGAUGACCAACAGCGUGGACGACGCCCUGAUCAACAGC<br>ACCAAGAUCUACAGCUACUUCCCCAGCGUGAUCAGCAAAGUGAACCAGGGCGCUCAGGGCAAGAAACUGGGCUCUAGCGGAGGGGGA<br>GGCUCUCCUGGCGGGGGAUCUAGCAUCGUGGGAAUUGUGGCAGGACUGGCAGUGCUGGCCGUGGUGGUGAUCGGAGCCGUGGUGGC<br>UACCGUGAUGUGCAGACGGAAGUCCAGCGGAGGCAAGGGCGGCAGCUACAGCCAGGCCGCCAGCUCUGAUAGCGCCCAGGGCAGCGAC<br>GUGUCACUGACAGCCUAGUAACUCGAGCUGGUACUGCAUGCACGCAAUGCUAGCUGCCCCUUUCCCGUCCUGGGUACCCCGAGUCUCC<br>CCCGACCUCGGGUCCCAGGUAUGCUCCCACCUCCACCUGCCCCACUCACCACCUCUGCUAGUUCCAGACACCUCCCAAGCACGCAGCAAU<br>GCAGCUCAAAACGCUUAGCCUAGCCACACCCCCACGGGAAACAGCAGUGAUUAACCUUUAGCAAUAAACGAAAGUUUAACUAAGCUAU<br>ACUAACCCCAGGGUUGGUCAAUUUCGUGCCAGCCACACCGAGACCUGGUCCAGAGUCGCUAGCCGCGUCGCUAAAAAAAAAAAAAAAA<br>AAAAAAAAAAAAAAGCAUAUGACUAAAAAAAAAAAAAAAAAAAAAAAAAAAAAAAAAAAAAAAAAAAAAAAAAAAAAAAAAAAAAAA |

TABLE 1-continued

| DESCRIPTION OF THE SEQUENCES | | |
|---|---|---|
| SEQ ID NO: | Description | SEQUENCE |
| | | AAAAAAA |
| | | HPV 18 |
| 5 | E6 | MRVMAPRTLILLLSGALALTETWAGSGGSGGGGSGGMARFEDPTRRPYKLPDLCTELNTSLQDIEITCVYCKTVLELTEVFEFAFKDLFVVYRDSIPH<br>AACHKCIDFYSRIRELRHYSDSVYGDTLEKLTNTGLYNLLIRCLRCQKPLNPAEKLRHLNEKRRFHNIAGHYRGQCHSCCNRARQERLQRRRETQVG<br>GSGGGGSGGKKQYIKANSKFIGITELKKLGGGKRGGGKKMTNSVDDALINSTKIYSYFPSVISKVNQGAQGKKLGSSGGGGSPGGGSSIVGIVAGL<br>AVLAVVVIGAVVATVMCRRKSSGGKGGSYSQAASSDSAQGSDVSLTA |
| 6 | E6 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGGCAAGAUUUGAA<br>GAUCCAACAAGAAGACCAUACAAACUGCCCGAUCUGUGCACAGAACUGAACACCUCUCUGCAAGAUAUUGAAAUCACCUGUGUGUACU<br>GUAAAACCGUGCUGGAACUGACCGAAGUGUUUGAAUUUGCUUUUAAAGACCUGUUUGUGGUGUACAGAGAUUCCAUUCCUCAUGCA<br>GCAUGUCACAAAUGUAUUGAUUUUUACUCAAGAAUCAGAGAACUGAGACAUUAUUCUGAUUCUGUGUAUGGAGAUACACUGGAGA<br>AACUGACAAAUACAGGACUGUACAAUCUGCUGAUUAGAUGUCUGAGAUGUCAGAAACCUCUGAACCCUGCUGAGAAACUGAGACAUC<br>UGAAUGAGAAAAGAAGAUUUCACAACAUUGCUGGCCAUUACAGAGGCCAGUGUCAUUCUUGUUGUAAUAGAGCAAGACAGGAAAGA<br>CUGCAAAGAAGAAGGGAAACCCAGGUGGGAGGAUCCGGUGGUGGCGGCAGCGGCGGCAAGAAGCAGUACAUCAAGGCCAACAGCAAG<br>UUCAUCGGCAUCACCGAGCUGAAGAAGCUGGGAGGGGGCAAACGGGGAGGCGGCAAAAAGAUGACCAACAGCGUGGACGACGCCCUG<br>AUCAACAGCACCAAGAUCUACAGCUACUUCCCCAGCGUGAUCAGCAAAGUGAACCAGGGCGCUCAGGGCAAGAAACUGGGCUCUAGCG<br>GAGGGGGAGGCUCUCCUGGCGGGGGAUCUAGCAUCGUGGGAAUUGUGGCAGGACUGGCAGUGCUGGCCGUGGUGGUGAUCGGAGCC<br>GUGGUGGCUACCGUGAUGUGCAGACGGAAGUCCAGCGGAGGCAAGGGCGGCAGCUACAGCCAGGCCGCCAGCUCUGAUAGCGCCCAG<br>GGCAGCGACGUGUCACUGACAGCCUAGUAACUCGAGCUGGUACUGCAUGCACGCAAUGCUAGCUGCCCCUUUCCCGUCCUGGGUACCC<br>CGAGUCUCCCCCGACCUCGGGUCCCAGGUAUGCUCCCACCUCCACCUGCCCCACUCACCACCUCUGCUAGUUCCAGACACCUCCCAAGCAC<br>GCAGCAAUGCAGCUCAAAACGCUUAGCCUAGCCACACCCCCACGGGAAACAGCAGUGAUUAACCUUUAGCAAUAAACGAAAGUUUAAC<br>UAAGCUAUACUAACCCCAGGGUUGGUCAAUUUCGUGCCAGCCACACCGAGACCUGGUCCAGAGUCGCUAGCCGCGUCGCUAAAAAAAA<br>AAAAAAAAAAAAAAAAAAAAAAGCAUAUGACUAAAAAAAAAAAAAAAAAAAAAAAAAAAAAAAAAAAAAAAAAAAAAAAAAAAAAAAAA<br>AAAAAAAAAAAAAAA |
| 7 | E7 | MRVMAPRTLILLLSGALALTETWAGSGGSGGGGSGGMHGPKATLQDIVLHLEPQNEIPVDLLCHEQLSDSEEENDEIDGVNHQHLPARRAEPQR<br>HTMLCMCCKCEARIELVVESSADDLRAFQQLFLNTLSFVCPWCASQQGGSGGGGSGGKKQYIKANSKFIGITELKKLGGGKRGGGKKMTNSVDD<br>ALINSTKIYSYFPSVISKVNQGAQGKKLGSSGGGGSPGGGSSIVGIVAGLAVLAVVVIGAVVATVMCRRKSSGGKGGSYSQAASSDSAQGSDVSLT<br>A |
| 8 | E7 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGCAUGGACCUAAG<br>GCAACAUUGCAAGACAUUGUAUUGCAUUUAGAGCCCCAAAAUGAAAUUCCGGUUGACCUUCUAUGUCACGAGCAAUUAAGCGACUCA<br>GAGGAAGAAAACGAUGAAAUAGAUGGAGUUAAUCAUCAACAUUUACCAGCCCGACGAGCCGAACCACAACGUCACACAAUGUUGUGU<br>AUGUGUUGUAAGUGUGAAGCCAGAAUUGAGCUAGUAGUAGAAAGCUCAGCAGACGACCUUCGAGCAUUCCAGCAGCUGUUUCUGAA<br>CACCCUGUCCUUUGUGUGUCCGUGGUGUGCAUCCCAGCAGGGAGGAUCCGGUGGUGGCGGCAGCGGCGGCAAGAAGCAGUACAUCAA<br>GGCCAACAGCAAGUUCAUCGGCAUCACCGAGCUGAAGAAGCUGGGAGGGGGCAAACGGGGAGGCGGCAAAAAGAUGACCAACAGCGU<br>GGACGACGCCCUGAUCAACAGCACCAAGAUCUACAGCUACUUCCCCAGCGUGAUCAGCAAAGUGAACCAGGGCGCUCAGGGCAAGAAA<br>CUGGGCUCUAGCGGAGGGGGAGGCUCUCCUGGCGGGGGAUCUAGCAUCGUGGGAAUUGUGGCAGGACUGGCAGUGCUGGCCGUGGU<br>GGUGAUCGGAGCCGUGGUGGCUACCGUGAUGUGCAGACGGAAGUCCAGCGGAGGCAAGGGCGGCAGCUACAGCCAGGCCGCCAGCUC<br>UGAUAGCGCCCAGGGCAGCGACGUGUCACUGACAGCCUAGUAACUCGAGCUGGUACUGCAUGCACGCAAUGCUAGCUGCCCCUUUCCC<br>GUCCUGGGUACCCCGAGUCUCCCCCGACCUCGGGUCCCAGGUAUGCUCCCACCUCCACCUGCCCCACUCACCACCUCUGCUAGUUCCAGA<br>CACCUCCCAAGCACGCAGCAAUGCAGCUCAAAACGCUUAGCCUAGCCACACCCCCACGGGAAACAGCAGUGAUUAACCUUUAGCAAUAA<br>ACGAAAGUUUAACUAAGCUAUACUAACCCCAGGGUUGGUCAAUUUCGUGCCAGCCACACCGAGACCUGGUCCAGAGUCGCUAGCCGCG |

TABLE 1-continued

DESCRIPTION OF THE SEQUENCES

| SEQ ID NO: | Description | SEQUENCE |
|---|---|---|
| | | UCGCUAAAAAAAAAAAAAAAAAAAAAAAAAAAAAAGCAUAUGACUAAAAAAAAAAAAAAAAAAAAAAAAAAAAAAAAAAAAAAAAAA<br>AAAAAAAAAAAAAAAAAAAAAAAAAAAA |
| | | HPV 31 |
| 9 | E6 | MRVMAPRTLILLLSGALALTETWAGSGGSGGGGSGGMFKNPAERPRKLHELSSALEIPYDELRLNCVYCKGQLTETEVLDFAFTDLTIVYRDDTPYG<br>VCTKCLRFYSKVSEFRWYRYSVYGTTLEKLTNKGICDLLIRCITCQRPLCPEEKQRHLDKKKRFHNIGGRWTGRCIVCWRRPRTETQVGGSGGGGSG<br>GKKQYIKANSKFIGITELKKLGGGKRGGGKKMTNSVDDALINSTKIYSYFPSVISKVNQGAQGKKLGSSGGGGSPGGGSSIVGIVAGLAVLAVVVIG<br>AVVATVMCRRKSSGGKGGSYSQAASSDSAQGSDVSLTA |
| 10 | E6 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGUUUAAAAAUCCA<br>GCAGAAAGACCAAGAAAACUGCAUGAACUGUCUUCUGCUCUGGAAAUUCCUUAUGAUGAACUGAGACUGAAUUGUGUGUAUUGUAA<br>AGGACAGCUGACAGAAACAGAAGUGCUGGAUUUUGCUUUUACAGAUCUGACAAUUGUGUAUAGAGAUGAUACACCUUAUGGAGUG<br>UGUACAAAAUGUCUGAGAUUUUAUUCCAAAGUGUCUGAAUUUAGAUGGUAUAGAUAUUCUGUGUAUGGAACAACAUUGGAAAAAU<br>UGACAAAUAAAGGAAUUUGUGAUCUGCUGAUUAGAUGUAUUACAUGUCAGAGACCUCUGUGUCCUGAAGAAAAACAGAGACAUCUG<br>GAUAAAAAGAAAAGAUUUCAUAAUAUUGGAGGAAGAUGGACAGGAAGAUGUAUUGUGUGUUGGAGAAGACCAAGAACAGAAACAC<br>AGGUGGGAGGAUCCGGUGGUGGCGGCAGCGGCGGCAAGAAGCAGUACAUCAAGGCCAACAGCAAGUUCAUCGGCAUCACCGAGCUGA<br>AGAAGCUGGGAGGGGGCAAACGGGGAGGCGGCAAAAAGAUGACCAACAGCGUGGACGACGCCCUGAUCAACAGCACCAAGAUCUACA<br>GCUACUUCCCCAGCGUGAUCAGCAAAGUGAACCAGGGCGCUCAGGGCAAGAAACUGGGCUCUAGCGGAGGGGGAGGCUCUCCUGGCG<br>GGGGAUCUAGCAUCGUGGGAAUUGUGGCAGGACUGGCAGUGCUGGCCGUGGUGGUGAUCGGAGCCGUGGUGGCUACCGUGAUGUG<br>CAGACGGAAGUCCAGCGGAGGCAAGGGCGGCAGCUACAGCCAGGCCGCCAGCUCUGAUAGCGCCCAGGGCAGCGACGUGUCACUGACA<br>GCCUAGUAACUCGAGCUGGUACUGCAUGCACGCAAUGCUAGCUGCCCCUUUCCCGUCCUGGGUACCCCGAGUCUCCCCCGACCUCGGG<br>UCCCAGGUAUGCUCCCACCUCCACCUGCCCCACUCACCACCUCUGCUAGUUCCAGACACCUCCCAAGCACGCAGCAAUGCAGCUCAAAAC<br>GCUUAGCCUAGCCACACCCCCACGGGAAACAGCAGUGAUUAACCUUUAGCAAUAAACGAAAGUUUAACUAAGCUAUACUAACCCCAGG<br>GUUGGUCAAUUUCGUGCCAGCCACACCGAGACCUGGUCCAGAGUCGCUAGCCGCGUCGCUAAAAAAAAAAAAAAAAAAAAAAAAAAAA<br>AAGCAUAUGACUAAAAAAAAAAAAAAAAAAAAAAAAAAAAAAAAAAAAAAAAAAAAAAAAAAAAAAAAAAAAAAAA |
| 11 | E7 | MRVMAPRTLILLLSGALALTETWAGSGGSGGGGSGGMRGETPTLQDYVLDLQPEATDLHCYEQLPDSSDEEDVIDSPAGQAKPDTSNYNIVTFCC<br>QCESTLRLCVQSTQVDIRILQELLMGSFGIVCPNCSTRLGGSGGGGSGGKKQYIKANSKFIGITELKKLGGGKRGGGKKMTNSVDDALINSTKIYSYF<br>PSVISKVNQGAQGKKLGSSGGGGSPGGGSSIVGIVAGLAVLAVVVIGAVVATVMCRRKSSGGKGGSYSQAASSDSAQGSDVSLTA |
| 12 | E7 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGAGAGGAGAGACA<br>CCCACAUUGCAGGAUUAUGUGUUGGAUUUGCAACCUGAGGCAACUGAUCUGCACUGUUAUGAACAGCUGCCCGAUUCUUCUGACGAA<br>GAAGAUGUGAUUGAUUCUCCAGCAGGACAGGCAAAACCAGAUACCUCCAAUUACAAUAUUGUGACCUUUUGUUGUCAGUGUGAAAG<br>CACACUGAGACUGUGUGUGCAGAGCACACAGGUGGAUAUUAGAAUUCUGCAAGAACUGCUGAUGGGCUCUUUUGGAAUUGUGUGUC<br>CAAAUUGUUCAACAAGACUGGGAGGAUCCGGUGGUGGCGGCAGCGGCGGCAAGAAGCAGUACAUCAAGGCCAACAGCAAGUUCAUCG<br>GCAUCACCGAGCUGAAGAAGCUGGGAGGGGGCAAACGGGGAGGCGGCAAAAAGAUGACCAACAGCGUGGACGACGCCCUGAUCAACA<br>GCACCAAGAUCUACAGCUACUUCCCCAGCGUGAUCAGCAAAGUGAACCAGGGCGCUCAGGGCAAGAAACUGGGCUCUAGCGGAGGGGG<br>AGGCUCUCCUGGCGGGGGAUCUAGCAUCGUGGGAAUUGUGGCAGGACUGGCAGUGCUGGCCGUGGUGGUGAUCGGAGCCGUGGUGG<br>CUACCGUGAUGUGCAGACGGAAGUCCAGCGGAGGCAAGGGCGGCAGCUACAGCCAGGCCGCCAGCUCUGAUAGCGCCCAGGGCAGCGA<br>CGUGUCACUGACAGCCUAGUAACUCGAGCUGGUACUGCAUGCACGCAAUGCUAGCUGCCCCUUUCCCGUCCUGGGUACCCCGAGUCUC<br>CCCCGACCUCGGGUCCCAGGUAUGCUCCCACCUCCACCUGCCCCACUCACCACCUCUGCUAGUUCCAGACACCUCCCAAGCACGCAGCAAU<br>GCAGCUCAAAACGCUUAGCCUAGCCACACCCCCACGGGAAACAGCAGUGAUUAACCUUUAGCAAUAAACGAAAGUUUAACUAAGCUAU<br>ACUAACCCCAGGGUUGGUCAAUUUCGUGCCAGCCACACCGAGACCUGGUCCAGAGUCGCUAGCCGCGUCGCUAAAAAAAAAAAAAAAA<br>AAAAAAAAAAAAAAGCAUAUGACUAAAAAAAAAAAAAAAAAAAAAAAAAAAAAAAAAAAAAAAAAAAAAAAAAAAAAAAAAAAAAA |

TABLE 1-continued

DESCRIPTION OF THE SEQUENCES

| SEQ ID NO: | Description | SEQUENCE |
|---|---|---|
| | | AAAAAAA |
| | | HPV 33 |
| 13 | E6 | MRVMAPRTLILLLSGALALTETWAGSGGSGGGGSGGMFQDTEEKPRTLHDLCQALETTIHNIELQCVECKKPLQRSEVYDFAFADLTVVYREGNPF<br>GICKLCLRFLSKISEYRHYNYSLYGNTLEQTVKKPLNEILIRCMICQRPLCPQEKKRHVDLNKRFHNISGRWAGRCAVCWRSRRRETALGGSGGGGS<br>GGKKQYIKANSKFIGITELKKLGGGKRGGGKKMTNSVDDALINSTKIYSYFPSVISKVNQGAQGKKLGSSGGGGSPGGGSSIVGIVAGLAVLAVVVI<br>GAVVATVMCRRKSSGGKGGSYSQAASSDSAQGSDVSLTA |
| 14 | E6 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGUUUCAGGAUACA<br>GAAGAAAAACCAAGAACACUUCAUGAUCUUUGUCAGGCUCUUGAAACAACAAUUCACAAUAUUGAAUUGCAGUGUGUGGAAUGUAA<br>GAAACCUUUGCAGAGAUCUGAAGUGUAUGAUUUUGCUUUUGCUGAUCUGACAGUGGUGUACAGAGAAGGAAAUCCUUUUGGAAUU<br>UGUAAACUGUGUCUGAGAUUUCUGUCAAAAAUUUCUGAAUACAGACAUUAUAAUUAUUCUCUGUAUGGAAAUACACUGGAACAGAC<br>AGUGAAAAAACCUCUGAAUGAAAUUCUGAUUAGAUGUAUGAUUUGUCAGAGACCAUUAUGUCCACAGGAAAAGAAAAGACAUGUGG<br>AUCUGAAUAAAAGAUUUCAUAAUAUUUCUGGAAGAUGGGCUGGAAGAUGUGCUGUGUGUUGGAGAUCAAGAAGAAGGGAAACAGC<br>UCUUGGAGGAUCCGGUGGUGGCGGCAGCGGCGGCAAGAAGCAGUACAUCAAGGCCAACAGCAAGUUCAUCGGCAUCACCGAGCUGAA<br>GAAGCUGGGAGGGGGCAAACGGGGAGGCGGCAAAAAGAUGACCAACAGCGUGGACGACGCCCUGAUCAACAGCACCAAGAUCUACAGC<br>UACUUCCCCAGCGUGAUCAGCAAAGUGAACCAGGGCGCUCAGGGCAAGAAACUGGGCUCUAGCGGAGGGGGAGGCUCUCCUGGCGGG<br>GGAUCUAGCAUCGUGGGAAUUGUGGCAGGACUGGCAGUGCUGGCCGUGGUGGUGAUCGGAGCCGUGGUGGCUACCGUGAUGUGCA<br>GACGGAAGUCCAGCGGAGGCAAGGGCGGCAGCUACAGCCAGGCCGCCAGCUCUGAUAGCGCCCAGGGCAGCGACGUGUCACUGACAGC<br>CUAGUAACUCGAGCUGGUACUGCAUGCACGCAAUGCUAGCUGCCCCUUUCCCGUCCUGGGUACCCCGAGUCUCCCCCGACCUCGGGUCC<br>CAGGUAUGCUCCCACCUCCACCUGCCCCACUCACCACCUCUGCUAGUUCCAGACACCUCCCAAGCACGCAGCAAUGCAGCUCAAAACGCU<br>UAGCCUAGCCACACCCCCACGGGAAACAGCAGUGAUUAACCUUUAGCAAUAAACGAAAGUUUAACUAAGCUAUACUAACCCCAGGGUU<br>GGUCAAUUUCGUGCCAGCCACACCGAGACCUGGUCCAGAGUCGCUAGCCGCGUCGCUAAAAAAAAAAAAAAAAAAAAAAAAAAAAAAAAG<br>CAUAUGACUAAAAAAAAAAAAAAAAAAAAAAAAAAAAAAAAAAAAAAAAAAAAAAAAAAAAAAAAAAAAAAAAAAAAAAAAAAAAAAA |
| 15 | E7 | MRVMAPRTLILLLSGALALTETWAGSGGSGGGGSGGMRGHKPTLKEYVLDLYPEPTDLYCYEQLSDSSDEDEGLDRPDGQAQPATADYYIVTCCH<br>TCNATVRLCVNSTASDLRTIQQLLMGTVNIVCPSCAQPGGSGGGGSGGKKQYIKANSKFIGITELKKLGGGKRGGGKKMTNSVDDALINSTKIYSYF<br>PSVISKVNQGAQGKKLGSSGGGGSPGGGSSIVGIVAGLAVLAVVVIGAVVATVMCRRKSSGGKGGSYSQAASSDSAQGSDVSLTA |
| 16 | E7 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGAGAGGACACAAG<br>CCAACGUUAAAGGAAUAUGUUUUAGAUUUAUAUCCUGAACCAACUGACCUAUACUGCUAUGAGCAAUUAAGUGACAGCUCAGAUGA<br>GGAUGAAGGCUUGGACCGGCCAGAUGGACAAGCACAACCAGCCACAGCUGAUUACUACAUUGUAACCUGUUGUCACACUUGUAACGC<br>CACAGUUCGUUUAUGUGUCAACAGUACAGCAAGUGACCUACGAACCAUACAGCAACUACUUAUGGGCACAGUUAAUAUUGUGUGCCC<br>UAGCUGUGCACAACCAGGAGGAUCCGGUGGUGGCGGCAGCGGCGGCAAGAAGCAGUACAUCAAGGCCAACAGCAAGUUCAUCGGCAU<br>CACCGAGCUGAAGAAGCUGGGAGGGGGCAAACGGGGAGGCGGCAAAAAGAUGACCAACAGCGUGGACGACGCCCUGAUCAACAGCACC<br>AAGAUCUACAGCUACUUCCCCAGCGUGAUCAGCAAAGUGAACCAGGGCGCUCAGGGCAAGAAACUGGGCUCUAGCGGAGGGGGAGGC<br>UCUCCUGGCGGGGGAUCUAGCAUCGUGGGAAUUGUGGCAGGACUGGCAGUGCUGGCCGUGGUGGUGAUCGGAGCCGUGGUGGCUAC<br>CGUGAUGUGCAGACGGAAGUCCAGCGGAGGCAAGGGCGGCAGCUACAGCCAGGCCGCCAGCUCUGAUAGCGCCCAGGGCAGCGACGUG<br>UCACUGACAGCCUAGUAACUCGAGCUGGUACUGCAUGCACGCAAUGCUAGCUGCCCCUUUCCCGUCCUGGGUACCCCGAGUCUCCCCCG<br>ACCUCGGGUCCCAGGUAUGCUCCCACCUCCACCUGCCCCACUCACCACCUCUGCUAGUUCCAGACACCUCCCAAGCACGCAGCAAUGCAG<br>CUCAAAACGCUUAGCCUAGCCACACCCCCACGGGAAACAGCAGUGAUUAACCUUUAGCAAUAAACGAAAGUUUAACUAAGCUAUACUA<br>ACCCCAGGGUUGGUCAAUUUCGUGCCAGCCACACCGAGACCUGGUCCAGAGUCGCUAGCCGCGUCGCUAAAAAAAAAAAAAAAAAAAA<br>AAAAAAAAAAGCAUAUGACUAAAAAAAAAAAAAAAAAAAAAAAAAAAAAAAAAAAAAAAAAAAAAAAAAAAAAAAAAAAAAAAAAAAA<br>AAA |

TABLE 1-continued

DESCRIPTION OF THE SEQUENCES

| SEQ ID NO: | Description | SEQUENCE |
|---|---|---|
| | | HPV 45 |
| 17 | E6 | MRVMAPRTLILLLSGALALTETWAGSGGSGGGGSGGMARFDDPTQRPYKLPDLCTELNTSLQDVSIACVYCKATLERTEVYQFAFKDLFIVYRDCIA<br>GSGGGGSGGKKQYIKANSKFIGITELKKLGGGKRGGGKKMTNSVDDALINSTKIYSYFPSVISKVNQGAQGKKLGSSGGGGSPGGGSSIVGIVAGL<br>YAACHKCIDFYSRIRELRYYSNSVYGETLEKITNTELYNLLIRCLRCQKPLNPAEKRRHLKDKRRFHSIAGQYRGQCNTCCDQARQERLRRRRETQVG<br>AVLAVVVIGAVVATVMCRRKSSGGKGGSYSQAASSDSAQGSDVSLTA |
| 18 | E6 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGGCAAGAUUUGAU<br>GAUCCAACACAGAGACCAUACAAACUGCCCGAUCUGUGUACAGAACUGAAUACAUCUCUGCAAGACGUGAGCAUUGCCUGUGUGUAU<br>UGUAAAGCCACACUGGAAAGAACAGAAGUGUACCAGUUUGCUUUUAAAGACCUGUUUAUCGUGUAUAGAGACUGUAUUGCUUAUGC<br>UGCUUGUCACAAAUGUAUUGAUUUUUAUUCUAGAAUUAGAGAACUGAGAUAUUAUUCCAAUUCUGUGUAUGGAGAAACACUGGAG<br>AAAAUCACAAAUACAGAGCUGUACAAUCUGCUGAUUAGAUGUCUGAGAUGUCAGAAACCACUGAACCCAGCUGAGAAAAGAAGACAU<br>CUUAAAGAUAAAAGAAGAUUUCAUUCCAUUGCUGGACAGUACAGAGGACAGUGUAAUACCUGUUGUGACCAGGCCAGACAGGAAAG<br>ACUGAGAAGAAGGAGAGAAACACAGGUGGGAGGAUCCGGUGGUGGCGGCAGCGGCGGCAAGAAGCAGUACAUCAAGGCCAACAGCAA<br>GUUCAUCGGCAUCACCGAGCUGAAGAAGCUGGGAGGGGGCAAACGGGGAGGCGGCAAAAAGAUGACCAACAGCGUGGACGACGCCCU<br>GAUCAACAGCACCAAGAUCUACAGCUACUUCCCCAGCGUGAUCAGCAAAGUGAACCAGGGCGCUCAGGGCAAGAAACUGGGCUCUAGC<br>GGAGGGGGAGGCUCUCCUGGCGGGGGAUCUAGCAUCGUGGGAAUUGUGGCAGGACUGGCAGUGCUGGCCGUGGUGGUGAUCGGAG<br>CCGUGGUGGCUACCGUGAUGUGCAGACGGAAGUCCAGCGGAGGCAAGGGCGGCAGCUACAGCCAGGCCGCCAGCUCUGAUAGCGCCCA<br>GGGCAGCGACGUGUCACUGACAGCCUAGUAACUCGAGCUGGUACUGCAUGCACGCAAUGCUAGCUGCCCCUUUCCCGUCCUGGGUACC<br>CCGAGUCUCCCCCGACCUCGGGUCCCAGGUAUGCUCCCACCUCCACCUGCCCCACUCACCACCUCUGCUAGUUCCAGACACCUCCCAAGCA<br>CGCAGCAAUGCAGCUCAAAACGCUUAGCCUAGCCACACCCCCACGGGAAACAGCAGUGAUUAACCUUUAGCAAUAAACGAAAGUUUAA<br>CUAAGCUAUACUAACCCCAGGGUUGGUCAAUUUCGUGCCAGCCACACCGAGACCUGGUCCAGAGUCGCUAGCCGCGUCGCUAAAAAAA<br>AAAAAAAAAAAAAAAAAAAAAAAAGCAUAUGACUAAAAAAAAAAAAAAAAAAAAAAAAAAAAAAAAAAAAAAAAAAAAAAAAAAAAAAAA<br>AAAAAAAAAAAAAAAA |
| 19 | E7 | MRVMAPRTLILLLSGALALTETWAGSGGSGGGGSGGMHGPQATLQEIVLHLEPQNELDPVDLLCYEQLSESEEENDEADGVSHAQLPARRAEPQ<br>RHKILCVCCKCDGRIELTVESSADDLRTLQQLFLSTLSFVCPWCATNQGGSGGGGSGGKKQYIKANSKFIGITELKKLGGGKRGGGKKMTNSVDDAL<br>INSTKIYSYFPSVISKVNQGAQGKKLGSSGGGGSPGGGSSIVGIVAGLAVLAVVVIGAVVATVMCRRKSSGGKGGSYSQAASSDSAQGSDVSLTA |
| 20 | E7 | GGGCGAACUAGUAUUCUUCUGGUCCCCACAGACUCAGAGAGAACCCGCCACCAUGAGAGUGAUGGCCCCCAGAACCCUGAUCCUGCUG<br>CUGUCUGGCGCCCUGGCCCUGACAGAGACAUGGGCCGGAAGCGGCGGCUCUGGAGGAGGCGGCUCCGGAGGCAUGCAUGGACCUCAG<br>GCAACACUUCAGGAAAUUGUGCUUCAUCUGGAACCUCAGAAUGAACUUGACCCUGUGGAUCUGCUGUGUUAUGAGCAGCUGUCUGA<br>GUCUGAGGAGGAGAAUGAUGAGGCAGAUGGAGUGUCUCAUGCACAGCUGCCUGCAAGAAGGGCAGAACCUCAGAGACACAAAAUUC<br>UGUGUGUGUGUUGUAAAUGUGAUGGAAGAAUUGAACUGACAGUGGAAUCUUCUGCUGAUGAUCUGAGAACACUGCAACAGCUGUU<br>UCUGUCUACACUGUCUUUUGUGUGUCCUUGGUGUGCAACAAAUCAGGGAGGAUCCGGUGGUGGCGGCAGCGGCGGCAAGAAGCAGU<br>ACAUCAAGGCCAACAGCAAGUUCAUCGGCAUCACCGAGCUGAAGAAGCUGGGAGGGGGCAAACGGGGAGGCGGCAAAAAGAUGACCA<br>ACAGCGUGGACGACGCCCUGAUCAACAGCACCAAGAUCUACAGCUACUUCCCCAGCGUGAUCAGCAAAGUGAACCAGGGCGCUCAGGG<br>CAAGAAACUGGGCUCUAGCGGAGGGGGAGGCUCUCCUGGCGGGGGAUCUAGCAUCGUGGGAAUUGUGGCAGGACUGGCAGUGCUGG<br>CCGUGGUGGUGAUCGGAGCCGUGGUGGCUACCGUGAUGUGCAGACGGAAGUCCAGCGGAGGCAAGGGCGGCAGCUACAGCCAGGCCG<br>CCAGCUCUGAUAGCGCCCAGGGCAGCGACGUGUCACUGACAGCCUAGUAACUCGAGCUGGUACUGCAUGCACGCAAUGCUAGCUGCCC<br>CUUUCCCGUCCUGGGUACCCCGAGUCUCCCCCGACCUCGGGUCCCAGGUAUGCUCCCACCUCCACCUGCCCCACUCACCACCUCUGCUAG<br>UUCCAGACACCUCCCAAGCACGCAGCAAUGCAGCUCAAAACGCUUAGCCUAGCCACACCCCCACGGGAAACAGCAGUGAUUAACCUUUA<br>GCAAUAAACGAAAGUUUAACUAAGCUAUACUAACCCCAGGGUUGGUCAAUUUCGUGCCAGCCACACCGAGACCUGGUCCAGAGUCGC<br>UAGCCGCGUCGCUAAAAAAAAAAAAAAAAAAAAAAAAAAAAAAAGCAUAUGACUAAAAAAAAAAAAAAAAAAAAAAAAAAAAAAAAA<br>AAAAAAAAAAAAAAAAAAAAAAAAAAAAAAAAAAAA |

TABLE 1-continued

| DESCRIPTION OF THE SEQUENCES | | |
|---|---|---|
| SEQ ID NO: | Description | SEQUENCE |
| | | HPV 58 |
| 21 | E6 | MRVMAPRTLILLLSGALALTETWAGSGGSGGGGSGGMFQDAEEKPRTLHDLCQALETSVHEIELKCVECKKTLQRSEVYDFTFADLRIVYRDGNPF AVCKVCLRLLSKISEYRHYNYSLYGDTLEQTLKKRLEEILIRCIICQRPLCPQEKKRHVDLNKRFHNISGRWTGRCAVCWRPRRRQTQVGGSGGGGS GGKKQYIKANSKFIGITELKKLGGGKRGGGKKMTNSVDDALINSTKIYSYFPSVISKVNQGAQGKKLGSSGGGGSPGGGSSIVGIVAGLAVLAVVVI GAVVATVMCRRKSSGGKGGSYSQAASSDSAQGSDVSLTA |
| 22 | E6 | GGGCGAACUAGUAUUCUUCUGGUCCCCACAGACUCAGAGAGAACCCGCCACCAUGAGAGUGAUGGCCCCCAGAACCCUGAUCCUGCUG CUGUCUGGCGCCCUGGCCCUGACAGAGACAUGGGCCGGAAGCGGCGGCUCUGGAGGAGGCGGCUCCGGAGGCAUGUUUCAGGAUGCU GAAGAAAAACCAAGAACACUGCAUGAUCUGUGUCAGGCUCUGGAAACAUCUGUGCAUGAAAUUGAACUGAAAUGUGUGGAAUGUAA GAAAACAUUACAGAGAUCUGAAGUGUAUGAUUUUACAUUUGCUGAUCUGAGAAUUGUGUACAGAGAUGGAAAUCCUUUUGCUGUG UGUAAAGUGUGUCUGAGACUGCUGUCUAAAAUUUCUGAAUACAGACAUUACAAUUACUCACUGUAUGGAGAUACACUGGAACAGAC ACUGAAGAAAAGACUGGAAGAAAUUCUGAUUAGAUGUAUUAUUUGUCAGAGACCUUUAUGUCCUCAGGAAAAGAAAAGACAUGUG GAUCUGAAUAAAAGAUUUCAUAAUAUUUCUGGAAGAUGGACAGGAAGAUGUGCUGUGUGUUGGAGACCAAGAAGAAGACAGACAC AGGUGGGAGGAUCCGGUGGUGGCGGCAGCGGCGGCAAGAAGCAGUACAUCAAGGCCAACAGCAAGUUCAUCGGCAUCACCGAGCUGA AGAAGCUGGGAGGGGGCAAACGGGGAGGCGGCAAAAAGAUGACCAACAGCGUGGACGACGCCCUGAUCAACAGCACCAAGAUCUACA GCUACUUCCCCAGCGUGAUCAGCAAAGUGAACCAGGGCGCUCAGGGCAAGAAACUGGGCUCUAGCGGAGGGGGAGGCUCUCCUGGCG GGGGAUCUAGCAUCGUGGGAAUUGUGGCAGGACUGGCAGUGCUGGCCGUGGUGGUGAUCGGAGCCGUGGUGGCUACCGUGAUGUG CAGACGGAAGUCCAGCGGAGGCAAGGGCGGCAGCUACAGCCAGGCCGCCAGCUCUGAUAGCGCCCAGGGCAGCGACGUGUCACUGACA GCCUAGUAACUCGAGCUGGUACUGCAUGCACGCAAUGCUAGCUGCCCCUUUCCCGUCCUGGGUACCCCGAGUCUCCCCCGACCUCGGG UCCCAGGUAUGCUCCCACCUCCACCUGCCCCACUCACCACCUCUGCUAGUUCCAGACACCUCCCAAGCACGCAGCAAUGCAGCUCAAAAC GCUUAGCCUAGCCACACCCCCACGGGAAACAGCAGUGAUUAACCUUUAGCAAUAAACGAAAGUUUAACUAAGCUAUACUAACCCCAGG GUUGGUCAAUUUCGUGCCAGCCACACCGAGACCUGGUCCAGAGUCGCUAGCCGCGUCGCUAAAAAAAAAAAAAAAAAAAAAAAAAAAA AAGCAUAUGACUAAAAAAAAAAAAAAAAAAAAAAAAAAAAAAAAAAAAAAAAAAAAAAAAAAAAAAAAAAAA |
| 23 | E7 | MRVMAPRTLILLLSGALALTETWAGSGGSGGGGSGGMRGNNPTLREYILDLHPEPTDLFCYEQLCDSSDEDEIGLDGPDGQAQPATANYYIVTCCY TCDATVRLCINSTATEVRTLQQLLMGTCTIVCPSCAQQGGSGGGGSGGKKQYIKANSKFIGITELKKLGGGKRGGGKKMTNSVDDALINSTKIYSYF PSVISKVNQGAQGKKLGSSGGGGSPGGGSSIVGIVAGLAVLAVVVIGAVVATVMCRRKSSGGKGGSYSQAASSDSAQGSDVSLTA |
| 24 | E7 | GGGCGAACUAGUAUUCUUCUGGUCCCCACAGACUCAGAGAGAACCCGCCACCAUGAGAGUGAUGGCCCCCAGAACCCUGAUCCUGCUG CUGUCUGGCGCCCUGGCCCUGACAGAGACAUGGGCCGGAAGCGGCGGCUCUGGAGGAGGCGGCUCCGGAGGCAUGAGAGGAAAUAAU CCAACACUGAGAGAAUACAUUCUGGAUCUGCAUCCAGAACCAACCGACCUGUUUUGUUAUGAACAGUUAUGUGACAGCAGCGAUGAA GAUGAAAUUGGACUGGAUGGACCAGAUGGACAGGCACAGCCAGCAACAGCAAAUUAUUACAUUGUGACAUGUUGUUACACAUGUGA UGCAACAGUGAGACUGUGUAUCAAUUCCACAGCCACAGAAGUGAGAACACUGCAACAGCUGCUGAUGGGAACAUGCACCAUUGUGUG UCCCUCUUGUGCCCAGCAGGGAGGAUCCGGUGGUGGCGGCAGCGGCGGCAAGAAGCAGUACAUCAAGGCCAACAGCAAGUUCAUCGG CAUCACCGAGCUGAAGAAGCUGGGAGGGGGCAAACGGGGAGGCGGCAAAAAGAUGACCAACAGCGUGGACGACGCCCUGAUCAACAGC ACCAAGAUCUACAGCUACUUCCCCAGCGUGAUCAGCAAAGUGAACCAGGGCGCUCAGGGCAAGAAACUGGGCUCUAGCGGAGGGGGA GGCUCUCCUGGCGGGGGAUCUAGCAUCGUGGGAAUUGUGGCAGGACUGGCAGUGCUGGCCGUGGUGGUGAUCGGAGCCGUGGUGGC UACCGUGAUGUGCAGACGGAAGUCCAGCGGAGGCAAGGGCGGCAGCUACAGCCAGGCCGCCAGCUCUGAUAGCGCCCAGGGCAGCGAC GUGUCACUGACAGCCUAGUAACUCGAGCUGGUACUGCAUGCACGCAAUGCUAGCUGCCCCUUUCCCGUCCUGGGUACCCCGAGUCUCC CCCGACCUCGGGUCCCAGGUAUGCUCCCACCUCCACCUGCCCCACUCACCACCUCUGCUAGUUCCAGACACCUCCCAAGCACGCAGCAAU GCAGCUCAAAACGCUUAGCCUAGCCACACCCCCACGGGAAACAGCAGUGAUUAACCUUUAGCAAUAAACGAAAGUUUAACUAAGCUAU ACUAACCCCAGGGUUGGUCAAUUUCGUGCCAGCCACACCGAGACCUGGUCCAGAGUCGCUAGCCGCGUCGCUAAAAAAAAAAAAAAAA AAAAAAAAAAAAAAGCAUAUGACUAAAAAAAAAAAAAAAAAAAAAAAAAAAAAAAAAAAAAAAAAAAAAAAAAAAAAAAAAAAAAAA AAAAAAA |

TABLE 1-continued

| SEQ ID NO: | Description | SEQUENCE |
|---|---|---|
| | | DESCRIPTION OF THE SEQUENCES |
| | | Sec/MITD |
| 25 | Sec (amino acid) | MRVMAPRTLILLLSGALALTETWAGS |
| 26 | MITD (amino acid) | IVGIVAGLAVLAVVVIGAVVATVMCRRKSSGGKGGSYSQAASSDSAQGSDVSLTA |
| | | P2P16 |
| 27 | P2P16 (amino acid) | KKQYIKANSKFIGITELKKLGGGKRGGGKKMTNSVDDALINSTKIYSYFPSVISKVNQGAQGKKL |
| | | GS Linker |
| 28 | GS Linker 1 | GGSGGGGSGG |
| 29 | GS Linker 2 | GSSGGGGSPGGGSS |
| | | 5'-UTR (hAg-Kozak) |
| 30 | 5'-UTR | AACUAGUAUUCUUCUGGUCCCCACAGACUCAGAGAGAACCCGCCACC |
| | | 3'-UTR (FI element) |
| 31 | 3'-UTR | CUGGUACUGCAUGCACGCAAUGCUAGCUGCCCCUUUCCCGUCCUGGGUACCCCGAGUCUCCCCCGACCUCGGGUCCCAGGUAUGCUCCC<br>ACCUCCACCUGCCCCACUCACCACCUCUGCUAGUUCCAGACACCUCCCAAGCACGCAGCAAUGCAGCUCAAAACGCUUAGCCUAGCCACA<br>CCCCCACGGGAAACAGCAGUGAUUAACCUUUAGCAAUAAACGAAAGUUUAACUAAGCUAUACUAACCCCAGGUUGGUCAAUUUCGU<br>GCCAGCCACACC |
| | | A30L70 |
| 32 | A30L70 | AAAAAAAAAAAAAAAAAAAAAAAAAAAAAAGCAUAUGACUAAAAAAAAAAAAAAAAAAAAAAAAAAAAAAAAAAAAAAAAAAAAAA<br>AAAAAAAAAAAAAAAAAAAAAAA |
| | | Helper epitopes |
| 33 | P2 | QYIKANSKFIGITEL |
| 34 | P16 | MTNSVDDALINSTKIYSYFPSVISKVNQGAQG |

DETAILED DESCRIPTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e., for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

Definitions

In the following, definitions will be provided which apply to all aspects of the present disclosure. The following terms have the following meanings unless otherwise indicated. Any undefined terms have their art recognized meanings.

Terms such as "reduce" or "inhibit" as used herein means the ability to cause an overall decrease, for example, of about 5% or greater, about 10% or greater, about 20% or greater, about 50% or greater, or about 75% or greater, in the level. The term "inhibit" or similar phrases includes a complete or essentially complete inhibition, i.e., a reduction to zero or essentially to zero.

Terms such as "increase" or "enhance" in one embodiment relate to an increase or enhancement by at least about 10%, at least about 20%, at least about 30%, at least about 40%, at least about 50%, at least about 80%, or at least about 100%.

"Physiological pH" as used herein refers to a pH of about 7.5.

The term "ionic strength" refers to the mathematical relationship between the number of different kinds of ionic species in a particular solution and their respective charges. Thus, ionic strength I is represented mathematically by the formula $$I = \frac{1}{2} \cdot \sum_i z_i^2 \cdot c_i$$

in which c is the molar concentration of a particular ionic species and z the absolute value of its charge. The sum 2 is taken over all the different kinds of ions (i) in solution.

According to the disclosure, the term "ionic strength" in one embodiment relates to the presence of monovalent ions. Regarding the presence of divalent ions, in particular divalent cations, their concentration or effective concentration (presence of free ions) due to the presence of chelating agents is in one embodiment sufficiently low so as to prevent degradation of the RNA. In one embodiment, the concentration or effective concentration of divalent ions is below the catalytic level for hydrolysis of the phosphodiester bonds between RNA nucleotides. In one embodiment, the concentration of free divalent ions is 20 UM or less.

In one embodiment, there are no or essentially no free divalent ions.

The term "freezing" relates to the solidification of a liquid, usually with the removal of heat.

The term "lyophilizing" or "lyophilization" refers to the freeze-drying of a substance by freezing it and then reducing the surrounding pressure to allow the frozen medium in the substance to sublimate directly from the solid phase to the gas phase.

The term “spray-drying” refers to spray-drying a substance by mixing (heated) gas with a fluid that is atomized (sprayed) within a vessel (spray dryer), where the solvent from the formed droplets evaporates, leading to a dry powder.

The term “cryoprotectant” relates to a substance that is added to a formulation in order to protect the active ingredients during the freezing stages.

The term “lyoprotectant” relates to a substance that is added to a formulation in order to protect the active ingredients during the drying stages.

The term “reconstitute” relates to adding a solvent such as water to a dried product to return it to a liquid state such as its original liquid state.

The term “recombinant” in the context of the present disclosure means “made through genetic engineering”. In one embodiment, a “recombinant object” in the context of the present disclosure is not occurring naturally.

The term “naturally occurring” as used herein refers to the fact that an object can be found in nature. For example, a peptide or nucleic acid that is present in an organism (including viruses) and can be isolated from a source in nature and which has not been intentionally modified by man in the laboratory is naturally occurring. The term “found in nature” means “present in nature” and includes known objects as well as objects that have not yet been discovered and/or isolated from nature, but that may be discovered and/or isolated in the future from a natural source.

In the context of the present disclosure, the term “particle” relates to a structured entity formed by molecules or molecule complexes. In one embodiment, the term “particle” relates to a micro- or nano-sized structure, such as a micro- or nano-sized compact structure. In the context of the present disclosure, the term “RNA lipoplex particle” relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

In particulate formulation, it is possible that each RNA species (e.g. RNA encoding HPV E6 vaccine antigen and RNA encoding HPV E7 vaccine antigen) is separately formulated as an individual particulate formulation. In that case, each individual particulate formulation will comprise one RNA species. The individual particulate formulations may be present as separate entities, e.g. in separate containers. Such formulations are obtainable by providing each RNA species separately (typically each in the form of an RNA-containing solution) together with a particle-forming agent, thereby allowing the formation of particles. Respective particles will contain exclusively the specific RNA species that is being provided when the particles are formed (individual particulate formulations). In one embodiment, a composition such as a pharmaceutical composition comprises more than one individual particle formulation. Respective pharmaceutical compositions are referred to as mixed particulate formulations. Mixed particulate formulations according to the invention are obtainable by forming, separately, individual particulate formulations, as described above, followed by a step of mixing of the individual particulate formulations. By the step of mixing, a formulation comprising a mixed population of RNA-containing particles is obtainable (for illustration: e.g. a first population of particles may contain RNA encoding HPV E6 vaccine antigen, and a second formulation of particles may contain RNA encoding HPV E7 vaccine antigen). Individual particulate populations may be together in one container, comprising a mixed population of individual particulate formulations. Alternatively, it is possible that all RNA species of the pharmaceutical composition (e.g. RNA encoding HPV E6 vaccine antigen and RNA encoding HPV E7 vaccine antigen) are formulated together as a combined particulate formulation. Such formulations are obtainable by providing a combined formulation (typically combined solution) of all RNA species together with a particle-forming agent, thereby allowing the formation of particles. As opposed to a mixed particulate formulation, a combined particulate formulation will typically comprise particles which comprise more than one RNA species. In a combined particulate composition different RNA species are typically present together in a single particle.

As used in the present disclosure, “nanoparticle” refers to a particle comprising RNA and at least one cationic lipid and having an average diameter suitable for intravenous administration.

The term “average diameter” refers to the mean hydrodynamic diameter of particles as measured by dynamic light scattering (DLS) with data analysis using the so-called cumulant algorithm, which provides as results the so-called $Z_{average}$ with the dimension of a length, and the polydispersity index (PI), which is dimensionless (Koppel, D., *J. Chem. Phys.* 57, 1972, pp 4814-4820, ISO 13321). Here “average diameter”, “diameter” or “size” for particles is used synonymously with this value of the $Z_{average}$.

The term “polydispersity index” is used herein as a measure of the size distribution of an ensemble of particles, e.g., nanoparticles. The polydispersity index is calculated based on dynamic light scattering measurements by the so-called cumulant analysis.

The term “ethanol injection technique” refers to a process, in which an ethanol solution comprising lipids is rapidly injected into an aqueous solution through a needle. This action disperses the lipids throughout the solution and promotes lipid structure formation, for example lipid vesicle formation such as liposome formation. Generally, the RNA lipoplex particles described herein are obtainable by adding RNA to a colloidal liposome dispersion. Using the ethanol injection technique, such colloidal liposome dispersion is, in one embodiment, formed as follows: an ethanol solution comprising lipids, such as cationic lipids like DOTMA and additional lipids, is injected into an aqueous solution under stirring. In one embodiment, the RNA lipoplex particles described herein are obtainable without a step of extrusion.

The term “extruding” or “extrusion” refers to the creation of particles having a fixed, cross-sectional profile. In particular, it refers to the downsizing of a particle, whereby the particle is forced through filters with defined pores.

The term “co-administered” or “co-administration” or the like as used herein refers to administration of two or more agents concurrently, simultaneously, or essentially at the same time, either as part of a single formulation or as multiple formulations that are administered by the same or different routes. “Essentially at the same time” as used herein means within about 1 minute, 5 minutes, 10 minutes, 15 minutes, 30 minutes, 1 hour, 2 hours, or 6 hours period of each other.

The disclosure describes nucleic acid sequences and amino acid sequences having a certain degree of identity to a given nucleic acid sequence or amino acid sequence, respectively (a reference sequence).

"Sequence identity" between two nucleic acid sequences indicates the percentage of nucleotides that are identical between the sequences. "Sequence identity" between two amino acid sequences indicates the percentage of amino acids that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970*, J. Mol. Biol.* 48, 443, with the aid of the similarity search algorithm by Pearson and Lipman, 1988*, Proc. Natl Acad. Sci. USA* 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi?PAGE_TYPE=BlastSearch&BLAST_SPEC=blast2seq&LINK_LOC=align2seq). In some embodiments, the algorithm parameters used for BLASTN algorithm on the NCBI website include: (i) Expect Threshold set to 10; (ii) Word Size set to 28; (iii) Max matches in a query range set to 0; (iv) Match/Mismatch Scores set to 1, −2; (v) Gap Costs set to Linear; and (vi) the filter for low complexity regions being used. In some embodiments, the algorithm parameters used for BLASTP algorithm on the NCBI website include: (i) Expect Threshold set to 10; (ii) Word Size set to 3; (iii) Max matches in a query range set to 0; (iv) Matrix set to BLOSUM62; (v) Gap Costs set to Existence: 11 Extension: 1; and (vi) conditional compositional score matrix adjustment.

Percentage identity is obtained by determining the number of identical positions at which the sequences to be compared correspond, dividing this number by the number of positions compared (e.g., the number of positions in the reference sequence) and multiplying this result by 100.

In some embodiments, the degree of identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments in continuous nucleotides. In some embodiments, the degree of identity is given for the entire length of the reference sequence.

Nucleic acid sequences or amino acid sequences having a particular degree of identity to a given nucleic acid sequence or amino acid sequence, respectively, may have at least one functional property of said given sequence, e.g., and in some instances, are functionally equivalent to said given sequence. One important property includes an immunogenic property, in particular when administered to a subject. In some embodiments, a nucleic acid sequence or amino acid sequence having a particular degree of identity to a given nucleic acid sequence or amino acid sequence is functionally equivalent to the given sequence.

RNA

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5'-untranslated region (5'-UTR), a peptide coding region and a 3'-untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In one embodiment, the RNA may have modified nucleosides. In some embodiments, the RNA comprises a modified nucleoside in place of at least one (e.g., every) uridine.

The term "uracil," as used herein, describes one of the nucleobases that can occur in the nucleic acid of RNA. The structure of uracil is:

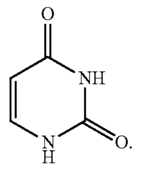

The term "uridine," as used herein, describes one of the nucleosides that can occur in RNA. The structure of uridine is:

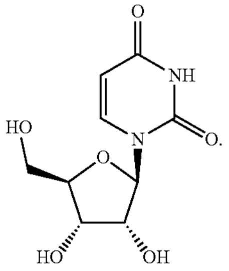 [SMILES: O=c1ccn([C@@H]2O[C@H](CO)[C@@H](O)[C@H]2O)c(=O)[nH]1]

UTP (uridine 5'-triphosphate) has the following structure:

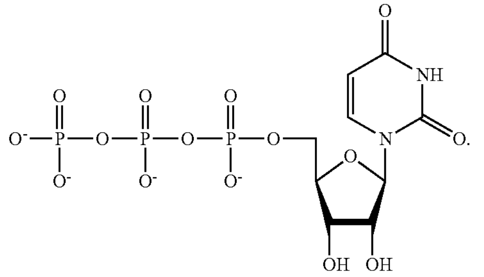

Pseudo-UTP (pseudouridine 5'-triphosphate) has the following structure:

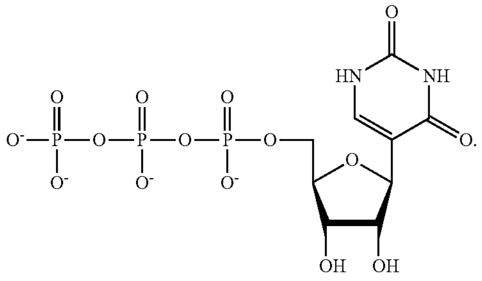

"Pseudouridine" is one example of a modified nucleoside that is an isomer of uridine, where the uracil is attached to the pentose ring via a carbon-carbon bond instead of a nitrogen-carbon glycosidic bond.

Another exemplary modified nucleoside is N1-methyl-pseudouridine (m1ψ), which has the structure:

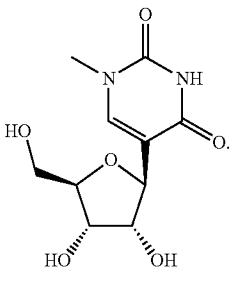 [SMILES: Cn1cc([C@@H]2O[C@H](CO)[C@@H](O)[C@H]2O)c(=O)[nH]c1=O]

N1-methyl-pseudo-UTP has the following structure:

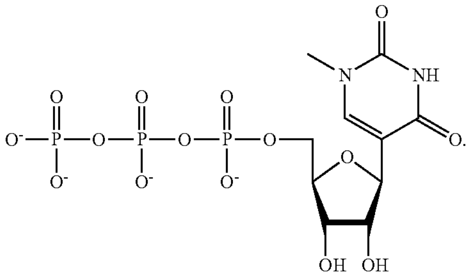

Another exemplary modified nucleoside is 5-methyl-uridine (m5U), which has the structure:

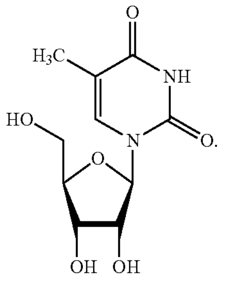

In some embodiments, one or more uridine in the RNA described herein is replaced by a modified nucleoside. In some embodiments, the modified nucleoside is a modified uridine. In some embodiments, the modified uridine replacing uridine is pseudouridine (+), N1-methyl-pseudouridine (m1ψ), or 5-methyl-uridine (m5U).

In some embodiments, the modified nucleoside replacing one or more uridine in the RNA may be any one or more of 3-methyl-uridine (m$^3$U), 5-methoxy-uridine (mo$^5$U), 5-aza-uridine, 6-aza-uridine, 2-thio-5-aza-uridine, 2-thio-uridine (s$^2$U), 4-thio-uridine (s$^4$U), 4-thio-pseudouridine, 2-thio-pseudouridine, 5-hydroxy-uridine (ho$^5$U), 5-aminoallyl-uridine, 5-halo-uridine (e.g., 5-iodo-uridineor 5-bromo-uridine), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s$^2$U), 5-aminomethyl-2-thio-uridine (nm$^5$s$^2$U), 5-methylaminomethyl-uridine (mnm$^5$U), 1-ethyl-pseudouridine, 5-methylaminomethyl-2-thio-uridine (mnm$^5$s$^2$U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s$^2$U), 5-propynyl-uridine, 1-propynyl-pseudouridine, 5-taurinomethyl-uridine (τm$^5$U), 1-taurinomethyl-pseudouridine, 5-taurinomethyl-2-thio-uridine (τm$^5$s$^2$U), 1-taurinomethyl-4-thio-pseudouridine), 5-methyl-2-thio-uridine (m$^5$s$^2$U), 1-methyl-4-thio-pseudouridine (m$^1$s$^4$ψ), 4-thio-1-methyl-pseudouridine, 3-methylpseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine ($acp^3U$), 1-methyl-3-(3-amino-3-carboxypropyl) pseudouridine ($acp^3$ ψ), 5-(isopentenylaminomethyl) uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (\m), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino) uridine, or any other modified uridine known in the art.

In some embodiments, at least one RNA comprises a modified nucleoside in place of at least one uridine. In some embodiments, at least one RNA comprises a modified nucleoside in place of each uridine. In some embodiments, each RNA comprises a modified nucleoside in place of at least one uridine. In some embodiments, each RNA comprises a modified nucleoside in place of each uridine.

In some embodiments, the modified nucleoside is independently selected from pseudouridine (ψ) N1-methyl-pseudouridine (m1ψ), and 5-methyl-uridine (m5U). In some embodiments, the modified nucleoside comprises pseudouridine (4). In some embodiments, the modified nucleoside comprises N1-methyl-pseudouridine (m1ψ). In some embodiments, the modified nucleoside comprises 5-methyl-uridine (m5U). In some embodiments, at least one RNA may comprise more than one type of modified nucleoside, and the modified nucleosides are independently selected from pseudouridine (4), N1-methyl-pseudouridine (m1ψ), and 5-methyl-uridine (m5U). In some embodiments, the modified nucleosides comprise pseudouridine (ψ) and N1-methyl-pseudouridine (m1ψ). In some embodiments, the modified nucleosides comprise pseudouridine (ψ) and 5-methyl-uridine (m5U). In some embodiments, the modified nucleosides comprise N1-methyl-pseudouridine (m1ψ) and 5-methyl-uridine (m5U). In some embodiments, the modified nucleosides comprise pseudouridine (ψ), N1-methyl-pseudouridine (m1ψ), and 5-methyl-uridine (m5U).

In one embodiment, the RNA comprises other modified nucleosides or comprises further modified nucleosides, e.g., modified cytidine. For example, in one embodiment, in the RNA 5-methylcytidine is substituted partially or completely, preferably completely, for cytidine. In one embodiment, the RNA comprises 5-methylcytidine and one or more selected from pseudouridine (ψ), N1-methyl-pseudouridine (m1ψ), and 5-methyl-uridine (m5U). In one embodiment, the RNA comprises 5-methylcytidine and N1-methyl-pseudouridine (m1ψ). In some embodiments, the RNA comprises 5-methylcytidine in place of each cytidine and N1-methyl-pseudouridine (m1ψ) in place of each uridine.

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5'- to 5'-triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes. In some embodiments, the building block cap for RNA is $m_2^{7,3'-O}$Gppp ($m_1^{2'-O}$)ApG (also sometimes referred to as $m_2^{7,3'O}$G(5')ppp(5') $m^{2'-O}$ApG), which has the following structure:

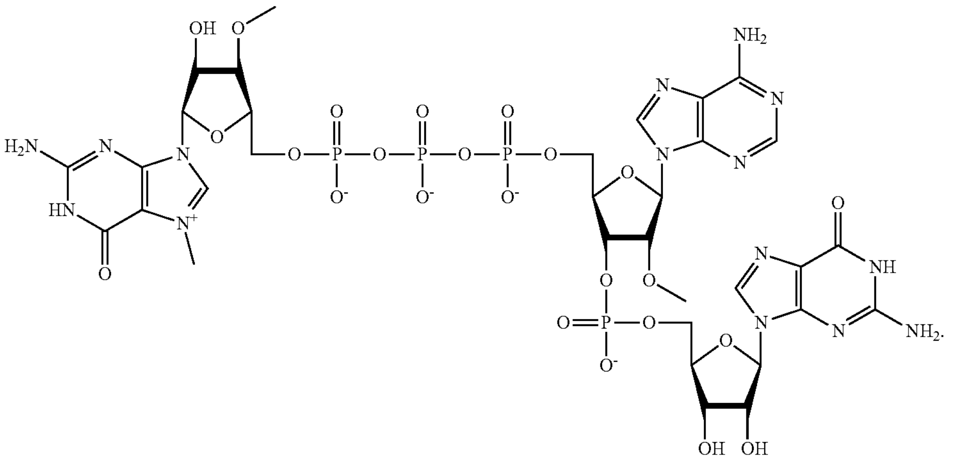

Below is an exemplary Cap1 RNA, which comprises RNA and $m_2^{7,3'O}$G(5')ppp(5') $m^{2'-O}$ApG:

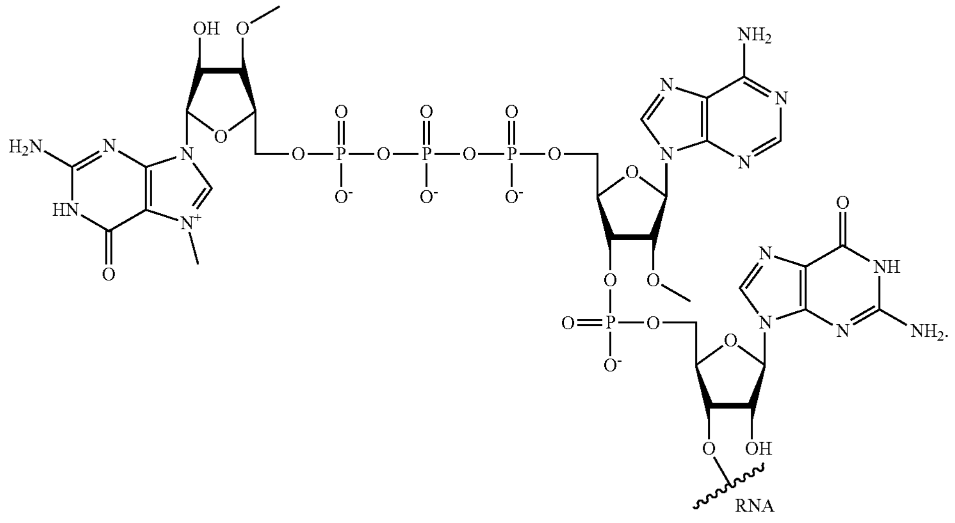
Below is another exemplary Cap1 RNA (no cap analog):
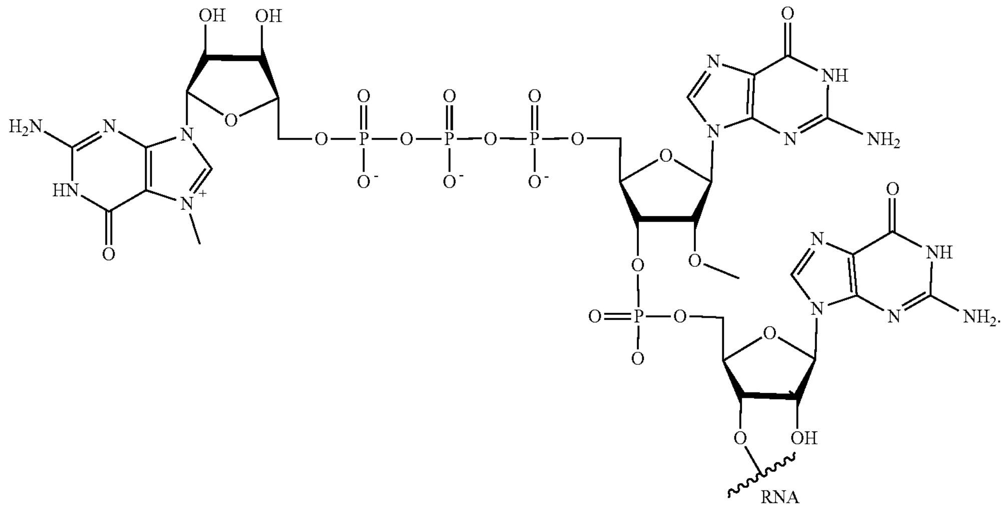
In some embodiments, the RNA is modified with "Cap0" structures using, in one embodiment, the cap analog anti-reverse cap (ARCA Cap ($m_2^{7,3'O}$G(5')ppp(5')G)) with the structure:
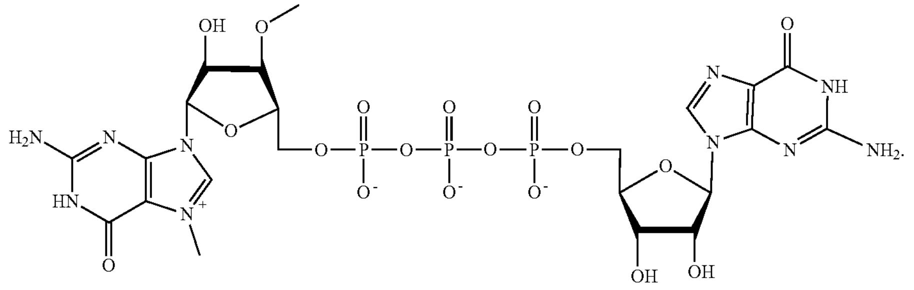
Below is an exemplary Cap0 RNA comprising RNA and $m_2^{7,3\,O}$G(5')ppp(5')G:

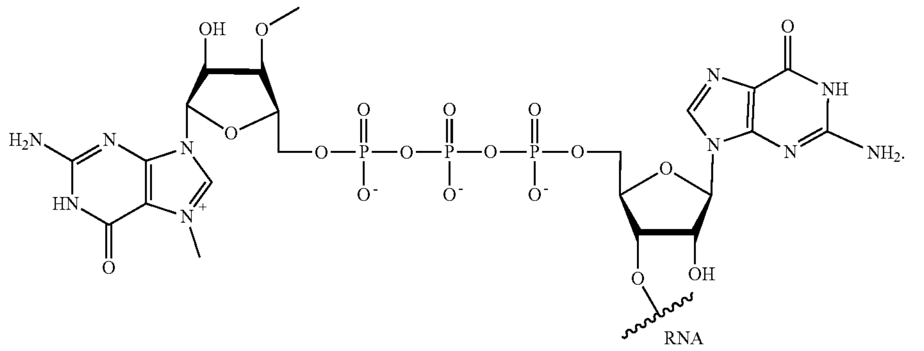

In some embodiments, the “Cap0” structures are generated using the cap analog Beta-S-ARCA ($m_2^{7,2'O}$G(5')ppSp(5')G) with the structure:

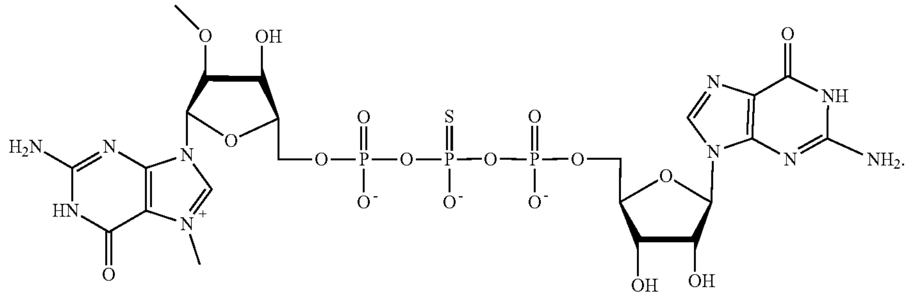

Below is an exemplary Cap0 RNA comprising Beta-S-ARCA ($m_2^{7,2\ O}$G(5')ppSp(5')G) and RNA:

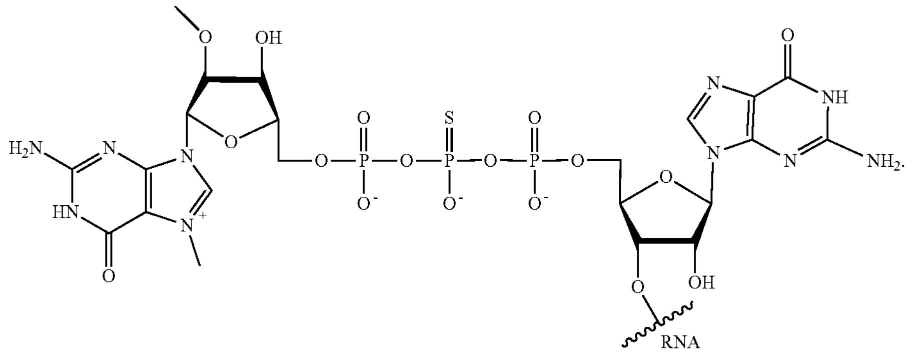

A particularly preferred Cap comprises the 5'-cap $m_2^{7,2'O}$G(5')ppSp(5')G. In some embodiments, at least one RNA described herein comprises the 5'-cap $m_2^{7,2\ O}$G(5')ppSp(5')G. In some embodiments, each RNA described herein comprises the 5'-cap $m_2^{7,2\ O}$G(5')ppSp(5')G. The “D1” diastereomer of beta-S-ARCA or “beta-S-ARCA (D1)” is the diastereomer of beta-S-ARCA which elutes first on an HPLC column compared to the D2 diastereomer of beta-S-ARCA (beta-S-ARCA (D2)) and thus exhibits a shorter retention time (cf., WO 2011/015347, herein incorporated by reference). A particularly preferred cap is beta-S-ARCA (D1) ($m_2^{7,2'-O}$GppSpG). In some embodiments, RNA according to the present disclosure comprises a 5'-UTR and/or a 3'-UTR. The term “untranslated region” or “UTR” relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5'-end, upstream of the start codon of a protein-encoding region. A 5'-UTR is downstream of the 5'-cap (if present), e.g., directly adjacent to the 5'-cap. A 3'-UTR, if present, is located at the 3'-end, downstream of the termination codon of a protein-encoding region, but the term “3'-UTR” does preferably not include the poly-A sequence. Thus, the 3'-UTR is upstream of the poly-A sequence (if present), e.g., directly adjacent to the poly-A sequence.

A particularly preferred 5'-UTR comprises the nucleotide sequence of SEQ ID NO: 30. A particularly preferred 3'-UTR comprises the nucleotide sequence of SEQ ID NO: 31.

In some embodiments, at least one RNA comprises a 5'-UTR comprising the nucleotide sequence of SEQ ID NO: 30, or a nucleotide sequence having at least 99%, 98%, 97%, 96%, 95%, 90%, 85%, or 80% identity to the nucleotide sequence of SEQ ID NO: 30. In some embodiments, each RNA comprises a 5'-UTR comprising the nucleotide sequence of SEQ ID NO: 30, or a nucleotide sequence having at least 99%, 98%, 97%, 96%, 95%, 90%, 85%, or 80% identity to the nucleotide sequence of SEQ ID NO: 30.

In some embodiments, at least one RNA comprises a 3'-UTR comprising the nucleotide sequence of SEQ ID NO: 31, or a nucleotide sequence having at least 99%, 98%, 97%, 96%, 95%, 90%, 85%, or 80% identity to the nucleotide sequence of SEQ ID NO: 31. In some embodiments, each RNA comprises a 3'-UTR comprising the nucleotide sequence of SEQ ID NO: 31, or a nucleotide sequence having at least 99%, 98%, 97%, 96%, 95%, 90%, 85%, or 80% identity to the nucleotide sequence of SEQ ID NO: 31.

As used herein, the term "poly-A tail" or "poly-A sequence" refers to an uninterrupted or interrupted sequence of adenylate residues which is typically located at the 3'-end of an RNA molecule. Poly-A tails or poly-A sequences are known to those of skill in the art and may follow the 3'-UTR in the RNAs described herein. An uninterrupted poly-A tail is characterized by consecutive adenylate residues. In nature, an uninterrupted poly-A tail is typical. RNAs disclosed herein can have a poly-A tail attached to the free 3'-end of the RNA by a template-independent RNA polymerase after transcription or a poly-A tail encoded by DNA and transcribed by a template-dependent RNA polymerase.

It has been demonstrated that a poly-A tail of about 120 A nucleotides has a beneficial influence on the levels of RNA in transfected eukaryotic cells, as well as on the levels of protein that is translated from an open reading frame that is present upstream (5') of the poly-A tail (Holtkamp et al., 2006, *Blood*, vol. 108, pp. 4009-4017).

The poly-A tail may be of any length. In some embodiments, a poly-A tail comprises, essentially consists of, or consists of at least 20, at least 30, at least 40, at least 80, or at least 100 and up to 500, up to 400, up to 300, up to 200, or up to 150 A nucleotides, and, in particular, about 120 A nucleotides. In this context, "essentially consists of" means that most nucleotides in the poly-A tail, typically at least 75%, at least 80%, at least 85%, at least 90%, at least 95%, at least 96%, at least 97%, at least 98%, or at least 99% by number of nucleotides in the poly-A tail are A nucleotides, but permits that remaining nucleotides are nucleotides other than A nucleotides, such as U nucleotides (uridylate), G nucleotides (guanylate), or C nucleotides (cytidylate). In this context, "consists of" means that all nucleotides in the poly-A tail, i.e., 100% by number of nucleotides in the poly-A tail, are A nucleotides. The term "A nucleotide" or "A" refers to adenylate.

In some embodiments, a poly-A tail is attached during RNA transcription, e.g., during preparation of in vitro transcribed RNA, based on a DNA template comprising repeated dT nucleotides (deoxythymidylate) in the strand complementary to the coding strand. The DNA sequence encoding a poly-A tail (coding strand) is referred to as poly(A) cassette.

In some embodiments, the poly(A) cassette present in the coding strand of DNA essentially consists of dA nucleotides, but is interrupted by a random sequence of the four nucleotides (dA, dC, dG, and dT). Such random sequence may be 5 to 50, 10 to 30, or 10 to 20 nucleotides in length. Such a cassette is disclosed in WO 2016/005324 A1, hereby incorporated by reference. Any poly(A) cassette disclosed in WO 2016/005324 A1 may be used in the present invention. A poly(A) cassette that essentially consists of dA nucleotides, but is interrupted by a random sequence having an equal distribution of the four nucleotides (dA, dC, dG, dT) and having a length of e.g., 5 to 50 nucleotides shows, on DNA level, constant propagation of plasmid DNA in *E. coli* and is still associated, on RNA level, with the beneficial properties with respect to supporting RNA stability and translational efficiency is encompassed. Consequently, in some embodiments, the poly-A tail contained in an RNA molecule described herein essentially consists of A nucleotides, but is interrupted by a random sequence of the four nucleotides (A, C, G, U). Such random sequence may be 5 to 50, 10 to 30, or 10 to 20 nucleotides in length.

In some embodiments, no nucleotides other than A nucleotides flank a poly-A tail at its 3'-end, i.e., the poly-A tail is not masked or followed at its 3'-end by a nucleotide other than A. In some embodiments, a poly-A tail comprises the sequence of SEQ ID NO: 32.

In some embodiments, at least one RNA comprises a poly-A tail. In some embodiments, each RNA comprises a poly-A tail. In some embodiments, the poly-A tail may comprise at least 20, at least 30, at least 40, at least 80, or at least 100 and up to 500, up to 400, up to 300, up to 200, or up to 150 nucleotides. In some embodiments, the poly-A tail may essentially consist of at least 20, at least 30, at least 40, at least 80, or at least 100 and up to 500, up to 400, up to 300, up to 200, or up to 150 nucleotides. In some embodiments, the poly-A tail may consist of at least 20, at least 30, at least 40, at least 80, or at least 100 and up to 500, up to 400, up to 300, up to 200, or up to 150 nucleotides. In some embodiments, the poly-A tail may comprise the poly-A tail shown in SEQ ID NO: 32. In some embodiments, the poly-A tail comprises at least 100 nucleotides. In some embodiments, the poly-A tail comprises about 150 nucleotides. In some embodiments, the poly-A tail comprises about 120 nucleotides.

In the context of the present disclosure, the term "transcription" relates to a process, wherein the genetic code in a DNA sequence is transcribed into RNA. Subsequently, the RNA may be translated into peptide or protein.

With respect to RNA, the term "expression" or "translation" relates to the process in the ribosomes of a cell by which a strand of mRNA directs the assembly of a sequence of amino acids to make a peptide or protein.

In one embodiment, after administration of the RNA described herein, e.g., formulated as RNA lipoplex particles, at least a portion of the RNA is delivered to a target cell. In one embodiment, at least a portion of the RNA is delivered to the cytosol of the target cell. In one embodiment, the RNA is translated by the target cell to produce the peptide or protein it enodes. In one embodiment, the target cell is a spleen cell. In one embodiment, the target cell is an antigen presenting cell such as a professional antigen presenting cell in the spleen. In one embodiment, the target cell is a dendritic cell or macrophage. RNA lipoplex particles described herein may be used for delivering RNA to such target cell. Accordingly, the present disclosure also relates to a method for delivering RNA to a target cell in a subject comprising the administration of the RNA lipoplex particles described herein to the subject. In one embodiment, the RNA is delivered to the cytosol of the target cell. In one embodiment, the RNA is translated by the target cell to produce the peptide or protein encoded by the RNA. According to the disclosure, the term "RNA encodes" means that the RNA, if present in the appropriate environment, such as within cells of a target tissue, can direct the assembly of amino acids to produce the peptide or protein it encodes during the process of translation. In one embodiment, RNA is able to interact with the cellular translation machinery allowing translation of the peptide or protein. A cell may produce the encoded peptide or protein intracellularly (e.g., in the cytoplasm and/or in the nucleus), may secrete the encoded peptide or protein, or may produce it on the surface.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" refers to large peptides, in particular peptides having at least about 151 amino acids, but the terms "peptide" and "protein" are used herein usually as synonyms.

The term "antigen" relates to an agent comprising an epitope against which an immune response can be generated. The term "antigen" includes, in particular, proteins and peptides.

In one embodiment, an antigen is presented by cells of the immune system such as antigen presenting cells like dendritic cells or macrophages. An antigen or a processing product thereof such as a T-cell epitope is in one embodiment bound by a T- or B-cell receptor, or by an immunoglobulin molecule such as an antibody. Accordingly, an antigen or a processing product thereof may react specifically with antibodies or T lymphocytes (T cells). In one embodiment, an antigen is a disease-associated antigen, such as a tumor antigen, in particular HPV E6 or HPV E7, and an epitope is derived from such antigen.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen or an epitope thereof may therefore be used for therapeutic purposes. Disease-associated antigens may be associated with cancer, typically tumors.

The term "tumor antigen" refers to a constituent of cancer cells. In particular, it refers to those antigens which are produced intracellularly or as surface antigens on tumor cells.

The term "epitope" refers to a part or fragment a molecule such as an antigen that is recognized by the immune system. For example, the epitope may be recognized by T cells, B cells or antibodies. An epitope of an antigen may include a continuous or discontinuous portion of the antigen and may be between about 5 and about 100 amino acids in length. In one embodiment, an epitope is between about 10 and about 25 amino acids in length. The term "epitope" includes T-cell epitopes.

The term "T-cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T-cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

In certain embodiments of the present disclosure, the RNA encodes at least one epitope. In certain embodiments, the epitope is derived from a tumor antigen as described herein.

Human Papillomavirus-Associated Malignancies

Human papillomavirus infection (HPV infection) is an infection caused by the human papillomavirus (HPV), a DNA virus from the papillomavirus family. HPV is the most frequently sexually transmitted viral infection. HPV infection has been established as a causative agent for a variety of cancers in the genital and head and neck region. All cervical cancers are HPV-positive, 88% of anal, 78% of vaginal and to a lesser extent vulva and penile cancers. Of the head and neck region, HPV-attributed cancers account for 30.8% of oropharyngeal cancers, whereas oral cavity and the larynx are affected to a much lesser extent. The incidence of HPV-negative oropharyngeal squamous cell carcinomas (OPSCC) decreased by 50% from 1988 to 2004, whereas HPV-positive oropharyngeal carcinomas increased more than two-fold. Over 100 different HPV types exist which can be classified as either "low" or "high" risk depending on their ability to mediate malignant transformation. High risk HPV16 and HPV18 are the most frequent oncogenic HPV types, with HPV16 accounting for 90% of all HPV-positive head and neck squamous cell carcinomas (HNSCC) and 66% of all cervical cancers.

High risk HPV viruses are non-enveloped double-stranded DNA viruses that owe their transforming capacity to their oncogenes E6 and E7. HPV infects the mucosal and cutaneous squamous epithelium and has an intra-epithelial infection cycle. HPV expresses six early (E1, E2, E4, E5, E6 and E7) and two late (L1 and L2) proteins. E1 and E2 are needed for the initiation of viral replication, whereas E2 also regulates the expression of E6 and E7 as a transcriptional repressor. During rolling circle genome integration, the E2 gene is disrupted, leading to higher expression of E6 and E7. L1 and L2 are viral capsid proteins that are crucial for virus assembly and, via the help of E4, release of viral particles. After an acute phase of viral infection, HPV gene products may remain within cells of the mucosal and cutaneous squamous epithelium with persistent expression of E6 and E7 that may drive malignant transformation. The HPV proteins E6 and E7 are able to deregulate the cell cycle, inhibit apoptosis and thus drive cancer progression. E6 possesses the ability to abrogate the function of the tumor suppressor protein p53, which governs cell cycle progression and apoptosis. The oncogenic potential of E7 is determined by its ability to regulate several cellular factors such as the retinoblastoma pocket protein (pRb), which is involved in G1 to S phase transition. E7 targets pRb family members to proteosomal degradation, resulting in impaired DNA repair, cell cycle checkpoints and loss of genomic integrity.

HPV-driven cancers are marked by the persistent expression of the viral oncogenes E6 and E7, which are key oncogenic drivers.

HNSCC is an aggressive and difficult to treat cancer type, associated with a reduction of life quality and significant morbidity. Although multiple vaccine formats have entered clinical testing, no HPV vaccine has been approved for therapeutic use in HPV-positive cervical or HNSCC cancer patients yet.

According to the disclosure, the term "HPV-positive cancer" includes cancers which are caused by HPV infection and/or wherein HPV or certain components, in particular HPV E6 and/or HPV E7, are detectable. Examples of such cancers include, but are not limited to, anogenital, cervical and penile cancers and cancer in the head and neck region such as cancer in the genital region or in the head and neck region. In one embodiment, a HPV-positive cancer is head and neck squamous cell carcinoma (HNSCC).

In some embodiments, compositions or medical preparations described herein comprise RNA encoding a HPV E6 vaccine antigen, and RNA encoding a HPV E7 vaccine antigen. Likewise, methods described herein comprise administration of RNA encoding a HPV E6 vaccine antigen, and RNA encoding a HPV E7 vaccine antigen.

Molecular Structure and Function of HPV E6 and HPV E7 Vaccine Antigens and RNA Coding Therefor HPV can induce a tumorigenic process through integration into a host genome. Furthermore, some of the "early genes" carried by the HPV virus, such as genes E6 and E7, act as oncogenes that promote tumor growth and malignant transformation. The two primary oncoproteins of high risk HPV types are E6 and E7. The "E" designation indicates that these two proteins are expressed early in the HPV life cycle. The E6/E7 proteins inactivate two tumor suppressor proteins, p53 (inactivated by E6) and pRb (inactivated by E7).

A HPV E6 protein or HPV E7 protein as described herein may be derived from any HPV, in particular any high risk HPV type such as HPV 16, 18, 31, 33, 45, or 58. In one embodiment, a HPV E6 protein or HPV E7 protein as described herein is derived from different HPV types. In one embodiment, a HPV E6 protein or HPV E7 protein as described herein is derived from the same HPV type. In one embodiment, the HPV type is HPV 16. In one embodiment, the HPV type is HPV 18. In one embodiment, the HPV type is HPV 31. In one embodiment, the HPV type is HPV 33. In one embodiment, the HPV type is HPV 45. In one embodiment, the HPV type is HPV 58.

In one embodiment, an amino acid sequence comprising human papillomavirus (HPV) E6 protein, an immunogenic variant thereof, or an immunogenic fragment of the HPV E6 protein or the immunogenic variant thereof, also termed "HPV E6 vaccine antigen herein" comprises an amino acid sequence of a HPV E6 protein, an amino acid sequence of an immunogenic variant of a HPV E6 protein, an amino acid sequence of an immunogenic fragment of a HPV E6 protein, or an amino acid sequence of an immunogenic fragment of an immunogenic variant of a HPV E6 protein.

In one embodiment, an amino acid sequence comprising human papillomavirus (HPV) E7 protein, an immunogenic variant thereof, or an immunogenic fragment of the HPV E7 protein or the immunogenic variant thereof, also termed "HPV E7 vaccine antigen herein" comprises an amino acid sequence of a HPV E7 protein, an amino acid sequence of an immunogenic variant of a HPV E7 protein, an amino acid sequence of an immunogenic fragment of a HPV E7 protein, or an amino acid sequence of an immunogenic fragment of an immunogenic variant of a HPV E7 protein.

In one embodiment, a HPV E6 protein is derived from HPV 16. In one embodiment, a HPV E6 vaccine antigen comprises the amino acid sequence of amino acids 37 to 194 of SEQ ID NO: 1, an amino acid sequence having at least 99%, 98%, 97%, 96%, 95%, 90%, 85%, or 80% identity to the amino acid sequence of amino acids 37 to 194 of SEQ ID NO: 1, or an immunogenic fragment of the amino acid sequence of amino acids 37 to 194 of SEQ ID NO: 1, or the amino acid sequence having at least 99%, 98%, 97%, 96%, 95%, 90%, 85%, or 80% identity to the amino acid sequence of amino acids 37 to 194 of SEQ ID NO: 1. In one embodiment, a HPV E6 vaccine antigen comprises the amino acid sequence of amino acids 37 to 194 of SEQ ID NO: 1.

In one embodiment, RNA encoding a HPV E6 vaccine antigen (i) comprises the nucleotide sequence of nucleotides 161 to 634 of SEQ ID NO: 2, a nucleotide sequence having at least 99%, 98%, 97%, 96%, 95%, 90%, 85%, or 80% identity to the nucleotide sequence of nucleotides 161 to 634 of SEQ ID NO: 2, or a fragment of the nucleotide sequence of nucleotides 161 to 634 of SEQ ID NO: 2, or the nucleotide sequence having at least 99%, 98%, 97%, 96%, 95%, 90%, 85%, or 80% identity to the nucleotide sequence of nucleotides 161 to 634 of SEQ ID NO: 2; and/or (ii) encodes an amino acid sequence comprising the amino acid sequence of amino acids 37 to 194 of SEQ ID NO: 1, an amino acid sequence having at least 99%, 98%, 97%, 96%, 95%, 90%, 85%, or 80% identity to the amino acid sequence of amino acids 37 to 194 of SEQ ID NO: 1, or an immunogenic fragment of the amino acid sequence of amino acids 37 to 194 of SEQ ID NO: 1, or the amino acid sequence having at least 99%, 98%, 97%, 96%, 95%, 90%, 85%, or 80% identity to the amino acid sequence of amino acids 37 to 194 of SEQ ID NO: 1. In one embodiment, RNA encoding a HPV E6 vaccine antigen (i) comprises the nucleotide sequence of nucleotides 161 to 634 of SEQ ID NO: 2; and/or (ii) encodes an amino acid sequence comprising the amino acid sequence of amino acids 37 to 194 of SEQ ID NO: 1.

In one embodiment, a HPV E6 protein is derived from HPV 18. In one embodiment, a HPV E6 vaccine antigen comprises the amino acid sequence of amino acids 37 to 194 of SEQ ID NO: 5, an amino acid sequence having at least 99%, 98%, 97%, 96%, 95%, 90%, 85%, or 80% identity to the amino acid sequence of amino acids 37 to 194 of SEQ ID NO: 5, or an immunogenic fragment of the amino acid sequence of amino acids 37 to 194 of SEQ ID NO: 5, or the amino acid sequence having at least 99%, 98%, 97%, 96%, 95%, 90%, 85%, or 80% identity to the amino acid sequence of amino acids 37 to 194 of SEQ ID NO: 5. In one embodiment, a HPV E6 vaccine antigen comprises the amino acid sequence of amino acids 37 to 194 of SEQ ID NO: 5.

In one embodiment, RNA encoding a HPV E6 vaccine antigen (i) comprises the nucleotide sequence of nucleotides 161 to 634 of SEQ ID NO: 6, a nucleotide sequence having at least 99%, 98%, 97%, 96%, 95%, 90%, 85%, or 80% identity to the nucleotide sequence of nucleotides 161 to 634 of SEQ ID NO: 6, or a fragment of the nucleotide sequence of nucleotides 161 to 634 of SEQ ID NO: 6, or the nucleotide sequence having at least 99%, 98%, 97%, 96%, 95%, 90%, 85%, or 80% identity to the nucleotide sequence of nucleotides 161 to 634 of SEQ ID NO: 6; and/or (ii) encodes an amino acid sequence comprising the amino acid sequence of amino acids 37 to 194 of SEQ ID NO: 5, an amino acid sequence having at least 99%, 98%, 97%, 96%, 95%, 90%, 85%, or 80% identity to the amino acid sequence of amino acids 37 to 194 of SEQ ID NO: 5, or an immunogenic fragment of the amino acid sequence of amino acids 37 to 194 of SEQ ID NO: 5, or the amino acid sequence having at least 99%, 98%, 97%, 96%, 95%, 90%, 85%, or 80% identity to the amino acid sequence of amino acids 37 to 194 of SEQ ID NO: 5. In one embodiment, RNA encoding a HPV E6 vaccine antigen (i) comprises the nucleotide sequence of nucleotides 161 to 634 of SEQ ID NO: 6; and/or (ii) encodes an amino acid sequence comprising the amino acid sequence of amino acids 37 to 194 of SEQ ID NO: 5.

In one embodiment, a HPV E6 protein is derived from HPV 31. In one embodiment, a HPV E6 vaccine antigen comprises the amino acid sequence of amino acids 37 to 185 of SEQ ID NO: 9, an amino acid sequence having at least 99%, 98%, 97%, 96%, 95%, 90%, 85%, or 80% identity to the amino acid sequence of amino acids 37 to 185 of SEQ ID NO: 9, or an immunogenic fragment of the amino acid sequence of amino acids 37 to 185 of SEQ ID NO: 9, or the amino acid sequence having at least 99%, 98%, 97%, 96%, 95%, 90%, 85%, or 80% identity to the amino acid sequence of amino acids 37 to 185 of SEQ ID NO: 9. In one embodiment, a HPV E6 vaccine antigen comprises the amino acid sequence of amino acids 37 to 185 of SEQ ID NO: 9.

In one embodiment, RNA encoding a HPV E6 vaccine antigen (i) comprises the nucleotide sequence of nucleotides 161 to 607 of SEQ ID NO: 10, a nucleotide sequence having at least 99%, 98%, 97%, 96%, 95%, 90%, 85%, or 80% identity to the nucleotide sequence of nucleotides 161 to 607 of SEQ ID NO: 10, or a fragment of the nucleotide sequence of nucleotides 161 to 607 of SEQ ID NO: 10, or the nucleotide sequence having at least 99%, 98%, 97%, 96%, 95%, 90%, 85%, or 80% identity to the nucleotide sequence of nucleotides 161 to 607 of SEQ ID NO: 10; and/or (ii) encodes an amino acid sequence comprising the amino acid sequence of amino acids 37 to 185 of SEQ ID NO: 9, an amino acid sequence having at least 99%, 98%, 97%, 96%, 95%, 90%, 85%, or 80% identity to the amino acid sequence of amino acids 37 to 185 of SEQ ID NO: 9, or an immunogenic fragment of the amino acid sequence of amino acids 37 to 185 of SEQ ID NO: 9, or the amino acid sequence having at least 99%, 98%, 97%, 96%, 95%, 90%, 85%, or 80% identity to the amino acid sequence of amino acids 37 to 185 of SEQ ID NO: 9. In one embodiment, RNA encoding a HPV E6 vaccine antigen (i) comprises the nucleotide sequence of nucleotides 161 to 607 of SEQ ID NO: 10; and/or (ii) encodes an amino acid sequence comprising the amino acid sequence of amino acids 37 to 185 of SEQ ID NO: 9.

In one embodiment, a HPV E6 protein is derived from HPV 33. In one embodiment, a HPV E6 vaccine antigen comprises the amino acid sequence of amino acids 37 to 185 of SEQ ID NO: 13, an amino acid sequence having at least 99%, 98%, 97%, 96%, 95%, 90%, 85%, or 80% identity to the amino acid sequence of amino acids 37 to 185 of SEQ ID NO: 13, or an immunogenic fragment of the amino acid sequence of amino acids 37 to 185 of SEQ ID NO: 13, or the amino acid sequence having at least 99%, 98%, 97%, 96%, 95%, 90%, 85%, or 80% identity to the amino acid sequence of amino acids 37 to 185 of SEQ ID NO: 13. In one embodiment, a HPV E6 vaccine antigen comprises the amino acid sequence of amino acids 37 to 185 of SEQ ID NO: 13.

In one embodiment, RNA encoding a HPV E6 vaccine antigen (i) comprises the nucleotide sequence of nucleotides 161 to 607 of SEQ ID NO: 14, a nucleotide sequence having at least 99%, 98%, 97%, 96%, 95%, 90%, 85%, or 80% identity to the nucleotide sequence of nucleotides 161 to 607 of SEQ ID NO: 14, or a fragment of the nucleotide sequence of nucleotides 161 to 607 of SEQ ID NO: 14, or the nucleotide sequence having at least 99%, 98%, 97%, 96%, 95%, 90%, 85%, or 80% identity to the nucleotide sequence of nucleotides 161 to 607 of SEQ ID NO: 14; and/or (ii) encodes an amino acid sequence comprising the amino acid sequence of amino acids 37 to 185 of SEQ ID NO: 13, an amino acid sequence having at least 99%, 98%, 97%, 96%, 95%, 90%, 85%, or 80% identity to the amino acid sequence of amino acids 37 to 185 of SEQ ID NO: 13, or an immunogenic fragment of the amino acid sequence of amino acids 37 to 185 of SEQ ID NO: 13, or the amino acid sequence having at least 99%, 98%, 97%, 96%, 95%, 90%, 85%, or 80% identity to the amino acid sequence of amino acids 37 to 185 of SEQ ID NO: 13. In one embodiment, RNA encoding a HPV E6 vaccine antigen (i) comprises the nucleotide sequence of nucleotides 161 to 607 of SEQ ID NO: 14; and/or (ii) encodes an amino acid sequence comprising the amino acid sequence of amino acids 37 to 185 of SEQ ID NO: 13.

In one embodiment, a HPV E6 protein is derived from HPV 45. In one embodiment, a HPV E6 vaccine antigen comprises the amino acid sequence of amino acids 37 to 194 of SEQ ID NO: 17, an amino acid sequence having at least 99%, 98%, 97%, 96%, 95%, 90%, 85%, or 80% identity to the amino acid sequence of amino acids 37 to 194 of SEQ ID NO: 17, or an immunogenic fragment of the amino acid sequence of amino acids 37 to 194 of SEQ ID NO: 17, or the amino acid sequence having at least 99%, 98%, 97%, 96%, 95%, 90%, 85%, or 80% identity to the amino acid sequence of amino acids 37 to 194 of SEQ ID NO: 17. In one embodiment, a HPV E6 vaccine antigen comprises the amino acid sequence of amino acids 37 to 194 of SEQ ID NO: 17.

In one embodiment, RNA encoding a HPV E6 vaccine antigen (i) comprises the nucleotide sequence of nucleotides 161 to 634 of SEQ ID NO: 18, a nucleotide sequence having at least 99%, 98%, 97%, 96%, 95%, 90%, 85%, or 80% identity to the nucleotide sequence of nucleotides 161 to 634 of SEQ ID NO: 18, or a fragment of the nucleotide sequence of nucleotides 161 to 634 of SEQ ID NO: 18, or the nucleotide sequence having at least 99%, 98%, 97%, 96%, 95%, 90%, 85%, or 80% identity to the nucleotide sequence of nucleotides 161 to 634 of SEQ ID NO: 18; and/or (ii) encodes an amino acid sequence comprising the amino acid sequence of amino acids 37 to 194 of SEQ ID NO: 17, an amino acid sequence having at least 99%, 98%, 97%, 96%, 95%, 90%, 85%, or 80% identity to the amino acid sequence of amino acids 37 to 194 of SEQ ID NO: 17, or an immunogenic fragment of the amino acid sequence of amino acids 37 to 194 of SEQ ID NO: 17, or the amino acid sequence having at least 99%, 98%, 97%, 96%, 95%, 90%, 85%, or 80% identity to the amino acid sequence of amino acids 37 to 194 of SEQ ID NO: 17. In one embodiment, RNA encoding a HPV E6 vaccine antigen (i) comprises the nucleotide sequence of nucleotides 161 to 634 of SEQ ID NO: 18; and/or (ii) encodes an amino acid sequence comprising the amino acid sequence of amino acids 37 to 194 of SEQ ID NO: 17.

In one embodiment, a HPV E6 protein is derived from HPV 58. In one embodiment, a HPV E6 vaccine antigen comprises the amino acid sequence of amino acids 37 to 185 of SEQ ID NO: 21, an amino acid sequence having at least 99%, 98%, 97%, 96%, 95%, 90%, 85%, or 80% identity to the amino acid sequence of amino acids 37 to 185 of SEQ ID NO: 21, or an immunogenic fragment of the amino acid sequence of amino acids 37 to 185 of SEQ ID NO: 21, or the amino acid sequence having at least 99%, 98%, 97%, 96%, 95%, 90%, 85%, or 80% identity to the amino acid sequence of amino acids 37 to 185 of SEQ ID NO: 21. In one embodiment, a HPV E6 vaccine antigen comprises the amino acid sequence of amino acids 37 to 185 of SEQ ID NO: 21.

In one embodiment, RNA encoding a HPV E6 vaccine antigen (i) comprises the nucleotide sequence of nucleotides 161 to 607 of SEQ ID NO: 22, a nucleotide sequence having at least 99%, 98%, 97%, 96%, 95%, 90%, 85%, or 80% identity to the nucleotide sequence of nucleotides 161 to 607 of SEQ ID NO: 22, or a fragment of the nucleotide sequence of nucleotides 161 to 607 of SEQ ID NO: 22, or the nucleotide sequence having at least 99%, 98%, 97%, 96%, 95%, 90%, 85%, or 80% identity to the nucleotide sequence of nucleotides 161 to 607 of SEQ ID NO: 22; and/or (ii) encodes an amino acid sequence comprising the amino acid sequence of amino acids 37 to 185 of SEQ ID NO: 21, an amino acid sequence having at least 99%, 98%, 97%, 96%, 95%, 90%, 85%, or 80% identity to the amino acid sequence of amino acids 37 to 185 of SEQ ID NO: 21, or an immunogenic fragment of the amino acid sequence of amino acids 37 to 185 of SEQ ID NO: 21, or the amino acid sequence having at least 99%, 98%, 97%, 96%, 95%, 90%, 85%, or 80% identity to the amino acid sequence of amino acids 37 to 185 of SEQ ID NO: 21. In one embodiment, RNA encoding a HPV E6 vaccine antigen (i) comprises the nucleotide sequence of nucleotides 161 to 607 of SEQ ID NO: 22; and/or (ii) encodes an amino acid sequence comprising the amino acid sequence of amino acids 37 to 185 of SEQ ID NO: 21.

In one embodiment, a HPV E7 protein is derived from HPV 16. In one embodiment, a HPV E7 vaccine antigen comprises the amino acid sequence of amino acids 37 to 134 of SEQ ID NO: 3, an amino acid sequence having at least 99%, 98%, 97%, 96%, 95%, 90%, 85%, or 80% identity to the amino acid sequence of amino acids 37 to 134 of SEQ ID NO: 3, or an immunogenic fragment of the amino acid sequence of amino acids 37 to 134 of SEQ ID NO: 3, or the amino acid sequence having at least 99%, 98%, 97%, 96%, 95%, 90%, 85%, or 80% identity to the amino acid sequence of amino acids 37 to 134 of SEQ ID NO: 3. In one embodiment, a HPV E7 vaccine antigen comprises the amino acid sequence of amino acids 37 to 134 of SEQ ID NO: 3.

In one embodiment, RNA encoding a HPV E7 vaccine antigen (i) comprises the nucleotide sequence of nucleotides 161 to 454 of SEQ ID NO: 4, a nucleotide sequence having at least 99%, 98%, 97%, 96%, 95%, 90%, 85%, or 80% identity to the nucleotide sequence of nucleotides 161 to 454 of SEQ ID NO: 4, or a fragment of the nucleotide sequence of nucleotides 161 to 454 of SEQ ID NO: 4, or the nucleotide sequence having at least 99%, 98%, 97%, 96%, 95%, 90%, 85%, or 80% identity to the nucleotide sequence of nucleotides 161 to 454 of SEQ ID NO: 4; and/or (ii) encodes an amino acid sequence comprising the amino acid sequence of amino acids 37 to 134 of SEQ ID NO: 3, an amino acid sequence having at least 99%, 98%, 97%, 96%, 95%, 90%, 85%, or 80% identity to the amino acid sequence of amino acids 37 to 134 of SEQ ID NO: 3, or an immunogenic fragment of the amino acid sequence of amino acids 37 to 134 of SEQ ID NO: 3, or the amino acid sequence having at least 99%, 98%, 97%, 96%, 95%, 90%, 85%, or 80% identity to the amino acid sequence of amino acids 37 to 134 of SEQ ID NO: 3. In one embodiment, RNA encoding a HPV E7 vaccine antigen (i) comprises the nucleotide sequence of nucleotides 161 to 454 of SEQ ID NO: 4; and/or (ii) encodes an amino acid sequence comprising the amino acid sequence of amino acids 37 to 134 of SEQ ID NO: 3.

In one embodiment, a HPV E7 protein is derived from HPV 18. In one embodiment, a HPV E7 vaccine antigen comprises the amino acid sequence of amino acids 37 to 141 of SEQ ID NO: 7, an amino acid sequence having at least 99%, 98%, 97%, 96%, 95%, 90%, 85%, or 80% identity to the amino acid sequence of amino acids 37 to 141 of SEQ ID NO: 7, or an immunogenic fragment of the amino acid sequence of amino acids 37 to 141 of SEQ ID NO: 7, or the amino acid sequence having at least 99%, 98%, 97%, 96%, 95%, 90%, 85%, or 80% identity to the amino acid sequence of amino acids 37 to 141 of SEQ ID NO: 7. In one embodiment, a HPV E7 vaccine antigen comprises the amino acid sequence of amino acids 37 to 141 of SEQ ID NO: 7.

In one embodiment, RNA encoding a HPV E7 vaccine antigen (i) comprises the nucleotide sequence of nucleotides 161 to 475 of SEQ ID NO: 8, a nucleotide sequence having at least 99%, 98%, 97%, 96%, 95%, 90%, 85%, or 80% identity to the nucleotide sequence of nucleotides 161 to 475 of SEQ ID NO: 8, or a fragment of the nucleotide sequence of nucleotides 161 to 475 of SEQ ID NO: 8, or the nucleotide sequence having at least 99%, 98%, 97%, 96%, 95%, 90%, 85%, or 80% identity to the nucleotide sequence of nucleotides 161 to 475 of SEQ ID NO: 8; and/or (ii) encodes an amino acid sequence comprising the amino acid sequence of amino acids 37 to 141 of SEQ ID NO: 7, an amino acid sequence having at least 99%, 98%, 97%, 96%, 95%, 90%, 85%, or 80% identity to the amino acid sequence of amino acids 37 to 141 of SEQ ID NO: 7, or an immunogenic fragment of the amino acid sequence of amino acids 37 to 141 of SEQ ID NO: 7, or the amino acid sequence having at least 99%, 98%, 97%, 96%, 95%, 90%, 85%, or 80% identity to the amino acid sequence of amino acids 37 to 141 of SEQ ID NO: 7. In one embodiment, RNA encoding a HPV E7 vaccine antigen (i) comprises the nucleotide sequence of nucleotides 161 to 475 of SEQ ID NO: 8; and/or (ii) encodes an amino acid sequence comprising the amino acid sequence of amino acids 37 to 141 of SEQ ID NO: 7.

In one embodiment, a HPV E7 protein is derived from HPV 31. In one embodiment, a HPV E7 vaccine antigen comprises the amino acid sequence of amino acids 37 to 134 of SEQ ID NO: 11, an amino acid sequence having at least 99%, 98%, 97%, 96%, 95%, 90%, 85%, or 80% identity to the amino acid sequence of amino acids 37 to 134 of SEQ ID NO: 11, or an immunogenic fragment of the amino acid sequence of amino acids 37 to 134 of SEQ ID NO: 11, or the amino acid sequence having at least 99%, 98%, 97%, 96%, 95%, 90%, 85%, or 80% identity to the amino acid sequence of amino acids 37 to 134 of SEQ ID NO: 11. In one embodiment, a HPV E7 vaccine antigen comprises the amino acid sequence of amino acids 37 to 134 of SEQ ID NO: 11.

In one embodiment, RNA encoding a HPV E7 vaccine antigen (i) comprises the nucleotide sequence of nucleotides 161 to 454 of SEQ ID NO: 12, a nucleotide sequence having at least 99%, 98%, 97%, 96%, 95%, 90%, 85%, or 80% identity to the nucleotide sequence of nucleotides 161 to 454 of SEQ ID NO: 12, or a fragment of the nucleotide sequence of nucleotides 161 to 454 of SEQ ID NO: 12, or the nucleotide sequence having at least 99%, 98%, 97%, 96%, 95%, 90%, 85%, or 80% identity to the nucleotide sequence of nucleotides 161 to 454 of SEQ ID NO: 12; and/or (ii) encodes an amino acid sequence comprising the amino acid sequence of amino acids 37 to 134 of SEQ ID NO: 11, an amino acid sequence having at least 99%, 98%, 97%, 96%, 95%, 90%, 85%, or 80% identity to the amino acid sequence of amino acids 37 to 134 of SEQ ID NO: 11, or an immunogenic fragment of the amino acid sequence of amino acids 37 to 134 of SEQ ID NO: 11, or the amino acid sequence having at least 99%, 98%, 97%, 96%, 95%, 90%, 85%, or 80% identity to the amino acid sequence of amino acids 37 to 134 of SEQ ID NO: 11. In one embodiment, RNA encoding a HPV E7 vaccine antigen (i) comprises the nucleotide sequence of nucleotides 161 to 454 of SEQ ID NO: 12; and/or (ii) encodes an amino acid sequence comprising the amino acid sequence of amino acids 37 to 134 of SEQ ID NO: 11.

In one embodiment, a HPV E7 protein is derived from HPV 33. In one embodiment, a HPV E7 vaccine antigen comprises the amino acid sequence of amino acids 37 to 133 of SEQ ID NO: 15, an amino acid sequence having at least 99%, 98%, 97%, 96%, 95%, 90%, 85%, or 80% identity to the amino acid sequence of amino acids 37 to 133 of SEQ ID NO: 15, or an immunogenic fragment of the amino acid sequence of amino acids 37 to 133 of SEQ ID NO: 15, or the amino acid sequence having at least 99%, 98%, 97%, 96%, 95%, 90%, 85%, or 80% identity to the amino acid sequence of amino acids 37 to 133 of SEQ ID NO: 15. In one embodiment, a HPV E7 vaccine antigen comprises the amino acid sequence of amino acids 37 to 133 of SEQ ID NO: 15.

In one embodiment, RNA encoding a HPV E7 vaccine antigen (i) comprises the nucleotide sequence of nucleotides 161 to 451 of SEQ ID NO: 16, a nucleotide sequence having at least 99%, 98%, 97%, 96%, 95%, 90%, 85%, or 80% identity to the nucleotide sequence of nucleotides 161 to 451 of SEQ ID NO: 16, or a fragment of the nucleotide sequence of nucleotides 161 to 451 of SEQ ID NO: 16, or the nucleotide sequence having at least 99%, 98%, 97%, 96%, 95%, 90%, 85%, or 80% identity to the nucleotide sequence of nucleotides 161 to 451 of SEQ ID NO: 16; and/or (ii) encodes an amino acid sequence comprising the amino acid sequence of amino acids 37 to 133 of SEQ ID NO: 15, an amino acid sequence having at least 99%, 98%, 97%, 96%, 95%, 90%, 85%, or 80% identity to the amino acid sequence of amino acids 37 to 133 of SEQ ID NO: 15, or an immunogenic fragment of the amino acid sequence of amino acids 37 to 133 of SEQ ID NO: 15, or the amino acid sequence having at least 99%, 98%, 97%, 96%, 95%, 90%, 85%, or 80% identity to the amino acid sequence of amino acids 37 to 133 of SEQ ID NO: 15. In one embodiment, RNA encoding a HPV E7 vaccine antigen (i) comprises the nucleotide sequence of nucleotides 161 to 451 of SEQ ID NO: 16; and/or (ii) encodes an amino acid sequence comprising the amino acid sequence of amino acids 37 to 133 of SEQ ID NO: 15.

In one embodiment, a HPV E7 protein is derived from HPV 45. In one embodiment, a HPV E7 vaccine antigen comprises the amino acid sequence of amino acids 37 to 142 of SEQ ID NO: 19, an amino acid sequence having at least 99%, 98%, 97%, 96%, 95%, 90%, 85%, or 80% identity to the amino acid sequence of amino acids 37 to 142 of SEQ ID NO: 19, or an immunogenic fragment of the amino acid sequence of amino acids 37 to 142 of SEQ ID NO: 19, or the amino acid sequence having at least 99%, 98%, 97%, 96%, 95%, 90%, 85%, or 80% identity to the amino acid sequence of amino acids 37 to 142 of SEQ ID NO: 19. In one embodiment, a HPV E7 vaccine antigen comprises the amino acid sequence of amino acids 37 to 142 of SEQ ID NO: 19.

In one embodiment, RNA encoding a HPV E7 vaccine antigen (i) comprises the nucleotide sequence of nucleotides 161 to 478 of SEQ ID NO: 20, a nucleotide sequence having at least 99%, 98%, 97%, 96%, 95%, 90%, 85%, or 80% identity to the nucleotide sequence of nucleotides 161 to 478 of SEQ ID NO: 20, or a fragment of the nucleotide sequence of nucleotides 161 to 478 of SEQ ID NO: 20, or the nucleotide sequence having at least 99%, 98%, 97%, 96%, 95%, 90%, 85%, or 80% identity to the nucleotide sequence of nucleotides 161 to 478 of SEQ ID NO: 20; and/or (ii) encodes an amino acid sequence comprising the amino acid sequence of amino acids 37 to 142 of SEQ ID NO: 19, an amino acid sequence having at least 99%, 98%, 97%, 96%, 95%, 90%, 85%, or 80% identity to the amino acid sequence of amino acids 37 to 142 of SEQ ID NO: 19, or an immunogenic fragment of the amino acid sequence of amino acids 37 to 142 of SEQ ID NO: 19, or the amino acid sequence having at least 99%, 98%, 97%, 96%, 95%, 90%, 85%, or 80% identity to the amino acid sequence of amino acids 37 to 142 of SEQ ID NO: 19. In one embodiment, RNA encoding a HPV E7 vaccine antigen (i) comprises the nucleotide sequence of nucleotides 161 to 478 of SEQ ID NO: 20; and/or (ii) encodes an amino acid sequence comprising the amino acid sequence of amino acids 37 to 142 of SEQ ID NO: 19.

In one embodiment, a HPV E7 protein is derived from HPV 58. In one embodiment, a HPV E7 vaccine antigen comprises the amino acid sequence of amino acids 37 to 134 of SEQ ID NO: 23, an amino acid sequence having at least 99%, 98%, 97%, 96%, 95%, 90%, 85%, or 80% identity to the amino acid sequence of amino acids 37 to 134 of SEQ ID NO: 23, or an immunogenic fragment of the amino acid sequence of amino acids 37 to 134 of SEQ ID NO: 23, or the amino acid sequence having at least 99%, 98%, 97%, 96%, 95%, 90%, 85%, or 80% identity to the amino acid sequence of amino acids 37 to 134 of SEQ ID NO: 23. In one embodiment, a HPV E7 vaccine antigen comprises the amino acid sequence of amino acids 37 to 134 of SEQ ID NO: 23.

In one embodiment, RNA encoding a HPV E7 vaccine antigen (i) comprises the nucleotide sequence of nucleotides 161 to 454 of SEQ ID NO: 24, a nucleotide sequence having at least 99%, 98%, 97%, 96%, 95%, 90%, 85%, or 80% identity to the nucleotide sequence of nucleotides 161 to 454 of SEQ ID NO: 24, or a fragment of the nucleotide sequence of nucleotides 161 to 454 of SEQ ID NO: 24, or the nucleotide sequence having at least 99%, 98%, 97%, 96%, 95%, 90%, 85%, or 80% identity to the nucleotide sequence of nucleotides 161 to 454 of SEQ ID NO: 24; and/or (ii) encodes an amino acid sequence comprising the amino acid sequence of amino acids 37 to 134 of SEQ ID NO: 23, an amino acid sequence having at least 99%, 98%, 97%, 96%, 95%, 90%, 85%, or 80% identity to the amino acid sequence of amino acids 37 to 134 of SEQ ID NO: 23, or an immunogenic fragment of the amino acid sequence of amino acids 37 to 134 of SEQ ID NO: 23, or the amino acid sequence having at least 99%, 98%, 97%, 96%, 95%, 90%, 85%, or 80% identity to the amino acid sequence of amino acids 37 to 134 of SEQ ID NO: 23. In one embodiment, RNA encoding a HPV E7 vaccine antigen (i) comprises the nucleotide sequence of nucleotides 161 to 454 of SEQ ID NO: 24; and/or (ii) encodes an amino acid sequence comprising the amino acid sequence of amino acids 37 to 134 of SEQ ID NO: 23.

According to certain embodiments, a signal peptide is fused, either directly or through a linker, e.g., a linker having the amino acid sequence according to SEQ ID NO: 28, to HPV E6/E7 protein, a variant thereof, or a fragment thereof, i.e., the antigenic peptide or protein. Accordingly, in one embodiment, a signal peptide is fused to the above described amino acid sequences derived from HPV E6/E7 protein or immunogenic fragments thereof (antigenic peptides or proteins) comprised by the vaccine antigens described above.

Such signal peptides are sequences, which typically exhibit a length of about 15 to 30 amino acids and are preferably located at the N-terminus of the antigenic peptide or protein, without being limited thereto. Signal peptides as defined herein preferably allow the transport of the antigenic peptide or protein as encoded by the RNA into a defined cellular compartment, preferably the cell surface, the endoplasmic reticulum (ER) or the endosomal-lysosomal compartment. In one embodiment, the signal peptide sequence as defined herein includes, without being limited thereto, the signal peptide sequence derived from the sequence encoding the human MHC class I complex (HLA-B51, haplotype A2, B27/B51, Cw2/Cw3), and preferably corresponds to the 78 bp fragment coding for the secretory signal peptide, which guides translocation of the nascent polypeptide chain into the endoplasmatic reticulum, and includes, in particular a sequence comprising the amino acid sequence of SEQ ID NO: 25 or a functional variant thereof.

In one embodiment, a signal sequence comprises the amino acid sequence of SEQ ID NO: 25, an amino acid sequence having at least 99%, 98%, 97%, 96%, 95%, 90%, 85%, or 80% identity to the amino acid sequence of SEQ ID NO: 25, or a functional fragment of the amino acid sequence of SEQ ID NO: 25, or the amino acid sequence having at least 99%, 98%, 97%, 96%, 95%, 90%, 85%, or 80% identity to the amino acid sequence of SEQ ID NO: 25. In one embodiment, a signal sequence comprises the amino acid sequence of SEQ ID NO: 25.

Such signal peptides are preferably used in order to promote secretion of the encoded antigenic peptide or protein. More preferably, a signal peptide as defined herein is fused to an encoded antigenic peptide or protein as defined herein. Accordingly, in particularly preferred embodiments, the RNA described herein comprises at least one coding region encoding an antigenic peptide or protein and a signal peptide, said signal peptide preferably being fused to the antigenic peptide or protein, more preferably to the N-terminus of the antigenic peptide or protein as described herein.

According to certain embodiments, an amino acid sequence enhancing antigen processing and/or presentation is fused, either directly or through a linker, to a HPV E6/E7 protein, a variant thereof, or a fragment thereof, i.e., the antigenic peptide or protein. Accordingly, in one embodiment, an amino acid sequence enhancing antigen processing and/or presentation is fused to the above described amino acid sequences derived from HPV E6/E7 or immunogenic fragments thereof (antigenic peptides or proteins) comprised by the vaccine antigens described above.

Such amino acid sequences enhancing antigen processing and/or presentation are preferably located at the C-terminus of the antigenic peptide or protein (and optionally at the C-terminus of an amino acid sequence which breaks immunological tolerance), without being limited thereto. Amino acid sequences enhancing antigen processing and/or presentation as defined herein preferably improve antigen processing and presentation. In one embodiment, the amino acid sequence enhancing antigen processing and/or presentation as defined herein includes, without being limited thereto, sequences derived from the human MHC class I complex (HLA-B51, haplotype A2, B27/B51, Cw2/Cw3), in particular a sequence comprising the amino acid sequence of SEQ ID NO: 26 or a functional variant thereof.

In one embodiment, an amino acid sequence enhancing antigen processing and/or presentation comprises the amino acid sequence of SEQ ID NO: 26, an amino acid sequence having at least 99%, 98%, 97%, 96%, 95%, 90%, 85%, or 80% identity to the amino acid sequence of SEQ ID NO: 26, or a functional fragment of the amino acid sequence of SEQ ID NO: 26, or the amino acid sequence having at least 99%, 98%, 97%, 96%, 95%, 90%, 85%, or 80% identity to the amino acid sequence of SEQ ID NO: 26. In one embodiment, an amino acid sequence enhancing antigen processing and/or presentation comprises the amino acid sequence of SEQ ID NO: 26.

Such amino acid sequences enhancing antigen processing and/or presentation are preferably used in order to promote antigen processing and/or presentation of the encoded antigenic peptide or protein. More preferably, an amino acid sequence enhancing antigen processing and/or presentation as defined herein is fused to an encoded antigenic peptide or protein as defined herein. Accordingly, in particularly preferred embodiments, the RNA described herein comprises at least one coding region encoding an antigenic peptide or protein and an amino acid sequence enhancing antigen processing and/or presentation, said amino acid sequence enhancing antigen processing and/or presentation preferably being fused to the antigenic peptide or protein, more preferably to the C-terminus of the antigenic peptide or protein as described herein.

Amino acid sequences derived from tetanus toxoid of *Clostridium tetani* may be employed to overcome self-tolerance mechanisms in order to efficiently mount an immune response to self-antigens by providing T-cell help during priming.

It is known that tetanus toxoid heavy chain includes epitopes that can bind promiscuously to MHC class II alleles and induce $CD4^+$ memory T cells in almost all tetanus vaccinated individuals. In addition, the combination of tetanus toxoid (TT) helper epitopes with tumor-associated antigens is known to improve the immune stimulation compared to application of tumor-associated antigen alone by providing $CD4^+$-mediated T-cell help during priming. To reduce the risk of stimulating $CD8^+$ T cells with the tetanus sequences which might compete with the intended induction of tumor antigen-specific T-cell response, not the whole fragment C of tetanus toxoid is used as it is known to contain $CD8^+$ T-cell epitopes. Two peptide sequences containing promiscuously binding helper epitopes were selected alternatively to ensure binding to as many MHC class II alleles as possible. Based on the data of the ex vivo studies the well-known epitopes p2 (QYIKANSKFIGITEL; TT 830-844) and p16 (MTNSVDDALINST-KIYSYFPSVISKVNQGAQG; TT578-609) were selected. The p2 epitope was already used for peptide vaccination in clinical trials to boost anti-melanoma activity. Present non-clinical data (unpublished) showed that RNA vaccines encoding both a tumor antigen plus promiscuously binding tetanus toxoid sequences lead to enhanced $CD8^+$ T-cell responses directed against the tumor antigen and improved break of tolerance.

Immunomonitoring data from patients vaccinated with vaccines including those sequences fused in frame with the tumor antigen-specific sequences reveal that the tetanus sequences chosen are able to induce tetanus-specific T-cell responses in almost all patients.

According to certain embodiments, an amino acid sequence which breaks immunological tolerance is fused, either directly or through a linker, e.g., a linker having the amino acid sequence according to SEQ ID NO: 28, to HPV E6/E7 protein, a variant thereof, or a fragment thereof, i.e., the antigenic peptide or protein. Accordingly, in one embodiment, an amino acid sequence which breaks immunological tolerance is fused to the above described amino acid sequences derived from HPV E6/E7 protein or immunogenic fragments thereof (antigenic peptides or proteins) comprised by the vaccine antigens described above.

Such amino acid sequences which break immunological tolerance are preferably located at the C-terminus of the antigenic peptide or protein (and optionally at the N-terminus of the amino acid sequence enhancing antigen processing and/or presentation, wherein the amino acid sequence which breaks immunological tolerance and the amino acid sequence enhancing antigen processing and/or presentation may be fused either directly or through a linker, e.g., a linker having the amino acid sequence according to SEQ ID NO: 29), without being limited thereto. Amino acid sequences which break immunological tolerance as defined herein preferably improve T cell responses. In one embodiment, the amino acid sequence which breaks immunological tolerance as defined herein includes, without being limited thereto, sequences derived from tetanus toxoid-derived helper sequences p2 and p16 (P2P16), in particular a sequence comprising the amino acid sequence of SEQ ID NO: 27 or a functional variant thereof.

In one embodiment, an amino acid sequence which breaks immunological tolerance comprises the amino acid sequence of SEQ ID NO: 27, an amino acid sequence having at least 99%, 98%, 97%, 96%, 95%, 90%, 85%, or 80% identity to the amino acid sequence of SEQ ID NO: 27, or a functional fragment of the amino acid sequence of SEQ ID NO: 27, or the amino acid sequence having at least 99%, 98%, 97%, 96%, 95%, 90%, 85%, or 80% identity to the amino acid sequence of SEQ ID NO: 27. In one embodiment, an amino acid sequence which breaks immunological tolerance comprises the amino acid sequence of SEQ ID NO: 27. Instead of using antigen RNAs fused with tetanus toxoid helper epitope, the tumor-antigen RNAs may be co-administered with a separate RNA coding for TT helper epitope during vaccination. Here, the TT helper epitope coding RNA will be added to each of the antigen-coding RNAs before preparation. In this way, mixed lipoplex nanoparticles are formed comprising both, antigen and helper epitope coding RNA in order to deliver both compounds to a given APC.

Accordingly, in some embodiments, compositions described herein may comprise RNA encoding Tetanus Toxoid-derived Helper Sequences p2 and p16 (P2P16). Likewise, methods described herein may comprise administration of RNA encoding Tetanus Toxoid-derived Helper Sequences p2 and p16 (P2P16).

Thus, a further aspect relates to a composition such as a pharmaceutical composition comprising particles such as lipoplex particles comprising:

(i) RNA encoding a vaccine antigen, and (ii) RNA encoding: an amino acid sequence which breaks immunological tolerance.

Such composition is useful in a method of inducing an immune response against the vaccine antigen and thus, against a disease-associated antigen.

A further aspect relates to a method of inducing an immune response comprising administering particles such as lipoplex particles comprising:

(i) RNA encoding a vaccine antigen, and (ii) RNA encoding: an amino acid sequence which breaks immunological tolerance.

In one embodiment, the amino acid sequence which breaks immunological tolerance comprises helper epitopes, preferably tetanus toxoid-derived helper epitopes.

In one embodiment, the RNA encoding a vaccine antigen is co-formulated as particles such as lipoplex particles with the RNA encoding an amino acid sequence which breaks immunological tolerance at a ratio of about 4:1 to about 16:1, about 6:1 to about 14:1, about 8:1 to about 12:1, or about 10:1.

In the following, embodiments of the HPV E6 or E7 vaccine RNAs are described, wherein certain terms used when describing elements thereof have the following meanings:

hAg-Kozak: 5'-UTR sequence of the human alpha-globin mRNA with an optimized 'Kozak sequence' to increase translational efficiency.

sec/MITD: Fusion-protein tags derived from the sequence encoding the human MHC class I complex (HLA-B51, haplotype A2, B27/B51, Cw2/Cw3), which have been shown to improve antigen processing and presentation. Sec corresponds to the 78 bp fragment coding for the secretory signal peptide, which guides translocation of the nascent polypeptide chain into the endoplasmatic reticulum. MITD corresponds to the transmembrane and cytoplasmic domain of the MHC class I molecule, also called MHC class I trafficking domain.

E6/E7: Sequences encoding the respective antigen of HPV.

Glycine-serine linker (GS): Sequences coding for short linker peptides predominantly consisting of the amino acids glycine (G) and serine(S), as commonly used for fusion proteins.

P2P16: Sequence coding for tetanus toxoid-derived helper epitopes to break immunological tolerance.

FI element: The 3'-UTR is a combination of two sequence elements derived from the "amino terminal enhancer of split" (AES) mRNA (called F) and the mitochondrial encoded 12S ribosomal RNA (called I). These were identified by an ex vivo selection process for sequences that confer RNA stability and augment total protein expression.

A30L70: A poly(A)-tail measuring 110 nucleotides in length, consisting of a stretch of 30 adenosine residues, followed by a 10 nucleotide linker sequence and another 70 adenosine residues designed to enhance RNA stability and translational efficiency in dendritic cells.

In one embodiment, vaccine RNA described herein has the structure:

beta-S-ARCA(D1)-hAg-Kozak-sec-GS(1)-E6/E7-GS(2)-P2P16-GS(3)-MITD-FI-A30L70

In one embodiment, vaccine antigen described herein has the structure:

sec-GS(1)-E6/E7-GS(2)-P2P16-GS(3)-MITD

In one embodiment, hAg-Kozak comprises the nucleotide sequence of SEQ ID NO: 30. In one embodiment, see comprises the amino acid sequence of SEQ ID NO: 25. In one embodiment, E6/E7 comprises the E6 or E7 sequences of a vaccine antigen described herein. In one embodiment, P2P16 comprises the the amino acid sequence of SEQ ID NO: 27. In one embodiment, MITD comprises the the amino acid sequence of SEQ ID NO: 26. In one embodiment, GS(1) comprises the amino acid sequence of SEQ ID NO: 28. In one embodiment, GS(2) comprises the amino acid sequence of SEQ ID NO: 28. In one embodiment, GS(3) comprises the amino acid sequence of SEQ ID NO: 29. In one embodiment, FI comprises the nucleotide sequence of SEQ ID NO: 31. In one embodiment, A30L70 comprises the nucleotide sequence of SEQ ID NO: 32.

In one embodiment, a HPV 16 E6 vaccine antigen comprises the amino acid sequence of SEQ ID NO: 1, an amino acid sequence having at least 99%, 98%, 97%, 96%, 95%, 90%, 85%, or 80% identity to the amino acid sequence of SEQ ID NO: 1, or an immunogenic fragment of the amino acid sequence of SEQ ID NO: 1, or the amino acid sequence having at least 99%, 98%, 97%, 96%, 95%, 90%, 85%, or 80% identity to the amino acid sequence of SEQ ID NO: 1. In one embodiment, a HPV 16 E6 vaccine antigen comprises the amino acid sequence of SEQ ID NO: 1.

In one embodiment, RNA encoding a HPV 16 E6 vaccine antigen (i) comprises the nucleotide sequence of SEQ ID NO: 2, a nucleotide sequence having at least 99%, 98%, 97%, 96%, 95%, 90%, 85%, or 80% identity to the nucleotide sequence of SEQ ID NO: 2, or a fragment of the nucleotide sequence of SEQ ID NO: 2, or the nucleotide sequence having at least 99%, 98%, 97%, 96%, 95%, 90%, 85%, or 80% identity to the nucleotide sequence of SEQ ID NO: 2; and/or (ii) encodes an amino acid sequence comprising the amino acid sequence of SEQ ID NO: 1, an amino acid sequence having at least 99%, 98%, 97%, 96%, 95%, 90%, 85%, or 80% identity to the amino acid sequence of SEQ ID NO: 1, or an immunogenic fragment of the amino acid sequence of SEQ ID NO: 1, or the amino acid sequence having at least 99%, 98%, 97%, 96%, 95%, 90%, 85%, or 80% identity to the amino acid sequence of SEQ ID NO: 1. In one embodiment, RNA encoding a HPV 16 E6 vaccine antigen (i) comprises the nucleotide sequence of SEQ ID NO: 2; and/or (ii) encodes an amino acid sequence comprising the amino acid sequence of SEQ ID NO: 1.

In one embodiment, a HPV 16 E7 vaccine antigen comprises the amino acid sequence of SEQ ID NO: 3, an amino acid sequence having at least 99%, 98%, 97%, 96%, 95%, 90%, 85%, or 80% identity to the amino acid sequence of SEQ ID NO: 3, or an immunogenic fragment of the amino acid sequence of SEQ ID NO: 3, or the amino acid sequence having at least 99%, 98%, 97%, 96%, 95%, 90%, 85%, or 80% identity to the amino acid sequence of SEQ ID NO: 3. In one embodiment, a HPV 16 E7 vaccine antigen comprises the amino acid sequence of SEQ ID NO: 3.

In one embodiment, RNA encoding a HPV 16 E7 vaccine antigen (i) comprises the nucleotide sequence of SEQ ID NO: 4, a nucleotide sequence having at least 99%, 98%, 97%, 96%, 95%, 90%, 85%, or 80% identity to the nucleotide sequence of SEQ ID NO: 4, or a fragment of the nucleotide sequence of SEQ ID NO: 4, or the nucleotide sequence having at least 99%, 98%, 97%, 96%, 95%, 90%, 85%, or 80% identity to the nucleotide sequence of SEQ ID NO: 4; and/or (ii) encodes an amino acid sequence comprising the amino acid sequence of SEQ ID NO: 3, an amino acid sequence having at least 99%, 98%, 97%, 96%, 95%, 90%, 85%, or 80% identity to the amino acid sequence of SEQ ID NO: 3, or an immunogenic fragment of the amino acid sequence of SEQ ID NO: 3, or the amino acid sequence having at least 99%, 98%, 97%, 96%, 95%, 90%, 85%, or 80% identity to the amino acid sequence of SEQ ID NO: 3. In one embodiment, RNA encoding a HPV 16 E7 vaccine antigen (i) comprises the nucleotide sequence of SEQ ID NO: 4; and/or (ii) encodes an amino acid sequence comprising the amino acid sequence of SEQ ID NO: 3.

In one embodiment, a HPV 18 E6 vaccine antigen comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5. In one embodiment, a HPV 18 E6 vaccine antigen comprises the amino acid sequence of SEQ ID NO: 5.

In one embodiment, RNA encoding a HPV 18 E6 vaccine antigen (i) comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) encodes an amino acid sequence comprising the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5. In one embodiment, RNA encoding a HPV 18 E6 vaccine antigen (i) comprises the nucleotide sequence of SEQ ID NO: 6; and/or (ii) encodes an amino acid sequence comprising the amino acid sequence of SEQ ID NO: 5.

In one embodiment, a HPV 18 E7 vaccine antigen comprises the amino acid sequence of SEQ ID NO: 7, an amino acid sequence having at least 99%, 98%, 97%, 96%, 95%, 90%, 85%, or 80% identity to the amino acid sequence of SEQ ID NO: 7, or an immunogenic fragment of the amino acid sequence of SEQ ID NO: 7, or the amino acid sequence having at least 99%, 98%, 97%, 96%, 95%, 90%, 85%, or 80% identity to the amino acid sequence of SEQ ID NO: 7. In one embodiment, a HPV 18 E7 vaccine antigen comprises the amino acid sequence of SEQ ID NO: 7.

In one embodiment, RNA encoding a HPV 18 E7 vaccine antigen (i) comprises the nucleotide sequence of SEQ ID NO: 8, a nucleotide sequence having at least 99%, 98%, 97%, 96%, 95%, 90%, 85%, or 80% identity to the nucleotide sequence of SEQ ID NO: 8, or a fragment of the nucleotide sequence of SEQ ID NO: 8, or the nucleotide sequence having at least 99%, 98%, 97%, 96%, 95%, 90%, 85%, or 80% identity to the nucleotide sequence of SEQ ID NO: 8; and/or (ii) encodes an amino acid sequence comprising the amino acid sequence of SEQ ID NO: 7, an amino acid sequence having at least 99%, 98%, 97%, 96%, 95%, 90%, 85%, or 80% identity to the amino acid sequence of SEQ ID NO: 7, or an immunogenic fragment of the amino acid sequence of SEQ ID NO: 7, or the amino acid sequence having at least 99%, 98%, 97%, 96%, 95%, 90%, 85%, or 80% identity to the amino acid sequence of SEQ ID NO: 7. In one embodiment, RNA encoding a HPV 18 E7 vaccine antigen (i) comprises the nucleotide sequence of SEQ ID NO: 8; and/or (ii) encodes an amino acid sequence comprising the amino acid sequence of SEQ ID NO: 7.

In one embodiment, a HPV 31 E6 vaccine antigen comprises the amino acid sequence of SEQ ID NO: 9, an amino acid sequence having at least 99%, 98%, 97%, 96%, 95%, 90%, 85%, or 80% identity to the amino acid sequence of SEQ ID NO: 9, or an immunogenic fragment of the amino acid sequence of SEQ ID NO: 9, or the amino acid sequence having at least 99%, 98%, 97%, 96%, 95%, 90%, 85%, or 80% identity to the amino acid sequence of SEQ ID NO: 9. In one embodiment, a HPV 31 E6 vaccine antigen comprises the amino acid sequence of SEQ ID NO: 9.

In one embodiment, RNA encoding a HPV 31 E6 vaccine antigen (i) comprises the nucleotide sequence of SEQ ID NO: 10, a nucleotide sequence having at least 99%, 98%, 97%, 96%, 95%, 90%, 85%, or 80% identity to the nucleotide sequence of SEQ ID NO: 10, or a fragment of the nucleotide sequence of SEQ ID NO: 10, or the nucleotide sequence having at least 99%, 98%, 97%, 96%, 95%, 90%, 85%, or 80% identity to the nucleotide sequence of SEQ ID NO: 10; and/or (ii) encodes an amino acid sequence comprising the amino acid sequence of SEQ ID NO: 9, an amino acid sequence having at least 99%, 98%, 97%, 96%, 95%, 90%, 85%, or 80% identity to the amino acid sequence of SEQ ID NO: 9, or an immunogenic fragment of the amino acid sequence of SEQ ID NO: 9, or the amino acid sequence having at least 99%, 98%, 97%, 96%, 95%, 90%, 85%, or 80% identity to the amino acid sequence of SEQ ID NO: 9. In one embodiment, RNA encoding a HPV 31 E6 vaccine antigen (i) comprises the nucleotide sequence of SEQ ID NO: 10; and/or (ii) encodes an amino acid sequence comprising the amino acid sequence of SEQ ID NO: 9.

In one embodiment, a HPV 31 E7 vaccine antigen comprises the amino acid sequence of SEQ ID NO: 11, an amino acid sequence having at least 99%, 98%, 97%, 96%, 95%, 90%, 85%, or 80% identity to the amino acid sequence of SEQ ID NO: 11, or an immunogenic fragment of the amino acid sequence of SEQ ID NO: 11, or the amino acid sequence having at least 99%, 98%, 97%, 96%, 95%, 90%, 85%, or 80% identity to the amino acid sequence of SEQ ID NO: 11.

In one embodiment, a HPV 31 E7 vaccine antigen comprises the amino acid sequence of SEQ ID NO: 11.

In one embodiment, RNA encoding a HPV 31 E7 vaccine antigen (i) comprises the nucleotide sequence of SEQ ID NO: 12, a nucleotide sequence having at least 99%, 98%, 97%, 96%, 95%, 90%, 85%, or 80% identity to the nucleotide sequence of SEQ ID NO: 12, or a fragment of the nucleotide sequence of SEQ ID NO: 12, or the nucleotide sequence having at least 99%, 98%, 97%, 96%, 95%, 90%, 85%, or 80% identity to the nucleotide sequence of SEQ ID NO: 12; and/or (ii) encodes an amino acid sequence comprising the amino acid sequence of SEQ ID NO: 11, an amino acid sequence having at least 99%, 98%, 97%, 96%, 95%, 90%, 85%, or 80% identity to the amino acid sequence of SEQ ID NO: 11, or an immunogenic fragment of the amino acid sequence of SEQ ID NO: 11, or the amino acid sequence having at least 99%, 98%, 97%, 96%, 95%, 90%, 85%, or 80% identity to the amino acid sequence of SEQ ID NO: 11. In one embodiment, RNA encoding a HPV 31 E7 vaccine antigen (i) comprises the nucleotide sequence of SEQ ID NO: 12; and/or (ii) encodes an amino acid sequence comprising the amino acid sequence of SEQ ID NO: 11.

In one embodiment, a HPV 33 E6 vaccine antigen comprises the amino acid sequence of SEQ ID NO: 13, an amino acid sequence having at least 99%, 98%, 97%, 96%, 95%, 90%, 85%, or 80% identity to the amino acid sequence of SEQ ID NO: 13, or an immunogenic fragment of the amino acid sequence of SEQ ID NO: 13, or the amino acid sequence having at least 99%, 98%, 97%, 96%, 95%, 90%, 85%, or 80% identity to the amino acid sequence of SEQ ID NO: 13.

In one embodiment, a HPV 33 E6 vaccine antigen comprises the amino acid sequence of SEQ ID NO: 13.

In one embodiment, RNA encoding a HPV 33 E6 vaccine antigen (i) comprises the nucleotide sequence of SEQ ID NO: 14, a nucleotide sequence having at least 99%, 98%, 97%, 96%, 95%, 90%, 85%, or 80% identity to the nucleotide sequence of SEQ ID NO: 14, or a fragment of the nucleotide sequence of SEQ ID NO: 14, or the nucleotide sequence having at least 99%, 98%, 97%, 96%, 95%, 90%, 85%, or 80% identity to the nucleotide sequence of SEQ ID NO: 14;

and/or (ii) encodes an amino acid sequence comprising the amino acid sequence of SEQ ID NO: 13, an amino acid sequence having at least 99%, 98%, 97%, 96%, 95%, 90%, 85%, or 80% identity to the amino acid sequence of SEQ ID NO: 13, or an immunogenic fragment of the amino acid sequence of SEQ ID NO: 13, or the amino acid sequence having at least 99%, 98%, 97%, 96%, 95%, 90%, 85%, or 80% identity to the amino acid sequence of SEQ ID NO: 13. In one embodiment, RNA encoding a HPV 33 E6 vaccine antigen (i) comprises the nucleotide sequence of SEQ ID NO: 14; and/or (ii) encodes an amino acid sequence comprising the amino acid sequence of SEQ ID NO: 13.

In one embodiment, a HPV 33 E7 vaccine antigen comprises the amino acid sequence of SEQ ID NO: 15, an amino acid sequence having at least 99%, 98%, 97%, 96%, 95%, 90%, 85%, or 80% identity to the amino acid sequence of SEQ ID NO: 15, or an immunogenic fragment of the amino acid sequence of SEQ ID NO: 15, or the amino acid sequence having at least 99%, 98%, 97%, 96%, 95%, 90%, 85%, or 80% identity to the amino acid sequence of SEQ ID NO: 15.

In one embodiment, a HPV 33 E7 vaccine antigen comprises the amino acid sequence of SEQ ID NO: 15.

In one embodiment, RNA encoding a HPV 33 E7 vaccine antigen (i) comprises the nucleotide sequence of SEQ ID NO: 16, a nucleotide sequence having at least 99%, 98%, 97%, 96%, 95%, 90%, 85%, or 80% identity to the nucleotide sequence of SEQ ID NO: 16, or a fragment of the nucleotide sequence of SEQ ID NO: 16, or the nucleotide sequence having at least 99%, 98%, 97%, 96%, 95%, 90%, 85%, or 80% identity to the nucleotide sequence of SEQ ID NO: 16; and/or (ii) encodes an amino acid sequence comprising the amino acid sequence of SEQ ID NO: 15, an amino acid sequence having at least 99%, 98%, 97%, 96%, 95%, 90%, 85%, or 80% identity to the amino acid sequence of SEQ ID NO: 15, or an immunogenic fragment of the amino acid sequence of SEQ ID NO: 15, or the amino acid sequence having at least 99%, 98%, 97%, 96%, 95%, 90%, 85%, or 80% identity to the amino acid sequence of SEQ ID NO: 15. In one embodiment, RNA encoding a HPV 33 E7 vaccine antigen (i) comprises the nucleotide sequence of SEQ ID NO: 16; and/or (ii) encodes an amino acid sequence comprising the amino acid sequence of SEQ ID NO: 15.

In one embodiment, a HPV 45 E6 vaccine antigen comprises the amino acid sequence of SEQ ID NO: 17, an amino acid sequence having at least 99%, 98%, 97%, 96%, 95%, 90%, 85%, or 80% identity to the amino acid sequence of SEQ ID NO: 17, or an immunogenic fragment of the amino acid sequence of SEQ ID NO: 17, or the amino acid sequence having at least 99%, 98%, 97%, 96%, 95%, 90%, 85%, or 80% identity to the amino acid sequence of SEQ ID NO: 17.

In one embodiment, a HPV 45 E6 vaccine antigen comprises the amino acid sequence of SEQ ID NO: 17.

In one embodiment, RNA encoding a HPV 45 E6 vaccine antigen (i) comprises the nucleotide sequence of SEQ ID NO: 18, a nucleotide sequence having at least 99%, 98%, 97%, 96%, 95%, 90%, 85%, or 80% identity to the nucleotide sequence of SEQ ID NO: 18, or a fragment of the nucleotide sequence of SEQ ID NO: 18, or the nucleotide sequence having at least 99%, 98%, 97%, 96%, 95%, 90%, 85%, or 80% identity to the nucleotide sequence of SEQ ID NO: 18; and/or (ii) encodes an amino acid sequence comprising the amino acid sequence of SEQ ID NO: 17, an amino acid sequence having at least 99%, 98%, 97%, 96%, 95%, 90%, 85%, or 80% identity to the amino acid sequence of SEQ ID NO: 17, or an immunogenic fragment of the amino acid sequence of SEQ ID NO: 17, or the amino acid sequence having at least 99%, 98%, 97%, 96%, 95%, 90%, 85%, or 80% identity to the amino acid sequence of SEQ ID NO: 17. In one embodiment, RNA encoding a HPV 45 E6 vaccine antigen (i) comprises the nucleotide sequence of SEQ ID NO: 18; and/or (ii) encodes an amino acid sequence comprising the amino acid sequence of SEQ ID NO: 17.

In one embodiment, a HPV 45 E7 vaccine antigen comprises the amino acid sequence of SEQ ID NO: 19, an amino acid sequence having at least 99%, 98%, 97%, 96%, 95%, 90%, 85%, or 80% identity to the amino acid sequence of SEQ ID NO: 19, or an immunogenic fragment of the amino acid sequence of SEQ ID NO: 19, or the amino acid sequence having at least 99%, 98%, 97%, 96%, 95%, 90%, 85%, or 80% identity to the amino acid sequence of SEQ ID NO: 19.

In one embodiment, a HPV 45 E7 vaccine antigen comprises the amino acid sequence of SEQ ID NO: 19.

In one embodiment, RNA encoding a HPV 45 E7 vaccine antigen (i) comprises the nucleotide sequence of SEQ ID NO: 20, a nucleotide sequence having at least 99%, 98%, 97%, 96%, 95%, 90%, 85%, or 80% identity to the nucleotide sequence of SEQ ID NO: 20, or a fragment of the nucleotide sequence of SEQ ID NO: 20, or the nucleotide sequence having at least 99%, 98%, 97%, 96%, 95%, 90%, 85%, or 80% identity to the nucleotide sequence of SEQ ID NO: 20; and/or (ii) encodes an amino acid sequence comprising the amino acid sequence of SEQ ID NO: 19, an amino acid sequence having at least 99%, 98%, 97%, 96%, 95%, 90%, 85%, or 80% identity to the amino acid sequence of SEQ ID NO: 19, or an immunogenic fragment of the amino acid sequence of SEQ ID NO: 19, or the amino acid sequence having at least 99%, 98%, 97%, 96%, 95%, 90%, 85%, or 80% identity to the amino acid sequence of SEQ ID NO: 19. In one embodiment, RNA encoding a HPV 45 E7 vaccine antigen (i) comprises the nucleotide sequence of SEQ ID NO: 20; and/or (ii) encodes an amino acid sequence comprising the amino acid sequence of SEQ ID NO: 19.

In one embodiment, a HPV 58 E6 vaccine antigen comprises the amino acid sequence of SEQ ID NO: 21, an amino acid sequence having at least 99%, 98%, 97%, 96%, 95%, 90%, 85%, or 80% identity to the amino acid sequence of SEQ ID NO: 21, or an immunogenic fragment of the amino acid sequence of SEQ ID NO: 21, or the amino acid sequence having at least 99%, 98%, 97%, 96%, 95%, 90%, 85%, or 80% identity to the amino acid sequence of SEQ ID NO: 21.

In one embodiment, a HPV 58 E6 vaccine antigen comprises the amino acid sequence of SEQ ID NO: 21.

In one embodiment, RNA encoding a HPV 58 E6 vaccine antigen (i) comprises the nucleotide sequence of SEQ ID NO: 22, a nucleotide sequence having at least 99%, 98%, 97%, 96%, 95%, 90%, 85%, or 80% identity to the nucleotide sequence of SEQ ID NO: 22, or a fragment of the nucleotide sequence of SEQ ID NO: 22, or the nucleotide sequence having at least 99%, 98%, 97%, 96%, 95%, 90%, 85%, or 80% identity to the nucleotide sequence of SEQ ID NO: 22;

and/or (ii) encodes an amino acid sequence comprising the amino acid sequence of SEQ ID NO: 21, an amino acid sequence having at least 99%, 98%, 97%, 96%, 95%, 90%, 85%, or 80% identity to the amino acid sequence of SEQ ID NO: 21, or an immunogenic fragment of the amino acid sequence of SEQ ID NO: 21, or the amino acid sequence having at least 99%, 98%, 97%, 96%, 95%, 90%, 85%, or 80% identity to the amino acid sequence of SEQ ID NO: 21. In one embodiment, RNA encoding a HPV 58 E6 vaccine antigen (i) comprises the nucleotide sequence of SEQ ID NO: 22; and/or (ii) encodes an amino acid sequence comprising the amino acid sequence of SEQ ID NO: 21.

In one embodiment, a HPV 58 E7 vaccine antigen comprises the amino acid sequence of SEQ ID NO: 23, an amino acid sequence having at least 99%, 98%, 97%, 96%, 95%, 90%, 85%, or 80% identity to the amino acid sequence of SEQ ID NO: 23, or an immunogenic fragment of the amino acid sequence of SEQ ID NO: 23, or the amino acid sequence having at least 99%, 98%, 97%, 96%, 95%, 90%, 85%, or 80% identity to the amino acid sequence of SEQ ID NO: 23.

In one embodiment, a HPV 58 E7 vaccine antigen comprises the amino acid sequence of SEQ ID NO: 23.

In one embodiment, RNA encoding a HPV 58 E7 vaccine antigen (i) comprises the nucleotide sequence of SEQ ID NO: 24, a nucleotide sequence having at least 99%, 98%, 97%, 96%, 95%, 90%, 85%, or 80% identity to the nucleotide sequence of SEQ ID NO: 24, or a fragment of the nucleotide sequence of SEQ ID NO: 24, or the nucleotide sequence having at least 99%, 98%, 97%, 96%, 95%, 90%, 85%, or 80% identity to the nucleotide sequence of SEQ ID NO: 24; and/or (ii) encodes an amino acid sequence comprising the amino acid sequence of SEQ ID NO: 23, an amino acid sequence having at least 99%, 98%, 97%, 96%, 95%, 90%, 85%, or 80% identity to the amino acid sequence of SEQ ID NO: 23, or an immunogenic fragment of the amino acid sequence of SEQ ID NO: 23, or the amino acid sequence having at least 99%, 98%, 97%, 96%, 95%, 90%, 85%, or 80% identity to the amino acid sequence of SEQ ID NO: 23. In one embodiment, RNA encoding a HPV 58 E7 vaccine antigen (i) comprises the nucleotide sequence of SEQ ID NO: 24; and/or (ii) encodes an amino acid sequence comprising the amino acid sequence of SEQ ID NO: 23.

The antigenic HPV E6/E7 protein or peptide encoded by a HPV E6 vaccine RNA/HPV E7 vaccine RNA may be derived from any HPV, in particular any high risk HPV type such as HPV 16, 18, 31, 33, 45, or 58. In one embodiment, the antigenic HPV E6/E7 protein or peptide encoded by a HPV E6 vaccine RNA/HPV E7 vaccine RNA is derived from different HPV types. In one embodiment, the antigenic HPV E6/E7 protein or peptide encoded by a HPV E6 vaccine RNA/HPV E7 vaccine RNA is derived from the same HPV type.

In one embodiment, the HPV E6 vaccine RNA/HPV E7 vaccine RNA combination is a combination of RNA encoding a HPV 16 E6 vaccine antigen and RNA encoding a HPV 16 E7 vaccine antigen.

In one embodiment, the HPV E6 vaccine RNA/HPV E7 vaccine RNA combination is a combination of RNA encoding a HPV 18 E6 vaccine antigen and RNA encoding a HPV 18 E7 vaccine antigen.

In one embodiment, the HPV E6 vaccine RNA/HPV E7 vaccine RNA combination is a combination of RNA encoding a HPV 31 E6 vaccine antigen and RNA encoding a HPV 31 E7 vaccine antigen.

In one embodiment, the HPV E6 vaccine RNA/HPV E7 vaccine RNA combination is a combination of RNA encoding a HPV 33 E6 vaccine antigen and RNA encoding a HPV 33 E7 vaccine antigen.

In one embodiment, the HPV E6 vaccine RNA/HPV E7 vaccine RNA combination is a combination of RNA encoding a HPV 45 E6 vaccine antigen and RNA encoding a HPV 45 E7 vaccine antigen.

In one embodiment, the HPV E6 vaccine RNA/HPV E7 vaccine RNA combination is a combination of RNA encoding a HPV 58 E6 vaccine antigen and RNA encoding a HPV 58 E7 vaccine antigen.

By "variant" herein is meant an amino acid sequence that differs from a parent amino acid sequence by virtue of at least one amino acid modification. The parent amino acid sequence may be a naturally occurring or wild type (WT) amino acid sequence, or may be a modified version of a wild type amino acid sequence. Preferably, the variant amino acid sequence has at least one amino acid modification compared to the parent amino acid sequence, e.g., from 1 to about 20 amino acid modifications, and preferably from 1 to about 10 or from 1 to about 5 amino acid modifications compared to the parent.

By "wild type" or "WT" or "native" herein is meant an amino acid sequence that is found in nature, including allelic variations. A wild type amino acid sequence, peptide or protein has an amino acid sequence that has not been intentionally modified.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all mutants, splice variants, posttranslationally modified variants, conformations, isoforms, allelic variants, species variants, and species homologs, in particular those which are naturally occurring.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

Preferably the degree of similarity, preferably identity between a given amino acid sequence and an amino acid sequence which is a variant of said given amino acid sequence will be at least about 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 100, at least about 120, at least about 140, at least about 160, at least about 180, or about 200 amino acids, preferably continuous amino acids. In preferred embodiments, the degree of similarity or identity is given for the entire length of the reference amino acid sequence.

"Sequence similarity" indicates the percentage of amino acids that either are identical or that represent conservative amino acid substitutions. "Sequence identity" between two amino acid sequences indicates the percentage of amino acids that are identical between the sequences.

An amino acid sequence (peptide, protein or polypeptide) "derived from" a designated amino acid sequence (peptide, protein or polypeptide) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof.

A peptide and protein antigen described herein (E6 protein, and E7 protein) when provided to a subject by administration of RNA encoding the antigen, i.e., a vaccine antigen, preferably results in stimulation, priming and/or expansion of T cells in the subject. Said stimulated, primed and/or expanded T cells are preferably directed against the target antigen, in particular the target antigen expressed by diseased cells, tissues and/or organs, i.e., the disease-associated antigen. Thus, a vaccine antigen may comprise the disease-associated antigen, or a fragment or variant thereof. In one embodiment, such fragment or variant is immunologically equivalent to the disease-associated antigen. In the context of the present disclosure, the term "fragment of an antigen" or "variant of an antigen" means an agent which results in stimulation, priming and/or expansion of T cells which stimulated, primed and/or expanded T cells target the disease-associated antigen, in particular when expressed on the surface of diseased cells, tissues and/or organs. Thus, the vaccine antigen administered according to the disclosure may correspond to or may comprise the disease-associated antigen, may correspond to or may comprise a fragment of the disease-associated antigen or may correspond to or may comprise an antigen which is homologous to the disease-associated antigen or a fragment thereof. If the vaccine antigen administered according to the disclosure comprises a fragment of the disease-associated antigen or an amino acid sequence which is homologous to a fragment of the disease-associated antigen said fragment or amino acid sequence may comprise an epitope of the disease-associated antigen or a sequence which is homologous to an epitope of the disease-associated antigen, wherein the T cells bind to said epitope. Thus, according to the disclosure, an antigen may comprise an immunogenic fragment of the disease-associated antigen or an amino acid sequence being homologous to an immunogenic fragment of the disease-associated antigen. An "immunogenic fragment of an antigen" according to the disclosure preferably relates to a fragment of an antigen which is capable of stimulating, priming and/or expanding T cells. It is preferred that the vaccine antigen (similar to the disease-associated antigen) provides the relevant epitope for binding by T cells. It is also preferred that the vaccine antigen (similar to the disease-associated antigen) is expressed on the surface of a cell such as an antigen-presenting cell so as to provide the relevant epitope for binding by the T cells. The vaccine antigen according to the invention may be a recombinant antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term "immunologically equivalent" is preferably used with respect to the immunological effects or properties of antigens or antigen variants. For example, an amino acid sequence is immunologically equivalent to a reference amino acid sequence, if said amino acid sequence when exposed to T cells binding to the reference amino acid sequence or cells expressing the reference amino acid sequence induces an immune reaction having a specificity of reacting with the reference amino acid sequence, in particular stimulation, priming and/or expansion of T cells. Thus, a molecule which is immunologically equivalent to an antigen exhibits the same or essentially the same properties and/or exerts the same or essentially the same effects regarding the stimulation, priming and/or expansion of T cells as the antigen to which the T cells are targeted.

"Activation" or "stimulation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "priming" refers to a process wherein a T cell has its first contact with its specific antigen and causes differentiation into effector T cells.

The term "clonal expansion" or "expansion" refers to a process wherein a specific entity is multiplied. In the context of the present disclosure, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

Lipoplex Particles

In certain embodiments of the present disclosure, the RNA described herein may be present in RNA lipoplex particles. The RNA lipoplex particles and compositions comprising RNA lipoplex particles described herein are useful for delivery of RNA to a target tissue after parenteral administration, in particular after intravenous administration. The RNA lipoplex particles may be prepared using liposomes that may be obtained by injecting a solution of the lipids in ethanol into water or a suitable aqueous phase. In one embodiment, the aqueous phase has an acidic pH. In one embodiment, the aqueous phase comprises acetic acid, e.g., in an amount of about 5 mM. In one embodiment, the liposomes and RNA lipoplex particles comprise at least one cationic lipid and at least one additional lipid. In one embodiment, the at least one cationic lipid comprises 1,2-di-O-octadecenyl-3-trimethylammonium propane (DOTMA) and/or 1,2-dioleoyl-3-trimethylammonium-propane (DOTAP). In one embodiment, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC). In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE). In one embodiment, the liposomes and RNA lipoplex particles comprise 1,2-di-O-octadecenyl-3-trimethylammonium propane (DOTMA) and 1,2-di-(9Z-octadecenoyl)-sn-glycero-3-phosphoethanolamine (DOPE). Liposomes may be used for preparing RNA lipoplex particles by mixing the liposomes with RNA.

Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

RNA Lipoplex Particle Diameter

RNA lipoplex particles described herein have an average diameter that in one embodiment ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

In one embodiment, RNA lipoplex particles described herein exhibit a polydispersity index less than about 0.5, less than about 0.4, or less than about 0.3. By way of example, the RNA lipoplex particles can exhibit a polydispersity index in a range of about 0.1 to about 0.3.

Lipid

In one embodiment, the lipid solutions, liposomes and RNA lipoplex particles described herein include a cationic lipid. As used herein, a "cationic lipid" refers to a lipid having a net positive charge. Cationic lipids bind negatively charged RNA by electrostatic interaction to the lipid matrix. Generally, cationic lipids possess a lipophilic moiety, such as a sterol, an acyl or diacyl chain, and the head group of the lipid typically carries the positive charge. Examples of cationic lipids include, but are not limited to 1,2-di-O-octadecenyl-3-trimethylammonium propane (DOTMA), dimethyldioctadecylammonium (DDAB); 1,2-dioleoyl-3- trimethylammonium propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 2,3-di(tetradecoxy) propyl-(2-hydroxyethyl)-dimethylazanium (DMRIE), 1,2-dimyristoyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2 (spermine carboxamide)ethyl]-N,N-dimethyl-l-propanamium trifluoroacetate (DOSPA). Preferred are DOTMA, DOTAP, DODAC, and DOSPA. In specific embodiments, the cationic lipid is DOTMA and/or DOTAP.

An additional lipid may be incorporated to adjust the overall positive to negative charge ratio and physical stability of the RNA lipoplex particles. In certain embodiments, the additional lipid is a neutral lipid. As used herein, a "neutral lipid" refers to a lipid having a net charge of zero. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, cholesterol, and cerebroside. In specific embodiments, the additional lipid is DOPE, cholesterol and/or DOPC.

In certain embodiments, the RNA lipoplex particles include both a cationic lipid and an additional lipid. In an exemplary embodiment, the cationic lipid is DOTMA and the additional lipid is DOPE. Without wishing to be bound by theory, the amount of the at least one cationic lipid compared to the amount of the at least one additional lipid may affect important RNA lipoplex particle characteristics, such as charge, particle size, stability, tissue selectivity, and bioactivity of the RNA. Accordingly, in some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

Charge Ratio

The electric charge of the RNA lipoplex particles of the present disclosure is the sum of the electric charges present in the at least one cationic lipid and the electric charges present in the RNA. The charge ratio is the ratio of the positive charges present in the at least one cationic lipid to the negative charges present in the RNA. The charge ratio of the positive charges present in the at least one cationic lipid to the negative charges present in the RNA is calculated by the following equation: charge ratio= [(cationic lipid concentration (mol))*(the total number of positive charges in the cationic lipid)]/[(RNA concentration (mol))*(the total number of negative charges in RNA)]. The concentration of RNA and the at least one cationic lipid amount can be determined using routine methods by one skilled in the art.

In one embodiment, at physiological pH the charge ratio of positive charges to negative charges in the RNA lipoplex particles is from about 1.6:2 to about 1:2, or about 1.6:2 to about 1.1:2. In specific embodiments, the charge ratio of positive charges to negative charges in the RNA lipoplex particles at physiological pH is about 1.6:2.0, about 1.5:2.0, about 1.4:2.0, about 1.3:2.0, about 1.2:2.0, about 1.1:2.0, or about 1:2.0.

It has been found that RNA lipoplex particles having such charge ratio may be used to preferentially target spleen tissue or spleen cells such as antigen-presenting cells, in particular dendritic cells. Accordingly, in one embodiment, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

Radiotherapy

Radiotherapy (RT) is the second most common treatment regimen used and given to approximately 50% of cancer patients. Different types of RT treatments exist, using high energy photons (X- and γ-ray), particle irradiation (e.g. protons, carbon ions) or radionuclides (cesium 137, iridium 192, iodine 125) to locally deliver radiation to malignant tissues. Local RT (LRT) faces an over 120 year-long history of technological improvements and radiation dose-refinement.

Ionizing radiation refers to radiation that has enough energy to ionize matter and can be divided into electromagnetic radiation (X- and γ-ray) and particulate radiation (a and B particles, protons, heavy ions). A natural source of ionizing radiation are radioisotopes that, upon radioactive decay, emit a unique spectrum of a ($He2^+$), B (e or e+) and y rays (high energy photons). The number of ionization events and tissue penetration depth is a function of the primary kinetic energy and, if charged, coulomb energy. The radiation dose is measured in gray (Gy) as the International Systems of Units (SI) unit for the absorbed radiation dose per unit mass of matter (1 J radiation/kg matter).

When ionizing radiation traverses biological matter, it is able to break chemical bonds and ionize molecules, with direct and severe effects on cells, tissues and the organism as a whole. Whereas all cellular structures may be harmed by radiation directly or indirectly (indirect ionization by radiation-induced reactive oxygen species (ROS)), DNA damage is regarded as the ultimate and most severe consequence. Ionizing radiation may cause different types of DNA damage, such as base damage, single-strand breaks (SSB) and double-strand breaks (DSB). The type and density of DNA damage is a function of radiation type (e.g. electromagnetic or particulate) and dose. The exact cellular fate, however, depends on cell-intrinsic factors such as cell type, cell cycle phase, repair capability and cell death-proficiency as a function of the DNA-damage response (DDR) initiated. First, if the cell is repair-proficient and the damage minimal, the cell may repair its damage. Base damages and SSB are repaired via base-excision repair (BER) or nucleotide excision repair (NER), whereas more severe DSB are repaired via non-homologous end-joining (NHEJ, all cell cycle phases) or homologous recombination (HR, only S and G2 phase). Second, the cell may try to repair the DNA damage, but fails to succeed and reproduces in its damaged form. Whereas unrepaired DSB can lead to cell death by mitotic catastrophe, misrepaired DSB give rise to chromosomal translocation and genomic instability and can cause secondary cancers. Third, the cell recognizes the damage and undergoes programmed cell death (apoptosis).

As most cancer cells exhibit aberrant DNA repair pathways and impaired cell cycle control, they might respond to ionizing radiation differently than their healthy counterparts. The linear-quadratic (LQ) model of cell killing is one of the key mathematical tools in radiation biology and physics, and provides a simple relationship between delivered dose and cell survival. Different radiation doses are applied in vitro and a cell's survival determined by its ability to produce a viable colony of progenitor cells, measured in a clonogenic survival assay. Clonogenic survival assays are the accepted gold standard to measure a cells survival in response to radiation, and is defined by $S=e^{-\alpha D-\beta D^2}$, with S being the surviving cell fraction, D the total dose, and $\alpha$ and $\beta$ the measure of a cell's radiosensitivity. The surviving fraction is plotted on a log scale against the radiation dose. The survival curve follows a linear slope ($\alpha$) at low doses and a curved slope ($\beta$) at higher doses. The early and late bent of this curve is a cell-intrinsic characteristic and expressed as the $\alpha/\beta$-ratio. Cells with a high $\alpha/\beta$-ratio experience a relatively constant rate of cell death across different doses, whereas cells with a low $\alpha/\beta$-ratio show a pronounced curvature and respond to high dose radiation with increased cell death. Slowly proliferating cells or tissues, such as most healthy cells, generally repair very well and have a low $\alpha/\beta$-ratio (late responding tissues). Rapidly proliferating cells or tissues, such as tumor cells, generally repair worse and have a high $\alpha/\beta$-ratio (acute responding tissues). Especially at low doses (<2-2.5 Gy), normal cells have a survival advantage over tumor cells due to slower growth and intact DNA repair. The higher radiosensitivity of tumor cells at low doses forms the basis of fractionated radiotherapy, which is still used in standard clinical practice today.

However, there are serious limitations of the LQ model to predict ionizing radiation effects: (i) It is an in vitro model used to predict in vivo radiation effects, (ii) it measures clonogenic survival, however no information is provided about the type of cell death induced, e.g. mitotic catastrophe, apoptosis, necrosis, necroptosis, autophagy or replicative senescence, (iii) it does not account for the reaction of the immune system and (iv) is not accurate at higher doses per fraction (>10 Gy).

For the radiotherapeutic treatment of tumors, two types of radiation machines are utilized: electromagnetic and particulate machines. Depending on the type (electromagnetic or particulate) and primary energy, radiation beams possess different dose-deposition profiles into tissues.

Whereas photons are not able to deeply penetrate tissues and, depending on their primary energy, deposit their energy within the first 5 to 10 cm of water, particulate beams like proton beams are able to deeper penetrate tissues. X-rays are most commonly used in conventional radiotherapy as they are relatively inexpensive, less deleterious as particulate irradiation and therefore considerate safer.

The therapeutic use of X-rays faces a long history of technological developments with many of the early radiation machines still being used today. The development of orthovoltage X-ray tubes (200-500 kilovolt (kV)) in the 1930s first allowed the external treatment of tumors with X-ray beams. Contrary to natural X- or $\gamma$-ray emitting radionuclides, an X-ray tube is a vacuum tube that generates X-rays from electrical input. Electrons are emitted from a cathode and accelerated through the vacuum towards an anode. Depending on the tube voltage (50 kV to 500 kV), electrons are accelerated to different speeds and X-rays of different energy produced. When electrons collide with the anode material, bremsstrahlung in the X-range is produced perpendicular to the electron beam. In contrast to naturally emitting radionuclides, radiation is only produced as long as the X-ray tube is turned on. The resulting X-ray energy is a function of tube voltage and anode material. Due to their low tissue penetration depth, orthovoltage X-rays are abandoned in clinical practice, yet they remain frequently applied in preclinical research.

Today, megavoltage X-rays (1 to 25 MeV) are in use, utilizing medical linear accelerators (LINAC) to generate high energy X-rays for therapeutic purposes. Size, shape and angle of the beam are controlled to cover the tumor while spearing healthy tissues. Conventional, 3D conformal RT (3D-CRT) and intensity modulated RT (IMRT) are different forms of external beam RT (EBRT). In conventional RT, the radiation dose is delivered from different angles in multiple overlapping beams. The highest dose is delivered at the beam intersection within the tumor and doses decline with distance from the intersection point. In 3D-CRT, a tumor 3D image (computed tomography (CT), magnetic resonance imaging (MRI) or positron emission tomography (PET)) is used to design radiation beams that are more conform to the shape of the tumor, and more accurately outline organs at risk. IMRT is an advanced form of 3D-CRT, in which the beam is divided in hundreds of beamlets of different intensities, enabling a highly conformal dose distribution and highly precise tumor targeting.

In contrast to electromagnetic irradiation, particle irradiation was introduced for therapeutic use in the 1970s, using proton or carbon beams. Particle irradiation is characterized by its good penetration potential and high energy deposition at the end of its range (Bragg peak). This allows extremely steep dose gradients with limited dose-deposition along the trajectory. Radiation machines are, however, very cost intensive and high dose-deposition is accompanied by a high risk of secondary cancers.

At times when radiation delivery and radiation machines were rudimentary, total radiation doses were fractionated to multiple smaller ones, not because of the appreciation of the underlying biology, but because of technical limitations and the desire to reduce off-target effects. Today, clinical LRT protocols are still based on fractionated LRT, applying daily 1.8 to 2 Gy (Monday to Friday) for six to eight weeks, accumulating total doses of 60 to 80 Gy.

Due to technological advances in radiation delivery, radiation doses can be delivered at high accuracy, reduced margins and high dose conformation. This allows the delivery of higher radiation doses in a single fraction at reduced risk, which is referred to as stereotactic body RT (SBRT). In addition, immunomodulatory effects of LRT became known, especially when high doses per fraction are applied. Due to the favorable immunological effects, a change is underway, increasingly applying high dose LRT alone or in conjunction with other immunomodulatory agents.

Immune Checkpoint Inhibitor

As used herein, "immune checkpoint" refers to regulators of the immune system, and, in particular, co-stimulatory and inhibitory signals that regulate the amplitude and quality of T cell receptor recognition of an antigen. In certain embodiments, the immune checkpoint is an inhibitory signal. In certain embodiments, the inhibitory signal is the interaction between PD-1 and PD-L1 and/or PD-L2. In certain embodiments, the inhibitory signal is the interaction between CTLA-4 and CD80 or CD86 to displace CD28 binding. In certain embodiments the inhibitory signal is the interaction between LAG-3 and MHC class II molecules. In certain embodiments, the inhibitory signal is the interaction between TIM-3 and one or more of its ligands, such as galectin 9, PtdSer, HMGB1 and CEACAM1. In certain embodiments, the inhibitory signal is the interaction between one or several KIRs and their ligands. In certain embodiments, the inhibitory signal is the interaction between TIGIT and one or more of its ligands, PVR, PVRL2 and PVRL3. In certain embodiments, the inhibitory signal is the interaction between CD94/NKG2A and HLA-E. In certain embodiments, the inhibitory signal is the interaction between VISTA and its binding partner(s). In certain embodiments, the inhibitory signal is the interaction between one or more Siglecs and their ligands. In certain embodiments, the inhibitory signal is the interaction between GARP and one or more of it ligands. In certain embodiments, the inhibitory signal is the interaction between CD47 and SIRPa. In certain embodiments, the inhibitory signal is the interaction between PVRIG and PVRL2. In certain embodiments, the inhibitory signal is the interaction between CSF1R and CSF1. In certain embodiments, the inhibitory signal is the interaction between BTLA and HVEM. In certain embodiments, the inhibitory signal is part of the adenosinergic pathway, e.g., the interaction between A2AR and/or A2BR and adenosine, produced by CD39 and CD73. In certain embodiments, the inhibitory signal is the interaction between B7-H3 and its receptor and/or B7-H4 and its receptor. In certain embodiments, the inhibitory signal is mediated by IDO, CD20, NOX or TDO.

The "Programmed Death-1 (PD-1)" receptor refers to an immuno-inhibitory receptor belonging to the CD28 family. PD-1 is expressed predominantly on previously activated T cells in vivo, and binds to two ligands, PD-L1 (also known as B7-H1 or CD274) and PD-L2 (also known as B7-DC or CD273). The term "PD-1" as used herein includes human PD-1 (hPD-1), variants, isoforms, and species homologs of hPD-1, and analogs having at least one common epitope with hPD-1. "Programmed Death Ligand-1 (PD-L1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The term "PD-L2" as used herein includes human PD-L2 (hPD-L2), variants, isoforms, and species homologs of hPD-L2, and analogs having at least one common epitope with hPD-L2. The ligands of PD-1 (PD-L1 and PD-L2) are expressed on the surface of antigen-presenting cells, such as dendritic cells or macrophages, and other immune cells. Binding of PD-1 to PD-L1 or PD-L2 results in downregulation of T cell activation. Cancer cells expressing PD-L1 and/or PD-L2 are able to switch off T cells expressing PD-1 what results in suppression of the anticancer immune response. The interaction between PD-1 and its ligands results in a decrease in tumor infiltrating lymphocytes, a decrease in T cell receptor mediated proliferation, and immune evasion by the cancerous cells. Immune suppression can be reversed by inhibiting the local interaction of PD-1 with PD-L1, and the effect is additive when the interaction of PD-1 with PD-L2 is blocked as well.

"Cytotoxic T Lymphocyte Associated Antigen-4 (CTLA-4)" (also known as CD152) is a T cell surface molecule and is a member of the immunoglobulin superfamily. This protein downregulates the immune system by binding to CD80 (B7-1) and CD86 (B7-2). The term "CTLA-4" as used herein includes human CTLA-4 (hCTLA-4), variants, isoforms, and species homologs of hCTLA-4, and analogs having at least one common epitope with hCTLA-4. CTLA-4 is a homolog of the stimulatory checkpoint protein CD28 with much higher binding affinity for CD80 and CD86. CTLA4 is expressed on the surface of activated T cells and its ligands are expressed on the surface of professional antigen-presenting cells. Binding of CTLA-4 to its ligands prevents the co-stimulatory signal of CD28 and produces an inhibitory signal. Thus, CTLA-4 downregulates T cell activation.

"T cell Immunoreceptor with Ig and ITIM domains" (TIGIT, also known as WUCAM or Vstm3) is an immune receptor on T cells and Natural Killer (NK) cells and binds to PVR (CD155) on DCs, macrophages etc., and PVRL2 (CD112; nectin-2) and PVRL3 (CD113; nectin-3) and regulates T cell-mediated immunity. The term "TIGIT" as used herein includes human TIGIT (hTIGIT), variants, isoforms, and species homologs of hTIGIT, and analogs having at least one common epitope with hTIGIT. The term "PVR" as used herein includes human PVR (hPVR), variants, isoforms, and species homologs of hPVR, and analogs having at least one common epitope with hPVR. The term "PVRL2" as used herein includes human PVRL2 (hPVRL2), variants, isoforms, and species homologs of hPVRL2, and analogs having at least one common epitope with hPVRL2. The term "PVRL3" as used herein includes human PVRL3 (hPVRL3), variants, isoforms, and species homologs of hPVRL3, and analogs having at least one common epitope with hPVRL3.

The "B7 family" refers to inhibitory ligands with undefined receptors. The B7 family encompasses B7-H3 and B7-H4, both upregulated on tumor cells and tumor infiltrating cells. The terms "B7-H3" and "B7-H4" as used herein include human B7-H3 (hB7-H3) and human B7-H4 (hB7-H4), variants, isoforms, and species homologs thereof, and analogs having at least one common epitope with B7-H3 and B7-H4, respectively.

"B and T Lymphocyte Attenuator" (BTLA, also known as CD272) is a TNFR family member expressed in Th1 but not Th2 cells. BTLA expression is induced during activation of T cells and is in particular expressed on surfaces of CD8+ T cells. The term "BTLA" as used herein includes human BTLA (hBTLA), variants, isoforms, and species homologs of hBTLA, and analogs having at least one common epitope with hBTLA. BTLA expression is gradually downregulated during differentiation of human CD8+ T cells to effector cell phenotype. Tumor-specific human CD8+T cells express high levels of BTLA. BTLA binds to "Herpesvirus entry mediator" (HVEM, also known as TNFRSF14 or CD270) and is involved in T cell inhibition. The term "HVEM" as used herein includes human HVEM (hHVEM), variants, isoforms, and species homologs of hHVEM, and analogs having at least one common epitope with hHVEM. BTLA-HVEM complexes negatively regulate T cell immune responses.

"Killer-cell Immunoglobulin-like Receptors" (KIRs) are receptors for MHC Class I molecules on NK T cells and NK cells that are involved in differentiation between healthy and diseased cells. KIRs bind to human leukocyte antigen (HLA) A, B and C, what suppresses normal immune cell activation. The term "KIRs" as used herein includes human KIRs (hKIRs), variants, isoforms, and species homologs of hKIRs, and analogs having at least one common epitope with a hKIR.

The term "HLA" as used herein includes variants, isoforms, and species homologs of HLA, and analogs having at least one common epitope with a HLA. KIR as used herein in particular refers to KIR2DL1, KIR2DL2, and/or KIR2DL3.

"Lymphocyte Activation Gene-3 (LAG-3)" (also known as CD223) is an inhibitory receptor associated with inhibition of lymphocyte activity by binding to MHC class II molecules. This receptor enhances the function of Treg cells and inhibits $CD8^+$ effector T cell function leading to immune response suppression. LAG-3 is expressed on activated T cells, NK cells, B cells and DCs. The term "LAG-3" as used herein includes human LAG-3 (hLAG-3), variants, isoforms, and species homologs of hLAG-3, and analogs having at least one common epitope.

"T Cell Membrane Protein-3 (TIM-3)" (also known as HAVcr-2) is an inhibitory receptor involved in the inhibition of lymphocyte activity by inhibition of Th1 cell responses. Its ligand is galectin 9 (GAL9), which is upregulated in various types of cancers. Other TIM-3 ligands include phosphatidyl serine (PtdSer), High Mobility Group Protein 1 (HMGB1) and Carcinoembryonic Antigen Related Cell Adhesion Molecule 1 (CEACAM1). The term "TIM-3" as used herein includes human TIM3 (hTIM-3), variants, isoforms, and species homologs of hTIM-3, and analogs having at least one common epitope. The term "GAL9" as used herein includes human GAL9 (hGAL9), variants, isoforms, and species homologs of hGAL9, and analogs having at least one common epitope. The term "PdtSer" as used herein includes variants and analogs having at least one common epitope. The term "HMGB1" as used herein includes human HMGB1 (hHMGB1), variants, isoforms, and species homologs of hHMGB1, and analogs having at least one common epitope. The term "CEACAM1" as used herein includes human CEACAM1 (hCEACAM1), variants, isoforms, and species homologs of hCEACAM1, and analogs having at least one common epitope.

"CD94/NKG2A" is an inhibitory receptor predominantly expressed on the surface of natural killer cells and of CD8+ T cells. The term "CD94/NKG2A" as used herein includes human CD94/NKG2A (hCD94/NKG2A), variants, isoforms, and species homologs of hCD94/NKG2A, and analogs having at least one common epitope. The CD94/NKG2A receptor is a heterodimer comprising CD94 and NKG2A. It suppresses NK cell activation and CD8+ T cell function, probably by binding to ligands such as HLA-E. CD94/NKG2A restricts cytokine release and cytotoxic response of natural killer cells (NK cells), Natural Killer T cells (NK-T cells) and T cells (a/B and y/8). NKG2A is frequently expressed in tumor infiltrating cells and HLA-E is overexpressed in several cancers.

"Indoleamine 2,3-dioxygenase" (IDO) is a tryptophan catabolic enzyme with immune-inhibitory properties. The term "IDO" as used herein includes human IDO (hIDO), variants, isoforms, and species homologs of hIDO, and analogs having at least one common epitope. IDO is the rate limiting enzyme in tryptophan degradation catalyzing its conversion to kynurenine. Therefore, IDO is involved in depletion of essential amino acids. It is known to be involved in suppression of T and NK cells, generation and activation of Tregs and myeloid-derived suppressor cells, and promotion of tumor angiogenesis. IDO is overexpressed in many cancers and was shown to promote immune system escape of tumor cells and to facilitate chronic tumor progression when induced by local inflammation.

In the "adenosinergic pathway" or "adenosine signaling pathway" as used herein ATP is converted to adenosine by the ectonucleotidases CD39 and CD73 resulting in inhibitory signaling through adenosine binding by one or more of the inhibitory adenosine receptors "Adenosine A2A Receptor" (A2AR, also known as ADORA2A) and "Adenosine A2B Receptor" (A2BR, also known as ADORA2B). Adenosine is a nucleoside with immunosuppressive properties and is present in high concentrations in the tumor microenvironment restricting immune cell infiltration, cytotoxicity and cytokine production. Thus, adenosine signaling is a strategy of cancer cells to avoid host immune system clearance. Adenosine signaling through A2AR and A2BR is an important checkpoint in cancer therapy that is activated by high adenosine concentrations typically present in the tumor microenvironment. CD39, CD73, A2AR and A2BR are expressed by most immune cells, including T cells, invariant natural killer cells, B cells, platelets, mast cells and eosinophils. Adenosine signaling through A2AR and A2BR counteracts T cell receptor mediated activation of immune cells and results in increased numbers of Tregs and decreased activation of DCs and effector T cells. The term "CD39" as used herein includes human CD39 (hCD39), variants, isoforms, and species homologs of hCD39, and analogs having at least one common epitope. The term "CD73" as used herein includes human CD73 (hCD73), variants, isoforms, and species homologs of hCD73, and analogs having at least one common epitope. The term "A2AR" as used herein includes human A2AR (hA2AR), variants, isoforms, and species homologs of hA2AR, and analogs having at least one common epitope. The term "A2BR" as used herein includes human A2BR (hA2BR), variants, isoforms, and species homologs of hA2BR, and analogs having at least one common epitope.

"V-domain Ig suppressor of T cell activation" (VISTA, also known as C10orf54) bears homology to PD-L1 but displays a unique expression pattern restricted to the hematopoietic compartment. The term "VISTA" as used herein includes human VISTA (hVISTA), variants, isoforms, and species homologs of hVISTA, and analogs having at least one common epitope. VISTA induces T cell suppression and is expressed by leukocytes within tumors.

The "Sialic acid binding immunoglobulin type lectin" (Siglec) family members recognize sialic acids and are involved in distinction between "self" and "non-self". The term "Siglecs" as used herein includes human Siglecs (hSiglecs), variants, isoforms, and species homologs of hSiglecs, and analogs having at least one common epitope with one or more hSiglecs. The human genome contains 14 Siglecs of which several are involved in immunosuppression, including, without limitation, Siglec-2, Siglec-3, Siglec-7 and Siglec-9. Siglec receptors bind glycans containing sialic acid, but differ in their recognition of the linkage regiochemistry and spatial distribution of sialic residues. The members of the family also have distinct expression patterns. A broad range of malignancies overexpress one or more Siglecs.

"CD20" is an antigen expressed on the surface of B and T cells. High expression of CD20 can be found in cancers, such as B cell lymphomas, hairy cell leukemia, B cell chronic lymphocytic leukemia, and melanoma cancer stem cells. The term "CD20" as used herein includes human CD20 (hCD20), variants, isoforms, and species homologs of hCD20, and analogs having at least one common epitope.

"Glycoprotein A repetitions predominant" (GARP) plays a role in immune tolerance and the ability of tumors to escape the patient's immune system. The term "GARP" as used herein includes human GARP (hGARP), variants, isoforms, and species homologs of hGARP, and analogs having at least one common epitope. GARP is expressed on lymphocytes including Treg cells in peripheral blood and tumor infiltrating T cells at tumor sites. It probably binds to latent "transforming growth factor β" (TGF-β). Disruption of GARP signaling in Tregs results in decreased tolerance and inhibits migration of Tregs to the gut and increased proliferation of cytotoxic T cells.

"CD47" is a transmembrane protein that binds to the ligand "signal-regulatory protein alpha" (SIRPα).

The term "CD47" as used herein includes human CD47 (hCD47), variants, isoforms, and species homologs of hCD47, and analogs having at least one common epitope with hCD47.

The term "SIRPα" as used herein includes human SIRPα (hSIRPα), variants, isoforms, and species homologs of hSIRPα, and analogs having at least one common epitope with hSIRPα. CD47 signaling is involved in a range of cellular processes including apoptosis, proliferation, adhesion and migration. CD47 is overexpressed in many cancers and functions as "don't eat me" signal to macrophages. Blocking CD47 signaling through inhibitory anti-CD47 or anti-SIRPα antibodies enables macrophage phagocytosis of cancer cells and fosters the activation of cancer-specific T lymphocytes.

"Poliovirus receptor related immunoglobulin domain containing" (PVRIG, also known as CD112R) binds to "Poliovirus receptor-related 2" (PVRL2). PVRIG and PVRL2 are overexpressed in a number of cancers. PVRIG expression also induces TIGIT and PD-1 expression and PVRL2 and PVR (a TIGIT ligand) are co-overexpressed in several cancers. Blockade of the PVRIG signaling pathway results in increased T cell function and CD8+ T cell responses and, therefore, reduced immune suppression and elevated interferon responses. The term "PVRIG" as used herein includes human PVRIG (hPVRIG), variants, isoforms, and species homologs of hPVRIG, and analogs having at least one common epitope with hPVRIG. "PVRL2" as used herein includes hPVRL2, as defined above.

The "colony-stimulating factor 1" pathway is another checkpoint that can be targeted according to the disclosure. CSF1R is a myeloid growth factor receptor that binds CSF1. Blockade of the CSF1R signaling can functionally reprogram macrophage responses, thereby enhancing antigen presentation and anti-tumor T cell responses. The term "CSF1R" as used herein includes human CSF1R (hCSF1R), variants, isoforms, and species homologs of hCSF1R, and analogs having at least one common epitope with hCSF1R. The term "CSF1" as used herein includes human CSF1 (hCSF1), variants, isoforms, and species homologs of hCSF1, and analogs having at least one common epitope with hCSF1.

"Nicotinamide adenine dinucleotide phosphate NADPH oxidase" refers to an enzyme of the NOX family of enzymes of myeloid cells that generate immunosuppressive reactive oxygen species (ROS). Five NOX enzymes (NOX1 to NOX5) have been found to be involved in cancer development and immunosuppression. Elevated ROS levels have been detected in almost all cancers and promote many aspects of tumor development and progression. NOX produced ROS dampens NK and T cell functions and inhibition of NOX in myeloid cells improves anti-tumor functions of adjacent NK cells and T cells. The term "NOX" as used herein includes human NOX (hNOX), variants, isoforms, and species homologs of hNOX, and analogs having at least one common epitope with hNOX.

Another immune checkpoint that can be targeted according to the disclosure is the signal mediated by "tryptophan-2,3-dioxygenase" (TDO). TDO represents an alternative route to IDO in tryptophan degradation and is involved in immune suppression. Since tumor cells may catabolize tryptophan via TDO instead of IDO, TDO may represent an additional target for checkpoint blockade. Indeed, several cancer cell lines have been found to upregulate TDO and TDO may complement IDO inhibition. The term "TDO" as used herein includes human TDO (hTDO), variants, isoforms, and species homologs of hTDO, and analogs having at least one common epitope with hTDO.

Many of the immune checkpoints are regulated by interactions between specific receptor and ligand pairs, such as those described above. Thus, immune checkpoint proteins mediate immune checkpoint signaling. For example, checkpoint proteins directly or indirectly regulate T cell activation, T cell proliferation and/or T cell function. Cancer cells often exploit these checkpoint pathways to protect themselves from being attacked by the immune system. Hence, the function of checkpoint proteins, which is modulated according to the present disclosure is typically the regulation of T cell activation, T cell proliferation and/or T cell function. Immune checkpoint proteins thus regulate and maintain self-tolerance and the duration and amplitude of physiological immune responses. Many of the immune checkpoint proteins belong to the B7: CD28 family or to the tumor necrosis factor receptor (TNFR) super family and, by binding to specific ligands, activate signaling molecules that are recruited to the cytoplasmic domain (Suzuki et al., 2016, Jap J Clin Onc, 46:191-203).

As used herein, the term "immune checkpoint modulator" or "checkpoint modulator" refers to a molecule or to a compound that modulates the function of one or more checkpoint proteins. Immune checkpoint modulators are typically able to modulate self-tolerance and/or the amplitude and/or the duration of the immune response. Preferably, the immune checkpoint modulator used according to the present disclosure modulates the function of one or more human checkpoint proteins and is, thus, a "human checkpoint modulator". In a preferred embodiment, the human checkpoint modulator as used herein is an immune checkpoint inhibitor.

As used herein, "immune checkpoint inhibitor" or "checkpoint inhibitor" refers to a molecule that totally or partially reduces, inhibits, interferes with or negatively modulates one or more checkpoint proteins or that totally or partially reduces, inhibits, interferes with or negatively modulates expression of one or more checkpoint proteins. In certain embodiments, the immune checkpoint inhibitor binds to one or more checkpoint proteins. In certain embodiments, the immune checkpoint inhibitor binds to one or more molecules regulating checkpoint proteins. In certain embodiments, the immune checkpoint inhibitor binds to precursors of one or more checkpoint proteins e.g., on DNA- or RNA-level. Any agent that functions as a checkpoint inhibitor according to the present disclosure can be used.

The term "partially" as used herein means at least 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% in the level, e.g., in the level of inhibition of a checkpoint protein.

In certain embodiments, the immune checkpoint inhibitor suitable for use in the methods disclosed herein, is an antagonist of inhibitory signals, e.g., an antibody which targets, for example, PD-1, PD-L1, CTLA-4, LAG-3, B7-H3, B7-H4, or TIM-3. These ligands and receptors are reviewed in Pardoll, D., Nature. 12:252-264, 2012. Further immune checkpoint proteins that can be targeted according the disclosure are described herein.

In certain embodiments, the immune checkpoint inhibitor prevents inhibitory signals associated with the immune checkpoint. In certain embodiments, the immune checkpoint inhibitor is an antibody, or fragment thereof that disrupts inhibitory signaling associated with the immune checkpoint. In certain embodiments, the immune checkpoint inhibitor is a small molecule inhibitor that disrupts inhibitory signaling. In certain embodiments, the immune checkpoint inhibitor is a peptide-based inhibitor that disrupts inhibitory signaling. In certain embodiments, the immune checkpoint inhibitor is an inhibitory nucleic acid molecule that disrupts inhibitory signaling.

In certain embodiments, the immune checkpoint inhibitor is an antibody, fragment thereof, or antibody mimic, that prevents the interaction between checkpoint blocker proteins, e.g., an antibody, or fragment thereof that prevents the interaction between PD-1 and PD-L1 or PD-L2. In certain embodiments, the immune checkpoint inhibitor is an antibody, fragment thereof, or antibody mimic, that prevents the interaction between CTLA-4 and CD80 or CD86. In certain embodiments, the immune checkpoint inhibitor is an antibody, fragment thereof, or antibody mimic, that prevents the interaction between LAG-3 and its ligands, or TIM-3 and its ligands. In certain embodiments, the immune checkpoint inhibitor prevents inhibitory signaling through CD39 and/or CD73 and/or the interaction of A2AR and/or A2BR with adenosine. In certain embodiments, the immune checkpoint inhibitor prevents interaction of B7-H3 with its receptor and/or of B7-H4 with its receptor. In certain embodiments, the immune checkpoint inhibitor prevents the interaction of BTLA with its ligand HVEM. In certain embodiments, the immune checkpoint inhibitor prevents the interaction of one or more KIRs with their respective ligands. In certain embodiments, the immune checkpoint inhibitor prevents the interaction of LAG-3 with one or more of its ligands. In certain embodiments, the immune checkpoint inhibitor prevents the interaction of TIM-3 with one or more of its ligands Galectin-9, PtdSer, HMGB1 and CEACAM1. In certain embodiments, the immune checkpoint inhibitor prevents the interaction of TIGIT with one or more of its ligands PVR, PVRL2 and PVRL3. In certain embodiments, the immune checkpoint inhibitor prevents the interaction of CD94/NKG2A with HLA-E. In certain embodiments, the immune checkpoint inhibitor prevents the interaction of VISTA with one or more of its binding partners. In certain embodiments, the immune checkpoint inhibitor prevents the interaction of one or more Siglecs and their respective ligands. In certain embodiments, the immune checkpoint inhibitor prevents CD20 signaling. In certain embodiments, the immune checkpoint inhibitor prevents the interaction of GARP with one or more of its ligands. In certain embodiments, the immune checkpoint inhibitor prevents the interaction of CD47 with SIRPα. In certain embodiments, the immune checkpoint inhibitor prevents the interaction of PVRIG with PVRL2. In certain embodiments, the immune checkpoint inhibitor prevents the interaction of CSF1R with CSF1. In certain embodiments, the immune checkpoint inhibitor prevents NOX signaling. In certain embodiments, the immune checkpoint inhibitor prevents IDO and/or TDO signaling. Inhibiting or blocking of inhibitory immune checkpoint signaling, as described herein, results in preventing or reversing immune-suppression and establishment or enhancement of T cell immunity against cancer cells. In one embodiment, inhibition of immune checkpoint signaling, as described herein, reduces or inhibits dysfunction of the immune system. In one embodiment, inhibition of immune checkpoint signaling, as described herein, renders dysfunctional immune cells less dysfunctional. In one embodiment, inhibition of immune checkpoint signaling, as described herein, renders a dysfunctional T cell less dysfunctional.

The term "dysfunction", as used herein, refers to a state of reduced immune responsiveness to antigenic stimulation. The term includes the common elements of both exhaustion and/or anergy in which antigen recognition may occur, but the ensuing immune response is ineffective to control infection or tumor growth. Dysfunction also includes a state in which antigen recognition is retarded due to dysfunctional immune cells.

The term "dysfunctional", as used herein, refers to an immune cell that is in a state of reduced immune responsiveness to antigen stimulation. Dysfunctional includes unresponsive to antigen recognition and impaired capacity to translate antigen recognition into downstream T cell effector functions, such as proliferation, cytokine production (e.g., IL-2) and/or target cell killing.

The term "anergy", as used herein, refers to the state of unresponsiveness to antigen stimulation resulting from incomplete or insufficient signals delivered through the T cell receptor (TCR). T cell anergy can also result upon stimulation with antigen in the absence of co-stimulation, resulting in the cell becoming refractory to subsequent activation by the antigen even in the context of co-stimulation. The unresponsive state can often be overridden by the presence of IL-2. Anergic T cells do not undergo clonal expansion and/or acquire effector functions.

The term "exhaustion", as used herein, refers to immune cell exhaustion, such as T cell exhaustion as a state of T cell dysfunction that arises from sustained TCR signaling that occurs during many chronic infections and cancer. It is distinguished from anergy in that it arises not through incomplete or deficient signaling, but from sustained signaling. Exhaustion is defined by poor effector function, sustained expression of inhibitory receptors and a transcriptional state distinct from that of functional effector or memory T cells. Exhaustion prevents optimal control of diseases (e.g., infection and tumors). Exhaustion can result from both extrinsic negative regulatory pathways (e.g., immunoregulatory cytokines) as well as cell intrinsic negative regulatory pathways (inhibitory immune checkpoint pathways, such as described herein).

"Enhancing T cell function" means to induce, cause or stimulate a T cell to have a sustained or amplified biological function, or renew or reactivate exhausted or inactive T cells. Examples of enhancing T cell function include increased secretion of y-interferon from CD8+ T cells, increased proliferation, increased antigen responsiveness (e.g., tumor clearance) relative to such levels before the intervention. In one embodiment, the level of enhancement is as least 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 200%, or more. Manners of measuring this enhancement are known to one of ordinary skill in the art.

The immune checkpoint inhibitor may be an inhibitory nucleic acid molecule. The term "inhibitory nucleic acid" or "inhibitory nucleic acid molecule" as used herein refers to a nucleic acid molecule, e.g., DNA or RNA, that totally or partially reduces, inhibits, interferes with or negatively modulates one or more checkpoint proteins. Inhibitory nucleic acid molecules include, without limitation, oligonucleotides, siRNA, shRNA, antisense DNA or RNA molecules, and aptamers (e.g., DNA or RNA aptamers).

The term "oligonucleotide" as used herein refers to a nucleic acid molecule that is able to decrease protein expression, in particular expression of a checkpoint protein, such as the checkpoint proteins described herein. Oligonucleotides are short DNA or RNA molecules, typically comprising from 2 to 50 nucleotides. Oligonucleotides may be single-stranded or double-stranded. A checkpoint inhibitor oligonucleotide may be an antisense-oligonucleotide. Antisense-oligonucleotides are single-stranded DNA or RNA molecules that are complementary to a given sequence, in particular to a sequence of the nucleic acid sequence (or a fragment thereof) of a checkpoint protein. Antisense RNA is typically used to prevent protein translation of mRNA, e.g., of mRNA encoding a checkpoint protein, by binding to said mRNA. Antisense DNA is typically used to target a specific, complementary (coding or non-coding) RNA. If binding takes place, such a DNA/RNA hybrid can be degraded by the enzyme RNase H. Moreover, morpholino antisense oligonucleotides can be used for gene knockdowns in vertebrates. For example, Kryczek et al., 2006 (J Exp Med, 203:871-81) designed B7-H4-specific morpholinos that specifically blocked B7-H4 expression in macrophages, resulting in increased T cell proliferation and reduced tumor volumes in mice with tumor associated antigen (TAA)-specific T cells.

The terms "siRNA" or "small interfering RNA" or "small inhibitory RNA" are used interchangeably herein and refer to a double-stranded RNA molecule with a typical length of 20-25 base pairs that interferes with expression of a specific gene, such as a gene coding for a checkpoint protein, with a complementary nucleotide sequence. In one embodiment, siRNA interferes with mRNA therefore blocking translation, e.g., translation of an immune checkpoint protein. Transfection of exogenous siRNA may be used for gene knockdown, however, the effect may be only transient, especially in rapidly dividing cells. Stable transfection may be achieved, e.g., by RNA modification or by using an expression vector. Useful modifications and vectors for stable transfection of cells with siRNA are known in the art. siRNA sequences may also be modified to introduce a short loop between the two strands resulting in a "small hairpin RNA" or "shRNA". shRNA can be processed into a functional siRNA by Dicer. shRNA has a relatively low rate of degradation and turnover. Accordingly, the immune checkpoint inhibitor may be a shRNA.

The term "aptamer" as used herein refers to a single-stranded nucleic acid molecule, such as DNA or RNA, typically in a length of 25-70 nucleotides that is capable of binding to a target molecule, such as a polypeptide. In one embodiment, the aptamer binds to an immune checkpoint protein such as the immune checkpoint proteins described herein. For example, an aptamer according to the disclosure can specifically bind to an immune checkpoint protein or polypeptide, or to a molecule in a signaling pathway that modulates the expression of an immune checkpoint protein or polypeptide. The generation and therapeutic use of aptamers is well known in the art (see, e.g., U.S. Pat. No. 5,475,096).

The terms "small molecule inhibitor" or "small molecule" are used interchangeably herein and refer to a low molecular weight organic compound, usually up to 1000 daltons, that totally or partially reduces, inhibits, interferes with, or negatively modulates one or more checkpoint proteins as described above. Such small molecular inhibitors are usually synthesized by organic chemistry, but may also be isolated from natural sources, such as plants, fungi, and microbes. The small molecular weight allows a small molecule inhibitor to rapidly diffuse across cell membranes. For example, various A2AR antagonists known in the art are organic compounds having a molecular weight below 500 daltons.

The immune checkpoint inhibitor may be an antibody, an antigen-binding fragment thereof, an antibody mimic or a fusion protein comprising an antibody portion with an antigen-binding fragment of the required specificity. Antibodies or antigen-binding fragments thereof are as described herein. Antibodies or antigen-binding fragments thereof that are immune checkpoint inhibitors include in particular antibodies or antigen-binding fragments thereof that bind to immune checkpoint proteins, such as immune checkpoint receptors or immune checkpoint receptor ligands. Antibodies or antigen-binding fragments may also be conjugated to further moieties, as described herein. In particular, antibodies or antigen-binding fragments thereof are chimerized, humanized or human antibodies. Preferably, immune checkpoint inhibitor antibodies or antigen-binding fragments thereof are antagonists of immune checkpoint receptors or of immune checkpoint receptor ligands.

In a preferred embodiment, an antibody that is an immune checkpoint inhibitor, is an isolated antibody.

The antibody that is an immune checkpoint inhibitor or the antigen-binding fragment thereof according to the present disclosure may also be an antibody that cross-competes for antigen binding with any known immune checkpoint inhibitor antibody. In certain embodiments, an immune checkpoint inhibitor antibody cross-competes with one or more of the immune checkpoint inhibitor antibodies described herein. The ability of antibodies to cross-compete for binding to an antigen indicates that these antibodies may bind to the same epitope region of the antigen or when binding to another epitope sterically hinder the binding of known immune checkpoint inhibitor antibodies to that particular epitope region. These cross-competing antibodies may have functional properties very similar to those they are cross-competing with as they are expected to block binding of the immune checkpoint to its ligand either by binding to the same epitope or by sterically hindering the binding of the ligand. Cross-competing antibodies can be readily identified based on their ability to cross-compete with one or more of known antibodies in standard binding assays such as Surface Plasmon Resoncance analysis, ELISA assays or flow cytometry (see, e.g., WO 2013/173223).

In certain embodiments, antibodies or antigen binding fragments thereof that cross-compete for binding to a given antigen with, or bind to the same epitope region of a given antigen as, one or more known antibodies are monoclonal antibodies. For administration to human patients, these cross-competing antibodies can be chimeric antibodies, or humanized or human antibodies. Such chimeric, humanized or human monoclonal antibodies can be prepared and isolated by methods well known in the art.

The checkpoint inhibitor may also be in the form of the soluble form of the molecules (or variants thereof) themselves, e.g., a soluble PD-L1 or PD-L1 fusion.

In the context of the disclosure, more than one checkpoint inhibitor can be used, wherein the more than one checkpoint inhibitors are targeting distinct checkpoint pathways or the same checkpoint pathway. Preferably, the more than one checkpoint inhibitors are distinct checkpoint inhibitors. Preferably, if more than one distinct checkpoint inhibitor is used, in particular at least 2, 3, 4, 5, 6, 7, 8, 9 or 10 distinct checkpoint inhibitors are used, preferably 2, 3, 4 or 5 distinct checkpoint inhibitors are used, more preferably 2, 3 or 4 distinct checkpoint inhibitors are used, even more preferably 2 or 3 distinct checkpoint inhibitors are used and most preferably 2 distinct checkpoint inhibitors are used. Preferred examples of combinations of distinct checkpoint inhibitors include combination of an inhibitor of PD-1 signaling and an inhibitor of CTLA-4 signaling, an inhibitor of PD-1 signaling and an inhibitor of TIGIT signaling, an inhibitor of PD-1 signaling and an inhibitor of B7-H3 and/or B7-H4 signaling, an inhibitor of PD-1 signaling and an inhibitor of BTLA signaling, an inhibitor of PD-1 signaling and an inhibitor of KIR signaling, an inhibitor of PD-1 signaling and an inhibitor of LAG-3 signaling, an inhibitor of PD-1 signaling and an inhibitor of TIM-3 signaling, an inhibitor of PD-1 signaling and an inhibitor of CD94/NKG2A signaling, an inhibitor of PD-1 signaling and an inhibitor of IDO signaling, an inhibitor of PD-1 signaling and an inhibitor of adenosine signaling, an inhibitor of PD-1 signaling and an inhibitor of VISTA signaling, an inhibitor of PD-1 signaling and an inhibitor of Siglec signaling, an inhibitor of PD-1 signaling and an inhibitor of CD20 signaling, an inhibitor of PD-1 signaling and an inhibitor of GARP signaling, an inhibitor of PD-1 signaling and an inhibitor of CD47 signaling, an inhibitor of PD-1 signaling and an inhibitor of PVRIG signaling, an inhibitor of PD-1 signaling and an inhibitor of CSF1R signaling, an inhibitor of PD-1 signaling and an inhibitor of NOX signaling, and an inhibitor of PD-1 signaling and an inhibitor of TDO signaling.

In certain embodiments, the inhibitory immunoregulator (immune checkpoint blocker) is a component of the PD-1/PD-L1 or PD-1/PD-L2 signaling pathway. Accordingly, certain embodiments of the disclosure provide for administering to a subject a checkpoint inhibitor of the PD-1 signaling pathway. In certain embodiments, the checkpoint inhibitor of the PD-1 signaling pathway is a PD-1 inhibitor. In certain embodiments, the checkpoint inhibitor of the PD-1 signaling pathway is a PD-1 ligand inhibitor, such as a PD-L1 inhibitor or a PD-L2 inhibitor. In a preferred embodiment, the checkpoint inhibitor of the PD-1 signaling pathway is an antibody or an antigen-binding portion thereof that disrupts the interaction between the PD-1 receptor and one or more of its ligands, PD-L1 and/or PD-L2. Antibodies which bind to PD-1 and disrupt the interaction between PD-1 and one or more of its ligands are known in the art. In certain embodiments, the antibody or antigen-binding portion thereof binds specifically to PD-1. In certain embodiments, the antibody or antigen-binding portion thereof binds specifically to PD-L1 and inhibits its interaction with PD-1, thereby increasing immune activity. In certain embodiments, the antibody or antigen-binding portion thereof binds specifically to PD-L2 and inhibits its interaction with PD-1, thereby increasing immune activity. In certain embodiments, the inhibitory immunoregulator is a component of the CTLA-4 signaling pathway. Accordingly, certain embodiments of the disclosure provide for administering to a subject a checkpoint inhibitor of the CTLA-4 signaling pathway. In certain embodiments, the checkpoint inhibitor of the CTLA-4 signaling pathway is a CTLA-4 inhibitor. In certain embodiments, the checkpoint inhibitor of the CTLA-4 signaling pathway is a CTLA-4 ligand inhibitor.

In certain embodiments, the inhibitory immunoregulator is a component of the TIGIT signaling pathway. Accordingly, certain embodiments of the disclosure provide for administering to a subject a checkpoint inhibitor of the TIGIT signaling pathway. In certain embodiments, the checkpoint inhibitor of the TIGIT signaling pathway is a TIGIT inhibitor. In certain embodiments, the checkpoint inhibitor of the TIGIT signaling pathway is a TIGIT ligand inhibitor.

In certain embodiments, the inhibitory immunoregulator is a component of the B7 family signaling pathway. In certain embodiments, the B7 family members are B7-H3 and B7-H4. Certain embodiments of the disclosure provide for administering to a subject a checkpoint inhibitor of B7-H3 and/or B7-4. Accordingly, certain embodiments of the disclosure provide for administering to a subject an antibody or an antigen-binding portion thereof that targets B7-H3 or B7-H4. The B7 family does not have any defined receptors but these ligands are upregulated on tumor cells or tumor-infiltrating cells. Preclinical mouse models have shown that blockade of these ligands can enhance anti-tumor immunity.

In certain embodiments, the inhibitory immunoregulator is a component of the BTLA signaling pathway. Accordingly, certain embodiments of the disclosure provide for administering to a subject a checkpoint inhibitor of the BTLA signaling pathway. In certain embodiments, the checkpoint inhibitor of the BTLA signaling pathway is a BTLA inhibitor. In certain embodiments, the checkpoint inhibitor of the BTLA signaling pathway is a HVEM inhibitor. In certain embodiments, the inhibitory immunoregulator is a component of one or more KIR signaling pathways. Accordingly, certain embodiments of the disclosure provide for administering to a subject a checkpoint inhibitor of one or more KIR signaling pathways. In certain embodiments, the checkpoint inhibitor of one or more KIR signaling pathways is a KIR inhibitor. In certain embodiments, the checkpoint inhibitor one or more KIR signaling pathways is a KIR ligand inhibitor. For example, the KIR inhibitor according to the present disclosure may be an anti-KIR antibody that binds to KIR2DL1, KIR2DL2, and/or KIR2DL3.

In certain embodiments, the inhibitory immunoregulator is a component of the LAG-3 signaling pathway. Accordingly, certain embodiments of the disclosure provide for administering to a subject a checkpoint inhibitor of LAG-3 signaling. In certain embodiments, the checkpoint inhibitor of the LAG-3 signaling pathway is a LAG-3 inhibitor. In certain embodiments, the checkpoint inhibitor of the LAG-3 signaling pathway is a LAG-3 ligand inhibitor.

In certain embodiments, the inhibitory immunoregulator is a component of the TIM-3 signaling pathway. Accordingly, certain embodiments of the disclosure provide for administering to a subject a checkpoint inhibitor of the TIM-3 signaling pathway. In certain embodiments, the checkpoint inhibitor of the TIM-3 signaling pathway is a TIM-3 inhibitor. In certain embodiments, the checkpoint inhibitor of the TIM-3 signaling pathway is a TIM-3 ligand inhibitor.

In certain embodiments, the inhibitory immunoregulator is a component of the CD94/NKG2A signaling pathway. Accordingly, certain embodiments of the disclosure provide for administering to a subject a checkpoint inhibitor of the CD94/NKG2A signaling pathway. In certain embodiments, the checkpoint inhibitor of the CD94/NKG2A signaling pathway is a CD94/NKG2A inhibitor. In certain embodiments, the checkpoint inhibitor of the CD94/NKG2A signaling pathway is a CD94/NKG2A ligand inhibitor.

In certain embodiments, the inhibitory immunoregulator is a component of the IDO signaling pathway. Accordingly, certain embodiments of the disclosure provide for administering to a subject a checkpoint inhibitor of the IDO signaling pathway, e.g., an IDO inhibitor.

In certain embodiments, the inhibitory immunoregulator is a component of the adenosine signaling pathway. Accordingly, certain embodiments of the disclosure provide for administering to a subject a checkpoint inhibitor of the adenosine signaling pathway. In certain embodiments, the checkpoint inhibitor of the adenosine signaling pathway is a CD39 inhibitor. In certain embodiments, the checkpoint inhibitor of the adenosine signaling pathway is a CD73 inhibitor. In certain embodiments, the checkpoint inhibitor of the adenosine signaling pathway is an A2AR inhibitor. In certain embodiments, the checkpoint inhibitor of the adenosine signaling pathway is an A2BR inhibitor.

In certain embodiments, the inhibitory immunoregulator is a component of the VISTA signaling pathway. Accordingly, certain embodiments of the disclosure provide for administering to a subject a checkpoint inhibitor of the VISTA signaling pathway. In certain embodiments, the checkpoint inhibitor of the VISTA signaling pathway is a VISTA inhibitor. In certain embodiments, the inhibitory immunoregulator is a component of one or more Siglec signaling pathways. Accordingly, certain embodiments of the disclosure provide for administering to a subject a checkpoint inhibitor of one or more Siglec signaling pathways. In certain embodiments, the checkpoint inhibitor of one or more Siglec signaling pathways is a Siglec inhibitor. In certain embodiments, the checkpoint inhibitor of one or more Siglec signaling pathways is a Siglec ligand inhibitor.

In certain embodiments, the inhibitory immunoregulator is a component of the CD20 signaling pathway. Accordingly, certain embodiments of the disclosure provide for administering to a subject a checkpoint inhibitor of the CD20 signaling pathway. In certain embodiments, the checkpoint inhibitor of the CD20 signaling pathway is a CD20 inhibitor.

In certain embodiments, the inhibitory immunoregulator is a component of the GARP signaling pathway. Accordingly, certain embodiments of the disclosure provide for administering to a subject a checkpoint inhibitor of the GARP signaling pathway. In certain embodiments, the checkpoint inhibitor of the GARP signaling pathway is a GARP inhibitor.

In certain embodiments, the inhibitory immunoregulator is a component of the CD47 signaling pathway. Accordingly, certain embodiments of the disclosure provide for administering to a subject a checkpoint inhibitor of the CD47 signaling pathway. In certain embodiments, the checkpoint inhibitor of the CD47 signaling pathway is a CD47 inhibitor. In certain embodiments, the checkpoint inhibitor of the CD47 signaling pathway is a SIRPα inhibitor. In certain embodiments, the inhibitory immunoregulator is a component of the PVRIG signaling pathway. Accordingly, certain embodiments of the disclosure provide for administering to a subject a checkpoint inhibitor of the PVRIG signaling pathway. In certain embodiments, the checkpoint inhibitor of the PVRIG signaling pathway is a PVRIG inhibitor. In certain embodiments, the checkpoint inhibitor of the PVRIG signaling pathway is a PVRIG ligand inhibitor.

In certain embodiments, the inhibitory immunoregulator is a component of the CSF1R signaling pathway. Accordingly, certain embodiments of the disclosure provide for administering to a subject a checkpoint inhibitor of the CSF1R signaling pathway. In certain embodiments, the checkpoint inhibitor of the CSF1R signaling pathway is a CSF1R inhibitor. In certain embodiments, the checkpoint inhibitor of the CSF1R signaling pathway is a CSF1 inhibitor.

In certain embodiments, the inhibitory immunoregulator is a component of the NOX signaling pathway. Accordingly, certain embodiments of the disclosure provide for administering to a subject a checkpoint inhibitor of the NOX signaling pathway, e.g., a NOX inhibitor. In certain embodiments, the inhibitory immunoregulator is a component of the TDO signaling pathway. Accordingly, certain embodiments of the disclosure provide for administering to a subject a checkpoint inhibitor of the TDO signaling pathway, e.g., a TDO inhibitor.

Exemplary PD-1 inhibitors include, without limitation, anti-PD-1 antibodies such as BGB-A317 (BeiGene; see U.S. Pat. No. 8,735,553, WO 2015/35606 and US 2015/0079109), cemiplimab (Regeneron; see WO 2015/112800) and lambrolizumab (e.g., disclosed as hPD109A and its humanized derivatives h409A1, h409A16 and h409A17 in WO2008/156712), AB137132 (Abcam), EH12.2H7 and RMP1-14 (#BE0146; Bioxcell Lifesciences Pvt. LTD.), MIH4 (Affymetrix eBioscience), nivolumab (OPDIVO, BMS-936558; Bristol Myers Squibb; see WO 2006/121168), pembrolizumab (KEYTRUDA; MK-3475; Merck; see WO 2008/156712), pidilizumab (CT-011; CureTech; see Hardy et al., 1994, Cancer Res., 54 (22): 5793-6 and WO 2009/101611), PDR001 (Novartis; see WO 2015/112900), MEDI0680 (AMP-514; AstraZeneca; see WO 2012/145493), TSR-042 (see WO 2014/179664), REGN-2810 (H4H7798N; cf. US 2015/0203579), JS001 (TAIZHOU JUNSHI PHARMA; see Si-Yang Liu et al., 2007, J. Hematol. Oncol. 70:136), AMP-224 (GSK-2661380; cf. Li et al., 2016, Int J Mol Sci 17 (7): 1151 and WO 2010/027827 and WO 2011/066342), PF-06801591 (Pfizer), BGB-A317 (BeiGene; see WO 2015/35606 and US 2015/0079109), BI 754091, SHR-1210 (see WO2015/085847), and antibodies 17D8, 2D3, 4H1, 4A11, 7D3, and 5F4 as described in WO 2006/121168, INCSHR1210 (Jiangsu Hengrui Medicine; also known as SHR-1210; see WO 2015/085847), TSR-042 (Tesaro Biopharmaceutical; also known as ANB011; see WO2014/179664), GLS-010 (Wuxi/Harbin Gloria Pharmaceuticals; also known as WBP3055; see Si-Yang et al., 2017, J. Hematol. Oncol. 70:136), STI-1110 (Sorrento Therapeutics; see WO 2014/194302), AGEN2034 (Agenus; see WO 2017/040790), MGA012 (Macrogenics; see WO 2017/19846), IBI308 (Innovent; see WO 2017/024465, WO 2017/025016, WO 2017/132825, and WO 2017/133540), anti-PD-1 antibodies as described, e.g., in U.S. Pat. Nos. 7,488,802, 8,008,449, 8,168,757, WO 03/042402, WO 2010/089411 (further disclosing anti-PD-L1 antibodies), WO 2010/036959, WO 2011/159877 (further disclosing antibodies against TIM-3), WO 2011/082400, WO 2011/161699, WO 2009/014708, WO 03/099196, WO 2009/114335, WO 2012/145493 (further disclosing antibodies against PD-L1), WO 2015/035606, WO 2014/055648 (further disclosing anti-KIR antibodies), US 2018/0185482 (further disclosing anti-PD-L1 and anti-TIGIT antibodies), U.S. Pat. Nos. 8,008,449, 8,779,105, 6,808,710, 8,168,757, US 2016/0272708, and U.S. Pat. No. 8,354,509, small molecule antagonists to the PD-1 signaling pathway as disclosed, e.g., in Shaabani et al., 2018, Expert Op Ther Pat., 28 (9): 665-678 and Sasikumar and Ramachandra, 2018, BioDrugs, 32 (5): 481-497, siRNAs directed to PD-1 as disclosed, e.g., in WO 2019/000146 and WO 2018/103501, soluble PD-1 proteins as disclosed in WO 2018/222711 and oncolytic viruses comprising a soluble form of PD-1 as described, e.g., in WO 2018/022831.

In a certain embodiment, the PD-1 inhibitor is nivolumab (OPDIVO; BMS-936558), pembrolizumab (KEYTRUDA; MK-3475), pidilizumab (CT-011), PDR001, MEDI0680 (AMP-514), TSR-042, REGN2810, JS001, AMP-224 (GSK-2661380), PF-06801591, BGB-A317, BI 754091, or SHR-1210.

Exemplary PD-1 ligand inhibitors are PD-L1 inhibitors and PD-L2 inhibitors and include, without limitation, anti-PD-L1 antibodies such as MEDI4736 (durvalumab; AstraZeneca; see WO 2011/066389), MSB-0010718C (see US 2014/0341917), YW243.55.S70 (see SEQ ID NO: 20 of WO 2010/077634 and U.S. Pat. No. 8,217,149), MIH1 (Affymetrix eBioscience; cf. EP 3 230 319), MDX-1105 (Roche/

Genentech; see WO2013019906 and U.S. Pat. No. 8,217,149) STI-1014 (Sorrento; see WO2013/181634), CK-301 (Checkpoint Therapeutics), KN035 (3D Med/Alphamab; see Zhang et al., 2017, Cell Discov. 3:17004), atezolizumab (TECENTRIQ; RG7446; MPDL3280A; R05541267; see U.S. Pat. No. 9,724,413), BMS-936559 (Bristol Myers Squibb; see U.S. Pat. No. 7,943,743, WO 2013/173223), avelumab (bavencio; cf. US 2014/0341917), LY3300054 (Eli Lilly Co.), CX-072 (Proclaim-CX-072; also called CytomX; see WO2016/149201), FAZ053, KN035 (see WO2017020801 and WO2017020802), MDX-1105 (see US 2015/0320859), anti-PD-L1 antibodies disclosed in U.S. Pat. No. 7,943,743, including 3G10, 12A4 (also referred to as BMS-936559), 10A5, 5F8, 10H10, 1B12, 7H1, 11E6, 12B7, and 13G4, anti-PD-L1 antibodies as described in WO 2010/077634, U.S. Pat. No. 8,217,149, WO 2010/036959, WO 2010/077634, WO 2011/066342, U.S. Pat. Nos. 8,217,149, 7,943,743, WO 2010/089411, U.S. Pat. Nos. 7,635,757, 8,217,149, US 2009/0317368, WO 2011/066389, WO2017/034916, WO2017/020291, WO2017/020858, WO2017/020801, WO2016/111645, WO2016/197367, WO2016/061142, WO2016/149201, WO2016/000619, WO2016/160792, WO2016/022630, WO2016/007235, WO2015/179654, WO2015/173267, WO2015/181342, WO2015/109124, WO 2018/222711, WO2015/112805, WO2015/061668, WO2014/159562, WO2014/165082, WO2014/100079.

Exemplary CTLA-4 inhibitors include, without limitation, the monoclonal antibodies ipilimumab (Yervoy; Bristol Myers Squibb) and tremelimumab (Pfizer/MedImmune), trevilizumab, AGEN-1884 (Agenus) and ATOR-1015, the anti-CTLA4 antibodies disclosed in WO 2001/014424, US 2005/0201994, EP 1212422, U.S. Pat. Nos. 5,811,097, 5,855,887, 6,051,227, 6,682,736, 6,984,720, WO 01/14424, WO 00/37504, US 2002/0039581, US 2002/086014, WO 98/42752, U.S. Pat. Nos. 6,207,156, 5,977,318, 7,109,003, and 7,132,281, the dominant negative proteins abatacept (Orencia; see EP 2 855 533), which comprises the Fe region of lgG 1 fused to the CTLA-4 ECD, and belatacept (Nulojix; see WO 2014/207748), a second generation higher-affinity CTLA-4-Ig variant with two amino acid substitutions in the CTLA-4 ECD relative to abatacept, soluble CTLA-4 polypeptides, e.g., RG2077 and CTLA4-IgG4m (see U.S. Pat. No. 6,750,334), anti-CTLA-4 aptamers and siRNAs directed to CTLA-4, e.g., as disclosed in US 2015/203848. Exemplary CTLA-4 ligand inhibitors are described in Pile et al., 2015 (Encyclopedia of Inflammatory Diseases, M. Parnham (ed.), doi: 10.1007/978-3-0348-0620-6_20).

Exemplary checkpoint inhibitors of the TIGIT signaling pathway include, without limitation, anti-TIGIT antibodies, such as BMS-986207, COM902 (CGEN-15137; Compugen), AB154 (Arcus Biosciences) or etigilimab (OMP-313M32; OncoMed Pharmaceuticals), or the antibodies disclosed in WO2017/059095, in particular “MAB10”, US 2018/0185482, WO 2015/009856, and US 2019/0077864.

Exemplary checkpoint inhibitors of B7-H3 include, without limitation, the Fc-optimized monoclonal antibody enoblituzumab (MGA271; Macrogenics; see US 2012/0294796) and the anti-B7-H3 antibodies MGD009 (Macrogenics) and pidilizumab (see U.S. Pat. No. 7,332,582).

Exemplary B7-H4 inhibitors include, without limitation, antibodies as described in Dangaj et al., 2013 (Cancer Research 73:4820-9) and in Smith et al., 2014 (Gynecol Oncol, 134:181-189), WO 2013/025779 (e.g., 2D1 encoded by SEQ ID NOs: 3 and 4, 2H9 encoded by SEQ ID NO: 37 and 39, and 2E11 encoded by SEQ ID NOs: 41 and 43) and in WO 2013/067492 (e.g., an antibody with an amino acid sequence selected from SEQ ID NOs: 1-8), morpholino antisense oligonucleotides, e.g., as described by Kryczek et al., 2006 (J Exp Med, 203:871-81), or soluble recombinant forms of B7-H4, such as disclosed in US 2012/0177645.

Exemplary BTLA inhibitors include, without limitation, the anti-BTLA antibodies described in Crawford and Wherry, 2009 (*J Leukocyte Biol* 86:5-8), WO 2011/014438 (e.g., 4C7 or an antibody comprising heavy and light chains according to SEQ ID NOs: 8 and 15 and/or SEQ ID NOs: 11 and 18), WO 2014/183885 (e.g., the antibody deposited under the number CNCM I-4752) and US 2018/155428.

Checkpoint inhibitors of KIR signaling include, without limitation, the monoclonal antibodies lirilumab (1-7F9; IPH2102; see see U.S. Pat. No. 8,709,411), IPH4102 (Innate Pharma; see Marie-Cardine et al., 2014, *Cancer* 74 (21): 6060-70), anti-KIR antibodies as disclosed, e.g., in US 2018/208652, US 2018/117147, US 2015/344576, WO 2005/003168, WO 2005/009465, WO 2006/072625, WO 2006/072626, WO 2007/042573, WO 2008/084106 (e.g., an antibody comprising heavy and light chains according to SEQ ID NOs: 2 and 3), WO 2010/065939, WO 2012/071411, WO 2012/160448 and WO 2014/055648.

LAG-3 inhibitors include, without limitation, the anti-LAG-3 antibodies BMS-986016 (Bristol-Myers Squibb; see WO 2014/008218 and WO 2015/116539), 25F7 (see US2011/0150892), IMP731 (see WO 2008/132601), H5L7BW (cf. WO2014140180), MK-4280 (28G-10; Merck; see WO 2016/028672), REGN3767 (Regneron/Sanofi), BAP050 (see WO 2017/019894), IMP-701 (LAG-525; Novartis) Sym022 (Symphogen), TSR-033 (Tesaro), MGD013 (a bispecific DART antibody targeting LAG-3 and PD-1 developed by MacroGenics), BI754111 (Boehringer Ingelheim), FS118 (a bispecific antibody targeting LAG-3 and PD-1 developed by F-star), GSK2831781 (GSK) and antibodies as disclosed in WO 2009/044273, WO 2008/132601, WO 2015/042246, EP 2 320 940, US 2019/169294, US 2019/169292, WO 2016/028672, WO 2016/126858, WO 2016/200782, WO 2015/200119, WO 2017/220569, WO 2017/087589, WO 2017/219995, WO 2017/019846, WO 2017/106129, WO 2017/062888, WO 2018/071500, WO 2017/087901, US 2017/0260271, WO 2017/198741, WO2017/220555, WO2017/015560, WO2017/025498, WO2017/149143, WO 2018/069500, WO2018/083087, WO2018/034227 WO2014/140180, the LAG-3 antagonistic protein AVA-017 (Avacta), the soluble LAG-3 fusion protein IMP321 (eftilagimod alpha; Immutep; see EP 2 205 257 and Brignone et al., 2007, *J. Immunol.,* 179:4202-4211), and soluble LAG-3 proteins disclosed in WO 2018/222711.

TIM-3 inhibitors include, without limitation, antibodies targeting TIM-3 such as F38-2E2 (BioLegend), cobolimab (TSR-022; Tesaro), LY3321367 (Eli Lilly), MBG453 (Novartis) and antibodies as disclosed in, e.g., WO 2013/006490, WO 2018/085469 (e.g., antibodies comprising heavy and light chain sequences encoded by nucleic acid sequences according to SEQ ID NOs: 3 and 4), WO 2018/106588, WO 2018/106529 (e.g., an antibody comprising heavy and light chain sequences according to SEQ ID NOs: 8-11).

TIM-3 ligand inhibitors include, without limitation, CEACAM1 inhibitors such as the anti-CEACAM1 antibody CM10 (cCAM Biotherapeutics; see WO 2013/054331), antibodies disclosed in WO 2015/075725 (e.g., CM-24, 26H7, 5F4, TEC-11, 12-140-4, Apr. 3, 2017, COL-4, F36-54, 34B1, YG-C28F2, D14HD11, M8.7.7, D11-AD11, HEA81, B I. I, CLB-gran-10, F34-187, T84.1, B6.2, B 1.13, YG-C94G7, 12-140-5, scFv DIATHIS1, TET-2; cCAM Biotherapeutics), antibodies described by Watt et al., 2001

(Blood, 98:1469-1479) and in WO 2010/12557 and PtdSer inhibitors such as bavituximab (Peregrine). CD94/NKG2A inhibitors include, without limitation, monalizumab (IPH2201; Innate Pharma) and the antibodies and method for their production as disclosed in U.S. Pat. No. 9,422,368 (e.g., humanized Z199; see EP 2 628 753), EP 3 193 929 and WO2016/032334 (e.g., humanized Z270; see EP 2 628 753).

IDO inhibitors include, without limitation, exiguamine A, epacadostat (INCB024360; InCyte; see U.S. Pat. No. 9,624, 185), indoximod (Newlink Genetics; CAS #: 110117-83-4), NLG919 (Newlink Genetics/Genentech; CAS #: 1402836-58-1), GDC-0919 (Newlink Genetics/Genentech; CAS #: 1402836-58-1), F001287 (Flexus Biosciences/BMS; CAS #: 2221034-29-1), KHK2455 (Cheong et al., 2018, Expert Opin Ther Pat. 28 (4): 317-330), PF-06840003 (see WO 2016/181348), navoximod (RG6078, GDC-0919, NLG919; CAS #: 1402837-78-8), linrodostat (BMS-986205;

Bristol-Myers Suibb; CAS #: 1923833-60-6), small molecules such as 1-methyl-tryptophan, pyrrolidine-2,5-dione derivatives (see WO 2015/173764) and the IDO inhibitors disclosed by Sheridan, 2015, Nat Biotechnol 33:321-322.

CD39 inhibitors include, without limitation, A001485 (Arcus Biosciences), PSB 069 (CAS #: 78510-31-3) and the anti-CD39 monoclonal antibody IPH5201 (Innate Pharma; see Perrot et al., 2019, Cell Reports 8:2411-2425.E9).

CD73 inhibitors include, without limitation, anti-CD73 antibodies such as CPI-006 (Corvus Pharmaceuticals), MEDI9447 (MedImmune; see WO2016075099), IPH5301 (Innate Pharma; see Perrot et al., 2019, Cell Reports 8:2411-2425.E9), the anti-CD73 antibodies described in WO2018/110555, the small molecule inhibitors PBS 12379 (Tocris Bioscience; CAS #: 1802226-78-3), A000830, A001190 and A001421 (Arcus Biosciences; see Becker et al., 2018, Cancer Research 78 (13 Supplement): 3691-3691, doi: 10.1158/1538-7445.AM2018-3691), CB-708 (Calithera Biosciences) and purine cytotoxic nucleoside analogue-based diphosphonates as described by Allard et al., 2018 (Immunol Rev., 276 (1): 121-144).

A2AR inhibitors include, without limitation, small molecule inhibitors such as istradefylline (KW-6002; CAS #: 155270-99-8), PBF-509 (Palobiopharma), ciforadenant (CPI-444: Corvus Pharma/Genentech; CAS #: 1202402-40-1), ST1535 ([2butyl-9-methyl-8-(2H-1,2,3-triazol 2-yl)-9H-purin-6-xylamine]; CAS #: 496955-42-1), ST4206 (see Stasi et al., 2015, *Europ J Pharm* 761:353-361; CAS #: 1246018-36-9), tozadenant (SYN115; CAS #: 870070-55-6), V81444 (see WO 2002/055082), preladenant (SCH420814; Merck; CAS #: 377727-87-2), vipadenant (BIIB014; CAS #: 442908-10-3), ST1535 (CAS #: 496955-42-1), SCH412348 (CAS #: 377727-26-9), SCH442416 (Axon 2283; Axon Medchem; CAS #: 316173-57-6), ZM241385 (4-(2-(7-amino-2-(2-furyl)-(1,2,4) triazolo (2,3-a)-(1,3,5)triazin-5-yl-amino)ethyl) phenol; Cas #: 139180-30-6), AZD4635 (AstraZeneca), AB928 (a dual A2AR/A2BR small molecule inhibitor; Arcus Biosciences) and SCH58261 (see Popoli et al., 2000, *Neuropsychopharm* 22:522-529; CAS #: 160098-96-4).

A2BR inhibitors include, without limitation, AB928 (a dual A2AR/A2BR small molecule inhibitor; Arcus Biosciences), MRS 1706 (CAS #: 264622-53-9), GS6201 (CAS #: 752222-83-6) and PBS 1115 (CAS #: 152529-79-8).

VISTA inhibitors include, without limitation, anti-VISTA antibodies such as JNJ-61610588 (onvatilimab; Janssen Biotech) and the small molecule inhibitor CA-170 (anti-PD-L1/L2 and anti-VISTA small molecule; CAS #: 1673534-76-3).

Siglec inhibitors include, without limitation, the anti-Sigle-7 antibodies disclosed in US 2019/023786 and WO 2018/027203 (e.g., an antibody comprising a variable heavy chain region according to SEQ ID NO: 1 and a variable light chain region according to SEQ ID NO: 15), the anti-Siglec-2 antibody inotuzumab ozogamicin (Besponsa; see U.S. Pat. Nos. 8,153,768 and 9,642,918), the anti-Siglec-3 antibody gemtuzumab ozogamicin (Mylotarg; see U.S. Pat. No. 9,359,442) or the anti-Siglec-9 antibodies disclosed in US 2019/062427, US 2019/023786, WO 2019/011855, WO 2019/011852 (e.g., an antibody comprising the CDRs according to SEQ ID NOs: 171-176, or 3 and 4, or 5 and 6, or 7 and 8, or 9 and 10, or 11 and 12, or 13 and 14, or 15 and 16, or 17 and 18, or 19 and 20, or 21 and 22, or 23 and 24, or 25 and 26), US 2017/306014 and EP 3 146 979.

CD20 inhibitors include, without limitation, anti-CD20 antibodies such as rituximab (RITUXAN; IDEC-102; IDEC-C2B8; see U.S. Pat. No. 5,843,439), ABP 798 (rituximab biosimilar), ofatumumab (2F2; see WO2004/035607), obinutuzumab, ocrelizumab (2h7; see WO 2004/056312), ibritumomab tiuxetan (Zevalin), tositumomab, ublituximab (LFB-R603; LFB Biotechnologies) and the antibodies disclosed in US 2018/0036306 (e.g., an antibody comprising light and heavy chains according to SEQ ID NOs: 1-3 and 4-6, or 7 and 8, or 9 and 10).

GARP inhibitors include, without limitation, anti-GARP antibodies such as ARGX-115 (arGEN-X) and the antibodies and methods for their production as disclosed in US 2019/127483, US 2019/016811, US 2018/327511, US 2016/251438, EP 3 253 796.

CD47 inhibitors include, without limitation, anti-CD47 antibodies such as HuF9-G4 (Stanford University/Forty Seven), CC-90002/INBRX-103 (Celgene/Inhibrx), SRF231 (Surface Oncology), IBI188 (Innovent Biologics), AO-176 (Arch Oncology), bispecific antibodies targeting CD47 including TG-1801 (NI-1701; bispecific monoclonal antibody targeting CD47 and CD19; Novimmune/TG Therapeutics) and NI-1801 (bispecific monoclonal antibody targeting CD47 and mesothelin; Novimmune), and CD47 fusion proteins such as ALX148 (ALX Oncology; see Kauder et al., 2019, PLoS One, doi: 10.1371/journal-.pone.0201832). SIRPα inhibitors include, without limitation, anti-SIRPα antibodies such as OSE-172 (Boehringer Ingelheim/OSE), FSI-189 (Forty Seven), anti-SIRPα fusion proteins such as TTI-621 and TTI-662 (Trillium Therapeutics; see WO 2014/094122).

PVRIG inhibitors include, without limitation, anti-PVRIG antibodies such as COM701 (CGEN-15029) and antibodies and method for their manufacture as disclosed in, e.g., WO 2018/033798 (e.g., CHA.7.518.1H4 (S241P), CHA.7.538.1.2.H4 (S241P), CPA.9.086H4 (S241P), CPA.9.083H4 (S241P), CHA.9.547.7.H4 (S241P), CHA.9.547.13.H4 (S241P) and antibodies comprising a variable heavy domain according to SEQ ID NO: 5 and a variable light domain according to SEQ ID NO: 10 of WO 2018/033798 or antibodies comprising a heavy chain according to SEQ ID NO:9 and a light chain according to SEQ ID NO: 14; WO 2018/033798 further discloses anti-TIGIT antibodies and combination therapies with anti-TIGIT and anti-PVRIG antibodies), WO2016134333, WO2018017864 (e.g., an antibody comprising a heavy chain according to SEQ ID NOs: 5-7 having at least 90% sequence identity to SEQ ID NO: 11 and/or a light chain according to SEQ ID NOs: 8-10 having at least 90% sequence identity to SEQ ID NO: 12, or an antibody encoded by SEQ ID NOs: 13 and/or 14 or SEQ ID NOs: 24 and/or 29, or another antibody disclosed in WO 2018/

017864) and anti-PVRIG antibodies and fusion peptides as disclosed in WO 2016/134335.

CSF1R inhibitors include, without limitation, anti-CSF1R antibodies cabiralizumab (FPA008; FivePrime; see WO 2011/140249, WO 2013/169264 and WO 2014/036357), IMC-CS4 (EliLilly), emactuzumab (R05509554; Roche), RG7155 (WO 2011/70024, WO 2011/107553, WO 2011/131407, WO 2013/87699, WO 2013/119716, WO 2013/132044) and the small molecule inhibitors BLZ945 (CAS #: 953769-46-5) and pexidartinib (PLX3397; Selleckchem; CAS #: 1029044-16-3).

CSF1 inhibitors include, without limitation, anti-CSF1 antibodies disclosed in EP 1 223 980 and Weir et al., 1996 (J Bone Mineral Res 11:1474-1481), WO 2014/132072, and antisense DNA and RNA as disclosed in WO 2001/030381.

Exemplary NOX inhibitors include, without limitation, NOX1 inhibitors such as the small molecule ML171 (Gianni et al., 2010, ACS Chem Biol 5 (10): 981-93, NOS31 (Yamamoto et al., 2018, Biol Pharm Bull. 41 (3): 419-426), NOX2 inhibitors such as the small molecules ceplene (histamine dihydrochloride; CAS #: 56-92-8), BJ-1301 (Gautam et al., 2017, Mol Cancer Ther 16 (10): 2144-2156; CAS #: 1287234-48-3) and inhibitors described by Lu et al., 2017, Biochem Pharmacol 143:25-38, NOX4 inhibitors such as the small molecule inhibitors VAS2870 (Altenhofer et al., 2012, Cell Mol Life Sciences 69 (14): 2327-2343), diphenylene iodonium (CAS #: 244-54-2) and GKT137831 (CAS #: 1218942-37-0; see Tang et al., 2018, 19 (10): 578-585). TDO inhibitors include, without limitation, 4-(indol-3-yl)-pyrazole derivatives (see U.S. Pat. No. 9,126,984 and US 2016/0263087), 3-indol substituted derivatives (see WO 2015/140717, WO 2017/025868, WO 2016/147144), 3-(indol-3-yl)-pyridine derivatives (see US 2015/0225367 and WO 2015/121812), dual IDO/TDO antagonist, such as small molecule dual IDO/TDO inhibitors disclosed in WO 2015/150097, WO 2015/082499, WO 2016/026772, WO 2016/071283, WO 2016/071293, WO 2017/007700, and the small molecule inhibitor CB548 (Kim, C, et al., 2018, Annals Oncol 29 (suppl_8): viii400-viii441).

According to the disclosure, the immune checkpoint inhibitor is an inhibitor of an inhibitory checkpoint protein but preferably not an inhibitor of a stimulatory checkpoint protein. As described herein, a number of CTLA-4, PD-1, TIGIT, B7-H3, B7-H4, BTLA, KIR, LAG-3, TIM-3, CD94/NKG2A, IDO, A2AR, A2BR, VISTA, Siglec, CD20, CD39, CD73, GARP, CD47, PVRIG, CSF1R, NOX and TDO inhibitors and inhibitors of respective ligands are known and several of them are already in clinical trials or even approved. Based on these known immune checkpoint inhibitors, alternative immune checkpoint inhibitors may be developed. In particular, known inhibitors of the preferred immune checkpoint proteins may be used as such or analogues thereof may be used, in particular chimerized, humanized or human forms of antibodies and antibodies cross-competing with any of the antibodies described herein.

It will be understood by one of ordinary skill in the art that other immune checkpoint targets can also be targeted by antagonists or antibodies, provided that the targeting results in the stimulation of an immune response such as an anti-tumor immune response as reflected in an increase in T cell proliferation, enhanced T cell activation, and/or increased cytokine production (e.g., IFN-γ, IL2).

Checkpoint inhibitors may be administered in any manner and by any route known in the art. The mode and route of administration will depend on the type of checkpoint inhibitor to be used.

Checkpoint inhibitors may be administered in the form of any suitable pharmaceutical composition as described herein.

Checkpoint inhibitors may be administered in the form of nucleic acid, such DNA or RNA molecules, encoding an immune checkpoint inhibitor, e.g., an inhibitory nucleic acid molecule or an antibody or fragment thereof. For example, antibodies can be delivered encoded in expression vectors, as described herein. Nucleic acid molecules can be delivered as such, e.g., in the form of a plasmid or mRNA molecule, or complexed with a delivery vehicle, e.g., a liposome, lipoplex or nucleic-acid lipid particles. Checkpoint inhibitors may also be administered via an oncolytic virus comprising an expression cassette encoding the checkpoint inhibitor. Checkpoint inhibitors may also be administered by administration of endogeneic or allogeneic cells able to express a checkpoint inhibitor, e.g., in the form of a cell based therapy.

The term "cell based therapy" refers to the transplantation of cells (e.g., T lymphocytes, dendritic cells, or stem cells) expressing an immune checkpoint inhibitor into a subject for the purpose of treating a disease or disorder (e.g., a cancer disease). In one embodiment, the cell based therapy comprises genetically engineered cells. In one embodiment, the genetically engineered cells express an immune checkpoint inhibitor, such as described herein. In one embodiment, the genetically engineered cells express an immune checkpoint inhibitor that is an inhibitory nucleic acid molecule, such as a siRNA, shRNA, an oligonucleotide, antisense DNA or RNA, an aptamer, an antibody or a fragment thereof or a soluble immune checkpoint protein or fusion. Genetically engineered cells may also express further agents that enhance T cell function. Such agents are known in the art. Cell based therapies for the use in inhibition of immune checkpoint signaling are disclosed, e.g., in WO 2018/222711, herein incorporated by reference in its entirety.

The term "oncolytic virus" as used herein, refers to a virus capable of selectively replicating in and slowing the growth or inducing the death of a cancerous or hyperproliferative cell, either in vitro or in vivo, while having no or minimal effect on normal cells. An oncolytic virus for the delivery of an immune checkpoint inhibitor comprises an expression cassette that may encode an immune checkpoint inhibitor that is an inhibitory nucleic acid molecule, such as a siRNA, shRNA, an oligonucleotide, antisense DNA or RNA, an aptamer, an antibody or a fragment thereof or a soluble immune checkpoint protein or fusion. The oncolytic virus preferably is replication competent and the expression cassette is under the control of a viral promoter, e.g., synthetic early/late poxvirus promoter. Exemplary oncolytic viruses include vesicular stomatitis virus (VSV), rhabdoviruses (e.g., picornaviruses such as Seneca Valley virus; SVV-001), coxsackievirus, parvovirus, Newcastle disease virus (NDV), herpes simplex virus (HSV; OncoVEX GMCSF), retroviruses (e.g., influenza viruses), measles virus, reovirus, Sinbis virus, vaccinia virus, as exemplarily described in WO 2017/209053 (including Copenhagen, Western Reserve, Wyeth strains), and adenovirus (e.g., Delta-24, Delta-24-RGD, ICOVIR-5, ICOVIR-7, Onyx-015, ColoAd1, H101, AD5/3-D24-GMCSF). Generation of recombinant oncolytic viruses comprising a soluble form of an immune checkpoint inhibitor and methods for their use are disclosed in WO 2018/022831, herein incorporated by reference in its entirety. Oncolytic viruses can be used as attenuated viruses.

As described herein, in one embodiment, HPV E6 vaccine RNA and HPV E7 vaccine RNA is administered together, i.e., co-administered, with a checkpoint inhibitor to a subject, e.g., a patient. In certain embodiments, the checkpoint inhibitor and the HPV E6 vaccine RNA/HPV E7 vaccine RNA are administered as a single composition to the subject. In certain embodiments, the checkpoint inhibitor and the HPV E6 vaccine RNA/HPV E7 vaccine RNA are administered concurrently (as separate compositions at the same time) to the subject. In certain embodiments, the checkpoint inhibitor and the HPV E6 vaccine RNA/HPV E7 vaccine RNA are administered separately to the subject. In certain embodiments, the checkpoint inhibitor is administered before the HPV E6 vaccine RNA/HPV E7 vaccine RNA to the subject. In certain embodiments, the checkpoint inhibitor is administered after the HPV E6 vaccine RNA/HPV E7 vaccine RNA to the subject. In certain embodiments, the checkpoint inhibitor and the HPV E6 vaccine RNA/HPV E7 vaccine RNA are administered to the subject on the same day. In certain embodiments, the checkpoint inhibitor and the HPV E6 vaccine RNA/HPV E7 vaccine RNA are administered to the subject on different days.

Platinum Compound

As used herein, the term "platinum compound" refers to compounds containing platinum in their structure such as platinum complexes. In some embodiments, this term refers to such compounds as used in platinum-based chemotherapy. In some embodiments, this term includes compounds such as cisplatin, carboplatin and oxaliplatin. In some embodiments, a platinum compound is cisplatin.

The term refers to "cisplatin" r "cisplatinum" the compound cis-diamminedichloroplatinum (II) (CDDP) of the following formula:

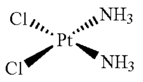

The term "carboplatin" refers to the compound cis-diammine (1,1-cyclobutanedicarboxylato) platinum (II) of the following formula:

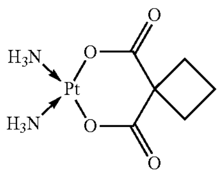

The term "oxaliplatin" refers to a compound which is a platinum compound that is complexed to a diaminocyclohexane carrier ligand of the following formula:

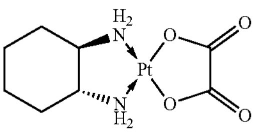

In particular, the term "oxaliplatin" refers to the compound [(1R,2R)-cyclohexane-1,2-diamine](ethanedioato-O, O') platinum (II). Oxaliplatin for injection is also marketed under the trade name Eloxatine.

A. Salt and Ionic Strength

According to the present disclosure, the compositions described herein may comprise salts such as sodium chloride. Without wishing to be bound by theory, sodium chloride functions as an ionic osmolality agent for preconditioning RNA prior to mixing with the at least one cationic lipid. Certain embodiments contemplate alternative organic or inorganic salts to sodium chloride in the present disclosure. Alternative salts include, without limitation, potassium chloride, dipotassium phosphate, monopotassium phosphate, potassium acetate, potassium bicarbonate, potassium sulfate, potassium acetate, disodium phosphate, monosodium phosphate, sodium acetate, sodium bicarbonate, sodium sulfate, sodium acetate, lithium chloride, magnesium chloride, magnesium phosphate, calcium chloride, and sodium salts of ethylenediaminetetraacetic acid (EDTA).

Generally, compositions comprising RNA lipoplex particles described herein comprise sodium chloride at a concentration that preferably ranges from 0 mM to about 500 mM, from about 5 mM to about 400 mM, or from about 10 mM to about 300 mM. In one embodiment, compositions comprising RNA lipoplex particles comprise an ionic strength corresponding to such sodium chloride concentrations.

B. Stabilizer

Compositions described herein may comprise a stabilizer to avoid substantial loss of the product quality and, in particular, substantial loss of RNA activity during freezing, lyophilization, spray-drying or storage such as storage of the frozen, lyophilized or spray-dried composition.

In an embodiment the stabilizer is a carbohydrate. The term "carbohydrate", as used herein refers to and encompasses monosaccharides, disaccharides, trisaccharides, oligosaccharides, and polysaccharides.

In embodiments of the disclosure, the stabilizer is mannose, glucose, sucrose or trehalose.

According to the present disclosure, the RNA lipoplex particle compositions described herein have a stabilizer concentration suitable for the stability of the composition, in particular for the stability of the RNA lipoplex particles and for the stability of the RNA.

C. pH and Buffer

According to the present disclosure, the RNA lipoplex particle compositions described herein have a pH suitable for the stability of the RNA lipoplex particles and, in particular, for the stability of the RNA. In one embodiment, the RNA lipoplex particle compositions described herein have a pH from about 5.5 to about 7.5.

According to the present disclosure, compositions that include buffer are provided. Without wishing to be bound by theory, the use of buffer maintains the pH of the composition during manufacturing, storage and use of the composition. In certain embodiments of the present disclosure, the buffer may be sodium bicarbonate, monosodium phosphate, disodium phosphate, monopotassium phosphate, dipotassium phosphate, [tris(hydroxymethyl)methylamino]propanesulfonic acid (TAPS), 2-(Bis(2-hydroxyethyl)amino) acetic acid (Bicine), 2-Amino-2-(hydroxymethyl) propane-1,3-diol (Tris), N-(2-Hydroxy-1,1-bis(hydroxymethyl)ethyl) glycine (Tricine), 3-[[1,3-dihydroxy-2-(hydroxymethyl) propan-2-yl]amino]-2-hydroxypropane-1-sulfonic acid (TAPSO), 2-[4-(2-hydroxyethyl) piperazin-1-yl]ethanesulfonic acid (HEPES), 2-[[1,3-dihydroxy-2-(hydroxymethyl) propan-2-yl]amino]ethanesulfonic acid (TES), 1,4-piperazinediethanesulfonic acid (PIPES), dimethylarsinic acid, 2-morpholin-4-ylethanesulfonic acid (MES), 3-morpholino-2-hydroxypropanesulfonic acid (MOPSO), or phosphate buffered saline (PBS). Other suitable buffers may be acetic acid in a salt, citric acid in a salt, boric acid in a salt and phosphoric acid in a salt.

In one embodiment, the buffer is HEPES.

In one embodiment, the buffer has a concentration from about 2.5 mM to about 15 mM.

D. Chelating Agent

Certain embodiments of the present disclosure contemplate the use of a chelating agent. Chelating agents refer to chemical compounds that are capable of forming at least two coordinate covalent bonds with a metal ion, thereby generating a stable, water-soluble complex. Without wishing to be bound by theory, chelating agents reduce the concentration of free divalent ions, which may otherwise induce accelerated RNA degradation in the present disclosure. Examples of suitable chelating agents include, without limitation, ethylenediaminetetraacetic acid (EDTA), a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriaminepentaacetic acid (DTPA), bis(aminoethyl)glycolether-N,N,N',N'-tetraacetic acid, iminodiacetic acid, citric acid, tartaric acid, fumaric acid, or a salt thereof. In certain embodiments, the chelating agent is EDTA or a salt of EDTA. In an exemplary embodiment, the chelating agent is EDTA disodium dihydrate.

In some embodiments, the EDTA is at a concentration from about 0.05 mM to about 5 mM.

E. Physical State of Compositions of the Disclosure

In embodiments, the composition of the present disclosure is a liquid or a solid. Non-limiting examples of a solid include a frozen form or a lyophilized form. In a preferred embodiment, the composition is a liquid.

Pharmaceutical Compositions of the Disclosure

The agents described herein, e.g., RNA described herein, e.g., formulated as RNA lipoplex particles, are useful as or for preparing pharmaceutical compositions or medicaments for therapeutic or prophylactic treatments.

The compositions of the present disclosure may be administered in the form of any suitable pharmaceutical composition.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation. In the context of the present disclosure, the pharmaceutical composition comprises the RNA described herein, e.g., formulated as RNA lipoplex particles. The pharmaceutical compositions of the present disclosure preferably comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cyctokines, such as monokines, lymphokines, interleukins, chemokines. The chemokines may be IL-1, IL-2, IL-3, IL-4, IL-5, IL-6, IL-7, IL-8, IL-9, IL-10, IL-12, INFa, INF-γ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

In some embodiments, an effective amount comprises an amount sufficient to cause a tumor/lesion to shrink. In some embodiments, an effective amount is an amount sufficient to decrease the growth rate of a tumor (such as to suppress tumor growth). In some embodiments, an effective amount is an amount sufficient to delay tumor development. In some embodiments, an effective amount is an amount sufficient to prevent or delay tumor recurrence. In some embodiments, an effective amount is an amount sufficient to increase a subject's immune response to a tumor, such that tumor growth and/or size and/or metastasis is reduced, delayed, ameliorated, and/or prevented. An effective amount can be administered in one or more administrations. In some embodiments, administration of an effective amount (e.g., of a composition comprising mRNAs) may: (i) reduce the number of cancer cells; (ii) reduce tumor size; (iii) inhibit, retard, slow to some extent and may stop cancer cell infiltration into peripheral organs; (iv) inhibit (e.g., slow to some extent and/or block or prevent) metastasis; (v) inhibit tumor growth; (vi) prevent or delay occurrence and/or recurrence of tumor; and/or (vii) relieve to some extent one or more of the symptoms associated with the cancer.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents, and/or excipients.

Suitable preservatives for use in the pharmaceutical compositions of the present disclosure include, without limitation, benzalkonium chloride, chlorobutanol, paraben, and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid, or solid suspension and/or mixing media. Examples of suitable diluents include ethanol, glycerol, and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients, or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

Routes of Administration of Pharmaceutical Compositions of the Disclosure

In one embodiment, pharmaceutical compositions described herein may be administered intravenously, intraarterially, subcutaneously, intradermally, intranodullary or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical composition is formulated for systemic administration. In another preferred embodiment, the systemic administration is by intravenous administration.

Use of Pharmaceutical Compositions of the Disclosure

The agents described herein, e.g., RNA described herein, e.g., formulated as RNA lipoplex particles, may be used in the therapeutic or prophylactic treatment of HPV-positive cancer.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating", or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g., mouse, rat, rabbit, dog, cat, cattle, swine, sheep, horse, or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In one embodiment of the disclosure, the aim is to provide an immune response against cancer cells expressing one or more HPV antigens, in particular HPV E6 and/or HPV E7, and to treat a cancer disease involving cells expressing one or more HPV antigens. In one embodiment, the cancer is HPV-positive cancer. In one embodiment, the cancer is anogenital, cervical or penile cancer, or cancer in the head and neck region such as cancer in the genital region or in the head and neck region. In one embodiment, the cancer is head and neck squamous cell carcinoma (HNSCC)

A pharmaceutical composition comprising RNA may be administered to a subject to elicit an immune response against one or more antigens or one or more epitopes encoded by the RNA in the subject which may be therapeutic or partially or fully protective. A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope, in particular HPV-positive cancer.

As used herein, "immune response" refers to an integrated bodily response to an antigen or a cell expressing an antigen and refers to a cellular immune response and/or a humoral immune response. A cellular immune response includes, without limitation, a cellular response directed to cells expressing an antigen and being characterized by presentation of an antigen with class I or class II MHC molecule. The cellular response relates to T lymphocytes, which may be classified as helper T cells (also termed $CD4^+$ T cells) that play a central role by regulating the immune response or killer cells (also termed cytotoxic T cells, $CD8^+$ T cells, or CTLs) that induce apoptosis in infected cells or cancer cells. In one embodiment, administering a pharmaceutical composition of the present disclosure involves stimulation of an anti-tumor $CD8^+$ T-cell response against cancer cells expressing one or more tumor antigens. In a specific embodiment, the tumor antigens are presented with class I MHC molecule.

The present disclosure contemplates an immune response that may be protective, preventive, prophylactic, and/or therapeutic. As used herein, "induces [or inducing] an immune response" may indicate that no immune response against a particular antigen was present before induction or it may indicate that there was a basal level of immune response against a particular antigen before induction, which was enhanced after induction. Therefore, "induces [or inducing] an immune response" includes "enhances [or enhancing] an immune response".

The term "immunotherapy" relates to the treatment of a disease or condition by inducing, or enhancing an immune response. The term "immunotherapy" includes antigen immunization or antigen vaccination.

The terms "immunization" or "vaccination" describe the process of administering an antigen to an individual with the purpose of inducing an immune response, for example, for therapeutic or prophylactic reasons.

In one embodiment, the present disclosure envisions embodiments wherein RNA lipoplex particles as described herein targeting spleen tissue are administered. The RNA encodes a peptide or protein comprising an antigen or an epitope as described, for example, herein. The RNA is taken up by antigen-presenting cells in the spleen such as dendritic cells to express the peptide or protein. Following optional processing and presentation by the antigen-presenting cells an immune response may be generated against the antigen or epitope resulting in a prophylactic and/or therapeutic treatment of a disease involving the antigen or epitope. In one embodiment, the immune response induced by the RNA lipoplex particles described herein comprises presentation of an antigen or fragment thereof, such as an epitope, by antigen presenting cells, such as dendritic cells and/or macrophages, and activation of cytotoxic T cells due to this presentation. For example, peptides or proteins encoded by the RNAs or procession products thereof may be presented by major histocompatibility complex (MHC) proteins expressed on antigen presenting cells. The MHC peptide complex can then be recognized by immune cells such as T cells or B cells leading to their activation. Thus, in one embodiment the RNA in the RNA lipoplex particles described herein, following administration, is delivered to the spleen and/or is expressed in the spleen. In one embodiment, the RNA lipoplex particles are delivered to the spleen for activating splenic antigen presenting cells. Thus, in one embodiment, after administration of the RNA lipoplex particles RNA delivery and/or RNA expression in antigen presenting cells occurs. Antigen presenting cells may be professional antigen presenting cells or non-professional antigen presenting cells. The professional antigen presenting cells may be dendritic cells and/or macrophages, even more preferably splenic dendritic cells and/or splenic macrophages. Accordingly, the present disclosure relates to RNA lipoplex particles or a pharmaceutical composition comprising RNA lipoplex particles as described herein for inducing or enhancing an immune response, preferably an immune response against HPV-positive cancer.

In one embodiment, systemically administering RNA lipoplex particles or a pharmaceutical composition comprising RNA lipoplex particles as described herein results in targeting and/or accumulation of the RNA lipoplex particles or RNA in the spleen and not in the lung and/or liver. In one embodiment, RNA lipoplex particles release RNA in the spleen and/or enter cells in the spleen. In one embodiment, systemically administering RNA lipoplex particles or a pharmaceutical composition comprising RNA lipoplex particles as described herein delivers the RNA to antigen presenting cells in the spleen. In a specific embodiment, the antigen presenting cells in the spleen are dendritic cells or macrophages.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen.

Peptides from degraded proteins are displayed on the macrophage cell surface where they can be recognized by T cells, and they can directly interact with antibodies on the B-cell surface, resulting in T- and B-cell activation and further stimulation of the immune response. Macrophages belong to the class of antigen presenting cells. In one embodiment, the macrophages are splenic macrophages.

The term "dendritic cell" (DC) refers to another subtype of phagocytic cells belonging to the class of antigen presenting cells. In one embodiment, dendritic cells are derived from hematopoietic bone marrow progenitor cells. These progenitor cells initially transform into immature dendritic cells. These immature cells are characterized by high phagocytic activity and low T-cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T-cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T-cell- or B-cell-related immune response. In one embodiment, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, such as antigen presenting cells to specific T cells.

The term "disease involving an antigen" or "disease involving an epitope" refers to any disease which implicates an antigen or epitope, e.g., a disease which is characterized by the presence of an antigen or epitope. The disease involving an antigen or epitope can be a cancer disease or simply cancer. As mentioned above, the antigen may be a disease-associated antigen, such as a tumor-associated antigen and the epitope may be derived from such antigen.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. One particular form of cancer that can be treated by the compositions and methods described herein is HPV-positive cancer. The term "cancer" according to the disclosure also comprises cancer metastases.

Combination strategies in cancer treatment may be desirable due to a resulting synergistic effect, which may be considerably stronger than the impact of a monotherapeutic approach.

In one embodiment, the pharmaceutical composition is administered with an immunotherapeutic agent. As used herein "immunotherapeutic agent" relates to any agent that may be involved in activating a specific immune response and/or immune effector function(s). The present disclosure contemplates the use of an antibody as an immunotherapeutic agent. Without wishing to be bound by theory, antibodies are capable of achieving a therapeutic effect against cancer cells through various mechanisms, including inducing apoptosis, block components of signal transduction pathways or inhibiting proliferation of tumor cells. In certain embodiments, the antibody is a monoclonal antibody. A monoclonal antibody may induce cell death via antibody-dependent cell mediated cytotoxicity (ADCC), or bind complement proteins, leading to direct cell toxicity, known as complement dependent cytotoxicity (CDC). Non-limiting examples of anti-cancer antibodies and potential antibody targets (in brackets) which may be used in combination with the present disclosure include: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Atezolizumab (PD-L1), Bavituximab (phosphatidylserine), Bectumomab (CD22), Belimumab (BAFF), Bevacizumab (VEGF-A), Bivatuzumab mertansine (CD44 v6), Blinatumomab (CD 19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin $\alpha v\beta 3$), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-$\beta$), Galiximab (CD80), Ganitumab (IGF-I), Gemtuzumab ozogamicin (CD33), Gevokizumab (IL-I$\beta$), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD 152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Namatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD 19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1 BB), Volociximab (integrin α5β1), Votumumab (tumor antigen CTAA 16.88), Zalutumumab (EGFR), and Zanolimumab (CD4).

In one embodiment, the immunotherapeutic agent is a PD-1 axis binding antagonist. A PD-1 axis binding antagonist includes but is not limited to a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific embodiment, PD-L1 binding partners are PD-1 and/or B7-1. In another embodiment, the PD-L2 binding antagonist is a molecule that inhibits the binding of PD-L2 to its binding partners. In a specific embodiment, the PD-L2 binding partner is PD-1. The PD-1 binding antagonist may be an antibody, an antigen binding fragment thereof, an immunoadhesin, a fusion protein, or oligopeptide. In some embodiments, the PD-1 binding antagonist is an anti-PD-1 antibody (e.g., a human antibody, a humanized antibody, or a chimeric antibody). Examples of an anti-PD-1 antibody include, without limitation, MDX-1106 (Nivolumab, OPDIVO), Merck 3475 (MK-3475, Pembrolizumab, KEYTRUDA), MEDI-0680 (AMP-514), PDR001, REGN2810, BGB-108, and BGB-A317.

In one embodiment, the PD-1 binding antagonist is an immunoadhesin that includes an extracellular or PD-1 binding portion of PD-L1 or PD-L2 fused to a constant region. In one embodiment, the PD-1 binding antagonist is AMP-224 (also known as B7-DCIg, is a PD-L2-Fc), which is fusion soluble receptor described in WO2010/027827 and WO201 1/066342.

In one embodiment, the PD-1 binding antagonist is an anti-PD-L1 antibody, including, without limitation, YW243.55.S70, MPDL3280A (Atezolizumab), MEDI4736 (Durvalumab), MDX-1105, and MSB0010718C (Avelumab).

In one embodiment, the immunotherapeutic agent is a PD-1 binding antagonist. In another embodiment, the PD-1 binding antagonist is an anti-PD-L1 antibody. In an exemplary embodiment, the anti-PD-L1 antibody is Atezolizumab.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Materials and Methods for Examples 1 to 4

Mice

Humanized, HLA-transgenic C57BL/6 A2DR1 embryos were obtained from CNRS Orleans and bred in house. Wild-type C57BL/6 mice were purchased from Charles River and Envigo. Throughout all experiments, age-matched (6-12 weeks) female animals were used. Procedures and experimental group sizes were approved by the regulatory authorities for animal welfare. All mice were kept in accordance with federal and state policies on animal research at the University of Mainz and BioNTech AG.

Tumor Cell Lines

The C57BL/6 TC-1 tumor cell line, derived from primary lung cells by immortalization and retroviral transduction with HPV16 E6/E7 (Lin, K. Y. et al., *Cancer Res.* 56, 21-26 (1996)), was obtained, together with the luciferase-transfected variant TC-1 luc, from T.-C. Wu (Johns Hopkins University). The C57BL/6 C3 tumor cell line, generated by immortalization and transfection of C57BL/6 mouse embryonic cells with the complete HPV16 genome (Feltkamp, M. C. W. et al., *Eur. J. Immunol.* 23, 2242-2249 (1993)), was a kind gift from S.H. van der Burg (Leiden University Medical Center, The Netherlands). Re-authentication of cells and generation of master and working cell banks were performed immediately upon receipt. Cells from third to ninth passages were used for tumor experiments.

RNA Constructs and In Vitro Transcription

Plasmid templates for in vitro transcription of antigen-encoding RNAs were based on the pST1-A120 and pST1-MITD vector (Holtkamp, S. et al., *Blood* 108, 4009-4017 (2006)) which feature 5' and 3 UTRs and poly(A) tails pharmacologically optimized for stability and protein translation. pST1-MITD features a signal sequence for routing to the endoplasmic reticulum and the major histocompatibility complex (MHC) class I transmembrane and cytoplasmic domains for improved presentation of MHC class I and II epitopes. pST1-eGFP-A120 (eGFP), pST1-OVA-MITD ($OVA_{257-264}$) and pST1-E7-MITD vectors were described previously (Holtkamp, S. et al., *Blood* 108, 4009-4017 (2006); Kreiter, S. et al., *J. Immunol.* 180, 309-318 (2007); Kranz, L. M. et al., *Nature* 534, 396-401 (2016); Kuhn, A. N. et al., *Gene Ther.* 17, 961-71 (2010)). pST1-OVA-MITD encodes the H-2Kb-restricted, immunodominant epitope $OVA_{257-264}$. pST1-E7-MITD encodes HPV16 full-length E7 protein and pST1-E6-MITD encodes HPV16 full-length E6 protein. Templates for in vitro transcription of mRNA were generated by cloning target sequences into the pST1-MITD vector. In vitro transcription and capping with β-Santi-reverse cap analog (ARCA) (Kuhn, A. N. et al., *Gene Ther.* 17, 961-71 (2010)) were performed as described previously (Holtkamp, S. et al., *Blood* 108, 4009-4017 (2006)).

Liposomes, RNA-LPX Preparation, and Immunization

Liposomes with cationic net charge comprised of the cationic lipid DOTMA and the helper lipid DOPE were used to complex RNA for the formation of RNA-LPX. Liposome manufacture and LPX formation were performed as previously described (Kranz, L. M. et al., *Nature* 534, 396-401 (2016)). In brief, RNA was stored in HEPES-buffered solution at an RNA concentration of 1 mg $mL^{-1}$. RNA-LPX were prepared by diluting the RNA with $H_2O$ and 1.5 M NaCl solution followed by adding an appropriate amount of liposome dispersion to reach a charge ratio of (+):(−) 1.3:2 at a final NaCl concentration of 150 mM. At the indicated charge ratio, RNA-LPX preparations (E7, eGFP, and $OVA_{257-264}$ RNA-LPX) had a particle size of 200-250 nm, a polydispersity index of ~0.25 and a zeta potential (mV) of −20-30 mV (Examples 2-4). If not mentioned otherwise, mice were immunized with 40 µg RNA-LPX. Control mice received RNA-LPX encoding for irrelevant protein (eGFP or $OVA_{257-264}$) or NaCl. Arrows in vaccination schemes indicate immunization.

Tumor Models and Treatment

For therapeutic tumor experiments, C57BL/6 mice were injected s.c. with $1\times10^5$ TC-1 tumor cells or $5\times10^5$ C3 tumor cells. Tumor sizes were measured unblinded with a caliper every three to four days for calculating tumor volumes using the equation $(a^2\times b)/2$ (a, width; b, length). For orthotopic tumor experiments, $5\times10^4$ TC-1 luc tumor cells were inoculated into the submucosa of the tongue. In some experiments, 200 µg of PD-L1 antibody (10F.9G2, BioXCell) or IgG2b isotype control (LF-2, BioXCell) were administered every three to four days intraperiotoneal. Animals were euthanized when predefined endpoints were reached.

Bioluminescence Imaging

Orthotopic TC-1 luc tumor growth was evaluated by in vivo bioluminescence imaging using the Xenogen IVIS Spectrum imaging system (Perkin Elmer, Waltham, MA, USA). An aqueous solution of L-luciferin (1.3 mg/mouse; BD Biosciences) was injected intraperitoneally. Emitted photons from live animals were quantified 5 min after luciferin administration. Regions of interest (ROI) were quantified as average radiance (photons $s^{-1}$ $cm^{-2}$ $sr^{-1}$) using IVIS Living Image 4.0 software.

Tissue Preparation

For the generation of single cell suspensions, tumors were excised, cut into pieces and subsequently incubated in digestion buffer containing 5 µg/ml collagenase (Roche Diagnostics), 500 units hyaluronidase (Sigma-Aldrich) and 50 µg/mL DNAse I (Roche Diagnostics) in PBS at 37° C. for 15 min. Tumor samples were forced through a 70 µm cell strainer (BD Falcon) using a plunger end of a syringe while rinsing with PBS. Cells were centrifuged at 460 g for 6 min and resuspended in fresh PBS. Erythrocytes were lysed with a hypotonic electrolyte solution for 5 min. Similarly, spleens were forced through a 70 µm cell strainer while rinsing with PBS and erythrocytes lysed with a hypotonic electrolyte solution. Peripheral blood (50 ul) was collected from the orbital sinus to obtain PBMCs for FACS staining.

IFNγ ELISpot

Enzyme-linked ImmunoSpot assay (ELISpot) was performed to detect T cell IFNγ release upon antigen encounter. In brief, spleens from A2DR1 mice were isolated, single cell suspensions generated and $5\times10^5$ splenocytes restimulated with media containing 2 µg/ml overlapping peptide pools of E6, E7 or a control protein (human herpesvirus type 5 (HHV5) protein pp65) overnight at 37° C. All samples were tested in triplicates. Overlapping peptide pools of E6, E7 and pp65 span the complete protein sequence (15-mers with 11 amino acid (aa) overlap) and were obtained from JPT Peptide Technologies.

Flow Cytometry

Flow cytometry staining was conducted on full blood, tumor, and spleen single cell suspension. Monoclonal antibodies for extracellular staining included CD45, CD8a CD4, CD44, CD86, PD-1, NK1.1, CD11b, PD-L1, I-A/I-E (BD Pharmingen), CD3, F4/80, Gr-1, (Biolegend), CD25 and (eBioscience). For intracellular staining, antibodies against IFNγ, Ki-67 (eBioscience), TNFα, Foxp3 (BD Pharmingen), granzyme B, iNOS (Invitrogen) and CD206 (BioLegend) were used. Flow cytometry staining was performed as follows: Live cells were stained with viability dyes (eBioscience) according to manufacturer's instructions. E7 specific $CD8^+$ T cells were stained with $E7_{49-57}$ H2-Db-restricted dextramers (Immudex) for 10 min at 4° C. in the dark. Extracellular targets were stained for 30 min at 4° C. in the dark. PBS containing 5% FCS and 5 mM EDTA was used as washing and staining buffer. For the staining of IFNγ, TNFα and granzyme B, samples were fixed and permeabilized with Cytofix/Cytoperm (BD Pharmingen), whereas for iNOS, CD206, Ki67 and Foxp3 staining, samples were fixed and permeabilized using Foxp3 Fixation Kit (eBioscience) according to manufacturer's instructions. Full blood was stained with MHC-dextramers prior to erythrocyte lysis using BD FACS lysing solution (BD Pharmingen). Immune cell populations were defined by pre-gating on viable cells and singlets and determined as follows: NK cells ($CD45^+$ $CD3^-$ $NK1.1^+$), $CD8^+$ T cells ($CD45^+$ $CD8^+$), $E7_{49-57}$ specific $CD8^+$ T cells ($CD45^+$ $CD8^+$ $E7_{49-57}$ multimer+), $CD4^+$ T cells ($CD45^+$ $CD4^+$), Treg ($CD45+CD4^+$ $Foxp3^+$ $CD25^+$), tumor-associated macrophages ($CD45^+$ CD11b+F4/$80^+$). Flow cytometric data was acquired on a FACS Canto II or LSR Fortessa flow cytometer (both BD Biosciences, Franklin Lakes, USA) and analyzed with FlowJo 7.6.5 or FlowJo 10.4 software (Tree Star).

Fluidigm qPCR Expression Analysis

Total RNA was extracted from cryo-conserved tumors using Tissue Lyser II (Quiagen). RNA was isolated by classical phenol/chloroform extraction following an initial RNA-cleanup on QIAcube using RNeasy mini spin columns. RNA was reverse-transcribed to cDNA using TAKARA PrimeScript™ RT Reagent Kit (Perfect Real Time). The cDNA was subjected to the Fluidigm BioMark HD system, following Fluidigm® Advanced Development Protocol 28-Fast Gene Expression Analysis using TaqMan® Gene Expression Assays (PN 100-2594 A2). Detection of 6-carboxyfluorescein signal, linear baseline correction, and the auto Ct threshold method were used for Ct-value determination. For data analysis, the R software package "qpcrPANEL" developed in-house was used. Raw Ct-values were read in and undetected Cts were set to the 0.975 quantiles of all Ct. ΔΔCt-values were calculated as described (Pfaffl, M. W., *Nucleic Acids Res.* 29, 45e-45 (2001)). Hypoxanthine-Guanine phosphoribosyltransferase (HPRT) was used as the reference gene to compute the ΔCt for each data point ($\Delta Ct_{i,j}=Ct_{i,j}-Ct_{HPRT,j}$) with i as gene and j as sample index. $\Delta Ct_{i,j}$ were calibrated with the ΔCt-value of the means (χ) of the control sample for each gene versus the mean of control samples in HPRT ($\Delta Ct_{i,calib}=\chi Ct_{i,control}-\chi Ct_{HPRT,control}$). Primer efficiencies were assumed to be equal and defined as $\Delta\Delta Ct=2-(-\Delta Ct_{i,j}-\Delta Ct_{i,calib})$. Differences in $\log_2$-fold changes of ΔΔCt-values were plotted to generate heat maps (GraphPad PRISM 7).

Next Generation Sequencing (NGS) and Gene Expression Analysis

Cryoconserved TC-1 tumors (liquid N2) were dry homogenized with the Tissue Lyser Il (Quiagen) for RNA extraction. RNA was isolated by classical phenol/chloroform extraction following a clean-up process on QIAcube using RNeasy mini spin columns. RNA was reverse-transcribed to cDNA using TAKARA PrimeScript™ RT Reagent Kit (Perfect Real Time). The procedure of NGS was in detail described by Castle and colleagues (Castle, J. C. et al., BMC Genomics 15, 190 (2014)). RNA-seq reads were mapped to the mouse genome applying the STAR algorithm (version 2.4.2) (Dobin A et al., Bioinformatics 29 (1), 15-21 (2013)). To quanify transcripts, the Python package "HTSeq with UCSC" (July 2007/NCBI37) annotation (Anders S. et al., Bioinformatics 31 (2), 166-169 (2015); Hsu F. et al., Bioinformatics 22 (9), 1036-1046 (2006)) was used and read counts normalized to Reads per kilobase per million mapped reads (RPKM) (Mortazavi A. et al., Nat Methods 5 (7), 621-628 (2008)). Normalization and differential expression (DE) analysis were performed with the R software package "DESeq2" (Love, M. I. et al., Genome Biol 15, 550 (2014)). A False discovery (FDR) rate of 0.01 and log 2-fold change of two was chosen to detect differentially expressed genes.

Statistical Analysis

Individual treatment and corresponding control group means were compared by unpaired, two-tailed Student's t test using corrected p values (Holm-Šidak approach) if appropriate. Two-way ANOVA was performed when both time and treatment were compared, and when significant ($p<0.05$), multiple comparisons were performed using Bonferroni posthoc tests. Survival benefit was determined with the log-rank test (Mantel-Cox). * $p\leq0.05$,  $p\leq0.01$, * $p\leq0.001$. If not mentioned otherwise, results are depicted as mean±SEM. All statistical analyses were performed with GraphPad PRISM 7.

Figure 1:
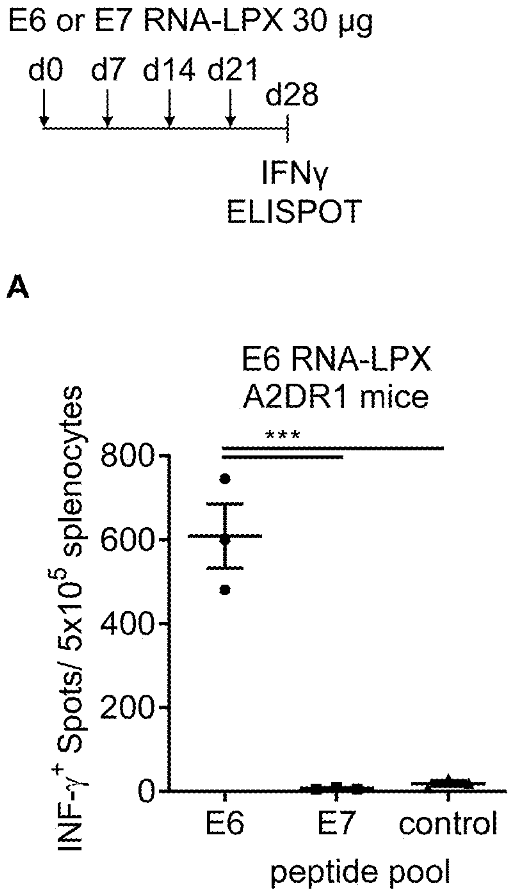
FIG. 1: Immunization with E6 and E7 RNA-LPX induces a strong E6 and E7 antigen-specific T cell response in humanized, HLA-transgenic A2DR1 mice A2DR1 mice (expressing human HLA-A*0201 and HLA-DRB1*01 molecules) (n=3/group) were immunized with 30 μg E6 or E7 RNA-LPX (do, d7, d14, d21) and spleens excised seven days after the last immunization (d28) to assess T cell reactivities against vaccine-encoded antigens in IFNγ ELISpot. T cell responses of (A) E6 RNA-LPX and (B) E7 RNA-LPX vaccinated A2DR1 mice were analyed against E6, E7 or control protein (pp65) overlapping peptide pools and IFNγ spots counted. Significance was determined using one-way ANOVA, Tukey's post-test. Mean±SEM.

Example 1: Immunization with E6 and E7 RNA-LPX Induces a Strong E6 and E7 Antigen-Specific T Cell Response in Humanized, HLA-Transgenic A2DR1 Mice To assess the immunogenicity of HPV16 E6 and E7 RNA-LPX, humanized, HLA-transgenic A2DR1 mice were used (Pajot A. et al., Eur J Immunol. 34 (11), 3060-3069 (2004)). These mice lack murine MHC class I and II molecules, bearing double knock-outs in β2m and IA $\beta^b$, but express human MHC class I and II molecules, being stabely transfected with human HLA-A2.1 and HLA-DRR. A2DR1 mice were vaccinated weekly with E6 or E7 RNA-LPX and splenic T cells isolated seven days after the 4th immunization to assess the T cell reactivity against vaccine encoded antigens in IFNγ ELISpot (FIG. 1A, B). E6 RNA-LPX vaccinated mice showed strong and selective T cell responses against the HPV16 E6 (FIG. 1A), whereas T cells from E7 RNA-LPX vaccinated mice selectively recognize HPV16 E7 (FIG. 1 B).

Together, these data indicate that both HPV16 E6 and E7 RNA-LPX efficiently prime and expand endogenous T cells against vaccine-encoded antigens in humanized, HLA-transgenic A2DR1 mice.

Example 2: E7 RNA-LPX Immunization Mediates Complete Remission of Progressing HPV16-Positive Tumors and Establishes Protective T Cell Memory We next assessed the anti-tumor efficacy of E7 RNA-LPX induced T cells in two HPV16 antigen-positive syngeneic mouse tumor models—TC-1 and C3—of which TC-1 has higher E7 expression levels than C3 (data not shown).

HPV-positive malignancies typically arise at sites of infection in oral or genital regions in the mucosa. As this poses a peculiar challenge for T cell trafficking (F., S. et al., *Cancer Research* (2013); Nizard, M. et al., *Nat. Commun.* 8, 15221 (2017)), we first explored the HPV16 E7 vaccine in an orthotopic tumor setting. TC-1 luc tumors were implanted submucosally at the base of the tongue. A few days after a single E7 RNA-LPX immunization dramatic tumor regression was observed in all mice (FIG. 2A). Nine days after immunization, orthotopic tumor lesions of RNA-LPX treated mice were found to be heavily infiltrated with leukocytes (FIG. 2B). Up to 42% of the infiltrating $CD8^+$ T cells were HPV 16 $E7_{49-57}$ specific (FIG. 2C). The majority of HPV 16 $E7_{49-57}$ specific T cells in orthotopic tumors were positive for the homing-associated integrin CD49α, whereas all antigen-specific $CD8^+$ T cells circulating in blood were CD49α negative (FIG. 2D), further supporting effective trafficking of primed T cells to tumors located at mucosal sites.

Next, tumor cells were implanted subcutaneously (s.c.) into the flank of mice and mice were dosed repeatedly i.v. with RNA-LPX encoding either HPV16 E7 or an irrelevant (irr.) antigen. All control-treated mice experienced progressive tumor growth and had to be sacrificed within 30 to 40 days after tumor challenge (FIGS. 2E, F and 2H, I). RNA-LPX immunization was associated with a rapid and complete rejection of tumors in all TC-1 tumor-bearing mice (FIG. 2E, F) and in 6 of 9 C3 tumor-bearing mice (FIG. 2H, I). The remaining three C3 tumor-bearing mice initially responded with tumor shrinkage but tumor growth eventually progressed (FIG. 2H, I). All mice with a complete anti-tumoral response to E7 RNA-LPX immunization remained tumor-free for the entire observation period (FIG. E, F). Mice rechallenged with TC-1 cells remained tumor-free, indicating the prevalence of a functional memory T cell response against the HPV16 E7 antigen (FIGS. 2G and J).

Collectively, these data indicate that E7 RNA-LPX efficiently primes T cells which infiltrate the tumor and execute anti-tumor activity in mucosal as well as s.c. $HPV16^+$ TC-1 and C3 tumors.

Figure 3:
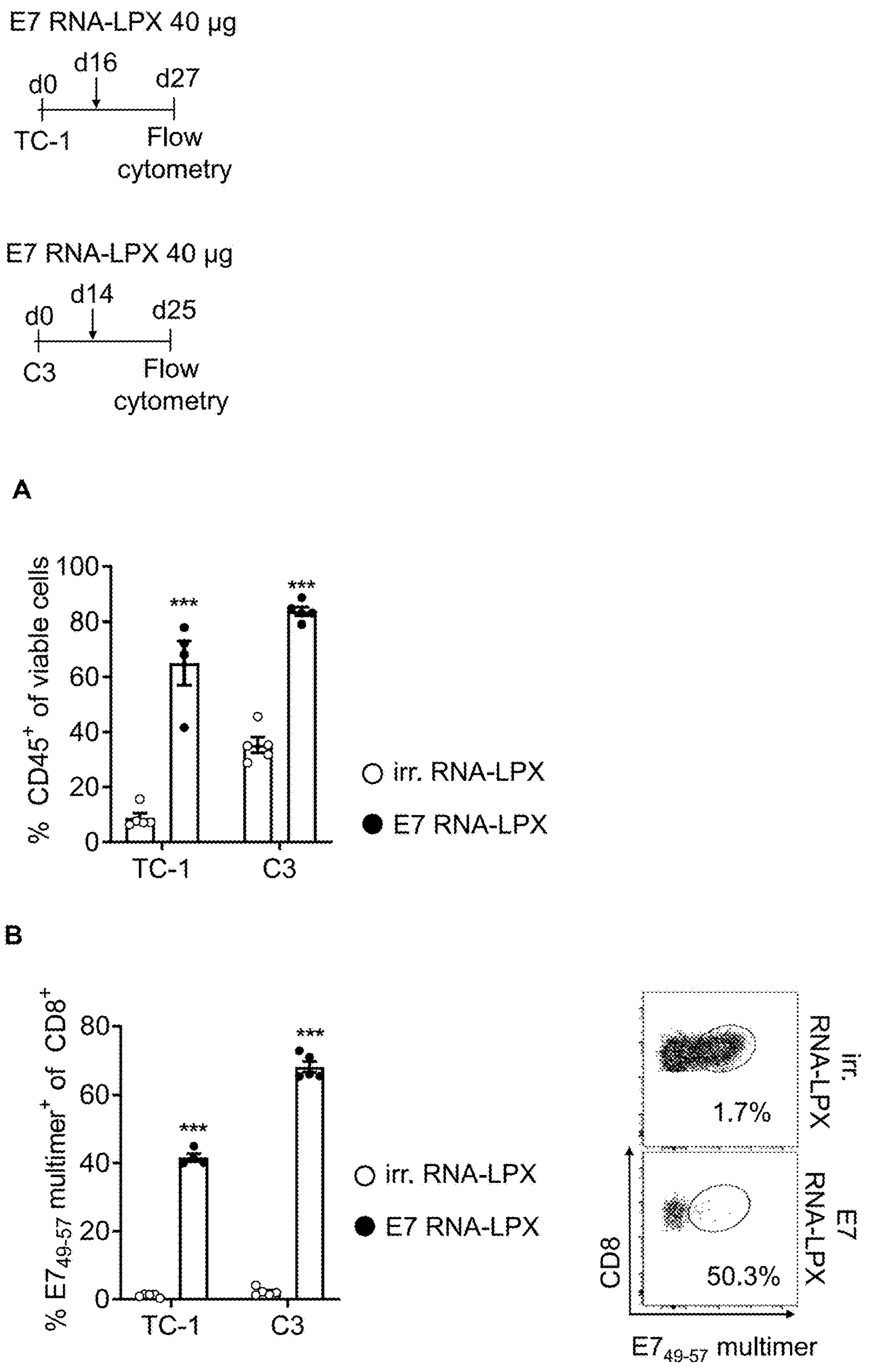
FIG. 3: Tumors of E7 RNA-LPX immunized mice have brisk immune infiltrates, E7-specific CD8+ T cells and a proinflammatory, cytotoxic and less immune-suppressive contexture Analysis of TIL in TC-1 (A, B, C-E) and C3 tumors (A, B, F-H) resected from mice (n=5/group) 11 days after one immunization with E7 RNA-LPX or irrelevant ($OVA_{257-264}$) RNA-LPX (TC-1: ~ 63 $mm^3$ and C3: ~ 65 $mm^3$ at therapy start). (A) Percentage of $CD45^+$ cells and (B) frequency of E749-57-specific $CD8^+$ T cells in TC-1 and C3 tumors as measured by flow cytometry. (B, right) Representative $E7_{49-57}$ multimer staining in TC-1 tumors. (C, F) Frequency of leukocyte subsets in (C) TC-1 and (F) C3 tumors. (D, G) $Ki67^+$ fraction of tumor-infiltrating $CD4^+$ and $CD8^+$ T cells in (D) TC-1 and (G) C3 tumors. (E, H) Expression of iNOS and CD206 in TAM of (E) TC-1 and (H) C3 tumors. (I) Gene expression analysis of selected genes in TC-1 (left) and C3 tumors (right) resected after two immunizations with E7 RNA-LPX or irrelevant ($OVA_{257-264}$) RNA-LPX determined by qRT-PCR. Tumor tissues were harvested two days after the last immunization. Heatmaps display log 2-fold changes calculated and normalized to irrelevant ($OVA_{257-264}$) RNA-LPX treated mice. (A-H) Significance was determined using unpaired, two-tailed Student's t-test and (I) Holm-Šidak multiple comparison test. Mean±SEM. TIL: Tumor-infiltrating lymphocytes; TAM: Tumor-associated macrophages; iNOS: Inducible nitric oxide synthase.
Figure 3:
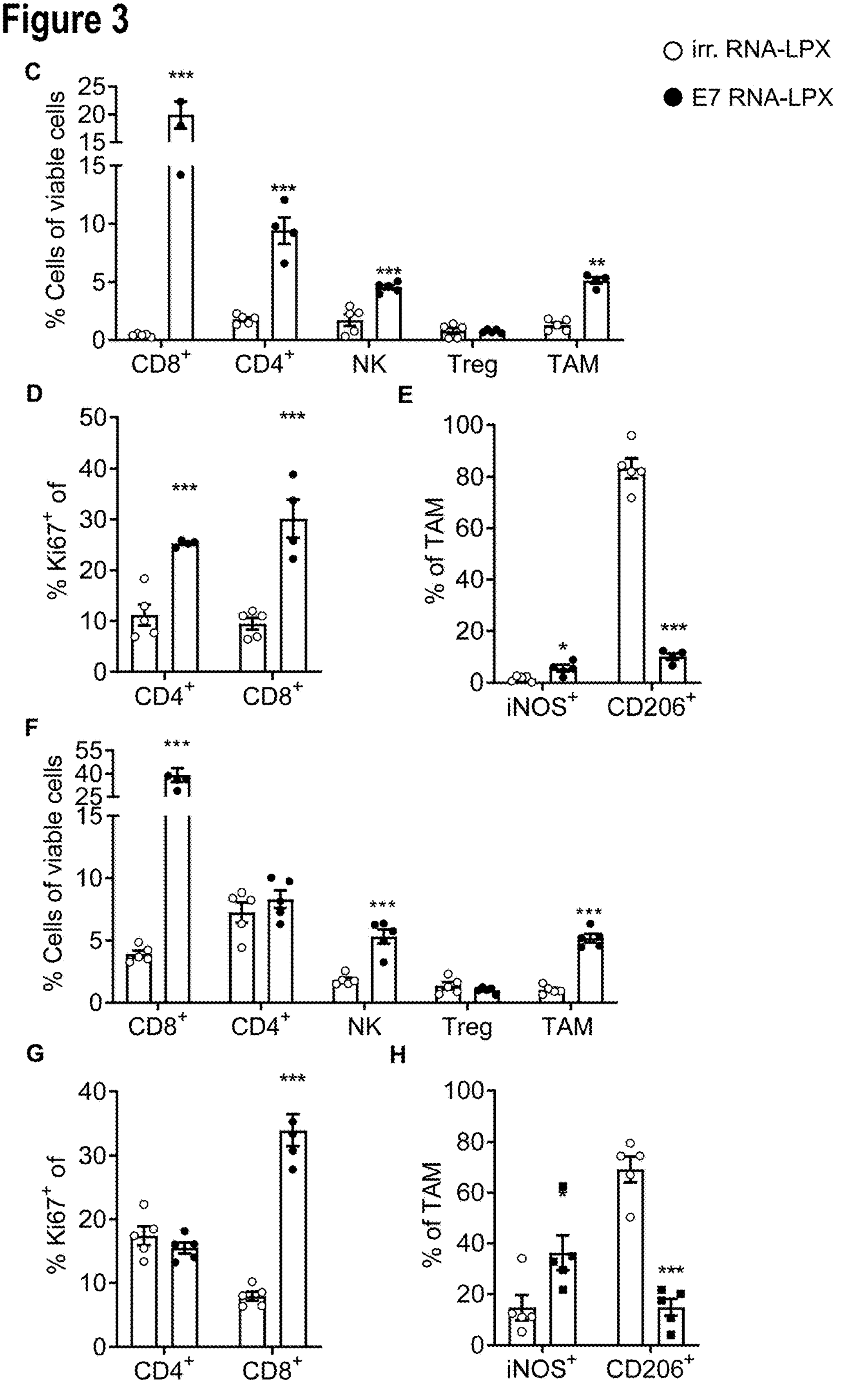
Figure 3:
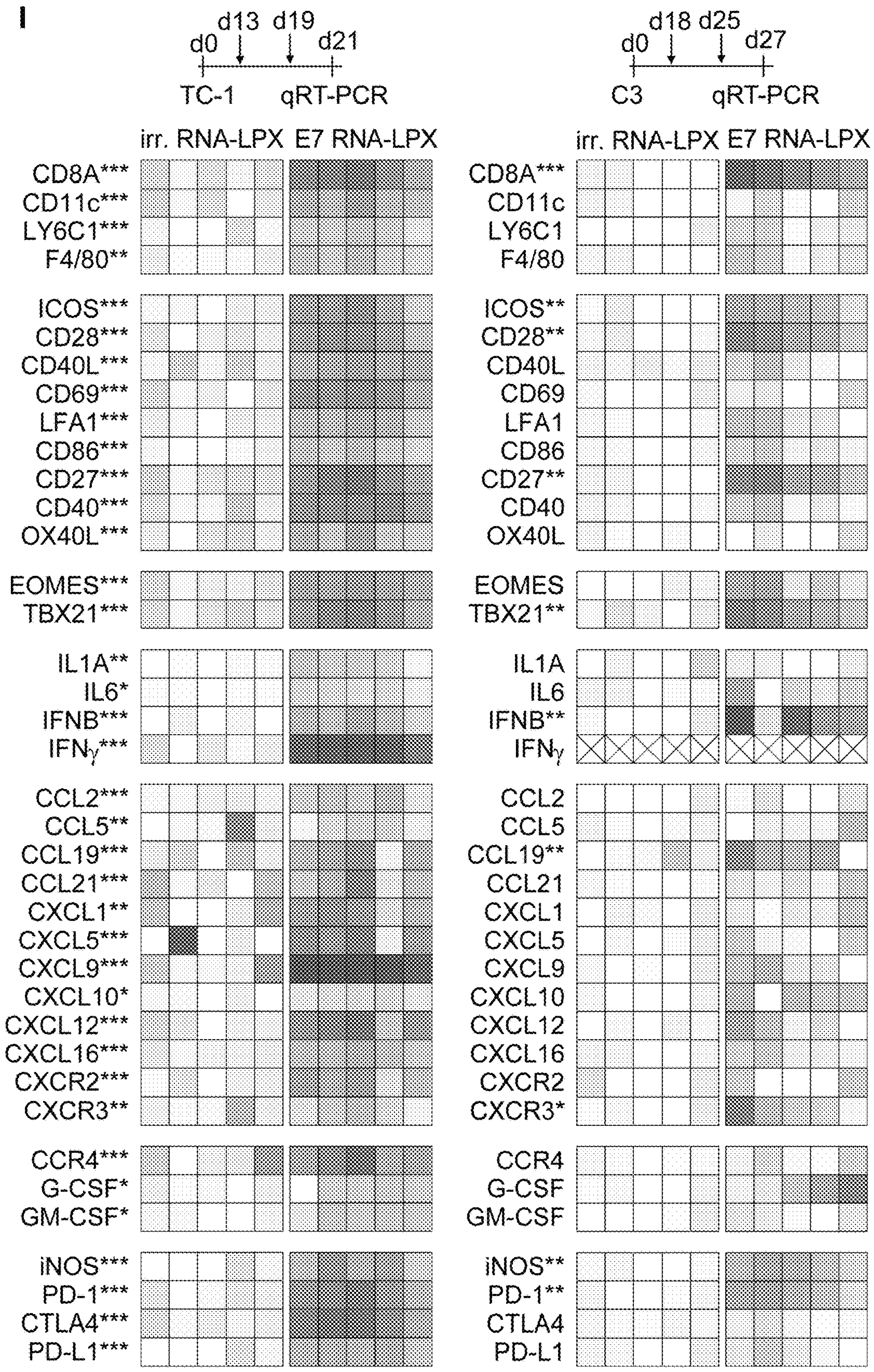

Example 3: Tumors of E7 RNA-LPX Immunized Mice have Brisk Immune Infiltrates, E7-Specific $CD8^+$ T Cells and a Proinflammatory, Cytotoxic and Less Immune-Suppressive Contexture Tumor-infiltrating cell populations from both TC-1 and C3 tumor-bearing mice were analyzed by flow cytometry 11 days after a single E7 RNA-LPX immunization or control treatment with irrelevant ($OVA_{257-264}$) RNA-LPX. In both tumor models, immunization was associated with early leukocyte infiltration (FIG. 3A) and strong expansion of E7-specific $CD8^+$ T cells (FIG. 3B). Tumor-infiltrating $CD8^+$ T cells of E7 RNA-LPX immunized, but not of control-treated mice, expressed high levels of IFNγ and granzyme B (GzmB) when stimulated ex vivo with $E7_{49-57}$ peptide (data not shown). TC-1 tumors of E7 RNA-LPX vaccinated mice had higher frequencies of tumor-infiltrating $CD8^+$ and $CD4^+$ T cells (FIG. 3C), which were also highly proliferative as measured by Ki-67 staining (FIG. 3D). In C3 tumors, this finding was confirmed for the $CD8^+$ T cell population, whereas the frequency and proliferative capacity of $CD4^+$ T cells were not affected by the E7 vaccine (FIGS. 3F and G). In both tumor models, E7 RNA-LPX was associated with a significant increase of NK cells and tumor-associated macrophages (TAM) (FIGS. 3C and F). TAMs were slightly skewed towards the proinflammatory iNOS-secreting M1-like phenotype, whereas the frequency of suppressive, $CD206^+$ M2-like macrophages were lower compared to control vaccinated mice (FIGS. 3E and H). Immunization had no effect on Tregs in either model (FIGS. 3C and F).

Gene expression analysis of bulk tumor samples of immunized mice confirmed and further extended the observations we made by flow cytometry on cellular level (FIG. 31). E7 RNA-LPX immunization was associated with the upregulation of markers for $CD8^+$ T cell function, attraction and Th1 development (Hertweck, A. et al., *Cell Rep.* 15, 2756-2770 (2016)), including T cell transcription factors EOMES and TBX21 (T-bet), T cell co-stimulatory molecules CD28, CD27, ICOS and chemokines such as CCL5, CXCL9 and CXCL12 together with their co-receptor CXCR3 known to be expressed on $CD8^+$ T cells (Hickman, H. D. et al., *Immunity* 42, 524-537 (2015)) and NK cells (Wendel, M., Galani, I. E., Suri-Payer, E. & Cerwenka, A., *Cancer Res.* 68, 8437-8445 (2008)). Proinflammatory molecules such as IL-1, IL-6, interferons and CCL2 were increased, as were PD-1 and iNOS. Most, but not all these markers were upregulated in both tumors models. Moreover, TC-1 tumors but not C3 tumors of vaccinated mice displayed a higher expression of DC activation markers such as CD86, CD40, markers for monocyte/macrophage recruitment, such as F4/80, CCL5 and GM-CSF, and the immune checkpoint molecules PD-L1 and CTLA-4.

In summary, vaccination with HPV16 E7 RNA-LPX was markedly associated with polarization towards a proinflammatory, cytotoxic and less immune-suppressive contexture, which was more pronounced in TC-1 compared to C3 tumors.

Figure 4:
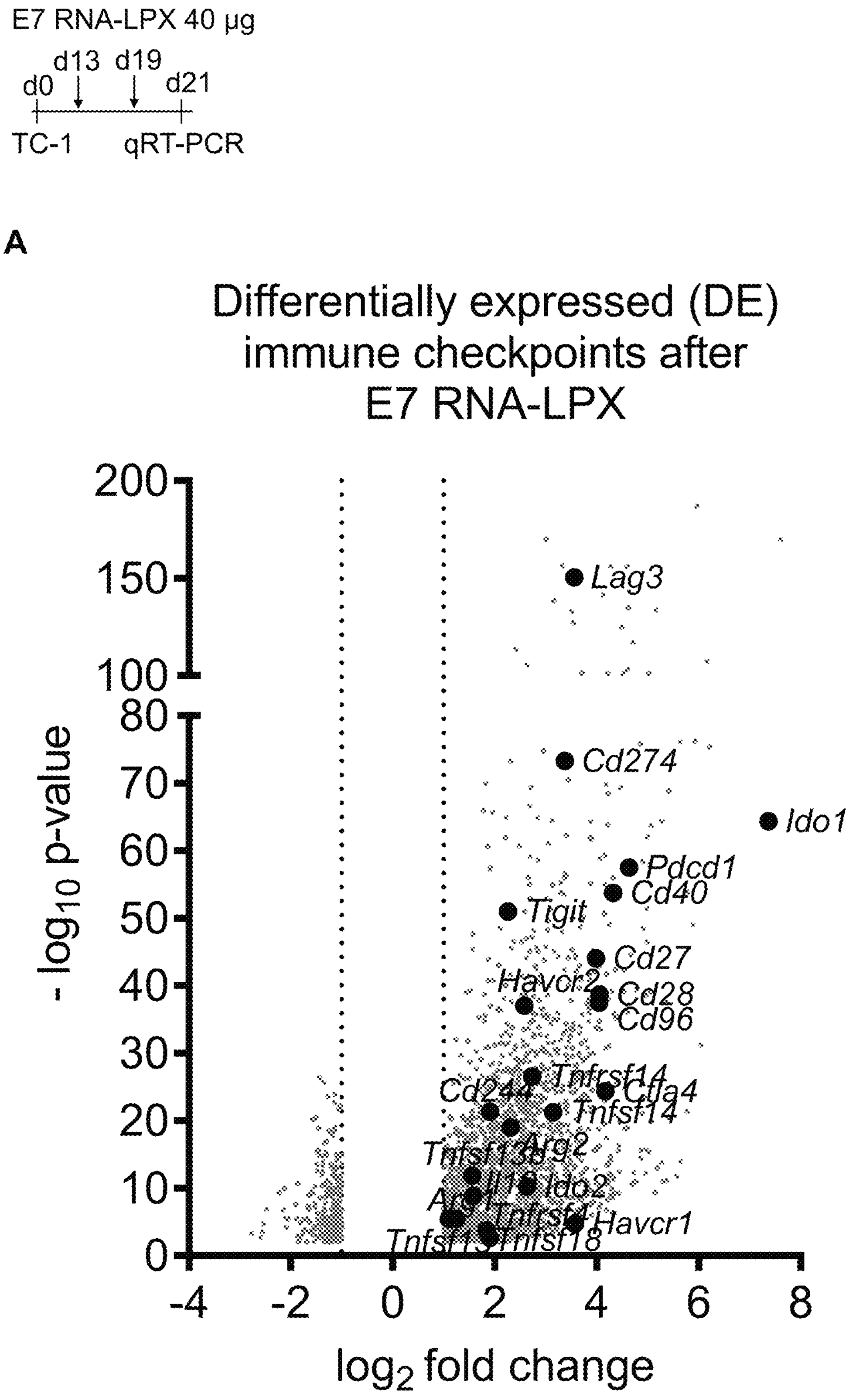
FIG. 4: E7 RNA-LPX immunization synergizes with checkpoint-blockade by rendering anti-PD-L1 refractory tumors responsive (A) Differential gene expression analysis in TC-1 tumors resected from TC-1 tumor-bearing mice (n=5/group) two days after the last immunization with E7 RNA-LPX or irrelevant ($OVA_{257}$-264) RNA-LPX (d13, d19). Volcano plot illustrates differentially expressed genes (log 2-fold change of >2, FDR 0.01) calculated and normalized to irrelevant ($OVA_{257-264}$) RNA-LPX treated mice. Genes encoding for druggable immune checkpoints are highlighted. (B-D) Tumor growth (B) and survival (C) of TC-1 tumor-bearing mice (n=14/group) immunized with E7 RNA-LPX or irrelevant ($OVA_{257-264}$) RNA-LPX (d11) and treated with anti-PD-L1 (aPD-L1) antibody or isotype control 3 to 4 days (d15, d18, d21, d25, d28). The average size of TC-1 tumors was ~120 $mm^3$ at treatment start. (D) Fraction of peripheral $E7_{49-57}$ multimer-positive $CD8^+$ T cell (d17, d25, d32). Significance was determined using (C) Mantel-cox log-rank test and (D) two-way ANOVA, Sidak's multiple comparison test, between E7 RNA-LPX and E7 RNA-LPX+aPD-L1 treated mice. (B) Ratios depict the fraction of mice with complete responses (CR). Mean±SEM. FDR=false discovery rate
Figure 4:
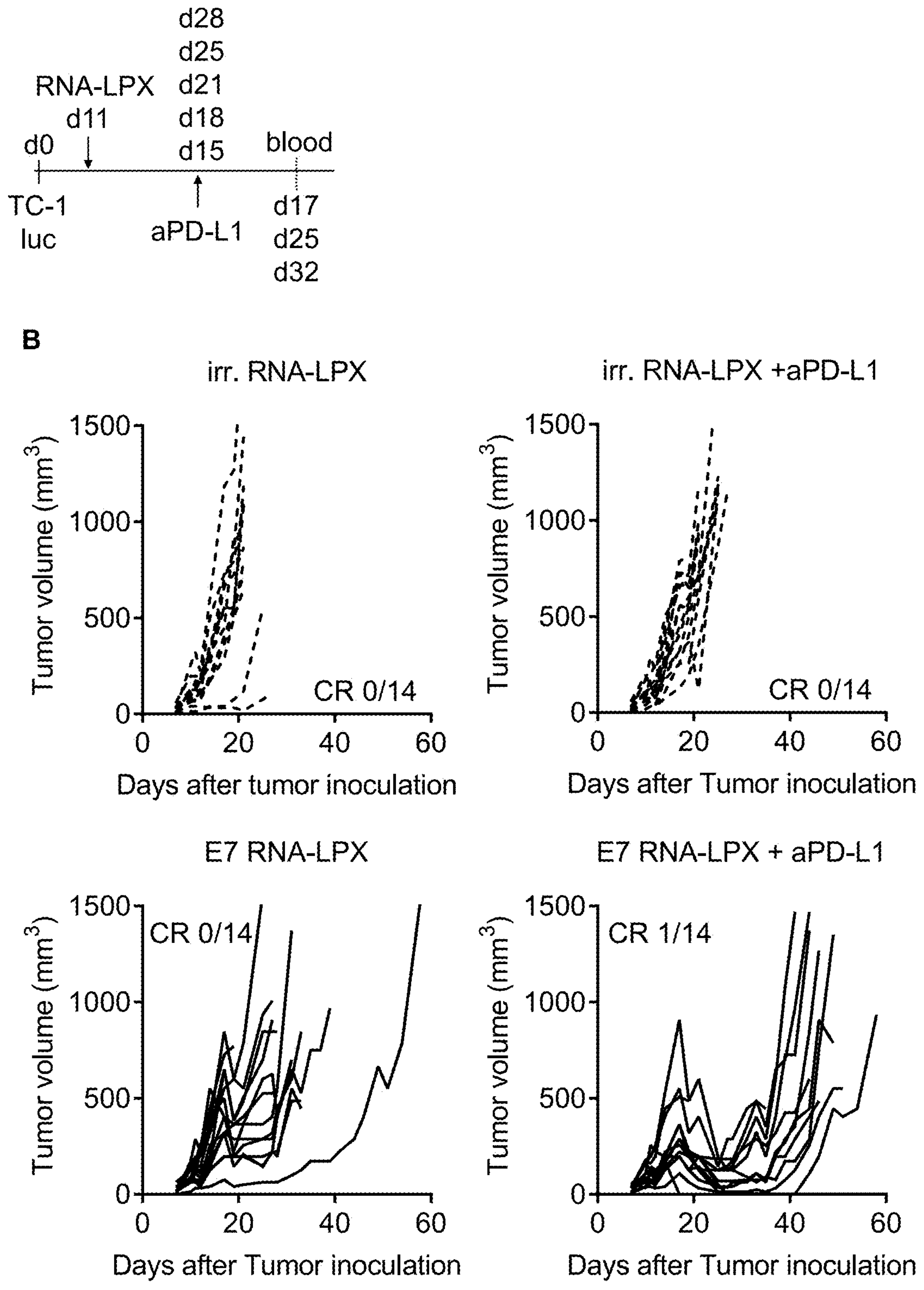
Figure 4:
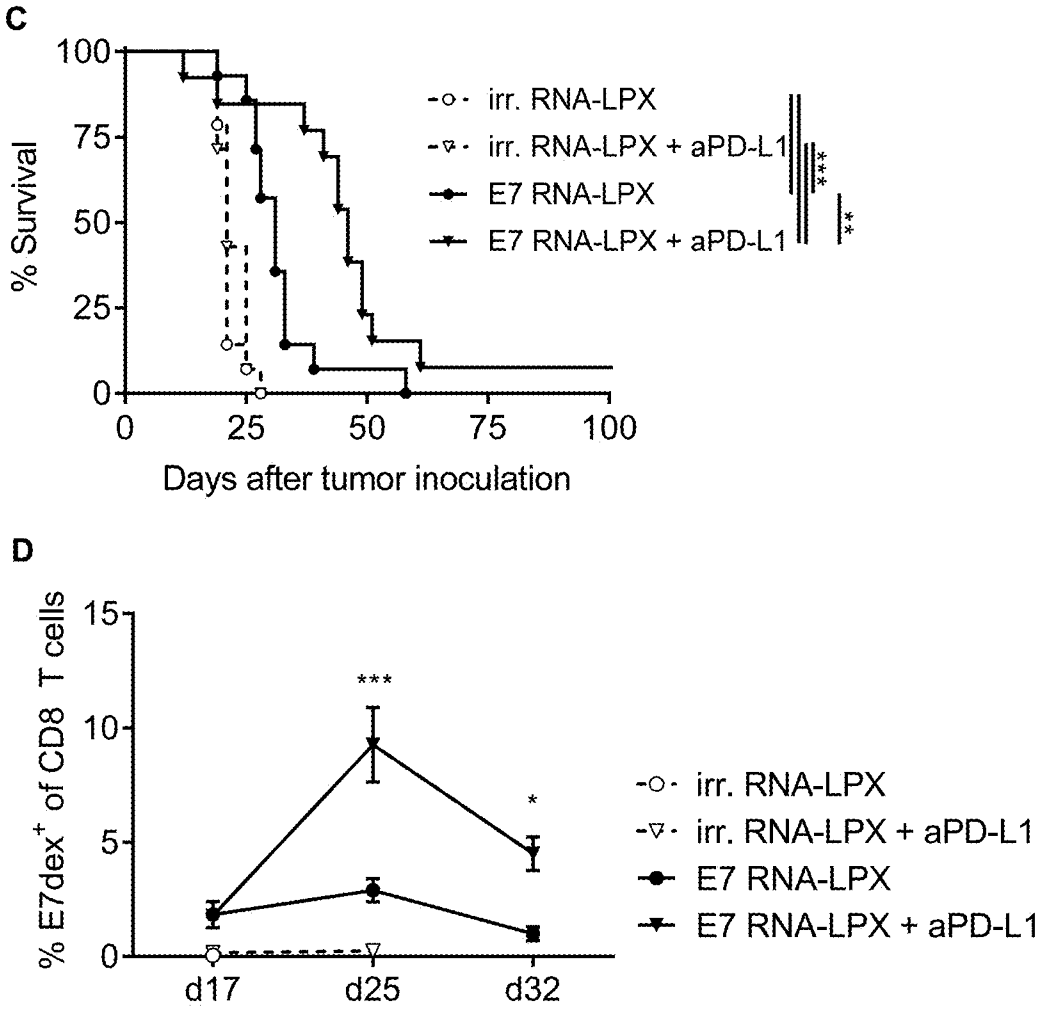

Example 4: E7 RNA-LPX Immunization Synergizes with Checkpoint-Blockade by Rendering Anti-PD-L1 Refractory Tumors Responsive E7 RNA-LPX vaccination strongly increased intratumoral T cell responses and mediated a global proinflammatory gene expression change. Strong inflammatory responses are often counter-regulated by strong inhibitory responses to keep an immunological balance. Hence, we analyzed the expression of known inhibitory receptors in E7 RNA-LPX-treated TC-1 tumors by gene expression analysis (FIG. 4A). E7 RNA-LPX vaccination induced differential expression (DE) of 2463 genes (log 2-fold>1, FDR 0.01) with a number of well known inhibitory T cell receptors such as Lag3, CD274 (PD-L1), Pdcd1 (PD-1), Tigit, Havcr2 (Tim-3) or metabolites such as Ido1 being strongly upregulated.

C3 and TC-1 tumors are known to be resistant to PD-L1/PD-1 immune checkpoint inhibitor (CPI) monotherapy (Badoual, C. et al., *Cancer Res.* (2013). doi: 10.1158/0008-5472.CAN-12-2606; Rice, A. E. et al., *Cancer Gene Ther.* (2015). doi: 10.1038/cgt.2015.40; Weir, G. M. et al., *J. Immunother. Cancer* (2016). doi: 10.1186/s40425-016-0169-2). E7 RNA-LPX vaccination appears to be associated with an array of immunologically favorable alterations in the tumor microenvironment including upregulation of PD-1 and of PD-L1 (FIG. 31, 4A), which correlates with IFNγ induction observed in HPV-antigen expressing TC-1 tumors (FIG. 31). Hypothesizing that increase in PD-L1 expression in conjunction with a stronger inflamed, non-excluded and less suppressed local milieu could convert a tumor refractory to PD-L1/PD-1 blockade to a susceptible one, we tested combination treatment of vaccine and anti-PD-L1 (aPD-L1) in mice. To allow a therapeutic window despite the efficacy of E7 RNA-LPX monotherapy, tumors were grown to a well advanced stage (tumor average size of 120 $mm^3$) and only a single dose of vaccine was administered followed by aPD-L1 treatment every 3-4 days.

In the TC-1 model, the majority of mice treated with aPD-L1 alone had to be sacrificed within 25 days, whereas with E7 RNA-LPX monotherapya significant survival benefit was observed (FIGS. 4B and C). Combined aPD-L1 further improved E7 RNA-LPX-mediated anti-tumoral responses and significantly enhanced the overall survival. As early tumor growth kinetics were largely comparable between E7 RNA-LPX vaccine and aPD-L1 combination therapy groups, the addition of aPD-L1 to the vaccine further prevented tumor outgrowth. In addition, anti-PD-L1 treatment significantly enhanced the expansion of E7-specific CD8 T cell responses after E7 RNA-LPX in the blood of treated mice (FIG. 4D). Findings suggest that HPV16-positive cancer patients could greatly benefit from the proposed combination of E7 RNA-LPX/aPD-L1 which collectively drives tumor rejection and tumor-specific T cell responses.

Materials and Methods for Examples 5 to 9

Mice

Female C57BL/6 wild-type mice were purchased from Envigo and age-matched (8-10 weeks) animals used throughout all experiments. Mice were kept in accordance with federal and state policies on animal research at BioNTech AG and procedures and experimental group sizes were approved by the regulatory authorities for animal welfare.

Tumor Cell Lines

The murine TC-1 tumor cell was derived from primary C57BL/6 lung cells by immortalization and retroviral transduction with HPV16 E6/E7 (Lin, K. Y. et al., *Cancer research* 56, 21-26 (1996)) and was obtained together with the luciferase-transfected variant TC-1 luc from T. C. Wu (Johns Hopkins University). The murine C3 tumor cell line was previously generated by immortalization and transfection of C57BL/6 embryonic cells with the complete HPV16 genome (Feltkamp, M. C. et al., *European journal of immunology* 23, 2242-2249 (1993)) and was a kind gift by S. H. van der Burg (Leiden University Medical Center). Re-authentication of cells and generation of master and working cell banks were performed immediately upon receipt. Cells from fifth to ninth passage were used for in vivo tumor experiments. For the irradiation of tumor cells, the orthovoltage X-ray source XRAD320 (Precision X-Ray Inc.) was used.

RNA Constructs and In Vitro Transcription

Plasmid templates for in vitro transcription of antigen-coding RNAs were generated by cloning target sequences into pST1-A120 and pST1-MITD vectors that feature 5' and 3'UTRs and poly(A) tails pharmacologically optimized for stability and protein translation (Holtkamp, S. et al., *Blood* 108, 4009-4017 (2006); Kreiter, S. et al., *Journal of immunology* (Baltimore, Md.: 1950) 180, 309-318 (2008)). pST1-MITD features a signal sequence for routing to the endoplasmic reticulum and MHC class I transmembrane and cytoplasmic domains for improved presentation of MHC class I and II epitopes (Kreiter, S. et al., *Journal of immunology* (Baltimore, Md.: 1950) 180, 309-318 (2008)). The following antigen-encoding vectors were used: E7 (encoding full-length HPV16 E7) (Grunwitz, C. et al., Oncoimmunology 8, e1629259 (2019)) and chicken ovalbumin (OVA, encoding the $H\text{-}2K^b$-restricted, immunodominant epitope $OVA_{257\text{-}264}$) (Kranz, L. M. et al., *Nature* 534, 396-401 (2016)). OVA RNA was used as a control RNA throughout all experiments. Antigen-encoding vectors were in vitro transcribed (IVT) and capped with the β-Santi-reverse cap analog (ARCA) as previously described (Kuhn, A. N. et al., *Gene therapy* 17, 961-971 (2010)).

RNA-LPX Preparation

RNA-lipoplexes (RNA-LPX) were generated by complexing negatively-charged IVT RNA with cationic liposomes consisting of the cationic lipid DOTMA and the helper lipid DOPE as previously described (Kranz, L. M. et al., *Nature* 534, 396-401 (2016)). HEPES-buffered RNA (1 mg $ml^{-1}$) was diluted in $H_2O$ and 1.5 M NaCl and liposomes added to reach a (+):(−) charge ratio of 1.3:2 at a final NaCl concentration of 150 mM. RNA-LPX preparations had a particle size of 200-250 nm, a polydispersity index of ~0.25 and a zeta potential (mV) of −20-30 mV.

Tumor Models and Treatment

For therapeutic tumor experiments, C57BL/6 mice were injected with $1\times10^5$ TC-1 or TC-1 luc tumor cells and $5\times10^5$ C3 tumor cells subcutaneously into to the right flank. Tumor growth was measured unblinded with a caliper every three to four days and tumor volumes calculated by ($a^2$ x b)/2 (a, width; b, length). Mice were immunized intravenously with 40 μg E7 or control (OVA) RNA-LPX. Arrows in vaccination schemes indicate immunization. Mice were randomized according to their tumor size prior RNA-LPX immunization. The orthovoltage X-ray source XRAD320 (Precision X-Ray Inc.) was used for tumor irradiation, irradiating tumors locally with different doses at a dose rate of 0.47 Gy/min. Biological effective doses were calculated using the formula $$BED = n \times d\left(1 + \frac{d}{\frac{\alpha}{\beta}}\right)$$

with n being the number of fractions, d being the dose per fraction and α/β being the tumor intrinsic radio-sensitivity (Gough, M. J., Crittenden, M. R. & Young, K. H., *Immunotherapy* 7, 847-849 (2015)). Tumor irradiation was performed under ketamine/xylazine narcosis. Normal tissue was shielded using a custom-made lead shield that spares a hole (1.5 cm diameter), allowing exposition of the tumor tissue only. For in vivo BrdU labelling, the BrdU base analogon was injected intraperitoneal at 1 mg/mouse, 24 h prior to organ excision (BrdU Flow Kit, BD Bioscience). The hypoxia probe pimonidazole (Hypoxyprobe Inc.) was injected intravenously at 1.2 mg/mouse 1 h prior organ excision. Animals were euthanized when the volume of the tumour exceeded 1500 $mm^3$ or when exhibiting signs of impaired health.

In some experiments, mice received 80 μg cisplatin chemotherapy or PBS intraperitoneal (i.p.) twice after RNA-LPX vaccination.

Tissue Preparation

For the generation of tumor single cell suspensions, tumors were cut and digested, using the mouse tumor dissociation kit and gentleMACS™ dissociator (Miltenyi Biotec). For the generation of lymph node single cell suspensions, lymph nodes were squeezed with forcepts and incubated with 1 mg mL-1 collagenase (Roche Diagnostics) and 10 μg mL-1 DNAseI (Roche Diagnostics). Tumor and lymph node single cell suspensions, as well as whole spleens, were forced through a 70 μm cell strainer (BD Falcon), using the plunger end of a syringe, while rinsing with PBS. Cells were centrifuged at 460 g for 6 min and erythrocytes lysed with a hypotonic electrolyte solution for 5 min. For the isolation CD8 TIL, target cells were magnetically enriched using the mouse CD8 (TIL) MicroBeads (Miltenyi Biotech) according to manufacturer's instructions.

Flow Cytometry

Flow cytometry staining was performed on tumor, tumor-draining lymph node and spleen single cell suspension as well as on CD8 T cell enriched tumor single cell suspensions. Monoclonal antibodies for extracellular staining included anti-mouse CD45, CD8a, CD4, CD44, NK1.1, PD-L1, cleaved caspase-3, Qa-$1^b$ (BD Pharmingen), PD-1, NKG2AB (Invitrogen), Tim-3, Fas, H-2 (pan MHC class I) (Biolegend) and CD25 (eBioscience). For intracellular staining, antibodies against IFNγ, IL-2 (eBioscience) and TNFα, Foxp3 (BD Pharmingen) were used. Flow cytometry staining was performed as follows: Live cells were stained with viability dyes (eBioscience) according to manufacturer's instructions. E7-specific $CD8^+$ T cells were stained with $E7_{49-57}$ H2-Db-restricted dextramers (Immudex) for 10 min at 4° C. in the dark. Extracellular targets were stained for 30 min at 4° C. in the dark. PBS containing 5% FCS and 5 mM EDTA was used as washing and staining buffer. For the staining of IFNγ, TNFα and IL-2, samples were fixed and permeabilized with Cytofix/Cytoperm (BD Pharmingen), whereas for Foxp3 staining, samples were fixed and permeabilized using Foxp3 Fixation Kit (eBioscience) according to manufacturer's instructions. Intracellular cytokine staining was performed as described earlier (Diken, M. et al., *Methods in molecular biology* (Clifton, N.J.) 1499, 223-236 (2017).), stimulating $CD8^+$ T cells with 2 μg/mL $E7_{49-57}$ (RAHYNIVTF, Jerini Peptide Technologies) peptide-loaded C57BL/6 BMDC in the presence of 10 μg/mL Brefeldin A (Sigma) for 5 h at 37° C. In vivo BrdU labelling and staining was performed using BD in vivo BrdU flow cytometry kit according to manufacturers instructions. Immune cell populations were defined by pre-gating on viable cells and singlets and determined as follows: NK cells ($CD45^+$ $NK1.1^+$), CD8 T cells ($CD45^+$ $CD8^+$), E7-specific CD8 T cells ($CD45^+$ $CD8^+$ $E7_{49-57}$ multimer+), CD4 T cells ($CD45^+$ $CD4^+$), Treg ($CD45^+$ $CD4^+$ $Foxp3^+$ $CD25^+$), tumor cells (CD45 $CD44^+$). Flow cytometric data was acquired on FACS Canto II or LSR Fortessa (BD Biosciences) and analyzed using FlowJo 10.4 (Tree Star).

Immunofluorescence Microscopy

8-μm sections of cryconserved tumors were fixed in 4% paraformaldehyde (PFA) for 10 min, permeabilized in tris-buffered saline (TBS) buffer containing 0.1% triton and blocked in DPBS supplemented with 1% bovine serum albumin (BSA), 5% mouse serum, 5% rat serum and 0.02% Nonident for 1 h, in the dark at room temperature. Fluorescence-labeled antibody against pimonidazole-thiole adducts (Hydroxyprobe™ Red584, Hydroxyprobe Inc.) were used to stain sections overnight at 4° C., followed by nuclear staining with Hoechst (Sigma-Aldrich). Immunofluorescence images were acquired using an epifluorescence microscope (Axio Scan.Z1, Zeiss, Oberkochen, Germany).

Statistical Analyses and Data Presentation

Single treatment and control group means were compared by unpaired, two-tailed student's t-test. If more than two experimental groups were compared, one-way analysis of variance (ANOVA) was performed, and when determined significant ($p<0.05$), Tukey's multiple comparison test run. Survival benefit was determined using log-rank test (Mantel-Cox). * p≤ 0.05,  p≤0.01, * p≤0.001. If not mentioned otherwise, results are depicted as mean±SEM. All statistical analyses were performed with GraphPad PRISM 8.

For Example 9, Statistical analysis was performed with GraphPad PRISM 9. For tumor growth analysis, two-way analysis of variance (ANOVA) was performed and when determined significant ($p<0.05$), Tukey's multiple comparison test run.

Figure 2:
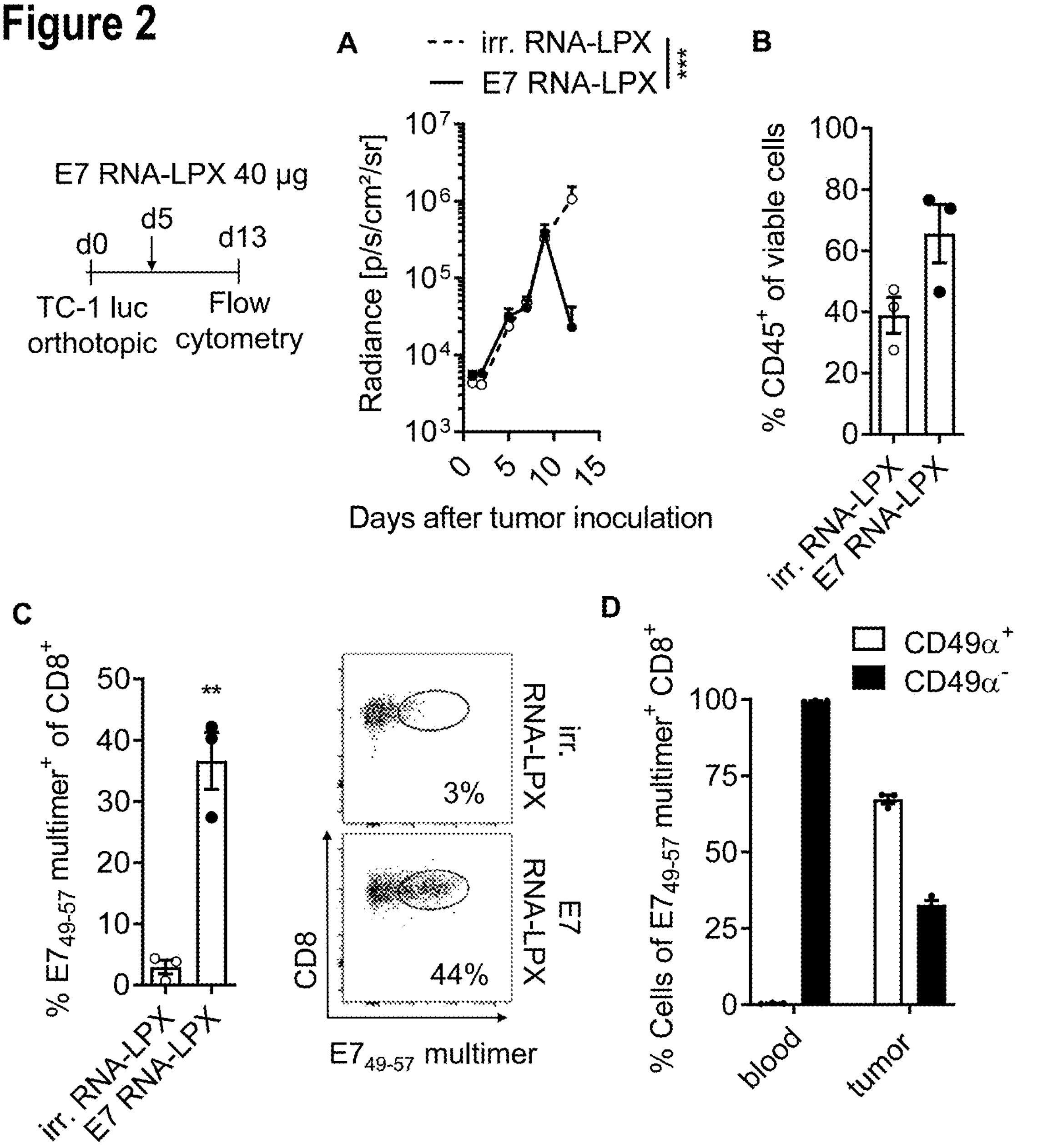
FIG. 2: E7 RNA-LPX immunization mediates complete remission of progressing HPV16-positive tumors and establishes protective T cell memory (A-D) TC-1 luc tumor cells were grafted into the submucosal lining of the tongue. Five days later mice were immunized with E7 RNA-LPX (n=13) or irrelevant ($OVA_{257-264}$) RNA-LPX (n=12). (A) TC-1 luc tumor growth kinetics as measured by in vivo bioluminescence. (B-D) Mice were sacrificed 13 days after tumor-challenge and tumor tissues harvested (n=3/group). The proportion of (B) $CD45^+$ and (C) $E7_{49-57}$ multimer$^+$ $CD8^+$ T cells in mice treated either with E7 RNA-LPX or irrelevant ($OVA_{257-264}$) RNA-LPX was measured by flow cytometry. (D) CD49a expression of $E7_{49-57}$ multimer$^+$ $CD8^+$ T cells of E7 RNA-LPX treated mice in blood and tumor. (E, F) TC-1 tumor growth (E) and survival (F) in mice (n=10/group) immunized three times (d4, d7, d13) with E7 RNA-LPX or irrelevant (eGFP) RNA-LPX. Average tumor size of ~6 $mm^3$ at start of treatment. (G) Survival of E7 RNA-LPX treated mice (n=10) rechallenged with TC-1 after initial TC-1 tumor challenge. Treatment-naive mice (n=10) served as control group. (H, I) C3 tumor growth (H) and survival (I) in mice immunized four times (d14, d21, d27, d33) with E7 RNA-LPX (n=9) or irrelevant ($OVA_{257-264}$) RNA-LPX (n=10). Average tumor size of ~25 $mm^3$ at start of treatment. (J) Survival of E7 RNA-LPX treated mice rechallenged with TC-1 after C3 tumor challenge (n=12/group). Treatment-naive mice (n=10) served as control group. Significance was determined using (A) two-way ANOVA, Sidak's multiple comparison test, (B, C) unpaired, two-tailed Student's t-test and (F, G, I, J) Mantel-cox log-rank test. Ratios depict the fraction of mice with complete responses (CR). Mean±SEM.
Figure 2:
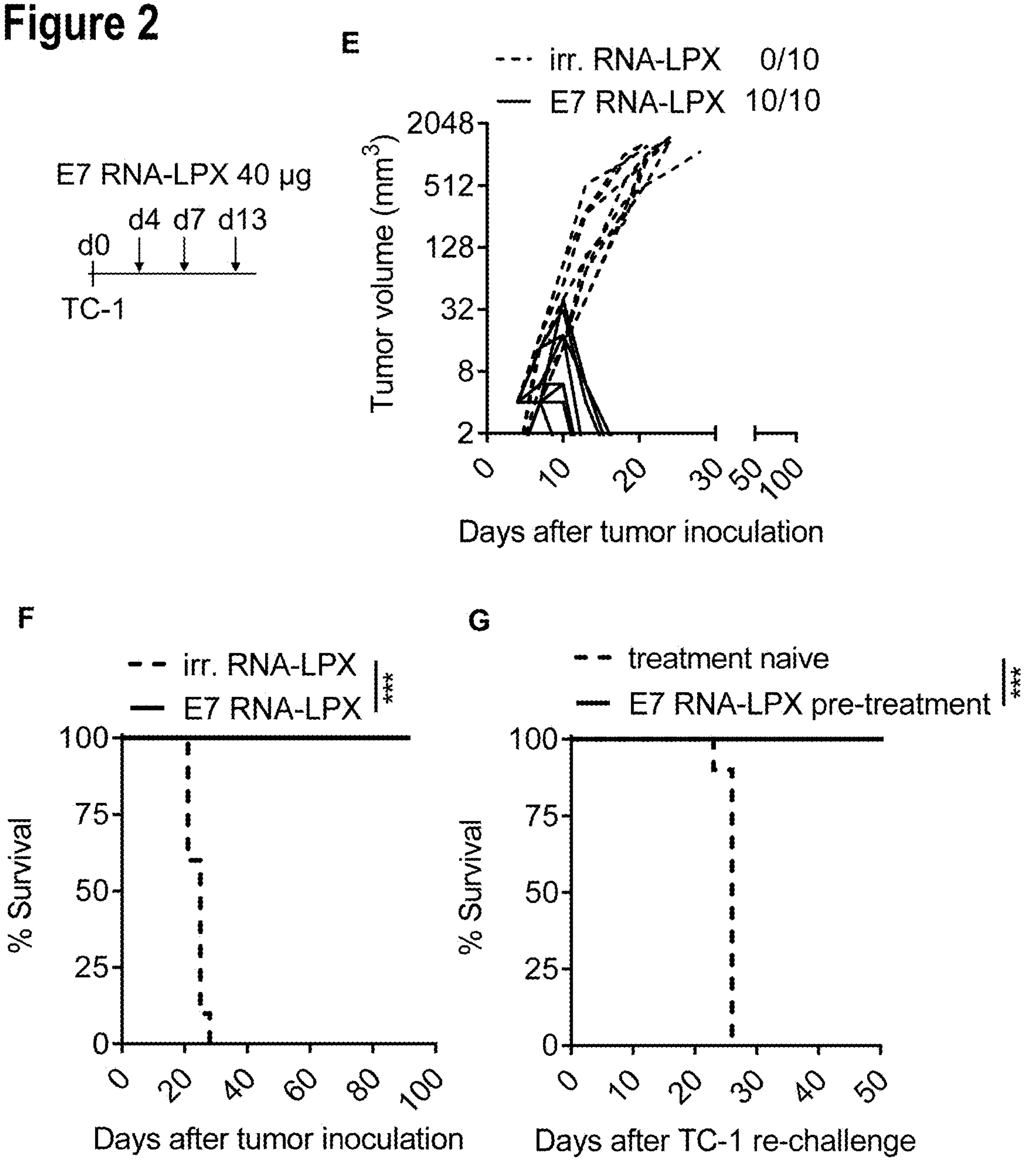
Figure 2:
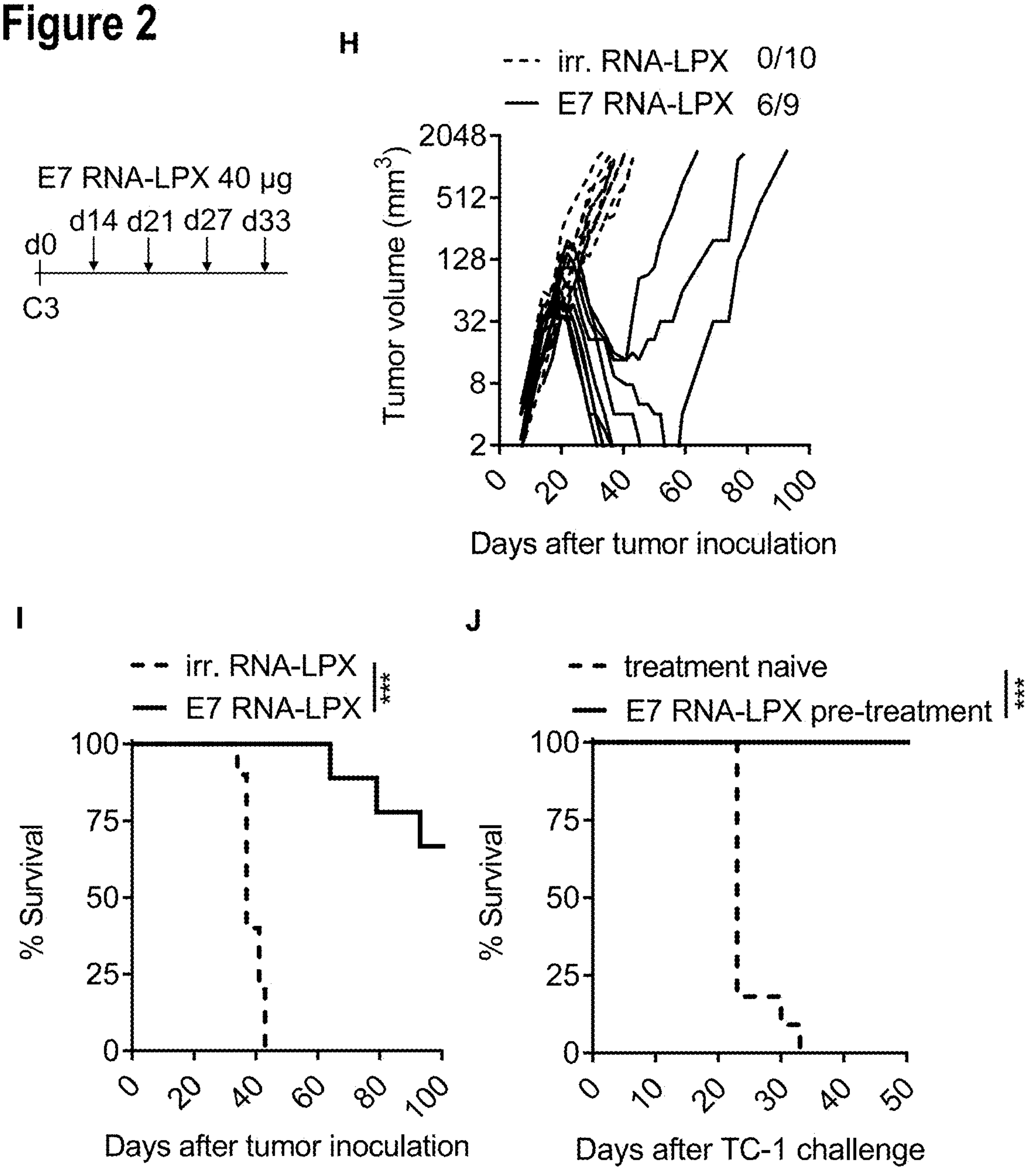
Figure 5:
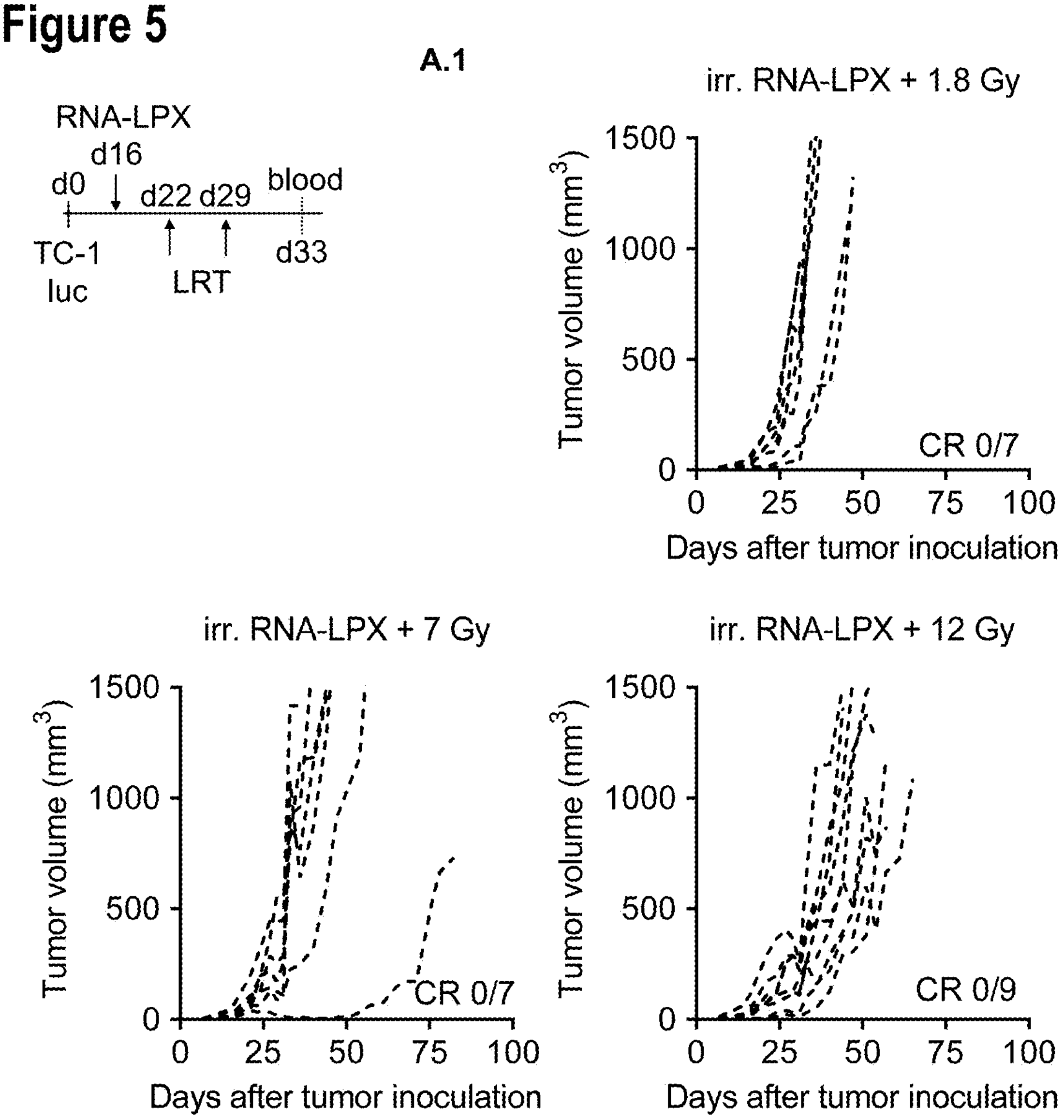
FIG. 5: LRT synergizes with E7 RNA-LPX vaccination to control established $HPV16^+$ tumors. (A-C) Antitumoral effects in s.c. TC-1 tumor-bearing C57BL/6 mice (n=6-14/group), immunized with E7 or control ($OVA_{257-264}$) RNA-LPX at a mean tumor volume of 75 $mm^3$, and tumors locally irradiated with 12 Gy, 7 Gy or 1.8 Gy. (A) Individual tumor growth curves. (B) Survival. (C) E7-multimer$^+$ $CD8^+$ T cells in the blood (n=4/group) as determined by flow cytometry. (D, E) Antitumoral effects in s.c. C3 tumor-bearing C57BL/6 mice (n=10-11/group), immunized with E7 or control ($OVA_{257-264}$) RNA-LPX at a mean tumor volume of 65 $mm^3$, and tumors locally irradiated with 12 Gy. (D) Survival. (E) Individual tumor growth curves. Significance in (B, D) was determined using Mantel-Cox log-rank test and in (C) one-way ANOVA, Tukey's multiple comparison test. (A, E) Ratios depict the fraction of mice with complete responses (CR). Mean±SEM.
Figure 5:
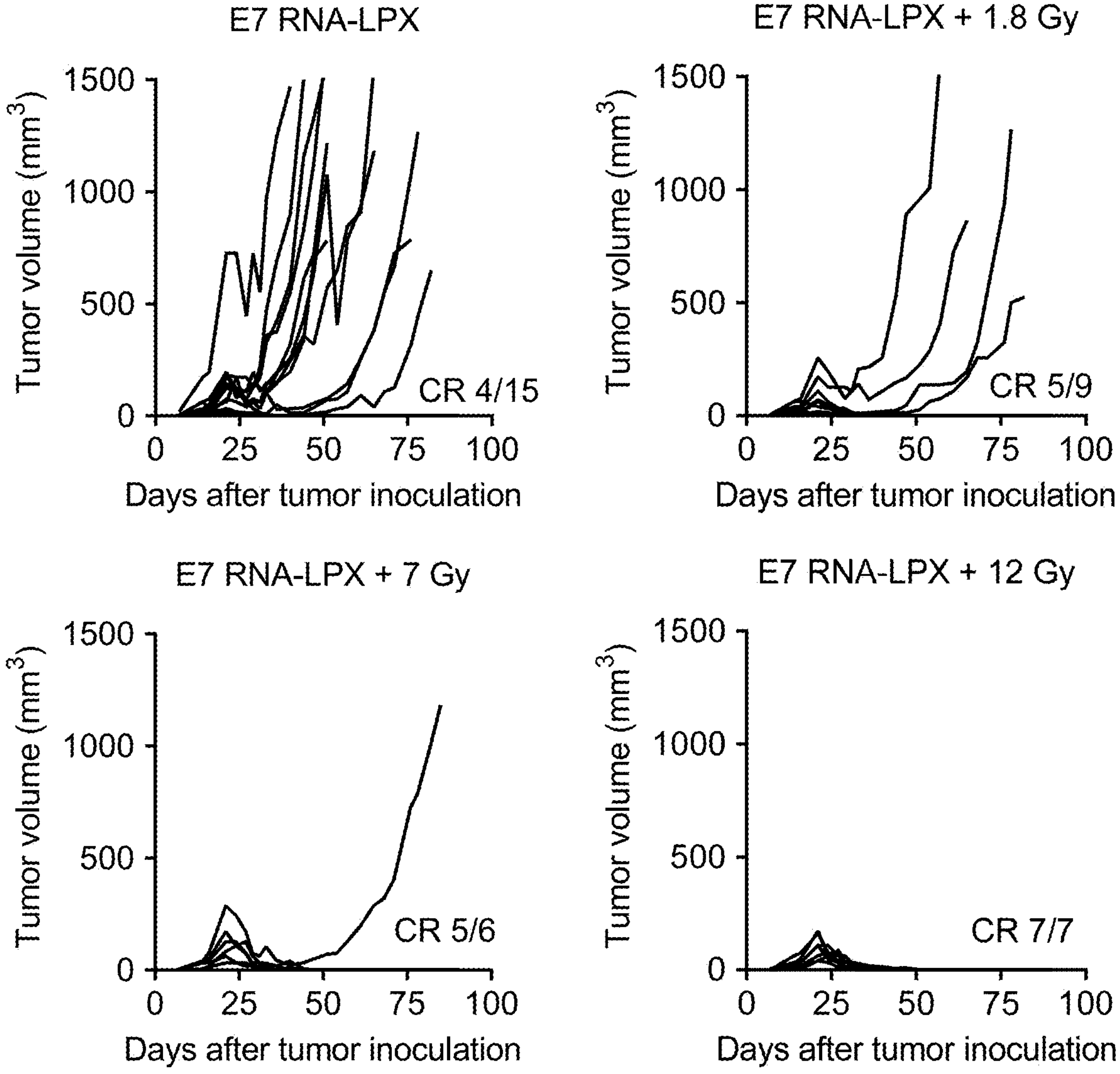
Figure 5:
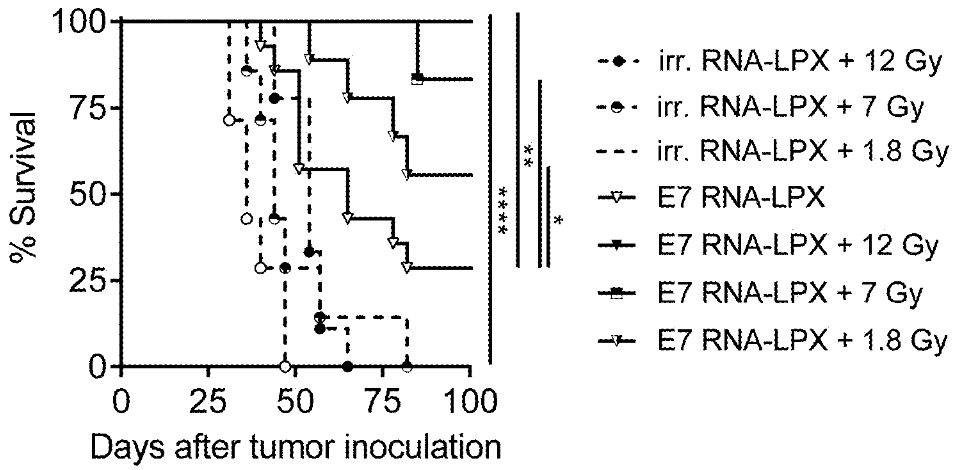
Figure 5:
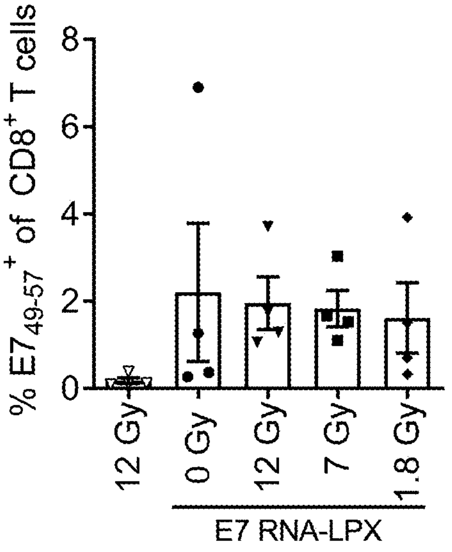
Figure 5:
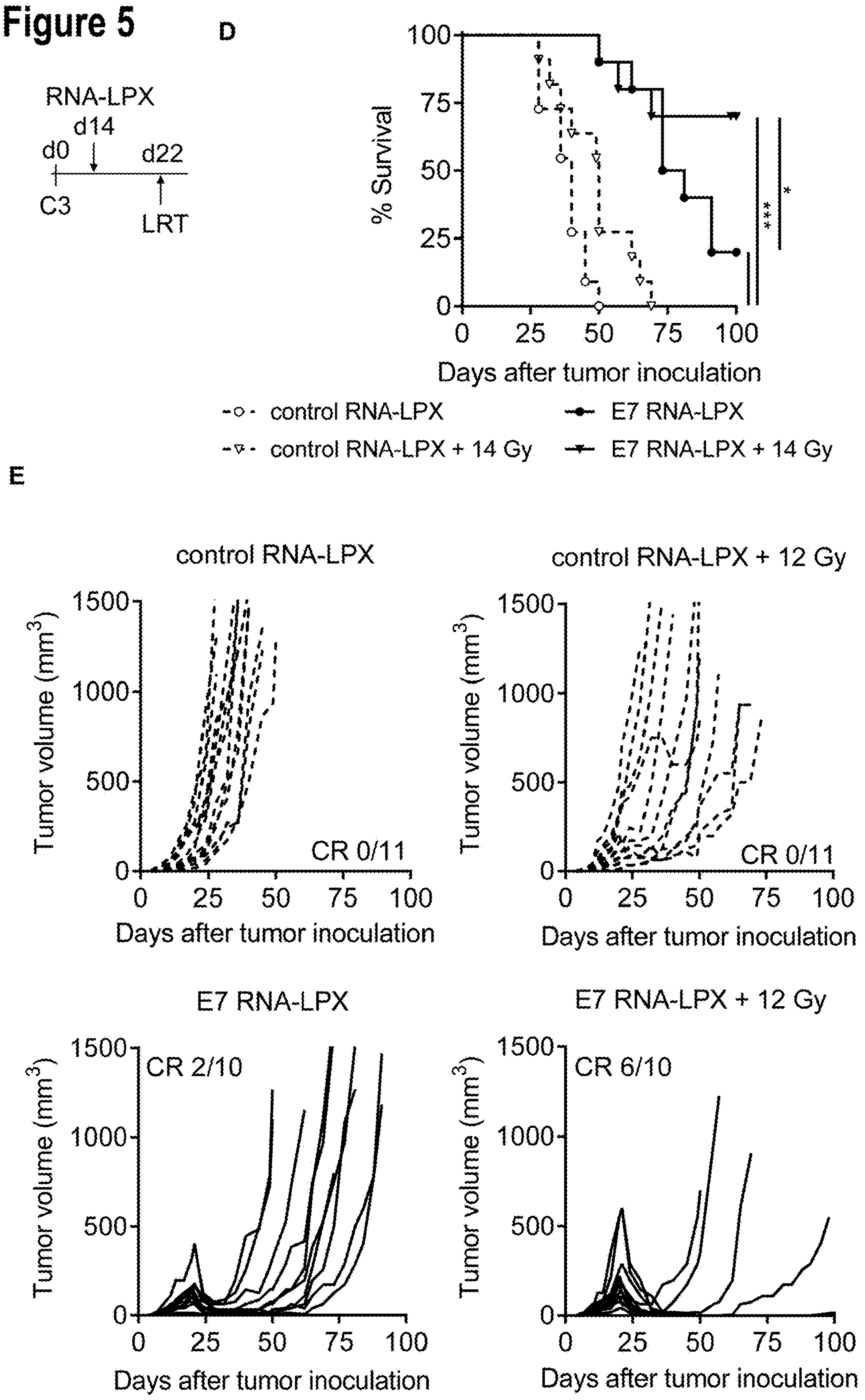

Example 5: LRT Synergizes with E7 RNA-LPX Vaccination to Control Established HPV16$^{+}$ Tumors To explore the combination of LRT and the E7 RNA-LPX vaccine format, we assessed different doses of local radiotherapy (LRT) (1.8 Gy, 7 Gy or 12 Gy) in the murine HPV16 E6/E7$^{+}$ tumor model TC-1. Single and late administrated E7 RNA-LPX vaccination significantly promoted tumor rejection (FIG. 5A2) and the survival of TC-1 tumor-bearing mice (FIG. 5B), however, the majority of TC-1 tumors relapsed. In contrast, LRT treatment had a marginal effect on tumor growth (FIG. 5A1, B), while when combined with the E7 RNA-LPX vaccine, displayed superior therapeutic effects, independent of the tested radiation dose (FIG. 5A2, B). Interestingly, in this tumor model, best therapeutic effects were achieved when E7 RNA-LPX was combined with high dose 12 Gy LRT, rendering 100% of mice tumor free up to 100 days after tumor inoculation (FIG. 5B). In parallel, the expansion of E7-specific CD8 T cells was monitored in the blood 17 days after E7 RNA-LPX and termed equal whether mice were irradiated or not, indicating an efficient priming of RNA-LPX-induced antigen-specific immune responses even when combined with cytotoxic LRT (FIG. 5C). Next we addressed, whether the same therapeutic efficacy of E7 RNA-LPX/LRT can be reached with a different LRT regimen, preserving the biologically effective dose. When 12 Gy LRT was fractionated to 3×6 Gy (data not shown) comparable antitumoral effects, and survival benefit were observed, indicating the relevance of total dose rather than LRT dose-fractionation to reach synergism with E7 RNA-LPX.

We tested then the antitumor efficacy of combined E7 RNA-LPX/LRT in a second HPV16$^{+}$ mouse tumor model, C3. Similar to TC-1, E7 RNA-LPX significantly enhanced the survival of C3 tumor-bearing mice, while 12 Gy LRT also only had a marginal effect on C3 tumor growth (FIG. 5D, E). Wheras all LRT-treated C3 tumor-bearing mice had to be sacrificed by day 75 after tumor challenge, combined E7 RNA-LPX/LRT lead to a significant survival benefit of C3 tumor-bearing mice (FIG. 5D) and enhanced the rate of complete responses to 60% (FIG. 5E). As for HPV16$^{+}$ TC-1 tumor-bearing mice, combined E7 RNA-LPX/LRT mediated superior tumor rejection of HPV16$^{+}$ C3 tumors, outperforming all other treatment groups.

Figure 6:
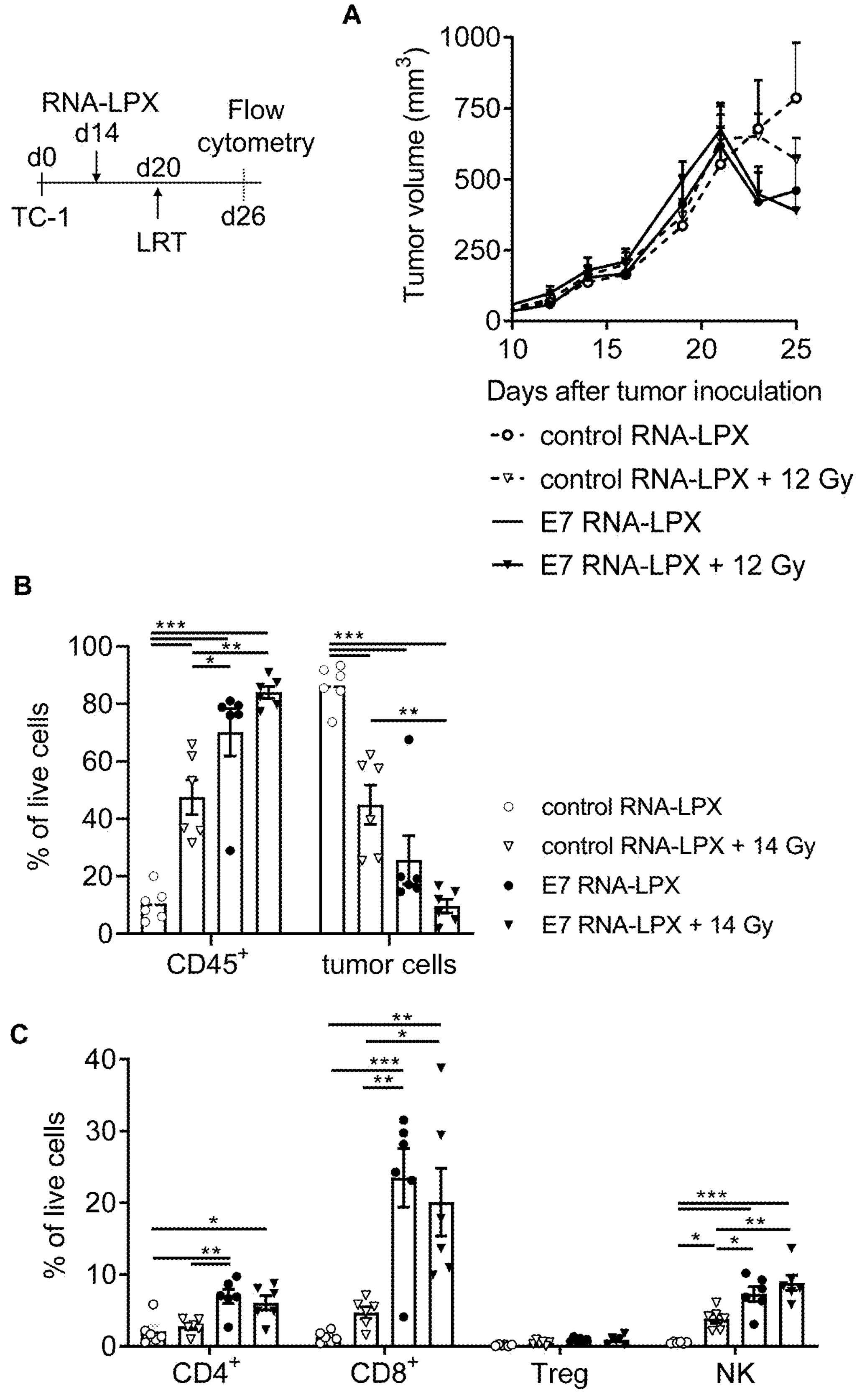
FIG. 6: Tumors of E7 RNA-LPX treated mice are highly infiltrated by effector immune cells. Flow cytometric characterization of s.c. TC-1 tumor, spleen and tumor-draining lymph node (inguinal) excised from s.c. TC-1 tumor-bearing C57BL/6 mice (n=6/group), vaccinated with E7 or control ($OVA_{257-264}$) RNA-LPX at a mean tumor volume of 165 $mm^3$ and locally irradiated with 12 Gy. (A) Mean tumor growth. (B) Fraction of tumor infiltrating $CD45^+$ leukocytes and tumor cells, and (C) of $CD4^+$, $CD8^+$, regulatory T (Treg) and NK cells. (D) Fraction of $E7_{49-57}$ multimer-positive $CD8^+$ T cells in tumor, spleen and tumor-draining lymph nodes. Representative pseudocolor plots show $E7_{49-57}$ multimer staining in TC-1 tumors. (E) Intracellular cytokine staining of IFNγ and TNFα on $CD8^+$ TIL after ex vivo restimulation with $E7_{49-57}$ peptides. Significance in (B-E) was determined using one-way ANOVA, Tukey's multiple comparison test. Mean±SEM. ns=non significant.
Figure 6:
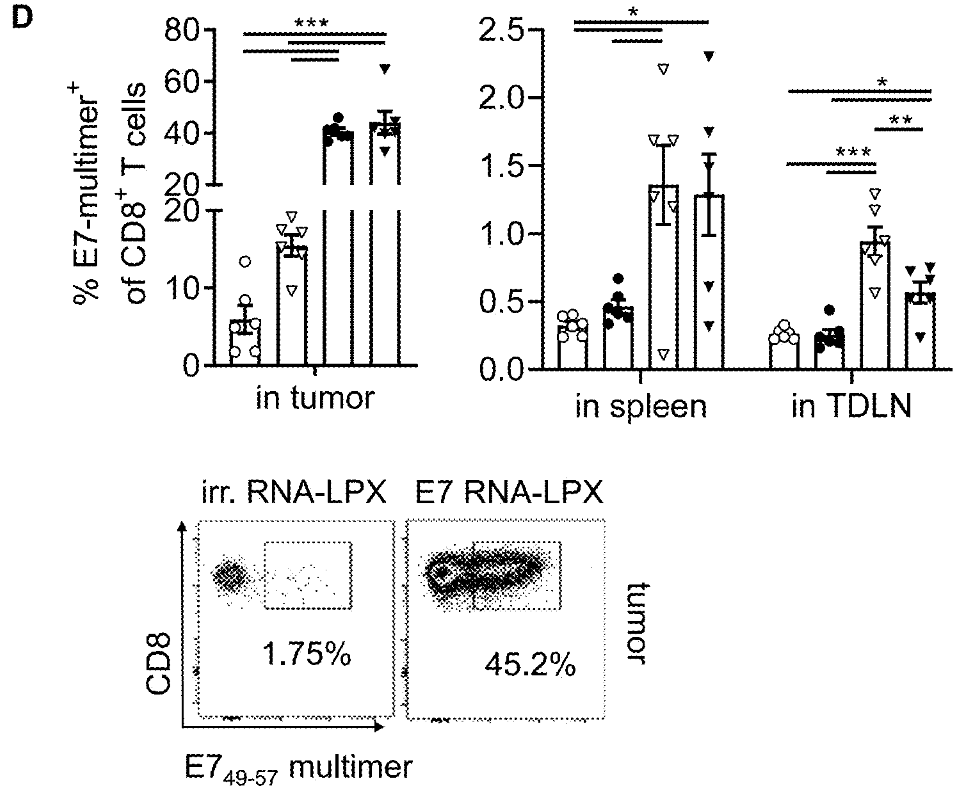
Figure 6:
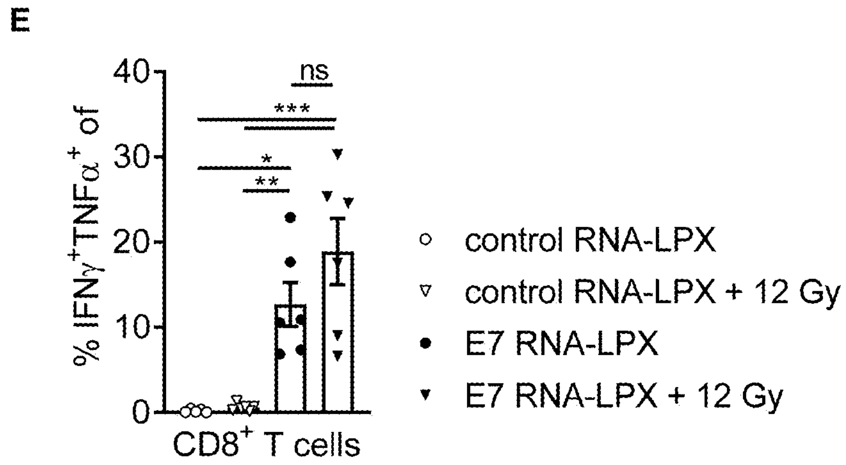

Example 6: Tumors of E7 RNA-LPX Treated Mice are Highly Infiltrated by Effector Immune Cells To characterize underlying cellular effects of superior tumor rejection after combined E7 RNA-LPX/LRT, we analyzed TC-1 tumor immune infiltrates by flow cytometry (FIG. 6). TC-1 tumors were excised twelve days after a single E7 RNA-LPX vaccination and five days after 12 Gy LRT, at a time point when tumor growth curves of single therapies started to diverge in respect to the control group, however, mice under E7 RNA-LPX/LRT therapy still displayed similar tumor sizes as E7 RNA-LPX vaccinated mice (FIG. 6A). Flow cytometry data showed that E7 RNA-LPX vaccination increased the infiltration of CD45$^{+}$ leukocytes from 10% at baseline (control RNA-LPX) to 70%, and reduced tumor cell contents from 90% to 20% (FIG. 6B).

LRT also mediated CD45$^{+}$ leukocyte infiltration and led to a decrease in tumor cell content, however, to a lesser extent than the E7 RNA-LPX vaccine. Further, E7 RNA-LPX vaccinated mice displayed a higher fraction of intratumoral CD4, CD8, NK cells (FIG. 6C) and E7-specific CD8 T cells in the tumor as well as in spleens and lymph nodes of treated mice (FIG. 6D), whereas LRT alone only mildly modulated these target populations. Immune infiltrates of E7 RNA-LPX/LRT-treated mice largely overlapped with those of E7 RNA-LPX-vaccinated mice (FIG. 6B, C, D). Upon in vitro restimulation of tumor infiltrating CD8 T cells (CD8 TIL) with E7 peptide-loaded BMDC, CD8 TIL from E7 RNA-LPX vaccinated mice secreted the highest level of IFNγ and TNFα effector cytokines, whether TC-1 tumors were irradiated or not (FIG. 6E).

At this early time point of analysis, E7 RNA-LPX seemed to dominantly contribute to the immune cell infiltration observed in E7 RNA-LPX/LRT-treated mice, whereas combined LRT did not add onto immunological effects observed.

Example 7: Combined LRT Enhances Tumor Cell Death, Reduces Local Immune Suppression and Promotes Vaccine-Induced CD8$^{+}$ T Cells Proliferation Besides characterizing infiltrating immune cell subsets, we investigated the effect of combined E7 RNA-LPX/LRT on TC-1 tumor cell content and their phenotype. As a cytotoxic therapy, LRT potently reduced TC-1 tumor cell counts by 3-fold (FIG. 7A), and increased the fraction of apoptotic tumor cells, characterized by expression of cleaved caspase-3 (CC3$^{+}$, FIG. 7B) and the death receptor Fas (FIG. 7C). The expression of major histocompatibility complex (MHC) class I (FIG. 7D), T cell inhibitory receptor PD-L1 (FIG. 7E), and T and NK cell inhibitory innate immune receptor Qa-1$^{b}$ (FIG. 7F) on tumor cells was only mildly modulated by LRT. E7 RNA-LPX vaccination on the other hand did not change total tumor cell content (FIG. 7A), only slightly increased the fraction of CC3$^{+}$ tumor cells (FIG. 7B), and expression of Fas on tumor cells (FIG. 7C), however, strongly modulated the expression of MHC class I (FIG. 7D), PD-L1 (FIG. 7E) and to a lesser extent Qa-1$^{b}$ (FIG. 7F) on tumor cells. TC-1 tumor cells from E7 RNA-LPX/LRT-treated mice shared all characteristics of E7 RNA-LPX-treated mice, except tumor content (FIG. 7A) and fraction of CC3$^{+}$ tumor cells (FIG. 7B). Tumor cell content was significantly and strongly reduced in the same manner as after LRT monotherapy and paired with a larger fraction of tumor cells undergoing apoptosis (CC3$^{+}$, FIGS. 7A and B).

Figure 7:
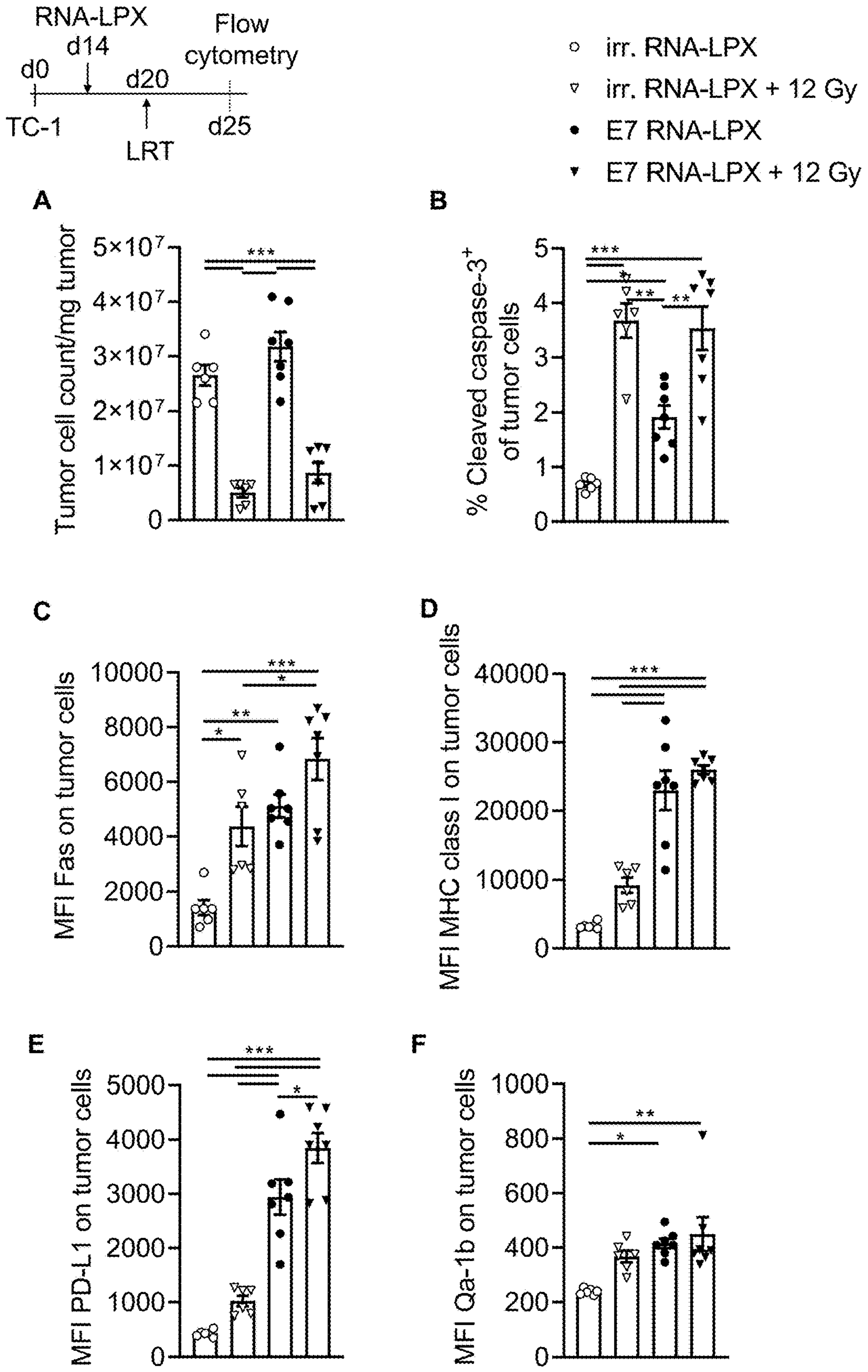
FIG. 7: Combined LRT enhances tumor cell death, reduces local immune suppression and promotes vaccine-induced $CD8^+$ T cells proliferation.
Figure 7:
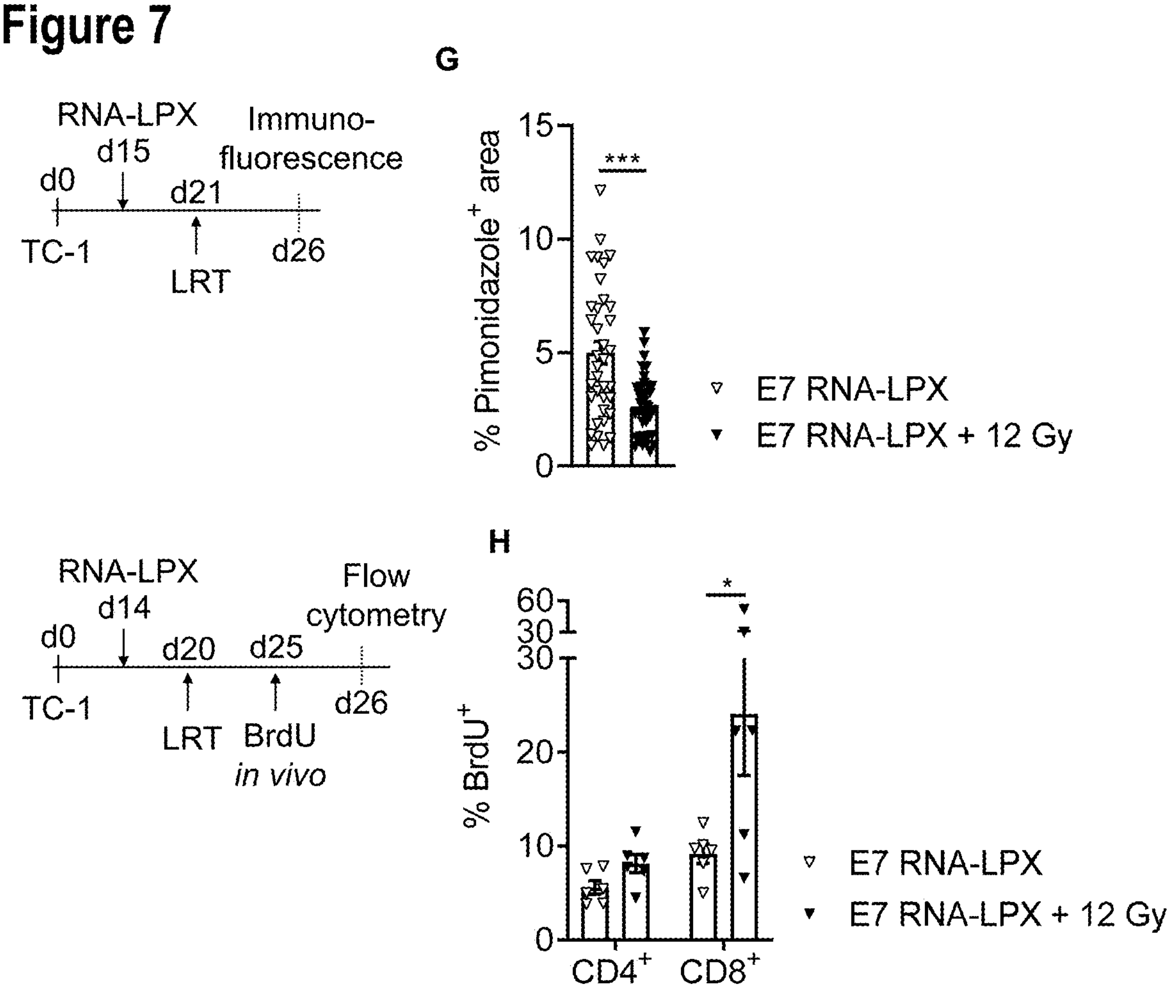

To further characterize the impact of irradiation during antigen-specific T cell responses, we performed an in vitro assay, co-culturing pre-irradiated TC-1 tumor cells with CD8 T cells isolated from spleens of E7 RNA-LPX vaccinated mice, and characterized tumor cell MHC class I, PD-L1 expression, fraction of cleaved caspase-3$^{+}$ tumor cells, as well as cytokine secretion by E7-specific CD8 T cells (data not shown). Different dose LRT (6 Gy and 12 Gy) mildly upregulated MHC class I and PD-L1 expression on tumor cells, being crucial parameters for the recognition and killing of tumor cells by antigen-specific CD8 T cells (data not shown). In sharp contrast, co-culture with E7-specific CD8 T cells highly elevated MHC class I and PD-L1 expression, independent of the radiation pre-treatment (data not shown), which may be a feedback mechanism of tumor cells sensing IFNγ, as it was also observed in vivo (FIG. 7 D, E). Despite similar extracellular expression of MHC class I and PD-L1, tumor cell killing ($CC3^+$ cells) by E7-specific CD8 T cells increased with the radiation dose applied (data not shown). Additionally, E7-specific $CD8^+$ T cells secreted more IFNγ when co-cultured with irradiated tumor cells, arguing for a better recognition of irradiated TC-1 tumor cells by E7-specific CD8 T cells (doses ≥4 Gy, data not shown). These in vitro data support the evidence that radiation renders tumor cells more susceptible to antigen-specific CD8 T cell-mediated killing.

Besides tumor cell phenotypes, we wanted to investigate if E7 RNA-LPX induced CD8 T cells would sense an altered local tumor microenvironment, such as tumor hypoxia, which is a commonly described factor involved in immunosuppression and linked to an aberrant and non-physiological vasculature in fast growing tumors (Li, Y., Patel, S. P., Roszik, J. & Qin, Y., *Frontiers in immunology* 9, 1591 (2018)). Thus, prior organ excision, the hypoxia probe pimonidazole (Varia, M. A. et al., *Gynecologic oncology* 71, 270-277 (1998)) was injected intravenously into E7 RNA-LPX- or E7 RNA-LPX/LRT-treated TC-1 tumor-bearing mice and hypoxic tumor areas analyzed by histology. Combined LRT significantly and strongly reduced TC-1 tumor hypoxia in E7 RNA-LPX-treated mice (FIG. 7G), and was interestingly associated with the highest proliferation rate of CD8 TIL in this treatment group (FIG. 7H) as shown by the higher incorporation of base analogue bromdeoxyuridine (BrdU) in CD8 TIL, but not in CD4 TIL.

Based on our observations, E7 RNA-LPX vaccination rendered lowly immune infiltrated and cold TC-1 tumors immunologically hot (FIG. 6B, C, D), whereas combined LRT reduced tumor cell content and additionally diminished intratumoral hypoxia (FIG. 7A, G), which seemed to foster the proliferative capacity of CD8 (FIG. 7H) and allowed late tumor rejection.

Example 8: LRT Renders E7-Specific $CD8^+$ T Cell Responses More Potent and Long-Lasting Previously we observed that E7-specific CD8 TIL, generated by E7 RNA-LPX vaccination, displayed the same secretion level of IFNγ and TNFα effector cytokines whether tumors were irradiated or not (FIG. 6E and, at this early time point, antitumoral effects were similar (FIG. 6A).

As combined LRT enhanced tumor rejection at later time points, we turned to characterize functional parameters of E7-specific CD8 T cells when tumor growth curves of E7 RNA-LPX- and E7 RNA-LPX/LRT-treated mice diverged as occurred 9 days after LRT (FIG. 8A). Flow cytometry data showed that E7 RNA-LPX- and E7 RNA-LPX/LRT-treated TC-1 tumor bearing mice displayed the same frequency of E7-specific CD8 T cells (FIG. 8B) as well as a similar expression of the inhibitory receptors Tim-3 (FIG. 8C) and PD-1 (FIG. 8D), however, a higher expression of the T cell inhibitory receptor NKG2AB was detectable in CD8 TIL isolated from E7 RNA-LPX/LRT-treated mice (FIG. 8E). Importantly, E7-specific CD8 TIL from combination therapy treated mice significantly secreted more IFNγ and TNFα effector cytokines (FIG. 8F), as well as IL-2 (FIG. 8G), upon antigenic restimulation, indicating a higher effector function and activation status of vaccine induced E7-specific CD8 T cells that correlates with their higher biological effect during tumor rejection. This higher biological effect was paired with reduced tumor content (data not shown) and a higher level of apoptotic tumor cells ($CC3^+$, data not shown), whereas other immunological parameters of tumor cell recognition, such as MHC class I, PD-L1 and Fas expression remained unchained (data not shown).

Overall the data indicate that LRT reduced tumor cell content and immunosuppressive factors within the TME and, hence, rendered vaccine-induced E7-specific CD8 TIL responses more potent and long lasting for augmented the rejection of $HPV16^+$ tumors.

Example 9: E7 RNA-LPX and Cisplatin Chemotherapy Synergize to Reject $HPV16^+$ TC-1 Tumors As chemotherapy is part of the standard of care in HNSCC cancer patients (PMID: 24273416), we assessed the combination of cisplatin chemotherapy—a chemotherapy most commonly used in HNSCC patients- and novel E7 RNA-LPX vaccines in $HPV16^+$ TC-1 tumor-bearing C57BL/6 mice as a potential future treatment regiment for $HPV^+$ HNSCC patients. TC-1 tumor bearing mice were treated with E7 RNA-LPX on day 16 and received two doses of cisplatin chemotherapy on day 22 and 28 (FIG. 9). Control mice were treated with control RNA-LPX coding for OVA not expressed by TC-1 tumors, or control RNA-LPX in combination with cisplatin. Whereas all control RNA-LPX vaccinated mice, had to be sacrificed by day 43, E7 RNA-LPX treatment enhanced the rate of complete responses (FIG. 9A), significantly slowed tumor growth (FIG. 9 B) and induced a survival benefit (FIG. 9 C). Cisplatin chemotherapy only slightly improved tumor growth in control RNA-LPX vaccinated mice (FIG. 9A, B), but strongly and significantly enhanced the therapeutic effects of E7 RNA-LPX vaccines with 10/12 mice being tumor free (FIG. 9A). In addition, combined E7 RNA-LPX and cisplatin chemotherapy significantly reduced tumor growth (FIG. 9 B) and mediated a strong survival benefit (FIG. 9 C), not observed in any of the monotherapy treated groups. Collectively, cisplatin augments the antitumor effects of E7 RNA-LPX vaccination. RNA-LPX vaccines and platinum-based chemotherapies can therefore serve as synergistic combination partners for improved cancer therapies.

The invention claimed is:

1. A composition or medical preparation comprising at least one RNA, wherein the at least one RNA encodes:

(i) an amino acid sequence comprising human papillomavirus (HPV) E6 protein, an immunogenic variant thereof, or an immunogenic fragment of the HPV E6 protein or the immunogenic variant thereof; and (ii) an amino acid sequence comprising HPV E7 protein, an immunogenic variant thereof, or an immunogenic fragment of the HPV E7 protein or the immunogenic variant thereof;

wherein (a) the RNA encoding the amino acid sequence under (i) comprises at least one of: the nucleotide sequence of SEQ ID NO: 2, a nucleotide sequence having at least 99%, 98%, 97%, 96%, 95%, 90%, 85%, or 80% identity to the nucleotide sequence of SEQ ID NO: 2, a nucleotide sequence encoding the amino acid sequence of amino acids 37 to 194 of SEQ ID NO: 1, and a nucleotide sequence encoding an amino acid sequence having at least 99%, 98%, 97%, 96%, 95%, 90%, 85%, or 80% identity to the amino acid sequence of amino acids 37 to 194 of SEQ ID NO: 1; or (b) the RNA encoding the amino acid sequence under (ii) comprises at least one of: the nucleotide sequence of SEQ ID NO: 4, a nucleotide sequence having at least 99%, 98%, 97%, 96%, 95%, 90%, 85%, or 80% identity to the nucleotide sequence of SEQ ID NO: 4, a nucleotide sequence encoding the amino acid sequence of amino acids 37 to 134 of SEQ ID NO: 3, and a nucleotide sequence encoding an amino acid sequence having at least 99%, 98%, 97%, 96%, 95%, 90%, 85%, or 80% identity to the amino acid sequence of amino acids 37 to 134 of SEQ ID NO: 3.

2. The composition or medical preparation of claim 1, wherein each of the amino acid sequences under (i), or (ii) is encoded by a separate RNA.

3. The composition or medical preparation of claim 1, wherein at least one amino acid sequence under (i), or (ii)

comprises an amino acid sequence enhancing at least one of: antigen processing, and presentation.

4. The composition or medical preparation of claim 3, wherein the amino acid sequence enhancing at least one of: antigen processing, and presentation comprises an amino acid sequence corresponding to the transmembrane and cytoplasmic domain of a MHC molecule, preferably a MHC class I molecule comprising the amino acid sequence of SEQ ID NO: 26, or an amino acid sequence having at least 99%, 98%, 97%, 96%, 95%, 90%, 85%, or 80% identity to the amino acid sequence of SEQ ID NO: 26.

5. The composition or medical preparation of claim 1, wherein at least one amino acid sequence under (i), or (ii) comprises an amino acid sequence which breaks immunological tolerance or at least one RNA is co-administered with RNA encoding an amino acid sequence which breaks immunological tolerance.

6. The composition or medical preparation of claim 5, wherein the amino acid sequence which breaks immunological tolerance comprises helper epitopes, preferably tetanus toxoid-derived helper epitopes comprising the amino acid sequence of SEQ ID NO: 27, or an amino acid sequence having at least 99%, 98%, 97%, 96%, 95%, 90%, 85%, or 80% identity to the amino acid sequence of SEQ ID NO: 27.

7. The composition or medical preparation of claim 1, wherein at least one of the amino acid sequences under (i), or (ii) is encoded by a coding sequence which modified by at least one of: codon-optimization and increase of the G/C content compared to wild type coding sequence, wherein the codon-optimization and the increase in the G/C content preferably does not change the sequence of the encoded amino acid sequence.

8. The composition or medical preparation of claim 1, wherein at least one RNA comprises at least one of:

(a) the 5' cap $m_2^{7,2'}$-OGppsp (5') G, (b) a 5' UTR comprising the nucleotide sequence of SEQ ID NO: 30, or a nucleotide sequence having at least 99%, 98%, 97%, 96%, 95%, 90%, 85%, or 80% identity to the nucleotide sequence of SEQ ID NO: 30, (c) a 3' UTR comprising the nucleotide sequence of SEQ ID NO: 31, or a nucleotide sequence having at least 99%, 98%, 97%, 96%, 95%, 90%, 85%, or 80% identity to the nucleotide sequence of SEQ ID NO: 31, and (d) a poly-A sequence, wherein the poly-A sequence comprises at least 100 nucleotides, wherein further the poly-A sequence comprises the nucleotide sequence of SEQ ID NO: 32.

9. The composition or medical preparation of claim 1, wherein the RNA is formulated as a liquid, formulated as a solid, or a combination thereof wherein the RNA is formulated for injection, wherein further the RNA is formulated for intravenous administration.

10. The composition or medical preparation of claim 1, wherein the RNA is formulated as lipoplex particles, wherein the RNA lipoplex particles are obtainable by mixing the RNA with liposomes.

11. The composition or medical preparation of claim 1, which further comprises an immune checkpoint inhibitor, wherein the immune checkpoint inhibitor is selected from a) a PD-1 inhibitor, b) a PD-L1 inhibitor, c) an anti-PD-1 antibody, d) an anti-PD-L1 antibody, (e) an anti-PD-1 antibody selected from: pembrolizumab (KEYTRUDA; MK-3475), nivolumab (OPDIVO; BMS-936558), pidilizumab (CT-011), cemiplimab (LIBTAYO, REGN2810), spartalizumab (PDR001), MEDI0680 (AMP-514), dostarlimab (TSR-042), cetrelimab (JNJ 63723283), toripalimab (JS001), AMP-224 (GSK-2661380), PF-06801591, tislelizumab (BGB-A317), ABBV-181, BI 754091, and SHR-1210, and (f) an anti-PD-L1 antibody selected from: atezolizumab (TECENTRIQ; RG7446; MPDL3280A; R05541267), durvalumab (MEDI4736), BMS-936559, avelumab (bavencio), lodapolimab (LY3300054), CX-072 (Proclaim-CX-072), FAZ053, KN035, and MDX-1105.

12. The composition or medical preparation of claim 1, which further comprises a platinum compound, wherein the platinum compound comprises cisplatin.

13. The composition or medical preparation of claim 1, which comprises an immune checkpoint inhibitor and a platinum compound.

14. The composition or medical preparation of claim 1, which is a pharmaceutical composition, wherein the pharmaceutical composition further comprises one or more compounds selected from pharmaceutically acceptable carriers, diluents and excipients.

15. The composition or medical preparation of claim 1, wherein the medical preparation is a kit.

16. The composition or medical preparation of claim 1 for pharmaceutical use.

17. The composition or medical preparation of claim 16, wherein the pharmaceutical use comprises a therapeutic or prophylactic treatment of a disease or disorder.

18. The composition or medical preparation of claim 17, wherein the therapeutic or prophylactic treatment of a disease or disorder comprises treating or preventing HPV-positive cancer.

19. The composition or medical preparation of claim 1, which is for administration to a human.

20. The composition or medical preparation of claim 17, wherein the therapeutic or prophylactic treatment of a disease or disorder further comprises administering radiotherapy, preferably local radiotherapy.

21. A method of treating HPV-positive cancer in a subject comprising administering the composition or medical preparation of claim 1.

22. The method of claim 21, wherein the RNA is administered by intravenous injection.

23. The method of claim 21, which further comprises administering to the subject an immune checkpoint inhibitor.

24. The method of claim 21, which further comprises administering to the subject a platinum compound.

25. The method of claim 21, which comprises administering to the subject an immune checkpoint inhibitor and a platinum compound.

26. The method of claim 21, wherein the subject is a human.

27. The method of claim 21, which further comprises administering to the subject radiotherapy, preferably local radiotherapy.

* * * * *